United States Patent [19]
Sakamoto et al.

[11] Patent Number: 5,872,137
[45] Date of Patent: Feb. 16, 1999

[54] DIHALOPROPENE COMPOUNDS, INSECTICIDAL/ACARICIDAL AGENTS CONTAINING SAME, AND INTERMEDIATES FOR THEIR PRODUCTION

[75] Inventors: Noriyasu Sakamoto, Osaka; Masaya Suzuki, Takarazuka; Kazunori Tsushima, Sanda; Kimitoshi Umeda, Takarazuka, all of Japan

[73] Assignee: Sumitomo Chemical Company, Limited, Osaka, Japan

[21] Appl. No.: 917,372

[22] Filed: Aug. 26, 1997

Related U.S. Application Data

[63] Continuation of Ser. No. 624,488, filed as PCT/JP95/01439 Jul. 20, 1995, abandoned.

[30] Foreign Application Priority Data

| Aug. 4, 1994 | [JP] | Japan | 6-183461 |
| Oct. 7, 1994 | [JP] | Japan | 6-243931 |
| Apr. 14, 1995 | [JP] | Japan | 7-089737 |

[51] Int. Cl.$^6$ .................................................. A01N 43/40
[52] U.S. Cl. .......................... 514/345; 568/649; 568/674; 424/406
[58] Field of Search ................................ 568/649, 674; 424/406; 514/345

[56] References Cited

U.S. PATENT DOCUMENTS

| 4,048,235 | 9/1977 | Karrer . |
| 4,061,683 | 12/1977 | Karrer . |
| 4,496,440 | 1/1985 | Campbell et al. . |
| 4,772,633 | 9/1988 | Matsuo et al. . |
| 5,302,619 | 4/1994 | Shuto et al. . |
| 5,530,015 | 6/1996 | Sakamoto et al. . |

FOREIGN PATENT DOCUMENTS

| 0203798 | 12/1986 | European Pat. Off. . |
| 0218543 | 4/1987 | European Pat. Off. . |
| 0227369 | 7/1987 | European Pat. Off. . |
| 55-120565 | 9/1980 | Japan . |
| 56-029504 | 3/1981 | Japan . |
| 1420171 | 1/1976 | United Kingdom . |
| 1424211 | 2/1976 | United Kingdom . |
| 1578412 | 11/1980 | United Kingdom . |

OTHER PUBLICATIONS

Head et al., J. Chem. Soc. (C), pp. 871–874 (1971).
Dorman, J. Org. Chem., vol. 31, pp.3666–3671 (1966).
English language abstract of Japanese Patent No. 55–120565 Aug. 3, 1979.
English language abstract of Japanese Patent No. 56–029504 Aug. 16, 1979.

*Primary Examiner*—Gary Geist
*Assistant Examiner*—Sreeni Padmanabhan
*Attorney, Agent, or Firm*—Birch, Stewart, Kolasch & Birch, LLP

[57] ABSTRACT

The dihalopropene compounds of the general formula [I] have excellent insecticidal/acaricidal activity, so that they are satisfactorily effective for the control of noxious insects, mites and ticks.

92 Claims, No Drawings

DIHALOPROPENE COMPOUNDS, INSECTICIDAL/ACARICIDAL AGENTS CONTAINING SAME, AND INTERMEDIATES FOR THEIR PRODUCTION

This application is a continuation of application Ser. No. 08/624,488 filed on Apr. 4, 1996, now abandoned.

This is the U.S. National stage Application of PCT/JP95/01439 filed Jul. 20, 1995 now WO96/04228 published Feb. 15, 1996.

1. Technical Field

The present invention relates to dihalopropene compounds, insecticidal/acaricidal agents containing these compounds as active ingredients, for their production.

2. Background Art

As disclosed in JP-A 48-86835/1973 and JP-A 49-1526/1974, for example, it is well known that some kinds of propene compounds can be used as an active ingredient of insecticides.

In view of their insecticidal/acaricidal activity, it cannot always be said that these compounds are satisfactorily active for the control of noxious insects, mites and ticks.

Disclosure of Invention

The present inventors have intensively studied to find a compound having excellent insecticidal/acaricidal activity. As a result, they have found that particular dihalopropene compounds have satisfactory insecticidal/acaricidal activity for the control of noxious insects, mites and ticks, thereby completing the present invention.

That is, the present invention provides a dihalopropene compound (hereinafter referred to as the present compound) of the general formula:

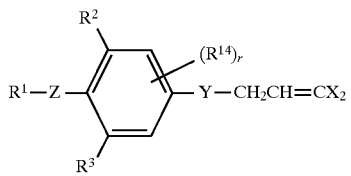

[I]

wherein $R^1$ is $C_1$–$C_{10}$ alkyl, $C_1$–$C_5$ haloalkyl, $C_2$–$C_{10}$ alkenyl, $C_2$–$C_6$ haloalkenyl, $C_3$–$C_9$ alkynyl, $C_3$–$C_5$ haloalkynyl, $C_2$–$C_7$ alkoxyalkyl, ($C_1$–$C_3$) alkoxy ($C_1$–$C_7$) carbonylalkyl, $C_2$–$C_7$ alkylthioalkyl; $C_3$–$C_6$ cycloalkyl which may be substituted with $C_1$–$C_4$ alkyl, $C_1$–$C_3$ alkoxy or $C_1$–$C_3$ haloalkoxy; $C_4$–$C_9$ cycloalkylalkyl which may be substituted with $C_1$–$C_4$ alkyl; $C_5$–$C_6$ cycloalkenyl which may be substituted with $C_1$–$C_4$ alkyl; $C_6$–$C_8$ cycloalkenylalkyl which may be substituted with $C_1$–$C_4$ alkyl; or $Q_1$, $Q_2$, $Q_3$, $Q_4$, $Q_5$, $Q_6$, $Q_7$, $Q_8$, $Q_9$ or $Q_{10}$ of the general formula:

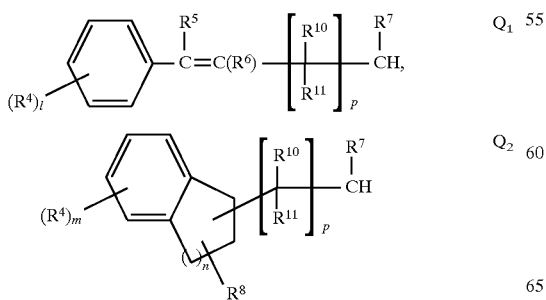

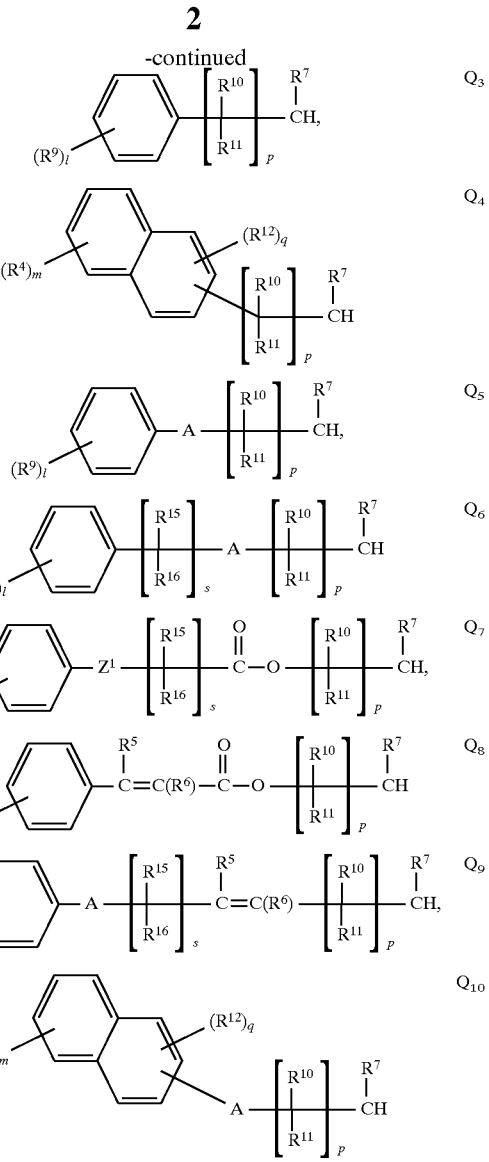

wherein $R^4$ and $R^{12}$ are independently halogen, $C_1$–$C_4$ alkyl, $C_1$–$C_3$ haloalkyl, $C_1$–$C_3$ alkoxy or $C_1$–$C_3$ haloalkoxy, $R^5$ and $R^6$ are independently hydrogen, $C_1$–$C_3$ alkyl, trifluoromethyl or halogen, $R^7$ is hydrogen or $C_1$–$C_3$ alkyl, $R^8$ is hydrogen, halogen or methyl, $R^9$ is halogen, cyano, nitro, hydroxy, pentafluorosulfanyl ($F_5S$), $C_1$–$C_8$ alkyl, $C_1$–$C_3$ haloalkyl, $C_1$–$C_8$ alkoxy, haloalkoxy, $C_1$–$C_3$ alkylthio, $C_1$–$C_3$ haloalkylthio, $C_3$–$C_6$ alkenyloxy, $C_3$–$C_6$ haloalkenyloxy, $C_1$–$C_3$ hydroxyalkyl, $C_2$–$C_4$ alkenyl, $C_2$–$C_4$ haloalkenyl, $C_2$–$C_4$ alkynyl, $C_2$–$C_4$ alkynyloxy, $C_2$–$C_4$ haloalkynyl, $C_2$–$C_4$ haloalkynyloxy, $C_2$–$C_4$ alkoxyalkyl, $C_2$–$C_4$ alkylthioalkyl, $C_3$–$C_6$ cycloalkyl, $C_5$–$C_6$ cycloalkenyl, $C_2$–$C_5$ alkoxycarbonyl, $C_3$–$C_6$ cycloalkyloxy, $C_5$–$C_6$ cycloalkenyloxy; phenyl which may be substituted with halogen, $C_1$–$C_4$ alkyl, $C_1$–$C_3$ haloalkyl, $C_1$–$C_3$ alkoxy, $C_1$–$C_3$ haloalkoxy, $C_3$–$C_6$ alkenyloxy or $C_3$–$C_6$ haloalkenyloxy; phenoxy which may be substituted with halogen, $C_1$–$C_4$ alkyl, $C_1$–$C_3$ haloalkyl, $C_1$–$C_3$ alkoxy, $C_1$–$C_3$ haloalkoxy, $C_3$–$C_6$ alkenyloxy or $C_3$–$C_6$ haloalkenyloxy; benzyl which may be substituted with halogen, $C_1$–$C_4$ alkyl, $C_1$–$C_3$ haloalkyl, $C_1$–$C_3$ alkoxy, $C_1$–$C_3$ haloalkoxy, $C_3$–$C_6$ alkenyloxy or $C_3$–$C_6$ haloalkenyloxy; benzyloxy which may be substituted with halogen, $C_1-C_4$ alkyl, $C_1-C_3$ haloalkyl, $C_1-C_3$ alkoxy, $C_1-C_3$ haloalkoxy, $C_3-C_6$ alkenyloxy or $C_3-C_6$ haloalkenyloxy; or pyridyloxy which may be substituted with halogen, $C_1-C_4$ alkyl, $C_1-C_3$ haloalkyl, $C_1-C_3$ alkoxy, $C_1-C_3$ haloalkoxy, $C_3-C_6$ alkenyloxy or $C_3-C_6$ haloalkenyloxy; or when l is an integer of 2 to 5, two adjacent $R^9$'s are taken together to form trimethylene, tetramethylene, methylenedioxy which may be substituted with halogen or $C_1-C_3$ alkyl; or ethylenedioxy which may be substituted with halogen or $C_1-C_3$ alkyl, $R^{10}$, $R^{11}$, $R^{15}$ and $R^{16}$ are independently hydrogen, $C_1-C_3$ alkyl or trifluoromethyl, A is oxygen, $S(O)_t$, $NR^{13}$, $C(=G^1)G^2$ or $G^1C(=G^2)$ wherein $G^1$ and $G^2$ are independently oxygen or sulfur, $R^{13}$ is hydrogen, acetyl or $C_1-C_3$ alkyl, and t is an integer of 0 to 2, $Z^1$ is oxygen, sulfur or $NR^{17}$ wherein $R^{17}$ is hydrogen, acetyl or $C_1-C_3$ alkyl, l is an integer of 0 to 5, m is an integer of 0 to 4, n is an integer of 1 or 2, p is an integer of 0 to 6, q is an integer of 0 to 3, and s is an integer of 1 to 6, $R^2$, $R^3$ and $R^{14}$ are independently halogen, $C_1-C_3$ haloalkyl or $C_1-C_3$ alkyl, r is an integer of 0 to 2, X's are independently chlorine or bromine, Y is oxygen, NH or sulfur, and Z is oxygen, sulfur or $NR^{13}$ wherein $R^{13}$ is hydrogen, acetyl or $C_1-C_3$ alkyl.

The present invention also provides an insecticidal/acaricidal agent containing the above dihalopropene compound as an active ingredient.

The present invention further provides the following compounds which are useful as intermediates for producing some of the present compounds:

a compound of the general formula:

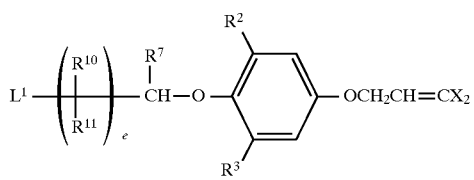

[II]

wherein $R^2$ and $R^3$ are independently halogen, $C_1-C_3$ alkyl or $C_1-C_3$ haloalkyl, $R^7$ is hydrogen or $C_1-C_3$ alkyl, $R^{10}$ and $R^{11}$ are independently hydrogen, $C_1-C_3$ alkyl or trifluoromethyl, X's are independently chlorine or bromine, $L^1$ is hydroxy, halogen, methanesulfonyloxy or p-toluenesulfonyloxy, and e is an integer of 2 to 4; and particularly, a compound wherein $R^7$, $R^{10}$ and $R^{11}$ are all hydrogen, and e is 2 or 3;

a compound of the general formula:

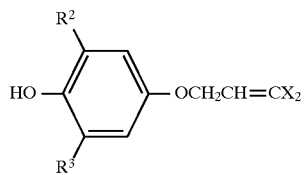

[III]

wherein $R^2$ and $R^3$ are independently halogen, $C_1-C_3$ alkyl or $C_1-C_3$ haloalkyl, and X's are independently chlorine or bromine;

a compound of the general formula:

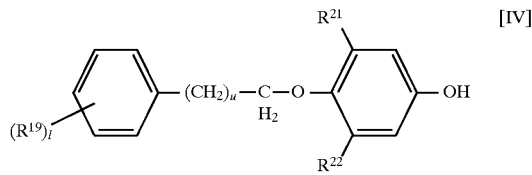

[IV]

wherein $R^{21}$ and $R^{22}$ are independently halogen or $C_1-C_3$ alkyl, $R^{19}$ is halogen, $C_1-C_3$ haloalkoxy or trifluoromethyl, u is 1 to 4, and l is an integer of 0 to 5;

a compound of the general formula:

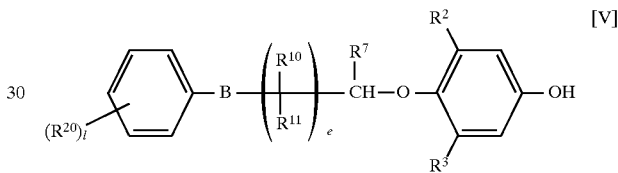

[V]

wherein $R^2$ and $R^3$ are independently halogen, $C_1-C_3$ alkyl or $C_1-C_3$ haloalkyl, $R^7$ is hydrogen or $C_1-C_3$ alkyl, $R^{10}$ and $R^{11}$ are independently hydrogen, $C_1-C_3$ alkyl or trifluoromethyl, $R^{20}$ is halogen, $C_1-C_3$ alkoxy, trifluoromethyl or $C_1-C_3$ haloalkoxy, l is an integer of 0 to 5, and e is an integer of 1 to 4; and particularly, a compound wherein B is oxygen; a compound wherein $R^2$ and $R^3$ are independently halogen or $C_1-C_3$ alkyl, $R^7$, $R^{10}$ and $R^{11}$ are all hydrogen, e is 1 to 4, and B is oxygen, $S(O)_t$ or $NR^{13}$ wherein $R^{13}$ is hydrogen, acetyl or $C_1-C_3$ alkyl, and t is an integer of 0 to 2.

DETAILED DESCRIPTION OF THE INVENTION

The variables in the above formulae for the present compounds and their intermediates can take the following specific examples.

Examples of the halogen atom represented by $R^2$, $R^3$, $R^4$, $R^5$, $R^6$, $R^8$, $R^9$ or $R^{12}$ or present in $R^9$ are fluorine, chlorine, bromine or iodine.

Examples of the $C_1-C_{10}$ alkyl group represented by $R^1$ are methyl, ethyl, n-propyl, isopropyl, n-butyl, isobutyl, sec-butyl, tert-butyl, n-pentyl, isopentyl, neopentyl, tert-pentyl, n-hexyl, n-heptyl, isohexyl, n-octyl, n-nonyl, n-decyl, 3-n-pentyl, 2-ethylbutyl, 1-methylpentyl, 1-ethylbutyl, 3-methylpentyl, 1,3-dimethylbutyl, 1-methylheptyl and 1-methyloctyl.

Examples of the $C_1-C_4$ alkyl group present in $R^1$ or $R^9$, or represented by $R^4$ or $R^{12}$, are methyl, ethyl, n-propyl, isopropyl, n-butyl, isobutyl, sec-butyl and tert-butyl.

Examples of the $C_1-C_3$ alkyl group represented by $R^2$, $R^3$, $R^5$, $R^6$, $R^7$, $R^{10}$, $R^{11}$, $R^{13}$, $R^{14}$, $R^{15}$ or $R^{16}$ are methyl, ethyl, n-propyl and isopropyl.

Examples of the $C_1$–$C_8$ alkyl group represented by $R^9$ are methyl, ethyl, n-propyl, isopropyl, n-butyl, isobutyl, sec-butyl, tert-butyl, n-pentyl, isopentyl, neopentyl, tert-pentyl, 1-ethylpropyl, n-hexyl, isohexyl, 2-ethylbutyl, 1-methylpentyl, 1-ethylbutyl, 3-methylpentyl, 1,3-dimethylbutyl, n-heptyl, n-octyl and 1-methylheptyl.

Examples of the $C_1$–$C_5$ haloalkyl group represented by $R^1$ are trifluoromethyl, difluoromethyl, bromodifluoromethyl, 2,2,2-trifluoroethyl, perfluoroethyl, 2-fluoroethyl, 2-chloroethyl, 2-bromoethyl, 2-iodoethyl, 2,2-dichloroethyl, 2-bromo-1,1,2,2-tetrafluoroethyl, 1,1,2,2,-tetrafluoroethyl, 2-chloro-1,1,2-trifluoroethyl, 2-bromo-1,1,2-trifluoroethyl, 2,2,2-trichloroethyl, 2,2,2-tribromoethyl, 3-chloropropyl, 3-bromopropyl, 3-fluoropropyl, 3-iodopropyl, 3,3,3-trifluoropropyl, 2,2,3,3,3-pentafluoropropyl, 1,1,2,3,3,3-hexafluoropropyl, 2-chloropropyl, 1-chloro-1-methylethyl, 1-bromo-1-methylethyl, 2-fluoro-1-(fluoromethyl)ethyl, 2-chloro-1-(chloromethyl)ethyl, 2-bromo- 1-(bromomethyl)ethyl, 2,2,2-trifluoro-1-(trifluoromethyl)ethyl, 2,3-dibromopropyl, 4-fluorobutyl, 4-bromobutyl, 4-chlorobutyl, 4-iodobutyl, 4-(bromomethyl)propyl, 3-chloro-2,2-dimethyl-n-propyl, 3-bromo-2,2-dimethylpropyl, 2,2,3,4,4, 4-hexafluorobutyl, 3-bromo-1-(bromomethyl)propyl and 2,2,3,3,4,4,5,5-octafluoropentyl.

Examples of the $C_1$–$C_3$ haloalkyl group presented by $R^2$, $R^3$, $R^4$, $R^9$ and $R^{14}$, or present in $R^9$, are trifluoromethyl, difluoromethyl, bromodifluoromethyl, 2,2,2-trifluoroethyl, 2-fluoroethyl, 2-chloroethyl, 2-bromoethyl, 1-fluoroethyl, 1-chloroethyl, 1-bromoethyl, 2,2,3,3,3-pentafluoropropyl, 3,3,3-trifluoropropyl, 1-fluoropropyl, 2-chloropropyl and 3-bromopropyl.

Examples of the $C_2$–$C_{10}$ alkenyl group represented by $R^1$ are vinyl, allyl, homoallyl, isopropenyl, 2-butenyl, 1-methyl-2-propenyl, 2-methyl-2-propenyl, 3-methyl-3-butenyl, 1-ethyl-2-propenyl, 2-ethyl-2-propenyl, 2-pentenyl, 2-methyl-2-butenyl, 1-methyl-2-butenyl, 2-methyl-3-butenyl, 4-pentenyl, 1-methyl-3-butenyl, 1-ethyl-2-propenyl, 1-propyl-2-propenyl, 3-hexenyl, 2-isopropyl-2-propenyl, 2-ethyl-2-butenyl, 2-methyl-2-pentenyl, 1-ethyl-2-butenyl, 1-methyl-4-pentenyl, 1,3-dimethyl-2-butenyl, 2-hexenyl, 4-hexenyl, 5-hexenyl, 1-n-propyl-2-propenyl, 1-allyl-3-butenyl, 2-heptenyl, 1,5-dimethyl-4-hexenyl, 1-pentyl-2-propenyl, 1,7-dimethyl-6-octenyl and geranyl.

Examples of the $C_2$–$C_6$ haloalkenyl group represented by $R^1$ are 2-chloroethenyl, 2,2-dichloroethenyl, 3-chloro-2-propenyl, 3-bromo-2-propenyl, 2-chloro-2-propenyl, 2-bromo-2-propenyl, 3,3-dichloro-2-propenyl, 3,3-dibromo-2-propenyl, 3,3-difluoro-2-propenyl, 2-(chloromethyl)-2-propenyl, 4-chloro-2-butenyl, 4-chloro-2-butenyl, 3-chloro-4,4,4-trifluoro-2-butenyl, 4-bromo-3-fluoro-4,4-difluoro-2-butenyl, 3,4,4,4-tetrafluoro-2-butenyl, 4,4-dichloro-3-butenyl, 4,4-dibromo-3-butenyl, 3-chloro-2-butenyl and 6,6-dichloro-5-hexenyl.

Examples of the $C_2$–$C_4$ alkenyl group represented by $R^9$ are vinyl, isopropenyl, 1-propenyl, 2-methyl-1-propenyl, 1-methyl-1-propenyl, allyl, 2-methyl-2-propenyl and 2-butenyl.

Examples of the $C_2$–$C_4$ haloalkenyl group represented by $R^9$ are 2,2-dichloroethenyl, 2,2-dibromoethenyl, 3,3-dichloroallyl, 3,3-dibromoallyl, 2,3-dichloroallyl, 2,3-dibromoallyl, 2-chloro-2-propenyl, 3-chloro-2-propenyl, 2-bromo-2-propenyl and 3-chloro-2-butenyl.

Examples of the $C_3$–$C_9$ alkynyl group represented by $R^1$ are 2-propynyl, 1-methyl-2-propynyl, 2-butynyl, 3-butynyl, 2-methyl-3-butynyl, 1-methyl-3-butynyl, 2-pentynyl, 4-pentynyl, 3-pentynyl, 1-ethyl-2-propynyl, 2-hexynyl, 3-hexynyl, 5-hexynyl, 1-pentyl-2-propynyl and 3-nonynyl.

Examples of the $C_3$–$C_5$ haloalkynyl group represented by $R^1$ are 3-chloro-2-propynyl, 3-bromo-2-propynyl, 4-chloro-2-butynyl, 3-chloro-1-methyl-2-propynyl, 3-bromo-1-methyl-2-propynyl, 4-chloro-3-butynyl, 4-bromo-3-butynyl, 4-chloro-2-methyl-3-butynyl, 4-bromo-2-methyl-3-butynyl, 1-methyl-4-chloro-3-butynyl, 1-methyl-4-bromo-3-butynyl, 5-chloro-4-pentynyl, 5-bromo-4-pentynyl, 1-ethyl-3-chloro-2-propynyl and 1-ethyl-3-bromo-2-propynyl.

Examples of the $C_2$–$C_4$ alkynyl group represented by $R^9$ are ethynyl, 1-propynyl, 2-propynyl and 1-methyl-2-propynyl.

Examples of the $C_2$–$C_4$ haloalkynyl group represented by $R^9$ are chloroethynyl, bromoethynyl, iodoethynyl, 3-chloro-2-propynyl, 3-bromo-2-propynyl, 3-iodo-2-propynyl, 1-methyl-3-chloro-2-propynyl, 1-methyl-3-bromo-2-propynyl and 1-methyl-3-iodo-2-propynyl.

Examples of the $C_2$–$C_4$ alkynyloxy group represented by $R^9$ are ethynyloxy, 1-propynyloxy, 2-propynyloxy and 1-methyl-2-propynyloxy.

Examples of the $C_2$–$C_4$ haloalkynyloxy group represented by $R^9$ are chloroethynyloxy, 3-chloro-2-propynyloxy, 3-bromo-2-propynyloxy, 1-methyl-3-chloro-2-propynyloxy and 1-methyl-3-bromo-2-propynyloxy.

Examples of the $C_2$–$C_7$ alkoxyalkyl group represented by $R^1$ are methoxymethyl, 2-methoxyethyl, ethoxymethyl, isopropoxymethyl, n-propoxymethyl, 1-methoxyethyl, 2-ethoxyethyl, 1-ethoxyethyl, 3-methoxypropyl, 2-methoxypropyl, 1-methoxypropyl, 2-methoxy-1-methylethyl, n-propoxyethyl, 2-ethoxypropyl, 2-ethoxy-1-methylethyl, 2-methoxybutyl, 2-methoxy-1-ethylethyl, 3-ethoxypropyl, 3-methoxy-n-butyl, 3-methoxy-2-methylpropyl, 3-methoxy-1-methylpropyl, 2-isopropoxyethyl, 3-methoxybutyl, 3-methyl-3-methoxybutyl, 2-butoxyethyl and 2-butoxy-1-methylethyl.

Examples of the $C_2$–$C_4$ alkoxyalkyl group represented by $R^9$ are methoxymethyl, ethoxymethyl, n-propyloxymethyl, isopropyloxymethyl, 2-methoxyethyl, 1-methoxyethyl, 2-ethoxyethyl, 1-ethoxyethyl, 3-methoxypropyl, 2-methoxypropyl, 1-methoxypropyl and 2-methoxy-1-methylethyl.

Examples of the $C_2$–$C_7$ alkylthioalkyl group represented by $R^1$ are methylthiomethyl, ethylthiomethyl, 2-methylthioethyl, 1-methylthioethyl, propylthiomethyl, isopropylthiomethyl, 2-ethylthioethyl, 1-ethylthioethyl, 3-(methylthio)propyl, 2-(methylthio)propyl, 1-(methylthio)propyl, 1-methyl-2-methylthioethyl, 2-isopropylthioethyl, 2-(propylthio)ethyl, 2-methylthio-1,2-dimethylethyl, 2-(methylthio)butyl, 1-ethyl-2-methylthioethyl, 2-(ethylthio)propyl, 2-ethylthio-1-methylethyl, 3-(ethylthio)propyl, 3-(methylthio)butyl, 2-methyl-3-(methylthio)propyl, 1-methyl-3-(methylthio)propyl, 2-tert-butylthioethyl, 2-isobutylthioethyl, 2-sec-butylthioethyl, 3-(tert-butylthio)propyl, 3-(isobutylthio)propyl and 3-(sec-butylthio)propyl.

Examples of the $C_2$–$C_4$ alkylthioalkyl group represented by $R^9$ are methylthiomethyl, ethylthiomethyl, propylthiomethyl, isopropylthiomethyl, 2-methylthioethyl, 1-methylthioethyl, 2-ethylthioethyl, 1-ethylthioethyl, 3-methylthiopropyl, 2-methylthiopropyl, 1-methylthiopropyl and 2-methylthio-1-methylethyl.

Examples of the $C_3$–$C_6$ cycloalkyl group represented by $R^1$, which may be substituted with $C_1$–$C_4$ alkyl, $C_1$–$C_3$ alkoxy or $C_1$–$C_3$ haloalkoxy, are cyclopropyl, cyclobutyl, 2-methoxycyclopentyl, 2-ethoxycyclopentyl, 2-propoxycyclopentyl, 2-isopropoxycyclohexyl, 2-butoxycyclopentyl, 2-isobutyloxycyclocpentyl, 2-secbutyloxycyclopentyl, 2-tert-butyloxycyclopentyl, cyclopentyl, 3-methylcyclopentyl, 2-methylcyclopentyl, 3-methoxycyclohexyl, 3-ethoxycyclohexyl, 3-propoxycyclohexyl, 3-isopropoxycyclohexyl, 3-butoxycyclohexyl, 3-isobutyloxycyclohexyl, 3-sec-butyloxycyclohexyl, 3-tert-butyloxycyclohexyl, 4-methoxycyclohexyl, 4-ethoxycyclohexyl, 4-propoxycyclohexyl, 4-isopropoxycyclohexyl, 4-butoxycyclohexyl, 4-isobutyloxycyclohexyl, 4-sec-butyloxycyclohexyl and 4-tert-butyloxycyclohexyl.

Examples of the $C_4$–$C_9$ cycloalkylalkyl group represented by $R^1$, which may be substituted with $C_1$–$C_4$ alkyl, are cyclopropylmethyl, cyclobutylmethyl, 1-cyclopropylethyl, 2-methylcyclopropylmethyl, 2-(2-methylcyclopropyl)ethyl, cyclopentylmethyl, cyclohexylmethyl, 2-cyclohexylethyl, 3-cyclopentylpropyl and 3-cyclohexylpropyl.

Examples of the $C_5$–$C_6$ cycloalkenyl group represented by $R^1$, which may be substituted with $C_1$–$C_4$ alkyl, are 2-cyclohexenyl, 3,5,5-trimethyl-2-cyclohexenyl, 3-methyl-2-cyclohexenyl, 3-cyclohexenyl, 2-cyclopentenyl and 3-cyclopentenyl.

Examples of the $C_6$–$C_8$ cycloalkenylalkyl group represented by $R^1$, which may be substituted with $C_1$–$C_4$ alkyl, are (1-cyclopentenyl)methyl, (3-cyclohexenyl)methyl and 2-(3-cyclohexenyl)ethyl.

Examples of the $C_3$–$C_6$ cycloalkyl group represented by $R^9$ are cyclopropyl, cyclobutyl, cyclopentyl and cyclohexyl.

Examples of the $C_5$–$C_6$ cycloalkenyl group represented by $R^9$ are 1-cyclopentenyl, 2-cyclopentenyl, 3-cyclopentenyl, 1-cyclohexenyl, 2-cyclohexenyl and 3-cyclohexenyl.

Examples of the $C_3$–$C_6$ cycloalkyloxy group represented by $R^9$ are cyclopropyloxy, cyclobutyloxy, cyclopentyloxy and cyclohexyloxy.

Examples of the $C_5$–$C_6$ cycloalkenyloxy group represented by $R^9$ are 1-cyclopentenyloxy, 2-cyclopentenyloxy, 3-cyclopentenyloxy, 1-cyclohexenyloxy, 2-cyclohexenyloxy and 3-cyclohexenyloxy.

Examples of the $C_1$–$C_3$ alkoxy group present in $R^1$ or $R^9$, or represented by $R^4$ or $R^{12}$ are methoxy, ethoxy, n-propoxy and isopropoxy.

Examples of the $(C_1$–$C_3)$alkoxy$(C_1$–$C_7)$carbonylalkyl group represented by $R^1$ are 1-(ethoxycarbonyl)methyl, 1-(methoxycarbonyl)methyl, 1-(n-propoxycarbonyl)methyl, 2-(methoxycarbonyl)ethyl, 1-(isopropoxycarbonyl)methyl, 3-(methoxycarbonyl)propyl, 4-(methoxycarbonyl)butyl, 5-(methoxycarbonyl)pentyl, 6-(methoxycarbonyl)hexyl and 7-(methoxycarbonyl)heptyl.

Examples of the $C_1$–$C_8$ alkoxy group represented by $R^9$ are methoxy, ethoxy, propoxy, isopropoxy, n-butoxy, sec-butoxy, isobutoxy, tert-butoxy, n-pentyloxy, isopentyloxy, neopentyloxy, tert-pentyloxy, (1-ethylpropyl)oxy, n-hexyloxy, octyloxy and n-heptyloxy.

Examples of the $C_1$–$C_3$ haloalkoxy group present in $R^1$ or represented by $R^4$ or $R^9$ are trifluoromethoxy, difluoromethoxy, bromodifluoromethoxy, 2-fluoroethoxy, 2,2,2-trifluoroethoxy, 2-chloroethoxy, 2-bromoethoxy, 2-chloro-1,1,2-trifluoroethoxy, 2-bromo-1,1,2-trifluoroethoxy, 1,1,2,2-tetrafluoroethoxy, 1,2,2,3,3,3-hexafluoropropoxy, 3-fluoropropoxy, 3-chloropropoxy, 3-bromopropoxy, 2,2,3,3,3-pentafluoropropoxy, 3,3,3-trifluoropropoxy and 1,1,2,2,2-pentafluoroethoxy.

Examples of the $C_1$–$C_3$ alkylthio group represented by $R^9$ are methylthio, ethylthio, n-propylthio and isopropylthio.

Examples of the $C_1$–$C_3$ haloalkylthio group represented by $R^9$ are trifluoromethylthio, difluoromethylthio, bromodifluoromethylthio, 2,2,2-trifluoroethylthio, 2-chloro-1,1,2-trifluoroethylthio, 2-bromo-1,1,2-trifluoroethylthio, 1,1,2,2-tetrafluoroethylthio, 2-chloroethylthio, 2-fluoroethylthio, 2-bromoethylthio, 3-fluoropropylthio, 3-chloropropylthio, (3-bromopropyl)thio, 2,2,3,3,3-pentafluoropropylthio and 3,3,3-trifluoropropylthio.

Examples of the $C_3$–$C_6$ alkenyloxy group represented by $R^9$ are allyloxy, 2-methylallyloxy, 2-butenyloxy, 3-methyl-2-butenyloxy, 2-methyl-2-butenyloxy, 2-pentenyloxy and 2-hexenyloxy.

Examples of the $C_3$–$C_6$ haloalkenyloxy group represented by $R^9$ are 3,3-dichloroallyloxy, 3,3-dibromoallyloxy, 2,3-dichloroallyloxy, 2,3-dibromoallyloxy, 2-chloro-2-propenyloxy, 3-chloro-2-propenyloxy, 2-bromo-2-propenyloxy and 3-chloro-2-butenyloxy.

Examples of the $C_1$–$C_3$ hydroxyalkyl group represented by $R^9$ are hydroxymethyl, 2-hydroxyethyl, 1-hydroxyethyl, 3-hydroxypropyl, 2-hydropropyl and 1-hydroxypropyl.

Examples of the $C_2$–$C_5$ alkoxycarbonyl group represented by $R^9$ are methoxycarbonyl, ethoxycarbonyl, n-propoxycarbonyl, isopropoxycarbonyl, n-butoxycarbonyl, isobutoxycarbonyl, sec-butoxycarbonyl and tert-butoxycarbonyl.

The following are preferred examples of the present compound:

dihalopropene compounds wherein $R^2$ and $R^3$ are independently halogen or $C_1$–$C_3$ alkyl, and r is 0;

dihalopropene compounds wherein $R^2$ and $R^3$ are independently chlorine, bromine, methyl, ethyl or isopropyl, and r is 0;

dihalopropene compounds wherein $R^2$ and $R^3$ are both chlorine, and r is 0;

dihalopropene compounds wherein $R^2$ is chlorine, $R^3$ is methyl, and r is 0;

dihalopropene compounds wherein $R^2$ is ethyl, $R^3$ is methyl, and r is 0;

dihalopropene compounds wherein $R^2$ is ethyl, $R^3$ is methyl, and r is 0;

dihalopropene compounds wherein $R^2$ and $R^3$ are both bromine, and r is 0;

dihalopropene compounds wherein $R^2$ and $R^3$ are both ethyl, and r is 0;

dihalopropene compounds wherein $R^2$ and $R^3$ are independently halogen or $C_1$–$C_3$ alkyl, r is 1 or 2, and $R^{14}$ is halogen or $C_1$–$C_3$ alkyl;

dihalopropene compounds wherein $R^2$ and $R^3$ are independently halogen or $C_1$–$C_3$ alkyl, r is 1 or 2, and $R^{14}$ is halogen;

dihalopropene compounds wherein Y and Z are both oxygen;

dihalopropene compounds wherein $R^1$ is $Q_3$;

dihalopropene compounds wherein $R^1$ is $Q_3$, p is 0, and $R^9$ is halogen, $C_1$–$C_4$ alkyl, $C_1$–$C_3$ haloalkyl, $C_1$–$C_4$ alkoxy, $C_1$–$C_3$ haloalkoxy, $C_1$–$C_3$ alkylthio, $C_1$–$C_3$ haloalkylthio, cyano, nitro or 3,4-methylenedioxy;

dihalopropene compounds wherein $R^1$ is $Q_3$, p is, 0, $R^9$ is phenyl which may be substituted with halogen, pentafluorosulfanyl, $C_1$–$C_4$ alkyl, $C_1$–$C_3$ haloalkyl, $C_1$–$C_3$ alkoxy or $C_1$–$C_3$ haloalkoxy; benzyl which may be substituted with halogen, pentafluorosulfanyl, $C_1$–$C_4$ alkyl, $C_1$–$C_3$ haloalkyl, $C_1$–$C_3$ alkoxy or $C_1$–$C_3$ haloalkoxy; phenoxy which may be substituted with halogen, pentafluorosulfanyl, $C_1$–$C_4$ alkyl, $C_1$–$C_3$ haloalkyl, $C_1$–$C_3$ alkoxy or $C_1$–$C_3$ haloalkoxy; or benzyloxy which may be substituted with halogen, pentafluorosulfanyl, $C_1$–$C_4$ alkyl, $C_1$–$C_3$ haloalkyl, $C_1$–$C_3$ alkoxy or $C_1$–$C_3$ haloalkoxy;

dihalopropene compounds wherein $R^1$ is $Q_3$, p is 1 to 3, $R^{10}$ and $R^{11}$ are both hydrogen, and $R^9$ is halogen, trifluoromethyl, pentafluorosulfanyl or $C_1$–$C_3$ haloalkoxy;

dihalopropene compounds wherein $R^1$ is $Q_5$;

dihalopropene compounds wherein $R^1$ is $Q_5$, p is 1 to 4, $R^{10}$ and $R^{11}$ are both hydrogen, and $R^9$ is halogen, trifluoromethyl, $C_1$–$C_3$ alkoxy, $C_1$–$C_3$ haloalkoxy, pentafluorosulfanyl or pentafluorosulfanyl;

dihalopropene compounds wherein $R^1$ is $Q_5$, p is 2 or 3, $R^{10}$ and $R^{11}$ are both hydrogen, $R^9$ is halogen, trifluoromethyl, isopropyloxy, $C_1$–$C_3$ haloalkoxy, pentafluorosulfanyl or difluoromethylenedioxy, and A is oxygen;

dihalopropene compounds wherein $R^1$ is $Q_5$, p is 2 or 3, $R^{10}$ and $R^{11}$ are both hydrogen, $R^9$ is halogen, trifluoromethyl, isopropyloxy or $C_1$–$C_3$ haloalkoxy, and A is oxygen; and dihalopropene compounds wherein $R^1$ is $C_1$–$C_{10}$ alkyl, $C_1$–$C_5$ haloalkyl, $C_2$–$C_{10}$ alkenyl, $C_2$–$C_6$ haloalkenyl, $C_3$–$C_9$ alkynyl, $C_3$–$C_5$ haloalkynyl, $C_2$–$C_7$ alkoxyalkyl, alkyl, $(C_1$–$C_3)$alkoxy$(C_1$–$C_7)$ carbonylalkyl or $C_2$–$C_7$ alkylthioalkyl; $C_3$–$C_6$ cycloalkyl which may be substituted with $C_1$–$C_4$ alkyl, $C_1$–$C_3$ alkoxy or $C_1$–$C_3$ haloalkoxy; $C_4$–$C_9$ cycloalkylalkyl which may be substituted with $C_1$–$C_4$ alkyl; $C_5$–$C_6$ cycloalkenyl which may be substituted with $C_1$–$C_4$ alkyl; or $C_6$–$C_8$ cycloalkenylalkyl which may be substituted with $C_1$–$C_4$ alkyl.

The following are particularly preferred examples of the present compound wherein numbers in parentheses are the corresponding compound numbers used below:

(100) 3,5-Dichloro-4-(3-(4-trifluoromethoxyphenoxy) propyloxy)-1-(3,3-dichloro-2-propenyloxy)benzene;

(166) 3,5-Dichloro-4-(3-(4-trifluoromethylphenoxy) propyl oxy)-1-(3,3-dichloro-2-propenyloxy)benzene;

(203) 3,5-Dichloro-4-(4-(4-isopropyloxyphenoxy)butyloxy) -1-(3,3-dichloro-2-propenyloxy)benzene;

(222) 3,5-Dichloro-4-(4-(4-chlorophenoxy)butyloxy)-1-(3, 3-dichloro-2-propenyloxy)benzene; and (284) 3-Ethyl-5-methyl-4-(3-(4-trifluoromethylphenoxy) propyloxy)-1-(3,3-dichloro-2-propenyloxy)benzene.

The present compounds can be produced, for example, by the following production processes A-G.

(Production Process A)

In this process, a compound of the general formula:

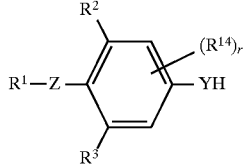 [VI]

wherein $R^1$, $R^2$, $R^3$, $R^{14}$, r, Y and Z are each as defined above, is reacted with a halide compound of the general formula:

 L—CH$_2$CH=CX$_2$ [VII]

wherein X is as defined above and L is halogen (e.g., chlorine, bromine, iodine), mesyloxy or tosyloxy.

The reaction is preferably effected in an inert solvent in the presence of a suitable base.

Examples of the solvent that can be used are ketones such as acetone, methyl ethyl ketone and cyclohexanone; ethers such as 1,2-dimethoxyethane, tetrahydrofuran, dioxane and dialkyl (e.g., $C_1$–$C_4$) ether (e.g., diethyl ether, diisopropyl ether); N,N-dimethylformamide, dimethylsulfoxide, hexamethylphophoric triamide, sulforane, acetonitrile, nitromethane; halogenated hydrocarbons such as dichloromethane, chloroform, 1,2-dichloroethane and chlorobenzene; hydrocarbons such as toluene, benzene and xylene; and water. If necessary, a mixture of these solvents can be used.

Examples of the base which can be used are hydroxides of alkali metals or alkaline earth metals, such as lithium hydroxide, sodium hydroxide, potassium hydroxide and calcium hydroxide; carbonates of alkali metals or alkaline earth metals, such as lithium carbonate, potassium carbonate, sodium carbonate and calcium carbonate; hydrides of alkali metals or alkaline earth metals, such as lithium hydride, sodium hydride, potassium hydride and calcium hydride; alkali metal alkoxides (e.g., $C_1$–$C_4$), such as sodium methoxide, sodium ethoxide and potassium tert-butoxide; and organic bases such as triethylamine and pyridine. If necessary, catalysts such as ammonium salts (e.g., triethylbenzylammonium chloride) may be added to the reaction system at a ratio of 0.01 to 1 mole per mole of the compound of the general formula [VI].

The reaction temperature is usually set within the range of −20° C. to 150° C. or the boiling point of a solvent used in the reaction, preferably −5° C. to 100° C. or the boiling point of a solvent used in the reaction.

The molar ratio of the starting materials and bases to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Further, purification can be carried out, if necessary, by an ordinary technique such as chromatography, distillation or recrystallization.

(Production Process B for the present compounds wherein Y is oxygen)

In this process, a compound of the general formula [VI] is reacted with an alcohol compound of the general formula:

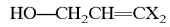 HO—CH$_2$CH=CX$_2$ [VIII]

wherein X is as defined above.

The reaction is preferably effected in an inert solvent, if necessary, in the presence of a suitable dehydrating agent.

Examples of the dehydrating agent which can be used are dicyclohexylcarbodiimide, and dialkyl (e.g., $C_1$–$C_4$) azodicarboxylates (e.g. diethylazodicarboxylate, diisopropylazodicarboxylate)-trialkyl (e.g., $C_1$–$C_{20}$) phosphine or triarylphosphine (e.g., triphenylphosphine, trioctylphosphine, tributylphosphine).

Examples of the solvent which can be used are hydrocarbons such as benzene, xylene and toluene; ethers such as diethyl ether, diisopropyl ether, tetrahydrofuran and dioxane; and halogenated hydrocarbons such as carbon tetrachloride, dichloromethane, chlorobenzene and dichlorobenzene.

The reaction temperature is usually set within the range of −20° C. to 200° C. or the boiling point of a solvent used in the reaction.

The molar ratio of the starting materials and dehydrating agents to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Further, purification can be carried out by an ordinary technique such as chromatography, distillation or recrystallization.

(Production Process C for the present compounds wherein Y is oxygen)

In this process, an aldehyde compound of the general formula:

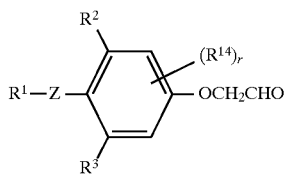

[IX]

wherein $R^1$, $R^2$, $R^3$, $R^{14}$, r and Z are each as defined above, is reacted with carbon tetrachloride or carbon tetrabromide.

The reaction is preferably effected in an inert solvent in the presence of a suitable trialkylphosphine or triarylphosphine, and if necessary, in the presence of metal zinc.

Examples of the solvent which can be used are hydrocarbons such as benzene, xylene and toluene; ethers such as diethyl ether, diisopropyl ether, tetrahydrofuran and dioxane; and halogenated hydrocarbons (exclusive of carbon tetrabromide and carbon tetrachloride) such as dichloromethane, 1,2-dichloroethane and chlorobenzene.

The reaction temperature is usually set within the range of −30° C. to 150° C. or the boiling point of a solvent used in the reaction.

Examples of the trialkyl (e.g., $C_1$–$C_{20}$) phosphine or triarylphosphine are triphenylphosphine and trioctylphosphine. The metal zinc which is used, if necessary, is preferably in dust form.

The molar ratio of the starting materials and reagents to be used in the reaction can be freely determined, but the ratio is preferably such that carbon tetrabromide or tetrachloride, trialkylphosphine or triarylphosphine, and zinc are 2 moles, 2 or 4 moles (2 moles when zinc is used), and 2 moles per mole of the aldehyde compound of the general formula [IX], or it is favorable to effect the reaction at a ratio closer thereto.

After completion of the reaction, the reaction mixture is subjected to ordinary post-treatments such as organic solvent extraction and concentration, and the desired compound of the present invention can be isolated. Further, purification can be carried out by an ordinary technique such as chromatography, distillation or recrystallization.

(Production Process D for the present compounds wherein Y and Z are both oxygen)

In this process, a compound of the general formula:

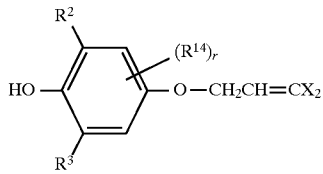

[X]

wherein $R^2$, $R^3$, $R^{14}$, r, Y and Z are each as defined above, is reacted with a compound of the general formula:

$R^1$—L  [XI]

wherein $R^1$ and L are each as defined above.

The reaction is preferably effected in an inert solvent in the presence of a suitable base.

Examples of the solvent which can be used are ketones such as acetone, methyl ethyl ketone and cyclohexanone; ethers such as 1,2-dimethoxyethane, tetrahydrofuran, dioxane and dialkyl (e.g., $C_1$–$C_4$) ethers (e.g., diethyl ether, diisopropyl ether); N,N-dimethylformamide, dimethylsulfoxide, hexamethylphosphoric triamide, sulforane, acetonitrile, nitromethane; halogenated hydrocarbons such as dichloromethane, chloroform, 1,2-dichloroethane and chlorobenzene; hydrocarbons such as toluene, benzene and xylene; and water. If necessary, a mixture of these solvents can be used.

Examples of the base which can be used are hydroxides of alkali metals or alkaline earth metals, such as lithium hydroxide, sodium hydroxide, potassium hydroxide and calcium hydroxide; carbonates of alkali metals or alkaline earth metals, such as lithium carbonate, potassium carbonate, sodium carbonate and calcium carbonate; hydrides of alkali metals or alkaline earth metals, such as lithium hydride, sodium hydride, potassium hydride and calcium hydride; alkali metal alkoxides (e.g., $C_1$–$C_4$) such as sodium methoxide, sodium ethoxide and potassium tert-butoxide; organic bases such as triethylamine and pyridine. If necessary, catalysts such as ammonium salts (e.g., triethylbenzylammonium chloride) may be added to the reaction system at a ratio of 0.01 to 1 mole per mole of the compound of the general formula [X].

The reaction temperature is usually set within the range of −20° C. to 150° C. or the boiling point of a solvent used in the reaction, preferably −5° C. to 100° C. or the boiling point of a solvent used in the reaction.

The molar ratio of the starting materials and dehydrating agents to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Further, purification can be carried out by an ordinary technique such as chromatography, distillation or recrystallization.

(Production Process E for the present compounds wherein Y and Z are both oxygen)

In this process, a compound of the general formula [X] is reacted with an alcohol compound of the general formula:

$R^1$—OH  [XII]

wherein $R^1$ is as defined above.

The reaction is preferably effected in an inert solvent, if necessary, in the presence of a suitable dehydrating agent.

Examples of the dehydrating agent which can be used are dicyclohexylcarbodiimide, and dialkyl (e.g., $C_1$–$C_4$) azodicarboxylates (e.g., diethylazodicarboxylate, diisopropylazodicarboxylate)-trialkyl (e.g., $C_1$–$C_{20}$) phosphine or triarylphosphine (e.g., triphenylphosphine, trioctylphosphine, tributylphosphine).

Examples of the solvent which can be used are hydrocarbons such as benzene, xylene and toluene; ethers such as diethyl ether, diisopropyl ether, tetrahydrofuran and dioxane; and halogenated hydrocarbons such as carbon tetrachloride, dichloromethane, chlorobenzene and dichlorobenzene.

The reaction temperature is usually set within the range of −20° C. to 200° C. or the boiling point of a solvent used in the reaction.

The molar ratio of the materials and dehydrating agents to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Further, purification can be carried out by an ordinary technique such as chromatography, distillation or recrystallization.

(Production Process F for the present compounds wherein Y and Z are both oxygen and $R^1$ is $Q_5$ (with the proviso that A is $A^2$), $Q_6$ (with the proviso that A is $A^2$), $Q_7$, $Q_8$ or $Q_{10}$ (with the proviso that A is $A^2$) [wherein $A^2$ is oxygen, sulfur or $NR^{13}$ and $R^{13}$ is as defined above])

In this process, a compound of the general formula:

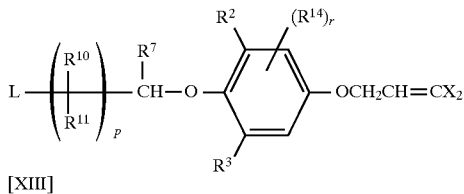

[XIII]

wherein $R^2$, $R^3$, $R^7$, $R^{10}$, $R^{11}$, $R^{14}$, X, L, p and r are each as defined above, is reacted with compound $Q_{51}$, $Q_{61}$, $Q_{71}$, $Q_{81}$ or $Q_{101}$ of the general formula:

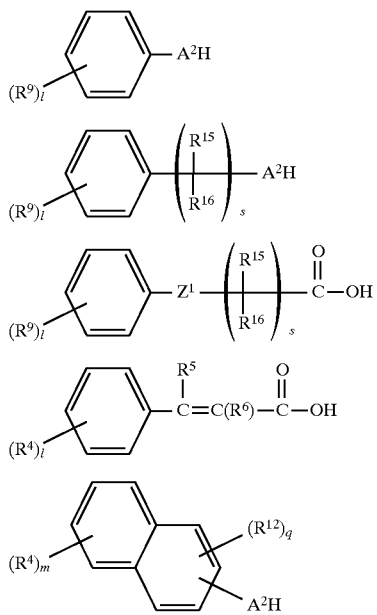

wherein $R^4$, $R^5$, $R^6$, $R^{12}$, $R^{15}$, $R^{16}$, $Z^1$, $A^2$1, m, q and s are each as defined above.

The reaction is preferably effected in an inert solvent in the presence of a suitable base.

Examples of the solvent which can be used are ketones such as acetone, methyl ethyl ketone and cyclohexanone; ethers such as 1,2-dimethoxyethane, tetrahydrofuran, dioxane and dialkyl (e.g., $C_1$–$C_4$ ethers (e.g., diethyl ether, diisopropyl ether); N,N-dimethylformamide, dimethylsulfoxide, hexamethylphosphoric triamide, sulforane, acetonitrile, nitromethane; halogenated hydrocarbons such as dichloromethane, chloroform, 1,2-dichloroethane and chlorobenzene; hydrocarbons such as toluene, benzene and xylene; and water. If necessary, a mixture of these solvents can be used.

Examples of the base which can be used are hydroxides of alkali metals or alkaline earth metals, such as lithium hydroxide, sodium hydroxide, potassium hydroxide and calcium hydroxide; carbonates of alkali metals or alkaline earth metals, such as lithium carbonate, potassium carbonate, sodium carbonate and calcium carbonate; hydrides of alkali metals or alkaline earth metals, such as lithium hydride, sodium hydride, potassium hydride and calcium hydride; alkali metal alkoxides (e.g., $C_1$–$C_4$) such as sodium methoxide, sodium ethoxide and potassium tert-butoxide; organic bases such as triethylamine and pyridine. If necessary, catalysts such as ammonium salts (e.g., triethylbenzylammonium chloride) may be added to the reaction system at a ratio of 0.01 to 1 mole per mole of the compound of the general formula [XIII].

The reaction temperature is usually set within the range of $-20°$ C. to $150°$ C. or the boiling point of a solvent used in the reaction, preferably $-5°$ C. to $100°$ C. or the boiling point of a solvent used in the reaction.

The molar ratio of the starting materials and dehydrating agents to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Further, purification can be carried out by an ordinary technique such as chromatography, distillation or recrystallization.

(Production Process G for the present compounds wherein Y and Z are both oxygen and $R^1$ is $Q_5$ (with the proviso that A is oxygen), $Q_6$ (with the proviso that A is oxygen), $Q_7$, $Q_8$ or $Q_{10}$ (with the proviso that A is oxygen))

In this process, a compound of the general formula:

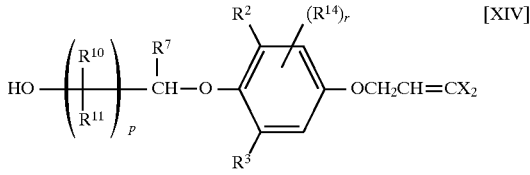

[XIV]

wherein $R^2$, $R^3$, $R^7$, $R^{10}$, $R^{11}$, $R^{14}$, X, p and r are each as defined above, is reacted with compound $Q_{52}$, $Q_{62}$, $Q_{71}$, $Q_{81}$ or $Q_{102}$ of the general formula:

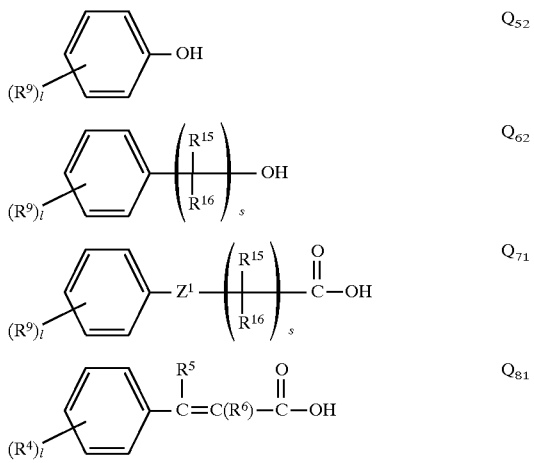

-continued

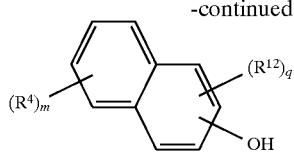

wherein $R^4$, $R^5$, $R^6$, R12 $R^{15}$, $R^{16}$, $Z^1$l, m, q and s are each as defined above.

The reaction is preferably effected in an inert solvent, if necessary, in the presence of a suitable dehydrating agent.

Examples of the dehydrating agent which can be used are dicyclohexylcarbodiimide, and dialkyl (e.g., $C_1$–$C_4$) azodicarboxylates (e.g., diethylazodicarboxylate, diisopropylazodicarboxylate)-trialkyl (e.g., $C_1$–$C_{20}$) phosphine or triarylphosphine (e.g., triphenylphosphine, trioctylphosphine, tributylphosphine).

Examples of the solvent which can be used are hydrocarbons such as benzene, xylene and toluene; ethers such as diethyl ether, diisopropyl ether, tetrahydrofuran and dioxane; and halogenated hydrocarbons such as carbon tetrachloride, dichloromethane, chlorobenzene and dichlorobenzene.

The reaction temperature is usually set within the range of −20° C. to 200° C. or the boiling point of a solvent used in the reaction.

The molar ratio of the materials and dehydrating agents to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Further, purification can be carried out by an ordinary technique such as chromatography, distillation or recrystallization.

When the present compound has an asymmetry carbon atom, it is to be construed to include its optically active isomers ((+)-form and (−)-form) having biological activity and their mixtures at any ratio. When the present compound exhibits geometrical isomerism, it is to be construed to include its geometrical isomers (cis-form and transform) and their mixtures at any ratio.

The following are typical examples of the present compound (wherein $R^1$ is as shown in Tables 1 to 17), which are not to be construed to limit the scope of the present invention.

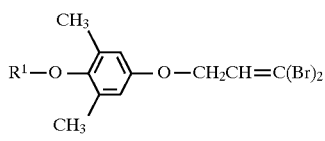

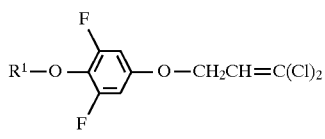

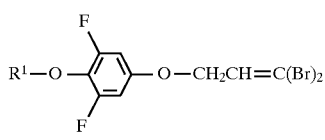

-continued

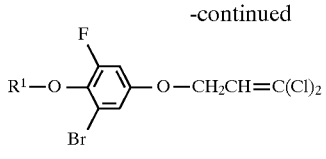

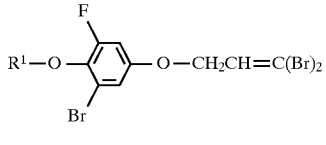

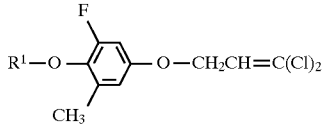

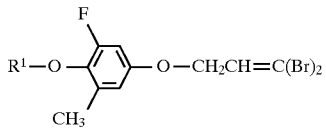

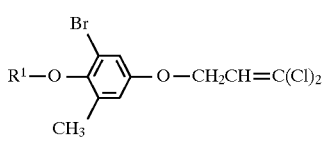

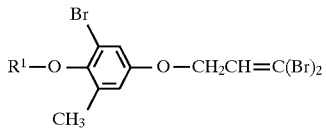

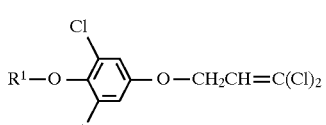

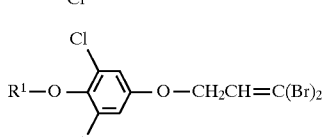

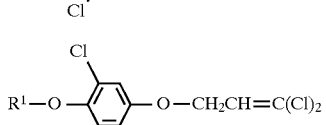

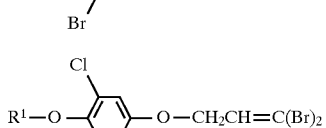

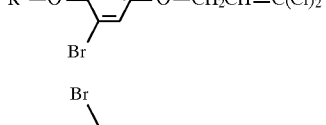

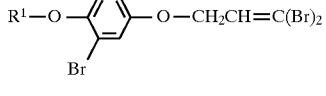

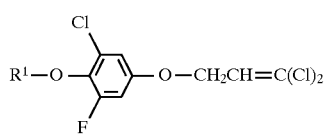
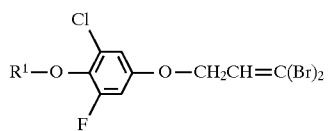
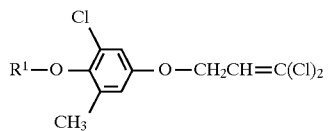
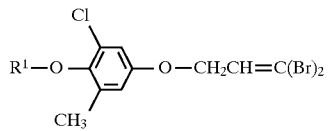
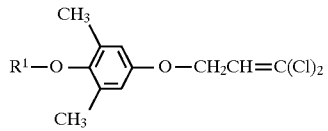
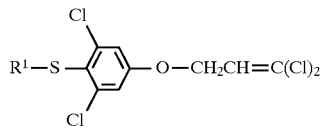
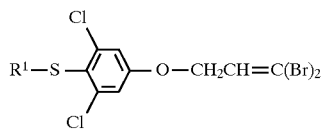
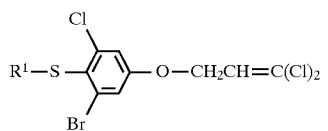
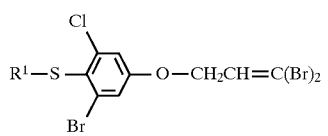
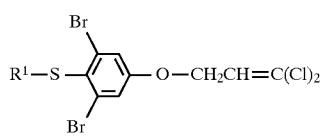
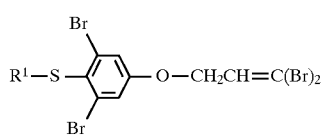
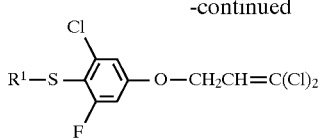
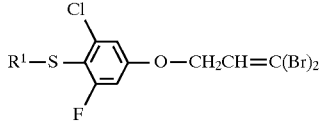
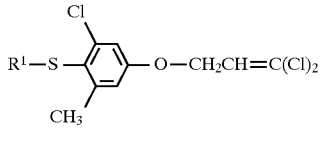
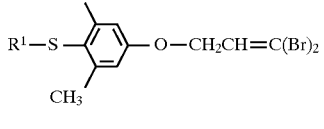
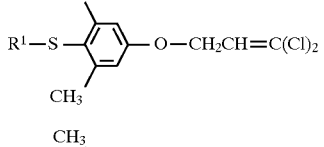
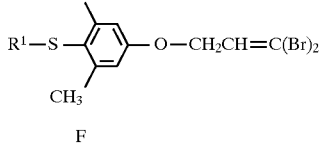
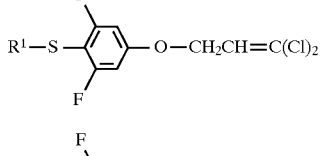
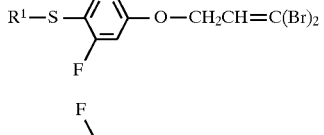
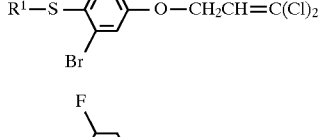

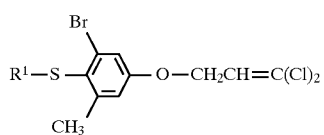
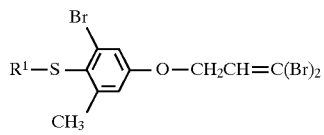
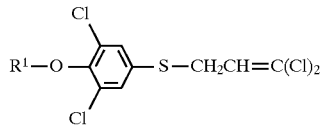
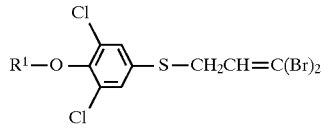
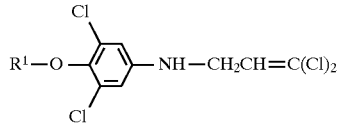
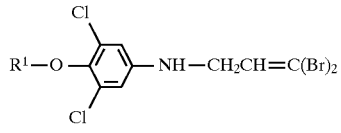
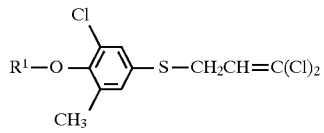
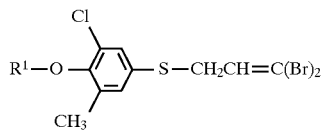
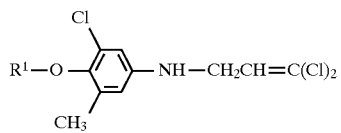
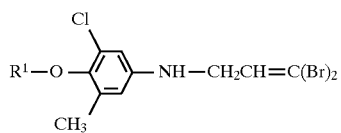
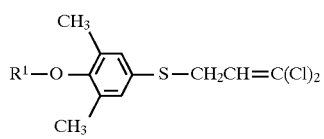
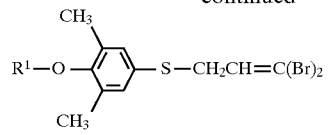
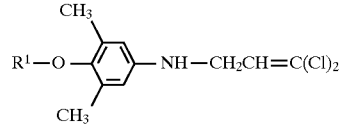
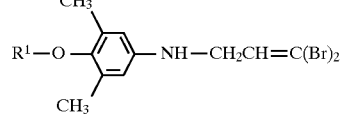
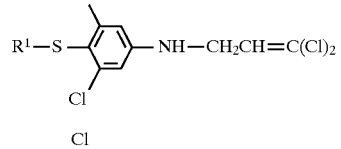
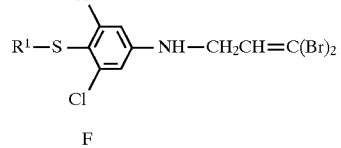
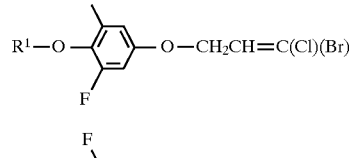
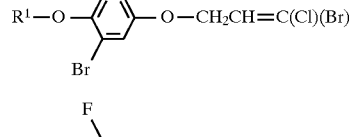
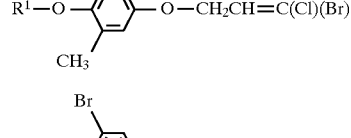
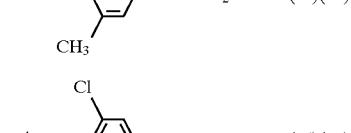
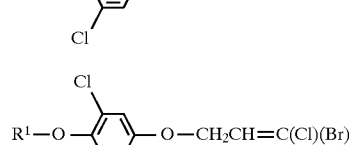
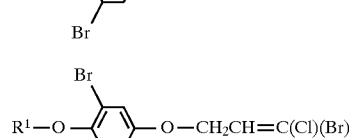

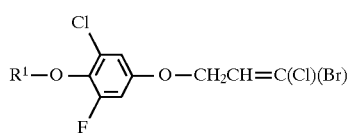
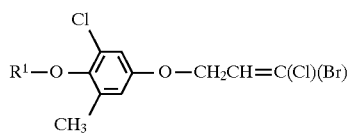
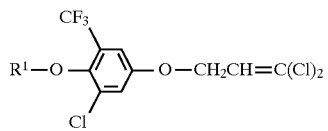
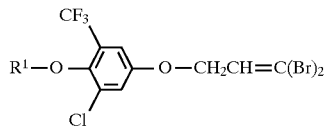
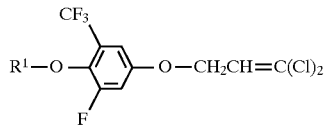
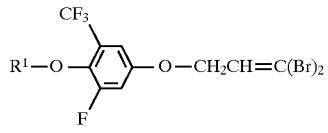
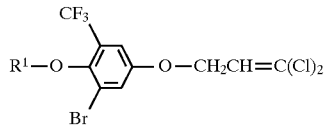
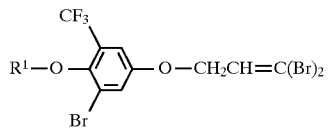
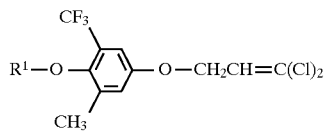
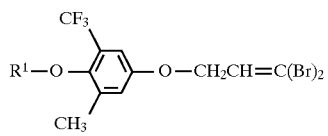
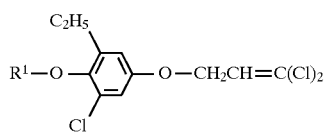
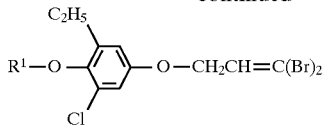
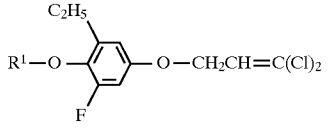
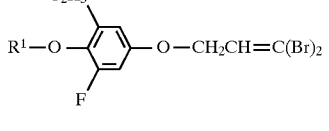
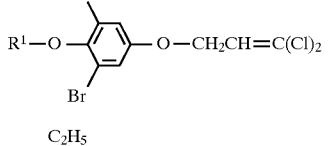
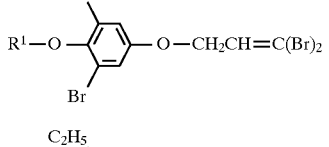
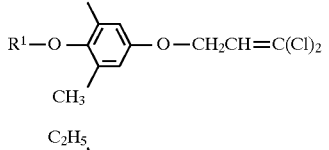
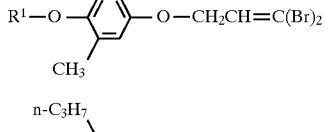
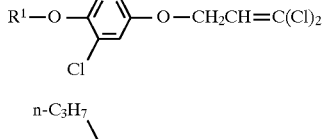
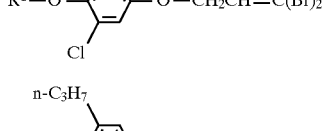
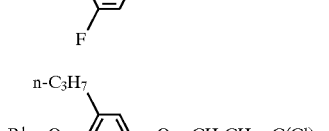

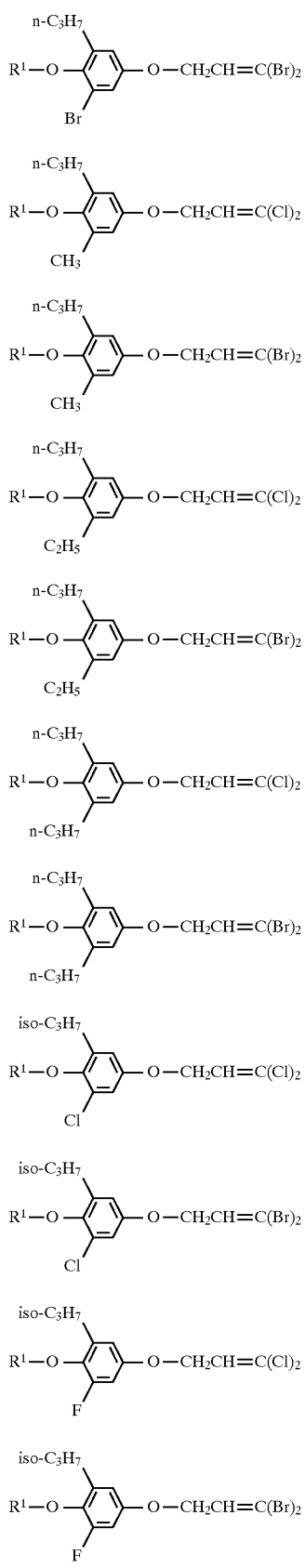
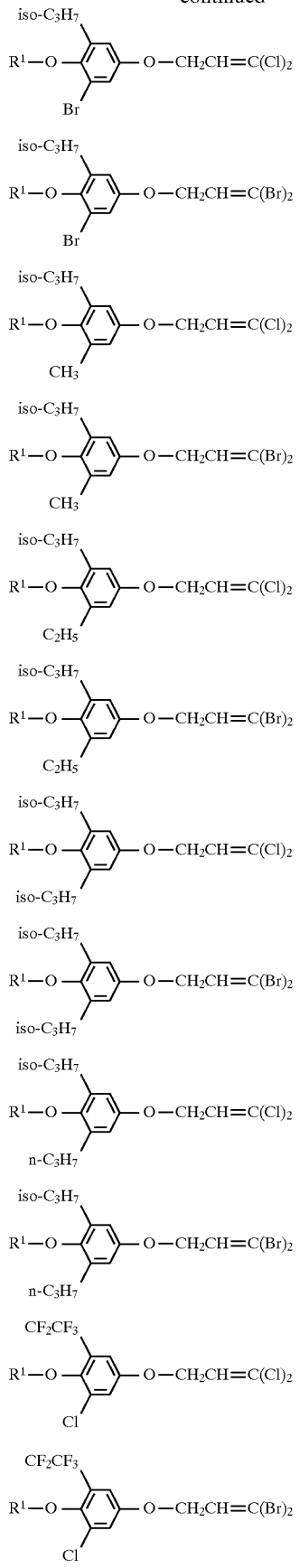

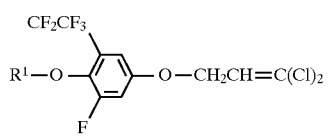
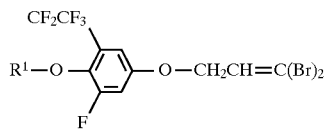
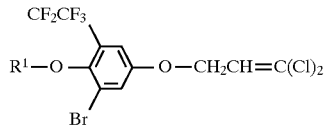
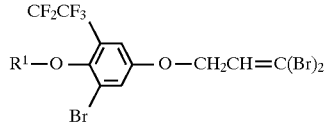
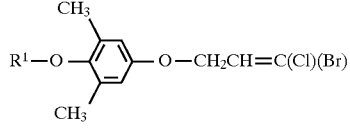
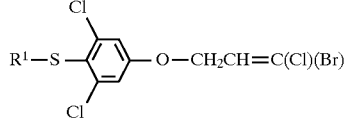
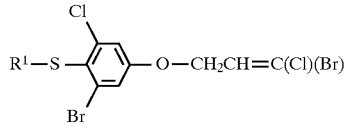
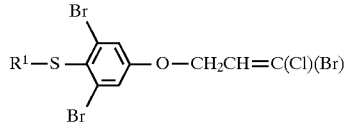
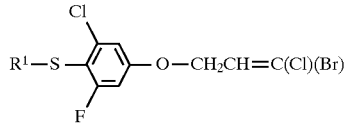
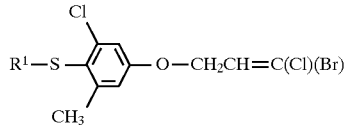
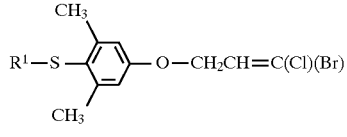
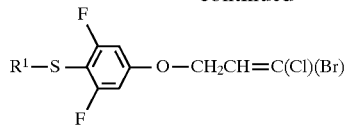
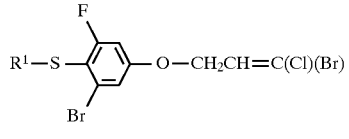
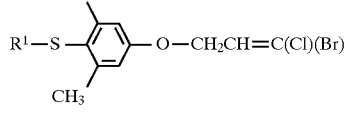
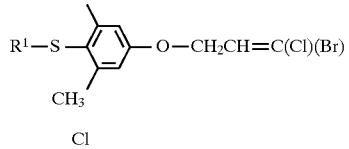
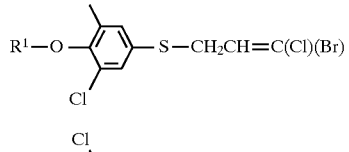
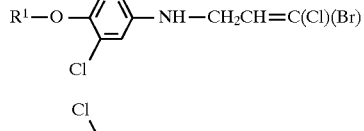
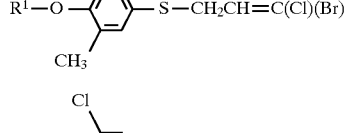
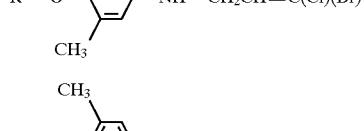
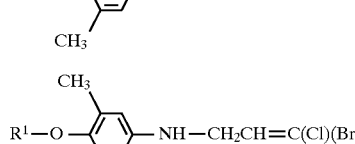
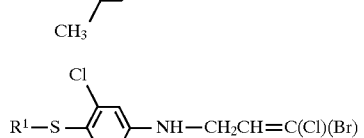
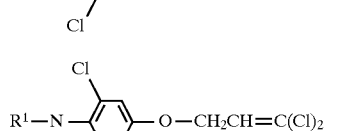

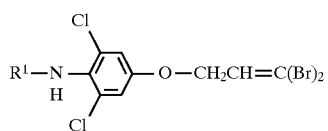
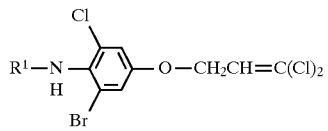
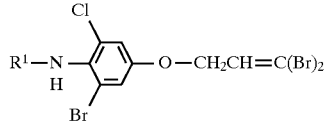
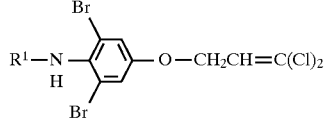
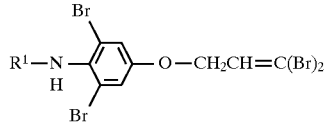
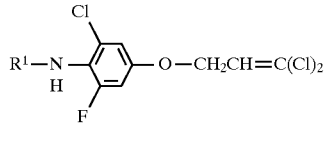
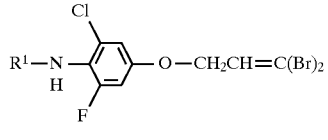
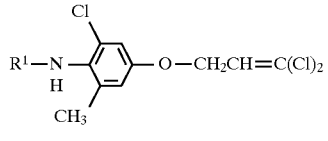
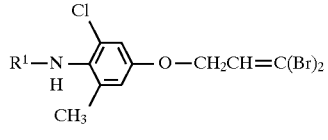
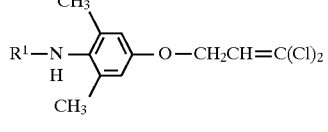
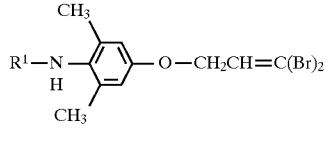
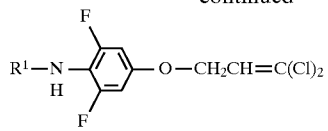
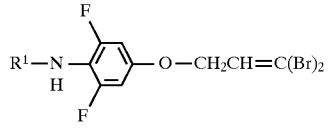
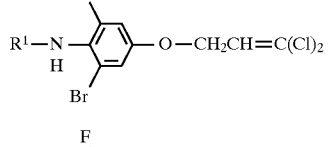
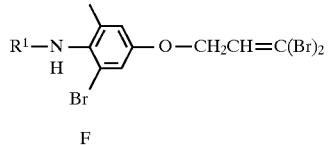
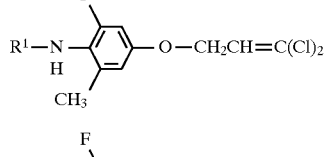
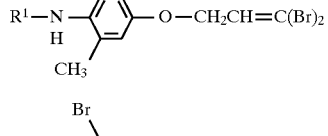
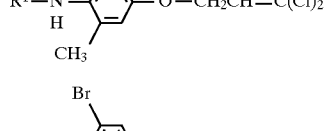
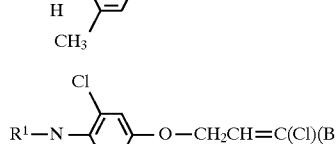
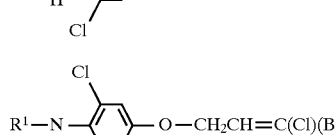
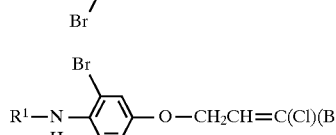
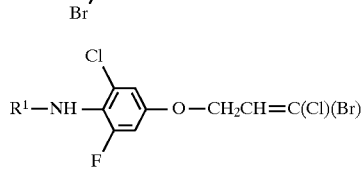

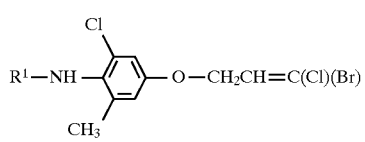
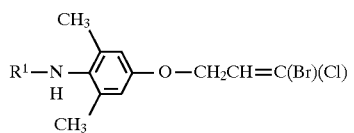
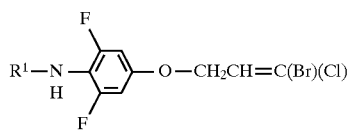
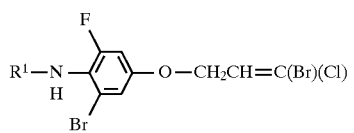
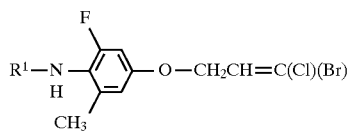
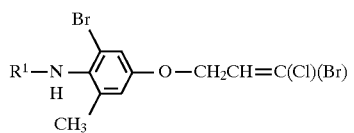
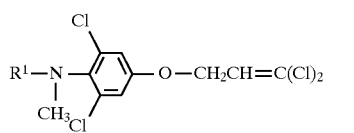
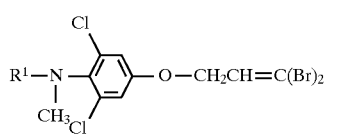
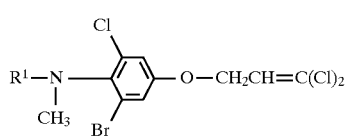
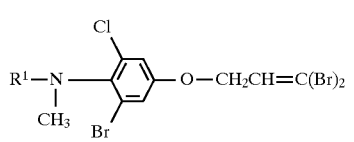
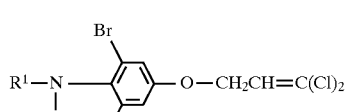
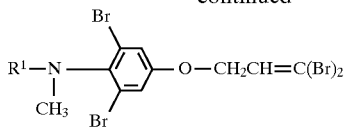
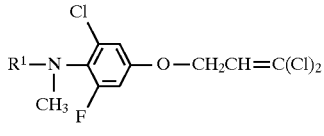
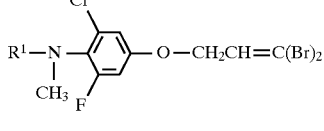
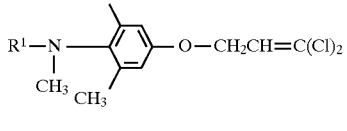
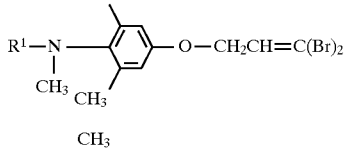
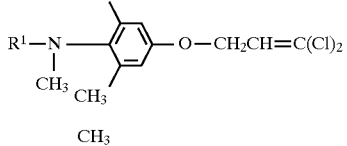
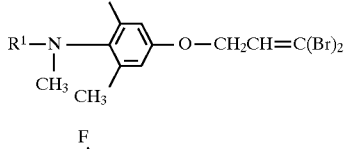
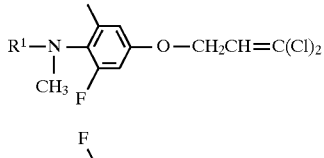
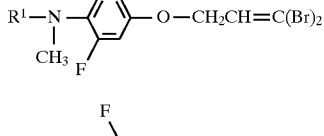
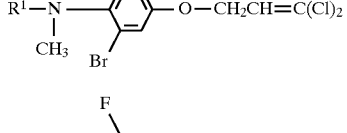
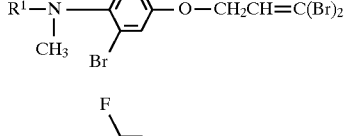
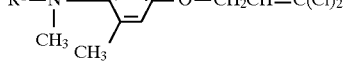

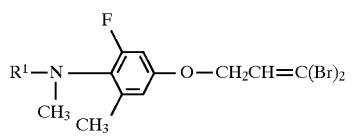
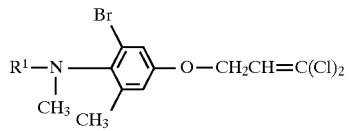
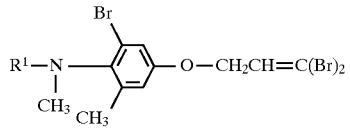
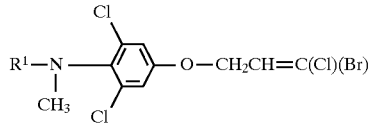
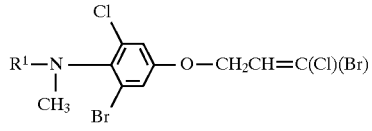
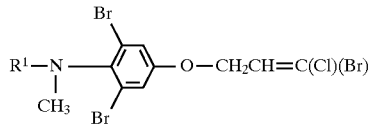
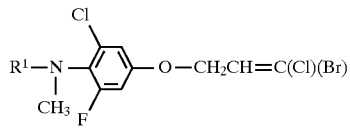
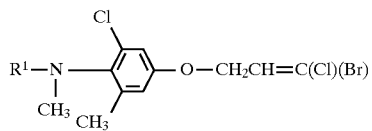
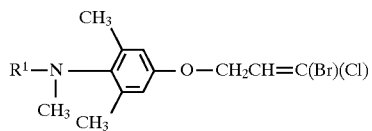
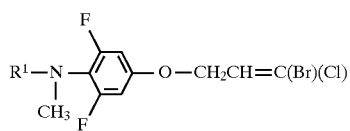
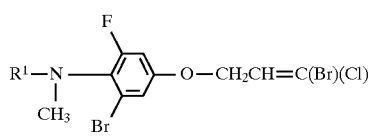
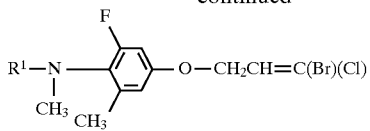
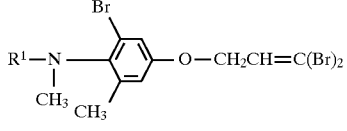
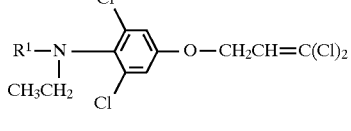
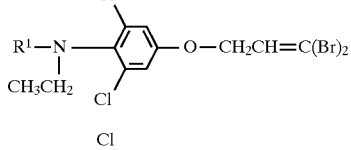
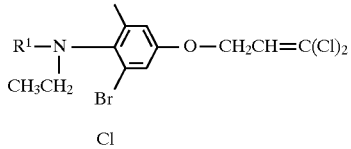
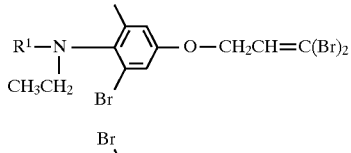
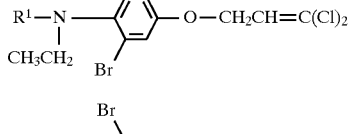
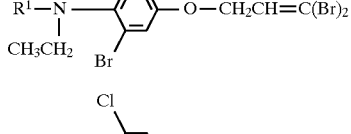
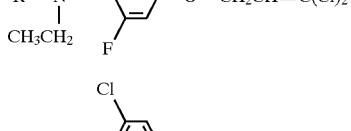
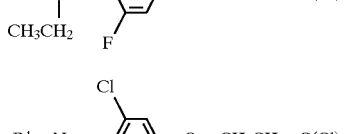
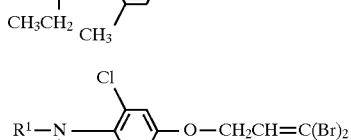

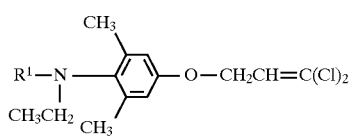
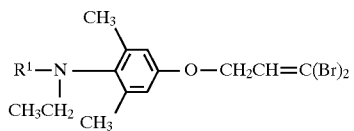
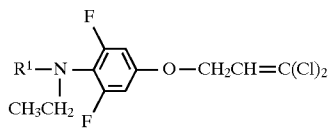
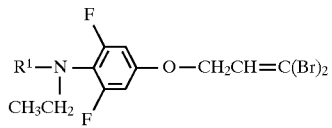
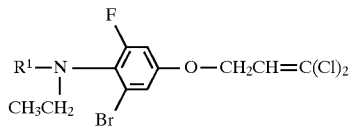
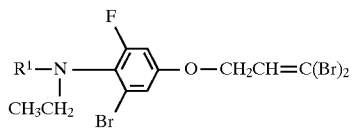
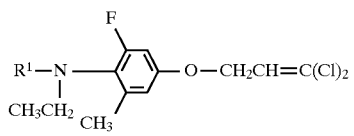
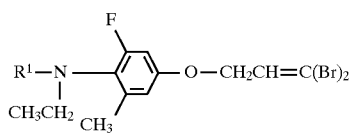
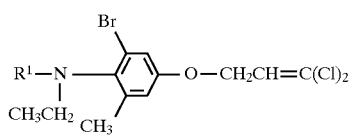
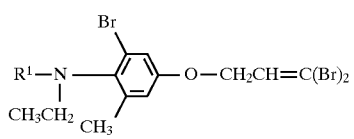
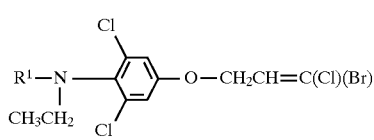
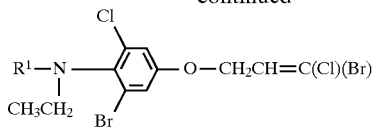
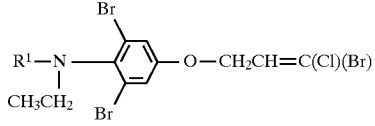
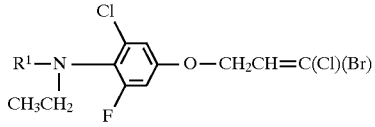
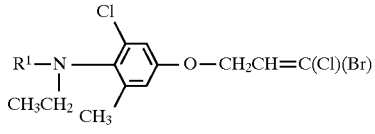
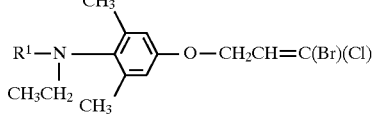
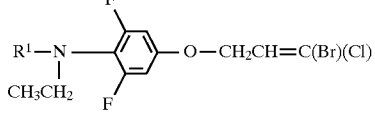
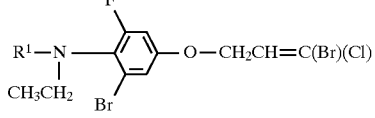
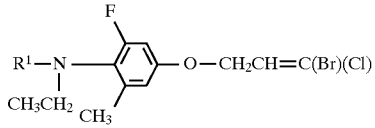
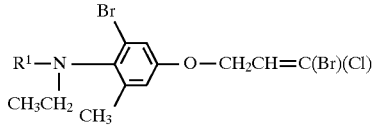
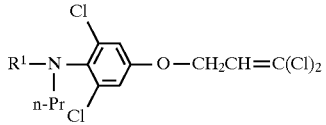
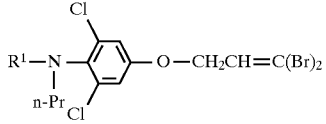
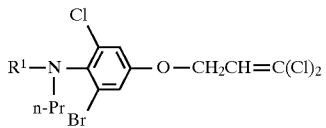

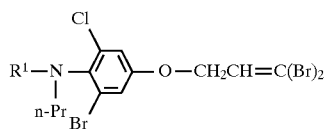
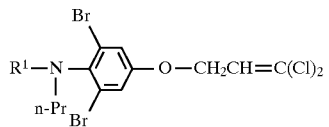
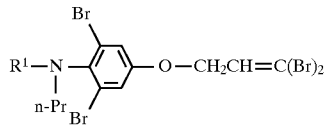
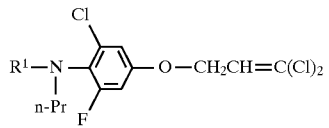
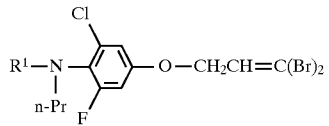
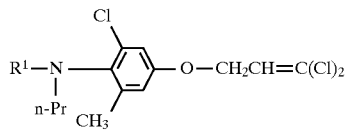
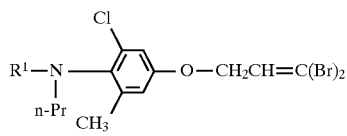
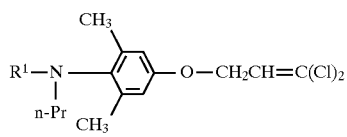
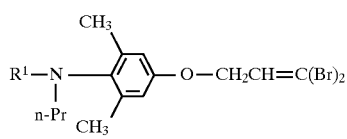
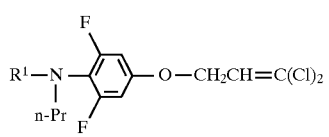
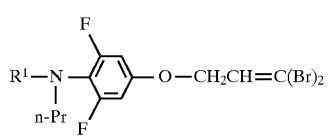
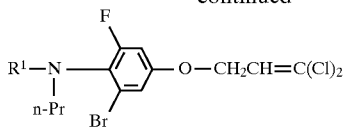
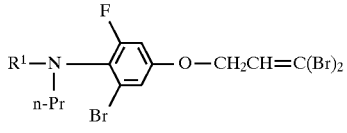
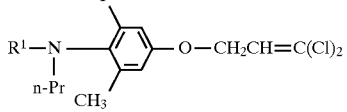
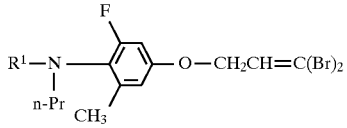
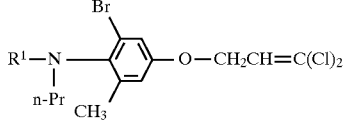
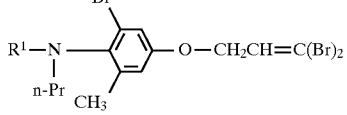
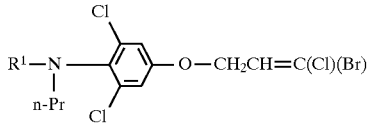
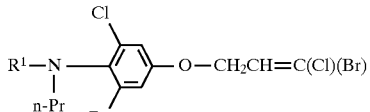
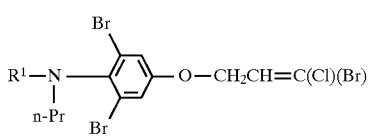
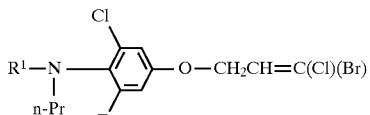
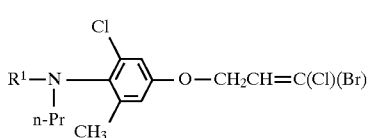
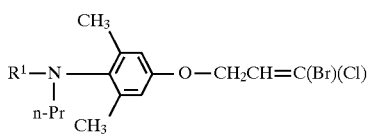

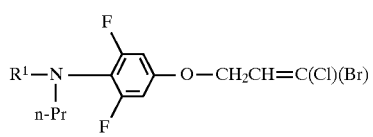
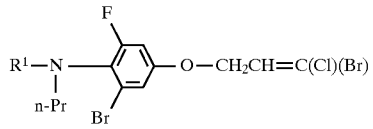
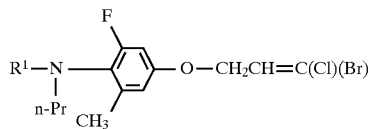
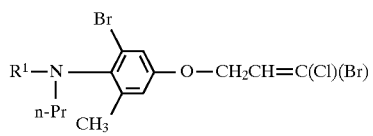
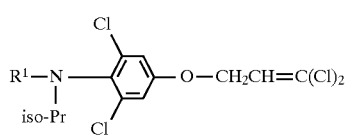
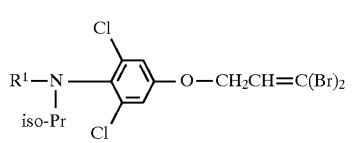
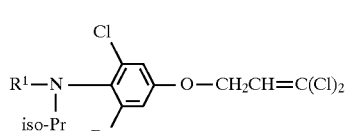
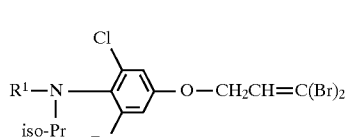
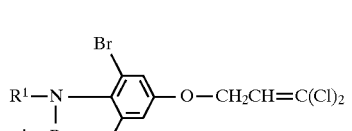
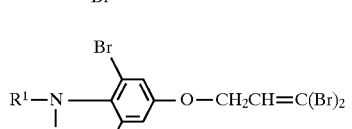
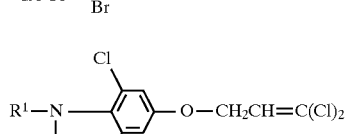
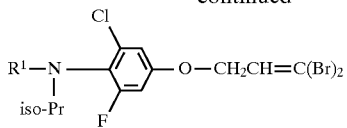
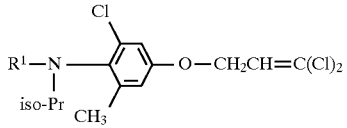
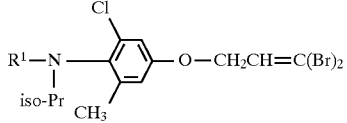
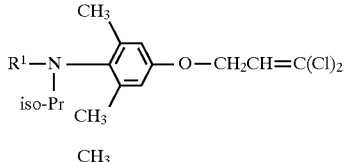
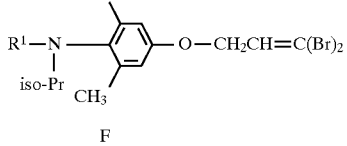
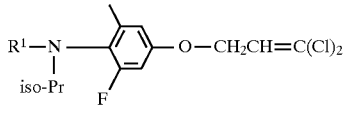
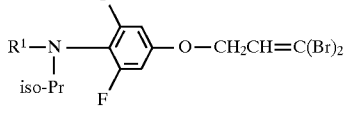
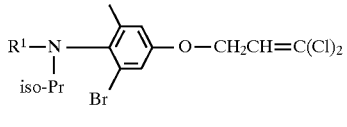
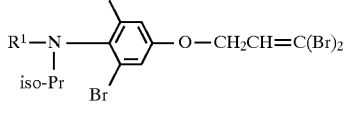
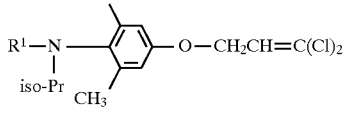
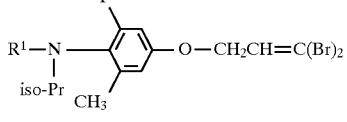
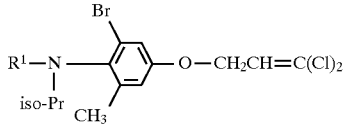

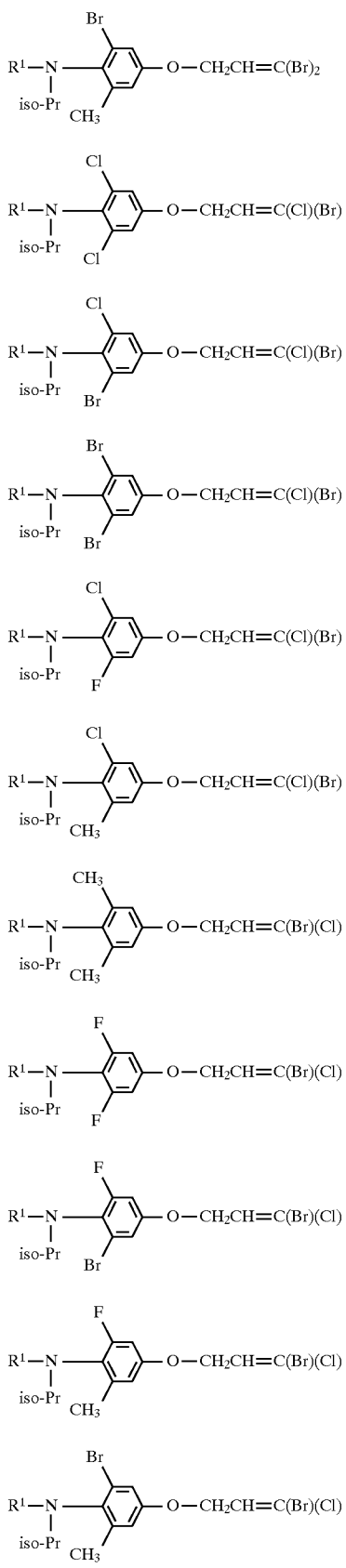
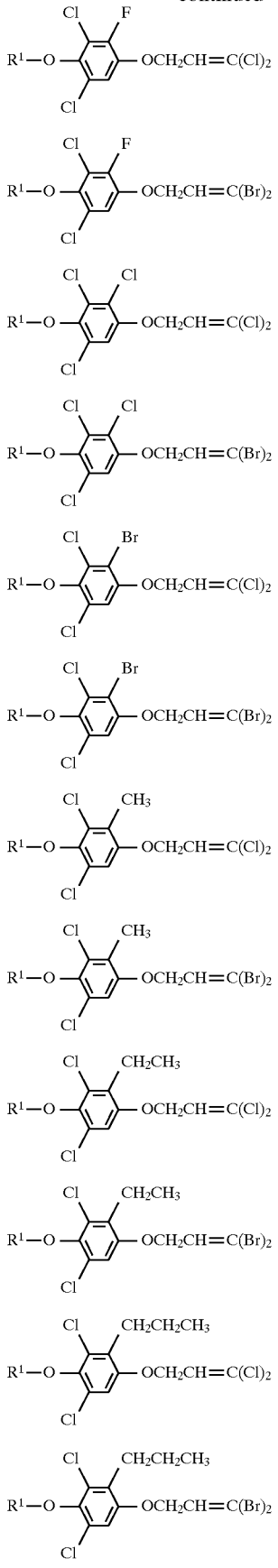

-continued
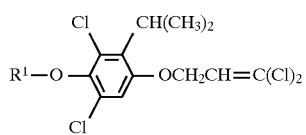
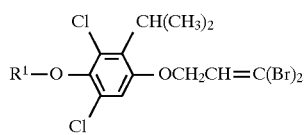
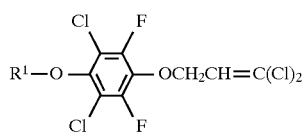
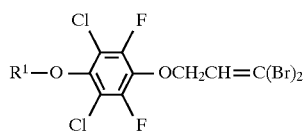
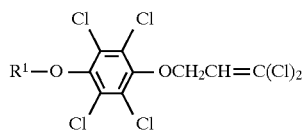
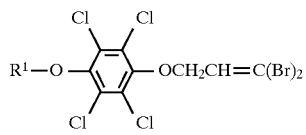
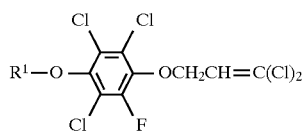
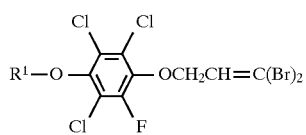
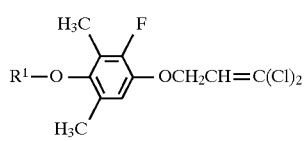
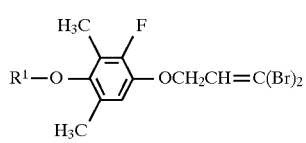
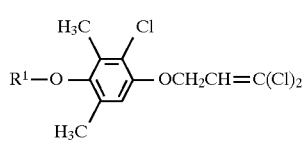
-continued
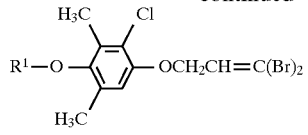
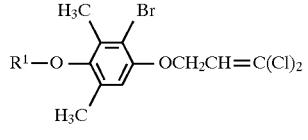
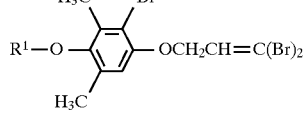
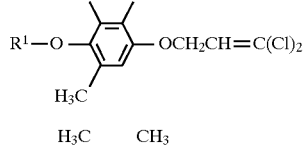
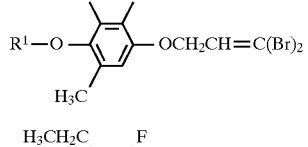
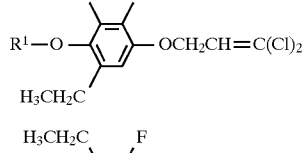
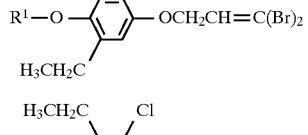
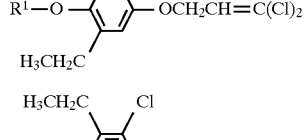
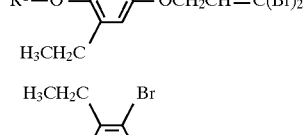
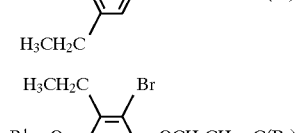
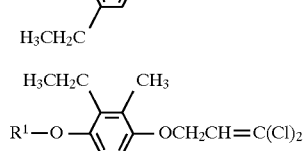

-continued

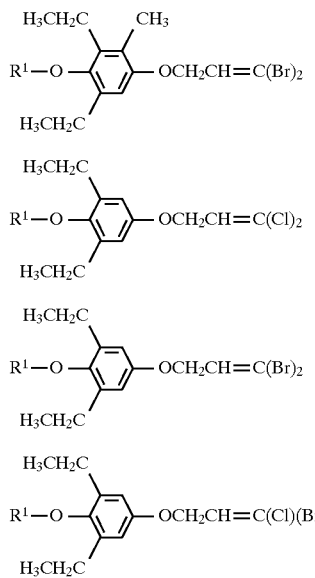

TABLE 1

| $R^1$ | $R^1$ |
|---|---|
| $CH_3-$ | $CH_3CH_2CH(CH_3)(CH_2)_2-$ |
| $C_2H_5-$ | $(CH_3)_2CHCH_2CH(CH_3)-$ |
| $CH_3CH_2CH_2-$ | $CH_3(CH_2)_5CH(CH_3)-$ |
| $(CH_3)_2CH-$ | $CH_3(CH_2)_6CH(CH_3)-$ |
| $CH_3(CH_2)_2CH_2-$ | $CF_3-$ |
| $(CH_3)_2CHCH_2-$ | $CF_2H-$ |
| $CH_3CH_2CH(CH_3)-$ | $CF_2Br-$ |
| $(CH_3)_3C-$ | $CF_3CH_2-$ |
| $CH_3(CH_2)_3CH_2-$ | $CF_3CF_2-$ |
| $(CH_3)_2CHCH_2CH_2-$ | $FCH_2CH_2-$ |
| $(CH_3)_3CCH_2-$ | $ClCH_2CH_2-$ |
| $CH_3CH_2C(CH_3)_2-$ | $BrCH_2CH_2-$ |
| $CH_3(CH_2)_4CH_2-$ | $ICH_2CH_2-$ |
| $(CH_3)_2CHCH_2CH_2CH_2-$ | $(Cl)_2CHCH_2-$ |

TABLE 1-continued

| $R^1$ | $R^1$ |
|---|---|
| $CH_3(CH_2)_5CH_2-$ | $BrCF_2CF_2-$ |
| $CH_3(CH_2)_6CH_2-$ | $CF_2HCF_2-$ |
| $CH_3(CH_2)_7CH_2-$ | $CFClHCF_2-$ |
| $CH_3(CH_2)_8CH_2-$ | $CF_2BrCFH-$ |
| $(C_2H_5)_2CH-$ | $ClCH_2CH_2CH_2-$ |
| $(C_2H_5)_2CHCH_2-$ | $BrCH_2CH_2CH_2-$ |
| $CH_3(CH_2)_3CH(CH_3)-$ | $FCH_2CH_2CH_2-$ |
| $CH_3(CH_2)_2CH(C_2H_5)-$ | $ICH_2CH_2CH_2-$ |

TABLE 2

| | |
|---|---|
| $CF_3CH_2CH_2-$ | $CH_2BrCH(CH_2Br)-$ |
| $CF_3CF_2CH_2-$ | $CH_2BrCH_2CH(CH_2Br)-$ |
| $CF_3CFHCF_2-$ | $CF_3CH(CF_3)-$ |
| $FCH_2(CH_2)_3-$ | $CH_2=CH-$ |
| $BrCH_2(CH_2)_3-$ | $CHCl=CH-$ |
| $ClCH_2(CH_2)_3-$ | $CCl_2=CH-$ |
| $ICH_2(CH_2)_3-$ | $CH_2=CHCH_2-$ |
| $ClC(CH_3)_2CH_2-$ | $CH_2=CHCH_2CH_2-$ |
| $FCH_2(CH_2)_4-$ | $(CH_3)_2C=CH(CH_2)_2(CH_3)C$ |
| $BrCH_2(CH_2)_4-$ | $=CHCH_2-$ |
| $ClCH_2(CH_2)_4-$ | $(CH_2=CH)(CH_3CH_2CH_2)CH-$ |
| $ICH_2(CH_2)_4-$ | $(CH_2=CHCH_2)_2CH-$ |
| $CH_3CHClCH_2-$ | $CH_2=C(CH_3)CH_2-$ |
| $CH_3CH(CH_2Br)CH_2-$ | $(CH_3)_2C=CHCH_2-$ |
| $CH_2ClC(CH_3)_2CH_2-$ | $CH_2=C(CH_3)CH_2CH_2-$ |
| $CH_2BrC(CH_3)_2CH_2-$ | $(CH_2=CH)(CH_3CH_2)CH-$ |
| $CH_2BrCHBrCH_2-$ | $ClCH=CHCH_2-$ |
| $CCl_3CH_2-$ | $CH_3CH=CHCH_2-$ |
| $CBr_3CH_2-$ | $BrCH=CHCH_2-$ |
| $CF_2HCF_2CH_2-$ | $CH_2=CClCH_2-$ |
| $CF_3CFHCF_2CH_2-$ | $CH_2=CBrCH_2-$ |
| $CF_2H(CF_2)_3CH_2-$ | $CH_2=C(CH_2Cl)CH_2-$ |
| $CH_2ClCH(CH_3)-$ | $ClCH_2CH=CHCH_2-$ |
| $CH_2BrCH(CH_3)-$ | $CH_3CH_2CH=CHCH_2CH_2-$ |
| $CH_2FCH(CH_2F)-$ | $ClCH_2CH=CHCH_2-$ |
| $CH_2ClCH(CH_2Cl)-$ | $(Cl_2)C=CHCH_2-$ |

TABLE 3

| | |
|---|---|
| $(Br)_2C=CHCH_2-$ | $CH_3CH=CH(CH_2)_2CH_2-$ |
| $(F)_2C=CHCH_2-$ | $CH_2=CH(CH_2)_3CH_2-$ |
| $(CF_3)(Cl)C=CHCH_2-$ | $CH_2=CHCH(CH_3CH_2CH_2)-$ |
| $(F)(CF_2Br)C=CHCH_2-$ | $(CH_3)_2C=CH(CH_2)_2CH(CH_3)-$ |
| $(CF_3)(F)C=CHCH_2CH_2-$ | $CH_3(CH_2)_3CH_2CH(CH=CH_3)-$ |
| $(Cl)_2C=CHCH_2CH_2-$ | $(CH_3)_2C=CH(CH_2)_2-CH(CH_3)CH_2CH_2-$ |
| $(Br)_2C=CHCH_2CH_2-$ | |
| $CH_2=C(CH(CH_3)_2)CH_2-$ | $(CH_3)(Cl)C=CHCH_2-$ |
| $CH_3CH=C(C_2H_5)CH_2-$ | $(Cl)_2C=CH(CH_2)_3CH_2-$ |
| $CH_2=C(C_2H_5)CH_2-$ | $CH\equiv CCH(CH_3)-$ |
| $C_2H_5CH=C(CH_3)CH_2-$ | $CH_3C\equiv CCH_2-$ |
| $C_2H_5CH=CHCH_2-$ | $HC\equiv CCH_2-$ |
| $CH_3CH=C(CH_3)CH_2-$ | $HC\equiv CCH_2CH_2-$ |
| $CH_3(CH_2)_3CH=CHCH_2-$ | $CH_3CH_2CH_2C\equiv CCH_2-$ |
| $CH_2=CHCH(CH_3)-$ | $CH_3CH_2C\equiv CCH_2CH_2-$ |
| $CH_3CH=CHCH(CH_3)-$ | $HC\equiv CCH(CH_3)CH_2-$ |
| $CH_3CH=CHCH(C_2H_5)-$ | $HC\equiv CCH(CH_3(CH_2)_4)-$ |
| $CH_2=CHCH_2CH_2CH(CH_3)-$ | $HC\equiv CCH_2CH(CH_3)-$ |
| $(CH_3)_2C=CHCH(CH_3)-$ | $CH_3CH_2C\equiv CCH_2-$ |
| $CF_3CH=CHCH_2-$ | $HC\equiv CCH_2CH_2CH_2-$ |
| $CH_2=CHCH(CH_3)CH_2-$ | $CH_3C\equiv CCH_2CH_2-$ |
| $CH_2=CHCH_2CH_2CH_2-$ | $HC\equiv CCH(C_2H_5)-$ |
| $CH_2=CHCH_2(CH_3)CH-$ | $HC\equiv CCH_2CH_2CH_2CH_2-$ |
| $CH_2=CHCH(C_2H_5)-$ | $CH_3(CH_2)_4C\equiv CCH_2CH_2-$ |
| $CH_3(CH_2)_2CH=CHCH_2$ | $ClCH_2C\equiv CCH-$ |

TABLE 4

| | |
|---|---|
| ClC≡CCH(CH₃)— | CH₃CH(OC₂H₅)— |
| BrC≡CCH(CH₃)— | CH₂(CH₃O)CH₂CH₂— |
| ClC≡CCH₂— | CH₃(CH₃O)CH₂— |
| BrC≡CCH₂— | CH₃CH₂CH(CH₃O)— |
| ClC≡CCH₂CH₂— | CH₃OCH₂CH(CH₃)— |
| BrC≡CCH₂CH₂— | CH₃(CH₂)₂OCH₂CH₂— |
| ClC≡CCH(CH₃)CH₂— | CH₃CH₂OCH(CH₃)CH₂— |
| BrC≡CCH(CH₃)CH₂— | CH₃CH₂OCH₂CH(CH₃)— |
| ClC≡CCH₂CH(CH₃)— | CH₃OCH(C₂H₅)CH₂— |
| BrC≡CCH₂CH(CH₃)— | CH₃OCH₂CH(C₂H₅)— |
| ClC≡CCH₂CH₂CH₂— | C₂H₅OCH₂CH₂CH₂— |
| BrC≡CCH₂CH₂CH₂— | CH₃OCH(CH₃)CH₂CH₂— |
| ClC≡CCH(C₂H₅)— | CH₃OCH₂CH(CH₃)CH₂— |
| BrC≡CCH(C₂H₅)— | CH₃OCH₂CH₂CH(CH₃)— |
| CH₃(CH₂)₃OCH₂CH(CH₃)— | CH₃SCH₂(CH₂)₂CH₂— |
| CH₃(CH₂)₃OCH₂CH₂— | CH₃SCH₂— |
| (CH₃)₂CHOCH₂CH₂— | CH₃CH₂SCH₂— |
| (CH₃)₂(CH₃O)CCH₂CH₂— | CH₃CH₂CH₂SCH₂— |
| CH₃(CH₃O)CHCH₂CH₂— | (CH₃)₂CHSCH₂— |
| CH₃OCH₂CH₂— | CH₃SCH₂CH₂— |
| CH₃CH₂OCH₂— | CH₃SCH(CH₃)— |
| CH₃OCH₂— | CH₃CH₂SCH₂CH₂— |
| (CH₃)₂CHOCH₂— | CH₃CH₂SCH(CH₃)— |
| CH₃CH₂CH₂OCH₂— | CH₃SCH₂CH₂CH₂— |
| CH₃CH(OCH₃)— | CH₃S(CH₃)CHCH₂— |
| CH₃CH₂OCH₂CH₂— | CH₃SCH(CH₃CH₂)— |

TABLE 5

| | |
|---|---|
| CH₃SCH₂CH(CH₃)— | 3-sec-butyloxycyclohexyl |
| (CH₃)₂CHSCH₂CH₂— | 3-tert-butyloxycyclohexyl |
| CH₃CH₂CH₂SCH₂CH₂— | 4-methoxycyclohexyl |
| CH₃SCH(CH₃)C(CH₃)H— | 4-ethoxycyclohexyl |
| CH₃SCH(C₂H₅)CH₂— | 4-propoxycyclohexyl |
| CH₃SCH(C₂H₅)— | 4-isopropoxycyclohexyl |
| CH₃CH₂SCH(CH₃)CH₂— | 4-butoxycyclohexyl |
| CH₃CH₂SCH₂CH(CH₃)— | 4-isobutyloxycyclohexyl |
| CH₃CH₂SCH₂CH₂CH₂— | 4-sec-butyloxycyclohexyl |
| CH₃SCH(CH₃)CH₂CH₂— | 4-tert-butyloxycyclohexyl |
| CH₃SCH₂CH(CH₃)CH₂— | 2-methoxycyclopentyl |
| CH₃SCH₂CH₂CH(CH₃)— | 2-ethoxycyclopentyl |
| (CH₃)₃CSCH₂CH₂— | 2-propoxycyclopentyl |
| (CH₃)₂CHCH₂SCH₂CH₂— | 2-isopropoxycyclopentyl |
| CH₃CH₂CH(CH₃)SCH₂CH₂— | 2-butoxycyclopentyl |
| (CH₃)₃CSCH₂CH₂CH₂— | 2-isobutyloxycyclopentyl |
| (CH₃)₂CHCH₂SCH₂CH₂CH₂— | 2-sec-butyloxycyclopentyl |
| CH₃CH₂CH(CH₃)SCH₂CH₂CH₂— | 2-tert-butyloxycyclopentyl |
| 3-methoxycyclohexyl | cyclopropyl |
| 3-ethoxycyclohexyl | cyclobutyl |
| 3-propoxycyclohexyl | cyclopentyl |
| 3-isopropoxycyclohexyl | |
| 3-butoxycyclohexyl | |
| 3-isobutyloxycyclohexyl | |

TABLE 6

| | |
|---|---|
| cyclohexyl | 3-(difluorobromomethoxy)cyclohexyl |
| 2,3-dimethylcyclohexyl | 4-(difluorobromomethoxy)cyclohexyl |
| 2-ethylcyclohexyl | 3-(difluorobromomethoxy)cyclopentyl |
| 3,3,5,5-tetramethylcyclohexyl | 3-(2,2,2-trifluoromethoxy)cyclohexyl |
| 3,4-dimethylcyclohexyl | 4-(2,2,2-trifluoroethoxy)cyclohexyl |
| 3,5-dimethylcyclohexy | 3-(2,2,2-trifluoroethoxy)cyclopentyl |
| 4-ethylcyclohexyl | |
| 2-methylcyclohexyl | |
| 3-methylcyclohexyl | |
| 4-methylcyclohexyl | |
| 3-methylcyclopentyl | cyclopentyl |
| 2-methylcyclopentyl | 3-(1,1,2,2,2-pentafluoroethoxy)cyclohexyl |
| 3-(trifluoromethoxy)cyclohexyl | 4-(1,1,2,2,2-pentafluoroethoxy)cyclohexyl |
| 4-(trifluoromethoxy)cyclohexyl | 3-(1,1,2,2,2-pentafluoroethoxy)cyclopentyl |
| 3-(trifluoromethoxy)cyclopentyl | 3-(2-chloroethoxy)cyclohexyl |
| 3-(difluoromethoxy)cyclohexyl | 3-(2-chloroethoxy)cyclopentyl |
| 4-(difluoromethoxy)cyclohexyl | 4-(2-chloroethoxy)cyclohexyl |
| 3-(difluoromethoxy)cyclopentyl | 3-(2-bromoethoxy)cyclohexyl |

TABLE 7

| | |
|---|---|
| 3-(2-bromoethoxy)cyclopentyl | 3-(1,2,2,3,3,3-hexafluoropropoxy)cyclopentyl |
| 4-(2-bromoethoxy)cyclohexyl | 4-(1,2,2,3,3,3-hexafluoropropoxy)cyclohexyl |
| 3-(2-chloro-1,1,2-trifluoroethoxy)cyclohexyl | 2-cyclohexylethyl |
| 3-(2-chloro-1,1,2-trifluoroethoxy)cyclopentyl | cyclobutylmethyl |
| 4-(2-chloro-1,1,2-trifluoroethoxy)cyclohexyl | cyclopropylmethyl |
| 3-(2-bromo-1,1,2-trifluoroethoxy)cyclohexyl | 1-cyclopropylmethyl |
| 3-(2-bromo-1,1,2-trifluoroethoxy)cyclopentyl | cyclohexylmethyl |
| 4-(2-bromo-1,1,2-trifluoroethoxy)cyclohexyl | cyclopentylmethyl |
| 3-(1,1,2,2-tetrafluoroethoxy)cyclohexyl | 2-methylcyclopropanemethyl |
| 3-(1,1,2,2-tetrafluoroethoxy)cyclopentyl | 3-cyclopentylpropyl |
| 4-(1,1,2,2-tetrafluoroethoxy)cyclohexyl | 3-cyclohexylpropyl |
| 3-(1,2,2,3,3,3-hexafluoropropoxy)cyclohexyl | 2-(2-methylcyclopropyl)ethyl |
| | 2-cyclohexenyl |
| | 3,5,5-trimethyl-2-cyclohexenyl |
| | 3-methyl-2-cyclohexenyl |
| | 2-(3-cyclohexenyl)ethyl |
| | (3-cyclohexenyl)methyl |
| | (1-cyclopentenyl)methyl |
| | 2-cyclopentenyl |
| | 3-cyclopentenyl |
| | 3-cyclohexenyl |
| CH₃OCOCH₂ | CH₃CH₂OCOCH₂CH₂ |
| CH₃OCOCH₂CH₂ | CH₃CH₂CH₂OCOCH₂ |
| CH₃OCOCH₂CH₂CH₂ | (CH₃)₂CHOCOCH₂CH₂ |
| CH₃OCOCH₂CH₂CH₂CH₂ | CH₃CH₂CH₂OCOCH₂CH₂ |
| CH₃OCOCH₂CH₂CH₂CH₂CH₂ | CH₃CH₂CH₂OCOCH₂CH₂ |
| CH₃OCOCH₂CH₂CH₂CH₂CH₂CH₂ | (CH₃)₂CHOCOCH₂CH₂CH₂ |
| CH₃OCOCH₂CH₂CH₂CH₂CH₂CH₂CH₂ | |

TABLE 8

$R^1 =$ naphthalene structure with positions 1-8, $(R^4)_m$ at 6, $(R^{12})_q$ at 1, $Q_4$ at position 3, substituent $[R^{10}R^{11}]_p$–CH(R^7)(R^{16})

| $(R^4)_m$ | $(R^{12})_a$ | position of $Q_4$ | $\left[\begin{array}{c}R^{10}\\R^{11}\end{array}\right]_p$ CH(R^7) | p | R^7 | R^16 | R^11 |
|---|---|---|---|---|---|---|---|
| H | H | 1 | | 1 | H | H | H |
| H | H | 1 | | 0 | H | H | H |
| H | H | 2 | | 0 | H | H | H |
| H | H | 2 | | 1 | H | H | H |
| H | H | 2 | | 0 | CH_3 | H | H |
| H | H | 1 | | 0 | CH_3 | H | H |
| 6-CH_3 | H | 2 | | 0 | CH_3 | H | H |
| 6-OCH_3 | H | 2 | | 0 | —CH_2CH_3 | H | H |
| H | 2-OCH_3 | 1 | | 0 | H | H | H |
| H | 4-F | 1 | | 0 | H | H | H |
| H | 2-OCH_2CH_3 | 1 | | 0 | H | H | H |
| H | 4-OCH_3 | 1 | | 0 | H | H | H |
| H | 3-OCH_3 | 2 | | 0 | H | H | H |
| H | 2-CH_3 | 1 | | 0 | H | H | H |
| 6-OCF_3 | H | 2 | | 0 | —CH_2CH_2 | H | H |
| 6-OCH_2CH_3 | H | 2 | | 0 | —CH_2CH_2 | H | H |
| 6-OCH(CH_3)_2 | H | 2 | | 0 | —CH_2CH_3 | H | H |
| 4-OCF_3 | H | 1 | | 0 | H | H | H |
| 4-OCH_2CH_3 | H | 1 | | 0 | H | H | H |
| 4-OCH(CH_3)_2 | H | 1 | | 0 | H | H | H |
| H | 1-CHF_2 | 2 | | 0 | H | H | H |
| H | H | 2 | | 1 | H | CH_3 | H |
| 6-OCF_3 | H | 2 | | 1 | H | CH_3 | H |
| 6-OCH(CH_3)_2 | H | 2 | | 1 | H | CH_3 | H |
| H | H | 3 | | 1 | H | CH_3 | H |
| 6-OCF_3 | H | 3 | | 1 | H | CH_3 | H |
| 6-OCH(CH_3)_2 | H | 3 | | 1 | H | CH_3 | H |

TABLE 9

$R^1 =$ tetrahydronaphthalene structure with positions 1-8, $(R^4)_m$ at 6, $R^8$ at position 2, substituent $[R^{10}R^{11}]_p$–CH(R^7) at position 1

| $(R^4)_m$ | R^7 | R^1 | position of $\left[\begin{array}{c}R^{10}\\R^{11}\end{array}\right]_p$ CH(R^7) | p | R^10 | R^11 |
|---|---|---|---|---|---|---|
| H | H | H | 1 | 0 | H | H |
| H | H | 1-CH_3 | 2 | 0 | H | H |
| H | H | 4-CH_3 | 1 | 0 | H | H |
| H | H | H | 2 | 0 | H | H |
| 6-OCH_3 | H | H | 2 | 0 | H | H |
| 6-OCH_3 | H | H | 3 | 0 | H | H |
| 6,7-(OCH_3)_2 | H | H | 2 | 0 | H | H |
| H | H | 2-CH_3 | 1 | 0 | H | H |
| 6,7-(OCH_3)_2 | H | H | 1 | 0 | H | H |
| 5,7-(CH_3)_3 | H | H | 1 | 0 | H | H |
| 7-(OCH_3) | H | H | 1 | 0 | H | H |
| 5-OCH_3 | H | H | 1 | 0 | H | H |
| 6-OCH_3 | H | H | 1 | 0 | H | H |
| 5-OCH_4 | H | H | 1 | 0 | H | H |

TABLE 9-continued

R¹ = [structure: tetrahydronaphthalene with (R⁴)ₘ at positions 5-8, connected at position 1 to [R¹⁰R¹¹C]ₚ-CHR⁷, R⁸ at position 2]

| (R⁴)ₘ | R⁷ | R¹ | position of [R¹⁰R¹¹C]ₚ-CHR⁷ | p | R¹⁰ | R¹¹ |
|---|---|---|---|---|---|---|
| 5-OCH₂CH₃ | H | H | 1 | 0 | H | H |
| 5-OCH₂CH₂CH₃ | H | H | 1 | 0 | H | H |
| 5-OCH(CH₃)₂ | H | H | 1 | 0 | H | H |
| 5-OCF₃ | H | H | 1 | 0 | H | H |
| 5-OCF₂H | H | H | 1 | 0 | H | H |
| 5-OCF₂Br | H | H | 1 | 0 | H | H |
| 5-OCH₂CF₃ | H | H | 1 | 0 | H | H |
| 5-OCF₂CF₃ | H | H | 1 | 0 | H | H |
| 5-OCH₂CH₂CF₃ | H | H | 1 | 0 | H | H |
| H | H | H | 2 | 1 | H | H |
| H | H | H | 2 | 2 | H | H |
| H | H | H | 1 | 1 | H | H |
| H | H | H | 1 | 2 | H | H |
| 6-OCH₃ | H | H | 2 | 1 | H | H |
| 6-OCH₃ | H | H | 2 | 2 | H | H |
| 6-OCH₂CH₃ | H | H | 2 | 1 | H | H |
| 6-OCH₂CH₃ | H | H | 2 | 2 | H | H |
| 6-OCH(CH₃)₂ | H | H | 2 | 1 | H | H |
| 6-OCH(CH₃)₂ | H | H | 2 | 2 | H | H |
| H | CH₃ | H | 2 | 1 | H | H |
| H | H | H | 2 | 1 | H | H |
| H | H | H | 2 | 1 | H | H |
| H | H | H | 1 | 1 | CH₃ | H |
| H | H | H | 2 | 1 | CH₃ | H |

TABLE 10

R¹ = [structure: indane with (R⁴)ₘ at positions 4-7, connected at position 1 to [R¹⁰R¹¹C]ₚ-CHR⁷, R⁸ at position 3]

| (R⁴)ₘ | R⁷ | R⁸ | position of [R¹⁰R¹¹C]ₚ-CHR⁷ | p | R¹⁶ | R¹¹ |
|---|---|---|---|---|---|---|
| H | H | 3-Br | 2 | 0 | H | H |
| H | H | H | 1 | 0 | H | H |
| H | H | H | 2 | 0 | H | H |
| H | H | H | 2 | 1 | H | H |
| H | H | H | 2 | 2 | H | H |
| H | H | H | 1 | 1 | H | H |
| H | H | H | 1 | 2 | H | H |
| 5-F | H | H | 1 | 0 | H | H |
| 5-F | H | H | 1 | 1 | H | H |
| 5-F | H | H | 1 | 2 | H | H |
| 5-OCH₃ | H | H | 2 | 0 | H | H |
| 5-OCH₃ | H | H | 1 | 0 | H | H |
| 5-OCH₃ | H | H | 1 | 1 | H | H |
| 5-OCH₃ | H | H | 1 | 2 | H | H |
| 6-OCH₃ | H | H | 1 | 0 | H | H |
| 6-OCH₃ | H | H | 1 | 1 | H | H |
| 6-OCH₃ | H | H | 1 | 2 | H | H |
| 5,6-(OCH₃)₂ | H | H | 1 | 0 | H | H |

TABLE 10-continued $R^1 =$ structure showing indane ring with positions 1-7, substituents $(R^4)_m$ at positions 4-6, $R^8$ at position 3, and $-[C(R^{10})(R^{11})]_p-CH(R^7)$ chain at position 1.

| $(R^4)_m$ | $R^7$ | $R^8$ | position of $[C(R^{10})(R^{11})]_p$ | p | $R^{16}$ | $R^{11}$ |
|---|---|---|---|---|---|---|
| 5,6-(OCH$_3$)$_2$ | H | H | 1 | 1 | H | H |
| 5,6-(OCH$_3$)$_2$ | H | H | 1 | 2 | H | H |
| H | CH$_3$ | H | 2 | 1 | H | H |
| H | H | H | 2 | 1 | H | H |
| H | H | H | 1 | 1 | H | H |
| H | H | H | 1 | 1 | CH$_3$ | H |
| H | H | H | 2 | 1 | CH$_3$ | H |

TABLE 11

Structure: phenyl ring with $(R^4)_l$ substituents and $Q_l$, attached at position 1 to $C(R^5)=C(R^6)-[C(R^{10})(R^{11})]_p-CH(R^7)$.

| $(R^4)l$ | $R^5$ | $R^6$ | $R^7$ | $R^{10}$ | $R^{11}$ | p |
|---|---|---|---|---|---|---|
| H | H | H | H | H | H | 0 |
| H | H | Cl | H | H | H | 0 |
| H | H | F | H | H | H | 0 |
| H | H | Br | H | H | H | 0 |
| H | H | CH$_3$ | H | H | H | 0 |
| H | Br | H | H | H | H | 0 |
| H | CH$_3$ | H | H | H | H | 0 |
| H | CH$_3$ | H | H | H | H | 0 |
| H | CH$_2$CH$_3$ | H | H | H | H | 0 |
| H | CH$_2$CH$_2$CH$_3$ | H | H | H | H | 0 |
| H | CH(CH$_3$)$_2$ | H | H | H | H | 0 |
| 4-Cl | H | H | CH$_3$ | H | H | 0 |
| H | H | H | CH$_3$ | H | H | 0 |
| 4-C(CH$_3$) | H | CH$_3$ | H | H | H | 0 |
| 2,4,5-(OCH$_3$)$_3$ | H | CH$_3$ | H | H | H | 0 |
| 2-OCH$_3$ | H | H | H | H | H | 0 |
| 2-F | H | H | H | H | H | 0 |
| 2-CF$_3$ | H | H | H | H | H | 0 |
| 2-Cl | H | H | H | H | H | 0 |
| 3-F | H | H | H | H | H | 0 |
| 3-Cl | H | H | H | H | H | 0 |
| 3-Br | H | H | H | H | H | 0 |
| 3-CF$_3$ | H | H | H | H | H | 0 |
| 3-OCH$_3$ | H | H | H | H | H | 0 |
| 4-F | H | H | H | H | H | 0 |
| 4-CF$_3$ | H | H | H | H | H | 0 |
| 4-Cl | H | H | H | H | H | 0 |
| 4-Br | H | H | H | H | H | 0 |
| 4-OCH$_3$ | H | H | H | H | H | 0 |
| 2,6-F$_2$ | H | H | H | H | H | 0 |
| 2,4-F$_2$ | H | H | H | H | H | 0 |
| 2,5-F$_2$ | H | H | H | H | H | 0 |
| 3,4-F$_2$ | H | H | H | H | H | 0 |
| 3,5-F$_2$ | H | H | H | H | H | 0 |
| 2,6-Cl$_2$ | H | H | H | H | H | 0 |
| 2,4-Cl$_2$ | H | H | H | H | H | 0 |
| 3,4-Cl$_2$ | H | H | H | H | H | 0 |
| 2-OCH$_3$, 5-Br | H | H | H | H | H | 0 |
| 2,3-(OCH$_3$)$_2$ | H | H | H | H | H | 0 |
| 2,4-(OCH$_3$)$_2$ | H | H | H | H | H | 0 |
| 2,5-(OCH$_3$)$_2$ | H | H | H | H | H | 0 |
| 3,4-(OCH$_3$)$_2$ | H | H | H | H | H | 0 |
| 3,5-(OCH)$_2$ | H | H | H | H | H | 0 |
| 3,4,5-(OCH$_3$)$_3$ | H | H | H | H | H | 0 |
| 2,4,5-(OCH$_3$)$_3$ | H | H | H | H | H | 0 |
| 2,3,4,5,6-F$_5$ | H | H | H | H | H | 0 |
| 4-OCH$_2$CH$_3$ | H | H | H | H | H | 0 |
| 3-OCH$_2$CH$_3$ | H | H | H | H | H | 0 |
| 3-OCH$_2$CH$_2$CH$_3$ | H | H | H | H | H | 0 |
| 3-(OCH(CH$_3$)$_2$ | H | H | H | H | H | 0 |
| 4-OCH$_2$CH | H | H | H | H | H | 0 |
| 4-OCH(CH$_3$)$_2$ | H | H | H | H | H | 0 |
| 3-OCF$_3$ | H | H | H | H | H | 0 |
| 4-OCF$_3$ | H | H | H | H | H | 0 |
| 3-OCHF$_2$ | H | H | H | H | H | 0 |
| 4-OCHF$_2$ | H | H | H | H | H | 0 |
| 3-OCF$_2$Br | H | H | H | H | H | 0 |
| 4-OCF$_2$Br | H | H | H | H | H | 0 |
| 3-OCH$_2$CF$_3$ | H | H | H | H | H | 0 |
| 4-OCH$_2$CF$_3$ | H | H | H | H | H | 0 |
| 3-OCF$_2$CF$_2$H | H | H | H | H | H | 0 |
| 4-OCF$_2$CF$_2$H | H | H | H | H | H | 0 |
| 3-OCH$_2$CH$_2$CF$_3$ | H | H | H | H | H | 0 |
| 4-OCH$_2$CH$_2$CF$_3$ | H | H | H | H | H | 0 |
| 3-OCF$_2$CPHCF$_3$ | H | H | H | H | H | 0 |
| 4-OCF$_2$CFHCF$_3$ | H | H | H | H | H | 0 |
| 3-CH$_3$ | H | H | H | H | H | 0 |
| 4-CH$_3$ | H | H | H | H | H | 0 |
| 3-CH$_2$CH$_3$ | H | H | H | H | H | 0 |
| 4-CH$_2$CH$_3$ | H | H | H | H | H | 0 |
| 2,4-(CH$_3$)$_2$ | H | H | H | H | H | 0 |
| 2-CF$_3$ | H | H | H | H | H | 0 |
| 2-CH$_3$ | H | H | H | H | H | 0 |
| 4-CH(CH$_3$)$_2$ | H | H | H | H | H | 0 |
| 3-CH$_3$ | H | H | H | H | H | 0 |
| 4-CF$_3$ | H | H | H | H | H | 0 |
| 3-CF$_3$ | H | H | H | H | H | 0 |
| 4-Cl | H | H | H | H | H | 1 |

TABLE 11-continued
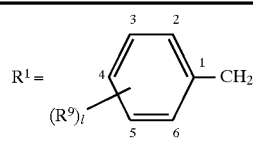
| (R⁴)l | R⁵ | R⁶ | R⁷ | R¹⁰ | R¹¹ | p |
|---|---|---|---|---|---|---|
| 4-CF₃ | H | H | H | H | H | 1 |
| 4-OCH(CH₃)₂ | H | H | H | H | H | 1 |
| 4-OCF₃ | H | H | H | H | H | 1 |
| 3-F | H | H | H | H | H | 1 |
| 3-CF₃ | H | H | H | H | H | 1 |
TABLE 12
R¹ = 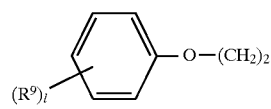
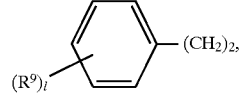
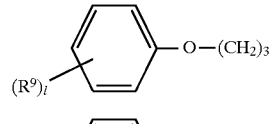
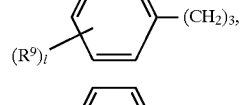
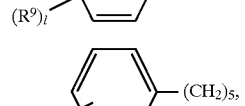
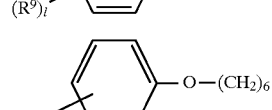
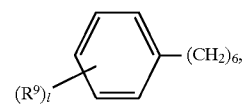
TABLE 12-continued
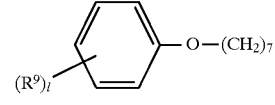
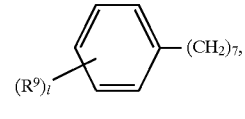
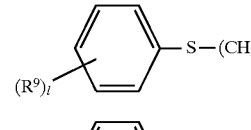
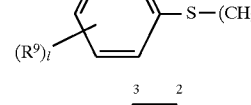
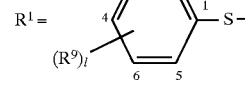
R¹ = 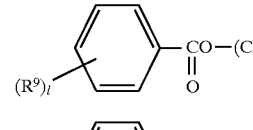
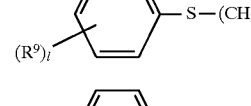
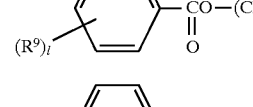
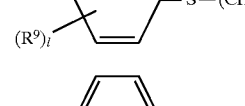
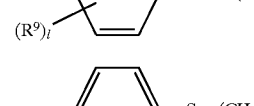
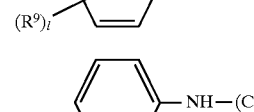
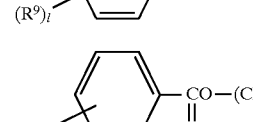

TABLE 12-continued (R⁹)ₗ—C₆H₄—NH—(CH₂)₄

(R⁹)ₗ—C₆H₄—CO—(CH₂)₃, with =O on CO (R⁹)ₗ—C₆H₄—NH—(CH₂)₅

(R⁹)ₗ—C₆H₄—CO—(CH₂)₄, with =O on CO (R⁹)ₗ—C₆H₄—NH—(CH₂)₆

(R⁹)ₗ—C₆H₄—CO—(CH₂)₅, with =O on CO (R⁹)ₗ—C₆H₄—NH—(CH₂)₇

$R^1 =$ (R⁹)ₗ-substituted phenyl (positions 1,2,3,4,5,6)—SO—(CH₂)₁, (R⁹)ₗ—C₆H₄—NCH₂CH₃—(CH₂)₃

(R⁹)ₗ—C₆H₄—SO—(CH₂)₂, (R⁹)ₗ—C₆H₄—NCH₂CH₃—(CH₂)₄

(R⁹)ₗ—C₆H₄—SO—(CH₂)₃, (R⁹)ₗ—C₆H₄—NCH₂CH₂CH₃—(CH₂)₃

(R⁹)ₗ—C₆H₄—SO—(CH₂)₄, (R⁹)ₗ—C₆H₄—NCH₂CH₂CH₃—(CH₂)₄

(R⁹)ₗ—C₆H₄—SO—(CH₂)₅, (R⁹)ₗ—C₆H₄—NCH(CH₃)₂—(CH₂)₄

(R⁹)ₗ—C₆H₄—SO—(CH₂)₆, (R⁹)ₗ—C₆H₄—NCH(CH₃)₂—(CH₂)₃

(R⁹)ₗ—C₆H₄—SO—(CH₂)₇, (R⁹)ₗ—C₆H₄—NCH(CH₃)₂—(CH₂)₄

(R⁹)ₗ—C₆H₄—SO₂—(CH₂)₁, (R⁹)ₗ—C₆H₄—OCO—(CH₂)₁

$R^1 =$ (R⁹)ₗ-substituted phenyl (positions 1,2,3,4,5,6)—SO₂—(CH₂)₂, (R⁹)ₗ—C₆H₄—OCO—(CH₂)₂

(R⁹)ₗ—C₆H₄—SO₂—(CH₂)₃, (R⁹)ₗ—C₆H₄—OCO—(CH₂)₃

(R⁹)ₗ—C₆H₄—SO₂—(CH₂)₄,

TABLE 12-continued

| Structure |
|---|
| (R⁹)_l —⟨phenyl⟩—OCO—(CH₂)₄ |
| (R⁹)_l —⟨phenyl⟩—SO₂—(CH₂)₅, |
| (R⁹)_l —⟨phenyl⟩—OCO—(CH₂)₅ |
| (R⁹)_l —⟨phenyl⟩—SO₂—(CH₂)₆, |
| (R⁹)_l —⟨phenyl⟩—OCO—(CH₂)₆ |
| (R⁹)_l —⟨phenyl⟩—SO₂—(CH₂)₇, |
| (R⁹)_l —⟨phenyl⟩—OCO—(CH₂)₇ |
| (R⁹)_l —⟨phenyl⟩—OCO—CH(CH₃), |
| (R⁹)_l —⟨phenyl⟩—CH₂CH(CH₃)CH(CH₃) |
| (R⁹)_l —⟨phenyl⟩—OCO—CH(CH₃)CH₂, |
| (R⁹)_l —⟨phenyl⟩—OCH₂CH₂CH₂CH(CH₃) |
| R¹ = (R⁹)_l —⟨phenyl, positions 1,2,3,4,5,6⟩—OCO—CH(CH₃)(CH₂)₂, |
| (R⁹)_l —⟨phenyl⟩—OCH₂CH₂CH(CH₃) |
| (R⁹)_l —⟨phenyl⟩—OCO—CH(CH₃)(CH₂)₃, |

TABLE 12-continued

| Structure |
|---|
| (R⁹)_l —⟨phenyl⟩—OCH₂CH(CH₃)CH₂ |
| (R⁹)_l —⟨phenyl⟩—OCO—CH(CH₃)(CH₂)₄, |
| (R⁹)_l —⟨phenyl⟩—OCH₂CH₂CH(CH₃)CH₂ |
| (R⁹)_l —⟨phenyl⟩—OCO—CH(CH₃)(CH₂)₅, |
| (R⁹)_l —⟨phenyl⟩—OCH₂CH(CH₃)CH₂CH₃ |
| (R⁹)_l —⟨phenyl⟩—OCO—CH(CH₃)(CH₂)₆, |
| (R⁹)_l —⟨phenyl⟩—OCH(CH₃)CH₂CH(CH₃) |
| (R⁹)_l —⟨phenyl⟩—CH₂CH(CH₃), |
| (R⁹)_l —⟨phenyl⟩—OCH₂C(CH₃)₂CH |
| (R⁹)_l —⟨phenyl⟩—CH(CH₃)CH(CH₃), |
| (R⁹)_l —⟨phenyl⟩—OCH(CH₃)CH(CH₃)CH₂ |
| (R⁹)_l —⟨phenyl⟩—CH(CH₃)CH(CH₃)CH₂CH₂, |
| (R⁹)_l —⟨phenyl⟩—CH(CH₃)CH₂CH₂CH(CH₃) |
| R¹ = (R⁹)_l —⟨phenyl, positions 1,2,3,4,5,6⟩—CH(CH₃)CH₂CH(CH₃)CH₂, |

TABLE 12-continued

| | |
|---|---|
| (R⁹)ₗ—⟨phenyl⟩— | CH₂CH(CH₃)CH(CH₃)CH₂ |
| (R⁹)ₗ—⟨phenyl⟩— | OCH(CH₃)CH(CH₃)CH₂CH₂, |
| (R⁹)ₗ—⟨phenyl⟩— | CH₂CH(CH₃)CH₂CH(CH₃) |
| (R⁹)ₗ—⟨phenyl⟩— | OCH(CH₃)CH₂CH₂CH(CH₃), |
| (R⁹)ₗ—⟨phenyl⟩— | CH₂OCH₂CH₂CH₂ |
| (R⁹)ₗ—⟨phenyl⟩— | OCH(CH₃)CH₂CH(CH₃)CH₂, |
| (R⁹)ₗ—⟨phenyl⟩— | OCH₂CO₂CH₂CH₂ |
| (R⁹)ₗ—⟨phenyl⟩— | OCH₂CH(CH₃)CH(CH₃)CH₂, |
| (R⁹)ₗ—⟨phenyl⟩— | OCH₂CO₂CH₂CH₂CH₂ |
| (R⁹)ₗ—⟨phenyl⟩— | OCH₂CH(CH₃)CH₂CH(CH₃), |
| (R⁹)ₗ—⟨phenyl⟩— | OCH₂CH₂CO₂CH₂CH₂ |
| (R⁹)ₗ—⟨phenyl⟩— | OCH₂CH₂CH(CH₃)CH(CH₃), |
| (R⁹)ₗ—⟨phenyl⟩— | OCH₂CH₂CO₂(CH₂)₂CH₂ |
| (R⁹)ₗ—⟨phenyl⟩— | CH₂CH₂OCH₂CH₂ |

TABLE 12-continued

| | |
|---|---|
| (R⁹)ₗ—⟨phenyl⟩— | CH₂CO₂CH₂CH₂ |
| R¹ = (R⁹)ₗ—⟨phenyl 1-6 positions⟩— | CH₂CH₂OCH₂CH₂CH₂, |
| (R⁹)ₗ—⟨phenyl⟩— | CH₂CO₂CH₂CH₂CH₂ |
| (R⁹)ₗ—⟨phenyl⟩— | CH₂CH₂CH₂OCH₂, |
| (R⁹)ₗ—⟨phenyl⟩— | CH₂CH₂CO₂CH₂CH₂ |
| (R⁹)ₗ—⟨phenyl⟩— | CH₂OCH₂CH₂, |
| (R⁹)ₗ—⟨phenyl⟩— | CH₂CH₂CO₂(CH₂)₂CH₂ |
| (R⁹)ₗ—⟨phenyl⟩— | CH₂OCH₂CH₂CH₂, |
| (R⁹)ₗ—⟨phenyl⟩— | C(=S)OCH₂CH₂ |
| (R⁹)ₗ—⟨phenyl⟩— | OCH₂CH=CHCH₂, |
| (R⁹)ₗ—⟨phenyl⟩— | C(=O)SCH₂CH₂ |
| (R⁹)ₗ—⟨phenyl⟩— | OCH(CH₃)CH=CHCH(CH₃), |
| (R⁹)ₗ—⟨phenyl⟩— | OC(=S)CH₂CH₂ |
| (R⁹)ₗ—⟨phenyl⟩— | OCH₂C(CH₃)=C(CH₃)CH₂, |

TABLE 12-continued

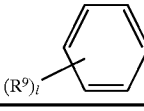

((R⁹)l in Table 12 is as defined below.)

(R⁹)l

H
2-CH₃
2-F
2-CF₃
2-Cl
2-Br
2-I
2-OCH₃
2-OCH₂CH₃
2-C₆H₅
2-NO₂
2-C₆H₄(p-CF₃)
2-CH₂C₆H₅
2-OC₆H₅
2-CN
3-CH₃
3-F
3-CF₃
3-Cl
3-Br
3-I
3-OCH₃
3-OC₆H₅
3-OCH₂C₆H₅
3-OCF₃
3-OCF₂CF₂H
3-NO₂
3-OC₆H₄(p-CH₃)
3-OC₆H₄(p-C(CH₃)3)
3-OC₆H₄(m-CF₃)
3-OC₆H₄(p-Cl)
3-OC₆H₃(3,4-Cl₂)
3-OC₆H₃(3,5-Cl₂)
3-OC₆H₄(p-OCH₃)
3-CN
3-CH₃
3-CH₂CH₃
3-CH₂CH₂CH₃
3-CH(CH₃)₂
3-C(CH₃)₃
3-OCF₂Br
3-OCF₂H
3-OCF₂CFHCF₃
3-OCH₂CF₃
3-OCH₂CH₃
3-OCH₂CH₂CH₃
3-OCH₂(CH₂)₂CH₃
3-OCH(CH₃)₂
3-OCH(CH₃)CH₂CH₃
3-OCH₂CH(CH₃)CH₃
3-OC(CH₃)₃
3-OCH₂CH=CH₂
3-OCH₂CH=C(Cl)₂
3-OCH₂CH=C(Br)₂
3-OCH₂CH=CH(Cl)
3-OCH₂C(Cl)=CH(Cl)
3-OCH₂CH=C(CH₃)₂
3-OCH₂CH=CH(CH₃)
3-OCH₂C(CH₃)=CH₂
3-OCH₂CBr=CH(Br)
3-CH₂OH
3-CH₂OCH₃
3-CH₂OCH₂CH₃
3-CH₂OCH₂CH₂CH₃
3-CH₂OCH₂(CH₃)₂
3-OCH₂C≡CH
3-OCH₂C≡C-Cl

TABLE 12-continued

3-OCH₂C≡C-Br
3-OCH₂C≡C-CH₃
3-OCH(CH₃)C≡CH
3-cyclopentyl
3-cyclohexyl
3-(3-cyclopentenyl)
3-(4-cyclopentenyl)

3-C(=O)—OCH₃

3-C(=O)—OCH₂CH₃

3-C(=O)—OCH₂CH₂CH₃

3-C(=O)—OCH(CH₃)₂

3-C(=O)—OC(CH₃)₃

3-cyclopropyloxy
3-cyclobutyloxy
3-cyclopentyloxy
3-cyclohexyloxy
3-(3-cyclohexenyl)
3-(4-cyclohexenyl)
3-(5-cyclohexenyl)
3-(3-cyclopentenyloxy)
3-(4-cyclopentenyloxy)
3-(3-cyclohexenyloxy)
3-(4-cyclohexenyloxy)
3-(5-cyclohexenyloxy)
3-CH₂C₆H₅
3-OCH₂CH=C(Cl)(CH₃)
3-OCH₂CH=C(CH₃)(CF₃)
3-OC₆H₄(o-Cl)
3-OC₆H₄(o-F)
3-OC₆H₄(o-CH₃)
3-OC₆H₄(m-Cl)
3-OC₆H₄(m-F)
3-OC₆H₄(m-CH₃)
3-OCH₂C₆H₄(o-Cl)
3-OCH₂C₆H₄(o-F)
3-OCH₂C₆H₄(o-Br)
3-OCH₂C₆H₄(o-CH₃)
3-OCH₂C₆H₄(o-CF₃)
3-OCH₂C₆H₄(m-Cl)
3-OCH₂C₆H₄(m-F)
3-OCH₂C₆H₄(m-Br)
3-OCH₂C₆H₄(m-CH₃)
3-OCH₂C₆H₄(m-CF₃)
3-OCH₂C₆H₄(p-Cl)
3-OCH₂C₆H₄(p-Br)
3-OCH₂C₆H₄(p-F)
3-OCH₂C₆H₄(p-CH₃)
3-OCH₂C₆H₄(p-CF₃)
3-SCF₂CF₂H
3-SCH₃
3-SCH₂CH₃
3-OCH₂C(Cl)=CH₂
4-CH₃
4-CH₂CH₃
4-CH(CH₃)₂
4-C(CH₃)₃
4-CH₂(CH₂)₂CH₃
4-F
4-CF₃
4-Cl
4-Br TABLE 12-continued 4-OCH$_3$
4-OCH$_2$CH$_3$
4-OCH$_2$(CH$_2$)$_2$CH$_3$
4-OCF$_3$
4-C$_6$H$_5$
4-OCH$_2$C$_6$H$_5$
4-OCH$_2$CH$_2$CH$_3$
4-OCF$_3$
4-SCH$_3$
4-NO$_2$
4-OC$_6$H$_5$
4-CH$_2$(CH$_2$)$_3$CH$_3$
4-CH$_2$(CH$_2$)$_4$CH$_3$
4-CH$_2$(CH$_2$)$_5$CH$_3$
4-CH$_2$(CH$_2$)$_6$CH$_3$
4-CH=CH$_2$
4-I
4-OCH$_2$(CH$_2$)$_3$CH$_3$
4-OCH$_2$(CH$_2$)$_4$CH$_3$
4-OCH$_2$(CH$_2$)$_5$CH$_3$
4-OCH(CH$_3$)$_2$
4-(2-cyclohexenyl)
4-SCH$_2$CH$_3$
4-C$_6$H$_4$(p-CH$_2$CH$_3$)
4-CN
4-OCF$_2$Br
4-OCF$_2$H
4-OCF$_2$CFHCF$_3$
4-OCH$_2$CF$_3$
4-OCF$_2$CF$_2$H
4-SCF$_2$CF$_2$H
4-SCH(CH$_3$)$_2$
4-OCH$_2$CH=CH$_2$
4-OCH$_2$CH=C(Cl)$_2$
4-OCH$_2$CH=C(Br)$_2$
4-OCH$_2$CH=CH(Cl)
4-OCH$_2$C(Cl)=CH(Cl)
4-OCH$_2$CH=C(CH$_3$)$_2$
4-OCH$_2$CH=CH(CH$_3$)
4-OCH$_2$C(CH$_3$)=CH$_2$
4-OCH$_2$C(Cl)=CH$_2$
4-OCH$_2$C(Br)=CH$_2$(Br)
4-CH$_2$OH
4-CH$_2$OCH$_3$
4-CH$_2$OCH$_2$CH$_3$
4-CH$_2$OCH$_2$CH$_2$CH$_3$
4-CH$_2$OCH(CH$_3$)$_2$
4-OCH$_2$C≡CH
4-OCH$_2$C≡C-Cl
4-OCH$_2$C≡C-Br
4-OCH$_2$C≡C-CH$_3$
4-OCH(CH$_3$)C≡CH
4-cyclopentyl
4-cyclohexyl
4-(3-cyclopentenyl)
4-(4-cyclopentenyl)

4-COCH$_3$
  ‖
  O

4-COCH$_2$CH$_3$
  ‖
  O

4-COCH$_2$CH$_2$CH$_3$
  ‖
  O

4-COCH(CH$_3$)$_2$
  ‖
  O

4-COC(CH$_3$)$_3$
  ‖
  O

TABLE 12-continued 4-cyclopropyloxy
4-cyclobutyloxy
4-cyclopentyloxy
4-cyclohexyloxy
4-(3-cyclohexenyl)
4-(4-cyclohexenyl)
4-(5-cyclohexenyl)
4-(3-cyclopentenyloxy)
4-(4-cyclopentenyloxy)
4-(3-cyclohexenyloxy)
4-(4-cyclohexenyloxy)
4-(5-cyclohexenyloxy)
4-CH$_2$C$_6$H$_5$
4-OCH$_2$CH=C(Cl)CH$_3$
4-OCH$_2$CH=C(CH$_3$)CF$_3$
4-OC$_6$H$_4$(o-Cl)
4-OC$_6$H$_4$(o-F)
4-OC$_6$H$_4$(o-CH$_3$)
4-OC$_6$H$_4$(m-Cl)
4-OC$_6$H$_4$(m-F)
4-OC$_6$H$_4$(m-CH$_3$)
4-OCH$_2$C$_6$H$_4$(o-Cl)
4-OCH$_2$C$_6$H$_4$(o-F)
4-OCH$_2$C$_6$H$_4$(o-Br)
4-OCH$_2$C$_6$H$_4$(o-CH$_3$)
4-OCH$_2$C$_6$H$_4$(o-CF$_3$)
4-OCH$_2$C$_6$H$_4$(m-Cl)
4-OCH$_2$C$_6$H$_4$(m-F)
4-OCH$_2$C$_6$H$_4$(m-Br)
4-OCH$_2$C$_6$H$_4$(m-CH$_3$)
4-OCH$_2$C$_6$H$_4$(m-CF$_3$)
4-OCH$_2$C$_6$H$_4$(p-Cl)
4-OCH$_2$C$_6$H$_4$(p-Br)
4-OCH$_2$C$_6$H$_4$(p-F)
4-OCH$_2$C$_6$H$_4$(p-CH$_3$)
4-OCH$_2$C$_6$H$_4$(p-CF$_3$)
4-SCF$_2$CF$_2$H
4-OCH$_2$C(Cl)=CH$_2$
2,6-F$_2$
2,3-F$_2$
2-F, 6-Cl
2,6-Cl$_2$
2,3-(OCH$_3$)$_2$
2,4-(CH$_3$)$_2$
3,4-(CH$_3$)$_2$
2,5-(CH$_3$)$_2$
3,4-F$_2$
2,4-F$_2$
2,5-F$_2$
2,4-Cl$_2$
3,4-Cl$_2$
2,5-Cl$_2$
2,4-(OCH$_3$)$_2$
2,5-(OCH$_3$)$_2$
2-OCH$_3$, 5-Br
3,4-OCH$_2$O—
3,5-(CH$_3$)$_2$
3,5-(CF$_3$)$_2$
3,5-F$_2$
3,5-Cl$_2$
3,5-(OCH$_3$)$_2$
2-CH$_3$, 4-C$_6$H$_5$
2-NO$_2$, 4-Cl
2-NO$_2$, 5-CH$_3$
3-CH$_3$, 4-NO$_2$
3-NO$_2$, 4-CH$_3$
2-NO$_2$, 4-Cl
3-NO$_2$, 4-Cl
2-Cl, 5-NO$_2$
2-NO$_2$, 5-Cl
3-OCH$_3$, 4-NO$_2$
2-CH$_3$, 3-F
2-F, 3-CF$_3$
2,3-Cl$_2$
2,6-(OCH$_3$)$_2$
2-Cl, 6-NO$_2$
2-NO$_2$, 3-OCH$_3$
2,6-(NO$_2$)$_2$

TABLE 12-continued

2-Cl, 5-CF$_3$
3-Cl, 4-F
2-Cl, 4-F
3-Br, 4-F
2-OCH$_3$, 5-Br
3,4-OCH$_2$CH$_2$O—
3-NO$_2$, 5-Cl
2,4-(NO$_2$)$_2$
3,5-(OCH$_2$C$_6$H$_5$)$_2$
3,4-(OCH$_2$C$_6$H$_5$)$_2$
2-F, 6-CF$_3$
2-F, 3-CF$_3$
2,6-(CF$_3$)$_2$
2-NO$_2$, 6-CH$_3$
2-NO$_2$, 3-CH$_3$
2-CH$_3$, 3-NO$_2$
2-NO$_2$, 3-Cl
2-Cl, 3-NO$_2$
2-Br, 3-NO$_2$
2-NO$_2$, 3-OCH$_3$
2-CH$_3$, 5-F
3-F, 4-CH$_3$
3-Br, 4-CH$_3$
2,4-(CF$_3$)$_2$
3-I, 4-CH$_3$
2-Cl, 5-CF$_3$
2,5-(CF$_3$)$_2$
2-F, 4-CF$_3$
2-Cl, 4-F
3-OCH$_3$, 4-CH$_3$
2-OCH$_3$, 4-Cl
2-OCH$_3$, 5-Cl
2-Br, 5-OCH$_3$
3,4-(OCH$_2$CH$_3$)$_2$
2-Cl, 5-SCH$_3$
2-OCH$_3$, 4-SCH$_3$
3-CH$_3$, 4-NO$_2$
2-CH$_3$, 5-NO$_2$
2-NO$_2$, 4-CF$_3$
2-F, 5-NO$_2$
2-Cl, 4-NO$_2$
3-NO$_2$, 4-F
2-Br, 5-NO$_2$
3-NO$_2$, 4-OCH$_3$
3,5-(C(CH$_3$)$_3$)$_2$
2,3(CH$_3$)$_2$, 4-OCH$_3$
3-CH$_3$, 2,4-(OCH$_3$)$_2$
2,3,4-(OCH$_3$)$_3$
3,4,5-(OCH$_3$)$_3$
2,3,4,5,6-F$_5$
2,4,6-(CH$_3$)$_3$
2,3,6-Cl$_3$
3,4-(OCH$_3$)$_2$, 5-Br
2,4,6-(OCH$_3$)$_3$
2,4-(OCH$_3$)$_2$, 5-Br
2-Br, 4,5-(OCH$_3$)$_2$
2,4,5-(OCH$_3$)$_3$
2-NO$_2$, 3,4-(OCH$_3$)$_2$
2-NO$_2$, 3,4-OCH$_2$O—
2,5-Cl$_2$, 4-CHF$_2$
2,3,4-F$_3$
2,3,6-Cl$_3$
2,3,5,6-F$_4$
2,3,6-F$_3$
2,4,6-F$_3$
3,4,5-F$_3$
2,4,6-Cl$_3$
2,3,5-Cl$_3$
2,3,5-I$_3$
2,4,5-F$_3$
2,4-Cl$_2$, 5-F
2,3,4,5-F$_4$
2,3,5,6-F$_4$, 4-CH$_3$
2,3,5,6-F$_4$, 4-Br
3-Cl, 4-OCH$_3$
3-Cl, 4-OCH$_2$CH$_3$
3-Cl, 4-OCH$_2$CH$_2$CH$_3$
3-Cl, 4-OCH(CH$_3$)$_2$
3-Cl, 4-OCH$_2$(CH$_2$)$_2$CH$_3$

3-Cl, 4-OCH(CH$_3$)CH$_2$CH$_3$
3-Cl, 4-OCH$_2$CH(CH$_3$)$_2$
3-Cl, 4-OC(CH$_3$)$_3$
3-Cl, 4-OCF$_3$
3-Cl, 4-OCF$_2$Br
3-Cl, 4-OCF$_2$H
3-Cl, 4-OCF$_2$CF$_2$H
3-Cl, 4-OCF$_2$CFHCF$_3$
3-Cl, 4-OCH$_2$CF$_3$
3-Cl, 4-OC$_6$H$_5$
3-Cl, 4-OCH$_2$C$_6$H$_5$
3-Cl, 4-cyclopentyloxy
3-Cl, 4-cyclohexyloxy
3-Br, 4-OCH$_3$
3-Br, 4-OCH$_2$CH$_3$
3-Br, 4-OCH$_2$CH$_2$CH$_3$
3-Br, 4-OCH(CH$_3$)$_2$
3-Br, 4-OCH$_2$(CH$_2$)$_2$CH$_3$
3-Br, 4-OCH(CH$_3$)CH$_2$CH$_3$
3-Br, 4-OCH$_2$CH(CH$_3$)$_2$
3-Br, 4-OC(CH$_3$)$_3$
3-Br, 4-OCF$_3$
3-Br, 4-OCF$_2$Br
3-Br, 4-OCF$_2$H
3-Br, 4-OCF$_2$CF$_2$H
3-Br, 4-OCF$_2$CFHCF$_3$
3-Br, 4-OCH$_2$CF$_3$
3-Br, 4-OC$_6$H$_5$
3-Br, 4-OCH$_2$C$_6$H$_5$
3-Br, 4-cyclopentyloxy
3-Br, 4-cyclohexyloxy
3-F, 4-OCH$_3$
3-F, 4-OCH$_2$CH$_3$
3-F, 4-OCH$_2$CH$_2$CH$_3$
3-F, 4-OCH(CH$_3$)$_2$
3-F, 4-OCH$_2$(CH$_2$)$_2$CH$_3$
3-F, 4-OCH(CH$_3$)CH$_2$CH$_3$
3-F, 4-OCH$_2$CH(CH$_3$)$_2$
3-F, 4-OC(CH$_3$)3
3-F, 4-OCF$_3$
3-F, 4-OCF$_2$Br
3-F, 4-OCF$_2$H
3-F, 4-OCF$_2$CF$_2$H
3-F, 4-OCF$_2$CFHCF$_3$
3-F, 4-OCH$_2$CF$_3$
3-F, 4-OC$_6$H$_5$
3-F, 4-OCH$_2$C$_6$H$_5$
3-F, 4-cyclopentyloxy
3-F, 4-cyclohexyloxy
3-CH$_3$, 4-OCH$_3$
3-CH$_3$, 4-OCH$_2$CH$_3$
3-CH$_3$, 4-OCH$_2$CH$_2$CH$_3$
3-CH$_3$, 4-OCH(CH$_3$)$_2$
3-CH$_3$, 4-OCH$_2$(CH$_2$)$_2$CH$_3$
3-CH$_3$, 4-OCH(CH$_3$)CH$_2$CH$_3$
3-CH$_3$, 4-OCH$_2$CH(CH$_3$)$_2$
3-CH$_3$, 4-OC(CH$_3$)$_3$
3-CH$_3$, 4-OCF$_3$
3-CH$_3$, 4-OCF$_2$Br
3-CH$_3$, 4-OCF$_2$H
3-CH$_3$, 4-OCF$_2$CF$_2$H
3-CH$_3$, 4-OCF$_2$CFHCF$_3$
3-CH$_3$, 4-OCH$_2$CF$_3$
3-CH$_3$, 4-OC$_6$H$_5$
3-CH$_3$, 4-OCH$_2$C$_6$H$_5$
3-CH$_3$, 4-cyclopentyloxy
3-CH$_3$, 4-cyclohexyloxy
3-OCH$_3$, 4-OCH$_3$
3-OCH$_3$, 4-OCH$_2$CH$_3$
3-OCH$_3$, 4-OCH$_2$CH$_2$CH$_3$
3-OCH$_3$, 4-OCH(CH$_3$)$_2$
3-OCH$_3$, 4-OCH$_2$(CH$_2$)$_2$CH$_3$
3-OCH$_3$, 4-OCH(CH$_3$)CH$_2$CH$_3$
3-OCH$_3$, 4-OCH$_2$CH(CH$_3$)$_2$
3-OCH$_3$, 4-OC(CH$_3$)$_3$
3-OCH$_3$, 4-OCF$_3$
3-OCH$_3$, 4-OCF$_2$Br
3-OCH$_3$, 4-OCF$_2$H
3-OCH$_3$, 4-OCF$_2$CF$_2$H

TABLE 12-continued

3-OCH$_3$, 4-OCF$_2$CFHCF$_3$
3-OCH$_3$, 4-OCH$_2$CF$_3$
3-OCH$_3$, 4-OC$_6$H$_5$
3-OCH$_3$, 4-OCH$_2$C$_6$H$_5$
3-OCH$_3$, 4-cyclopentyloxy
3-OCH$_3$, 4-cyclohexyloxy
3-OCH$_2$CH$_3$, 4-OCH$_3$
3-OCH$_2$CH$_3$, 4-OCH$_2$CH$_3$
3-OCH$_2$CH$_3$, 4-OCH$_2$CH$_2$CH$_3$
3-OCH$_2$CH$_3$, 4-OCH(CH$_3$)$_2$
3-OCH$_2$CH$_3$, 4-OCH$_2$(CH$_2$)$_2$CH$_3$
3-OCH$_2$CH$_3$, 4-OCH(CH$_3$)CH$_2$CH$_3$
3-OCH$_2$CH$_3$, 4-OCH$_2$CH(CH$_3$)$_2$
3-OCH$_2$CH$_3$, 4-OC(CH$_3$)$_3$
3-OCH$_2$CH$_3$, 4-OCF$_3$
3-OCH$_2$CH$_3$, 4-OCF$_2$Br
3-OCH$_2$CH$_3$, 4-OCF$_2$H
3-OCH$_2$CH$_3$, 4-OCF$_2$CF$_2$H
3-OCH$_2$CH$_3$, 4-OCF$_2$CFHCF$_3$
3-OCH$_2$CH$_3$, 4-OCH$_2$CF$_3$
3-OCH$_2$CH$_3$, 4-OC$_6$H$_5$
3-OCH$_2$CH$_3$, 4-OCH$_2$C$_6$H$_5$
3-OCH$_2$CH$_3$, 4-cyclopentyloxy
3-OCH$_2$CH$_3$, 4-cyclohexyloxy
4-Cl, 3-OCH$_3$
4-Cl, 3-OCH$_2$CH$_3$
4-Cl, 3-OCH$_2$CH$_2$CH$_3$
4-Cl, 3-OCH(CH$_3$)$_2$
4-Cl, 3-OCH$_2$(CH$_2$)$_2$CH$_3$
4-Cl, 3-OCH(CH$_3$)CH$_2$CH$_3$
4-Cl, 3-OCH$_2$CH(CH$_3$)$_2$
4-Cl, 3-OC(CH$_3$)$_3$
4-Cl, 3-OCF$_3$
4-Cl, 3-OCF$_2$Br
4-Cl, 3-OCF$_2$H
4-Cl, 3-OCF$_2$CF$_2$H
4-Cl, 3-OCF$_2$CFHCF$_3$
4-Cl, 3-OCH$_2$CF$_3$
4-Cl, 3-OC$_6$H$_5$
4-Cl, 3-OCH$_2$C$_6$H$_5$
4-Cl, 3-cyclopentyloxy
4-Cl, 3-cyclohexyloxy
4-Br, 3-OCH$_3$
4-Br, 3-OCH$_2$CH$_3$
4-Br, 3-OCH$_2$CH$_2$CH$_3$
4-Br, 3-OCH(CH$_3$)$_2$
4-Br, 3-OCH$_2$(CH$_2$)$_2$CH$_3$
4-Br, 3-OCH(CH$_3$)CH$_2$CH$_3$
4-Br, 3-OCH$_2$CH(CH$_3$)$_2$
4-Br, 3-OC(CH$_3$)$_3$
4-Br, 3-OCF$_3$
4-Br, 3-OCF$_2$Br
4-Br, 3-OCF$_2$H
4-Br, 3-OCF$_2$CF$_2$H
4-Br, 3-OCF$_2$CFHCF$_3$
4-Br, 3-OCH$_2$CF$_3$
4-Br, 3-OC$_6$H$_5$
4-Br, 3-OCH$_2$C$_6$H$_5$
4-Br, 3-cyclopentyloxy
4-Br, 3-cyclohexyloxy
4-F, 3-OCH$_3$
4-F, 3-OCH$_2$CH$_3$
4-F, 3-OCH$_2$CH$_2$CH$_3$
4-F, 3-OCH(CH$_3$)$_2$
4-F, 3-OCH$_2$(CH$_2$)$_2$CH$_3$
4-F, 3-OCH(CH$_3$)CH$_2$CH$_3$
4-F, 3-OCH$_2$CH(CH$_3$)$_2$
4-F, 3-OC(CH$_3$)$_3$
4-F, 3-OCF$_3$
4-F, 3-OCF$_2$Br
4-F, 3-OCF$_2$H
4-F, 3-OCF$_2$CF$_2$H
4-F, 3-OCF$_2$CFHCF$_3$
4-F, 3-OCH$_2$CF$_3$
4-F, 3-OC$_6$H$_5$
4-F, 3-OCH$_2$C$_6$H$_5$
4-F, 3-cyclopentyloxy
4-F, 3-cyclohexyloxy
4-CH$_3$, 3-OCH$_3$
4-CH$_3$, 3-OCH$_2$CH$_3$
4-CH$_3$, 3-OCH$_2$CH$_2$CH$_3$
4-CH$_3$, 3-OCH(CH$_3$)$_2$
4-CH$_3$, 3-OCH$_2$(CH$_2$)$_2$CH$_3$
4-CH$_3$, 3-OCH(CH$_3$)CH$_2$CH$_3$
4-CH$_3$, 3-OCH$_2$CH(CH$_3$)$_2$
4-CH$_3$, 3-OC(CH$_3$)$_3$
4-CH$_3$, 3-OCF$_3$
4-CH$_3$, 3-OCF$_2$Br
4-CH$_3$, 3-OCF$_2$H
4-CH$_3$, 3-OCF$_2$CF$_2$H
4-CH$_3$, 3-OCF$_2$CFHCF$_3$
4-CH$_3$, 3-OCH$_2$CF$_3$
4-CH$_3$, 3-OC$_6$H$_5$
4-CH$_3$, 3-OCH$_2$C$_6$H$_5$
4-CH$_3$, 3-cyclopentyloxy
4-CH$_3$, 3-cyclohexyloxy
2-Cl, 5-OCH$_3$
2-Cl, 5-OCH$_2$CH$_3$
2-Cl, 5-OCH$_2$CH$_2$CH$_3$
2-Cl, 5-OCH(CH$_3$)$_2$
2-Cl, 5-OCH$_2$(CH$_2$)$_2$CH$_3$
2-Cl, 5-OCH(CH$_3$)CH$_2$CH$_3$
2-Cl, 5-OCH$_2$CH(CH$_3$)$_2$
2-Cl, 5-OC(CH$_3$)$_3$
2-Cl, 5-OCF$_3$
2-Cl, 5-OCF$_2$Br
2-Cl, 5-OCF$_2$H
2-Cl, 5-OCF$_2$CF$_2$H
2-Cl, 5-OCF$_2$CFHCF$_3$
2-Cl, 5-OCH$_2$CF$_3$
2-Cl, 5-OC$_6$H$_5$
2-Cl, 5-OCH$_2$C$_6$H$_5$
2-Cl, 5-cyclopentyloxy
2-Cl, 5-cyclohexyloxy
2-Cl, 4-OCH$_3$
2-Cl, 4-OCH$_2$CH$_3$
2-Cl, 4-OCH$_2$CH$_2$CH$_3$
2-Cl, 4-OCH(CH$_3$)$_2$
2-Cl, 4-OCH$_2$(CH$_2$)$_2$CH$_3$
2-Cl, 4-OCH(CH$_3$)CH$_2$CH$_3$
2-Cl, 4-OCH$_2$CH(CH$_3$)$_2$
2-Cl, 4-OC(CH$_3$)$_3$
2-Cl, 4-OCF$_3$
2-Cl, 4-OCF$_2$Br
2-Cl, 4-OCF$_2$H
2-Cl, 4-OCF$_2$CF$_2$H
2-Cl, 4-OCF$_2$CFHCF$_3$
2-Cl, 4-OCH$_2$CF$_3$
2-Cl, 4-OC$_6$H$_5$
2-Cl, 4-OCH$_2$C$_6$H$_5$
2-Cl, 4-cyclopentyloxy
2-Cl, 4-cyclohexyloxy
4-OCH$_3$, 3-OCH$_2$CH$_2$CH$_3$
4-OCH$_3$, 3-OCH(CH$_3$)$_2$
4-OCH$_3$, 3-OCH$_2$(CH$_2$)$_2$CH$_3$
4-OCH$_3$, 3-OCH(CH$_3$)CH$_2$CH$_3$
4-OCH$_3$, 3-OCH$_2$CH(CH$_3$)$_2$
4-OCH$_3$, 3-OC(CH$_3$)$_3$
4-OCH$_3$, 3-OCF$_3$
4-OCH$_3$, 3-OCF$_2$Br
4-OCH$_3$, 3-OCF$_2$H
4-OCH$_3$, 3-OCF$_2$CF$_2$H
4-OCH$_3$, 3-OCF$_2$CFHCF$_3$
4-OCH$_3$, 3-OCH$_2$CF$_3$
4-OCH$_3$, 3-OC$_6$H$_5$
4-OCH$_3$, 3-OCH$_2$C$_6$H$_5$
4-OCH$_3$, 3-cyclopentyloxy
4-OCH$_3$, 3-cyclohexyloxy
2,5-(CH$_3$)$_2$, 4-OCH$_3$
2,5-(CH$_3$)$_2$, 4-OCH$_2$CH$_3$
2,5-(CH$_3$)$_2$, 4-OCH$_2$CH$_2$CH$_3$
2,5-(CH$_3$)$_2$, 4-OCH(CH$_3$)$_2$
2,5-(CH$_3$)$_2$, 4-OCH$_2$(CH$_2$)$_2$CH$_3$
2,5-(CH$_3$)$_2$, 4-OCH(CH$_3$)CH$_2$CH$_3$
2,5-(CH$_3$)$_2$, 4-OCH$_2$CH(CH$_3$)$_2$

TABLE 12-continued 2,5-(CH$_3$)$_2$, 4-OC(CH$_3$)$_3$
2,5-(CH$_3$)$_2$, 4-OCF$_3$
2,5-(CH$_3$)$_2$, 4-OCF$_2$Br
2,5-(CH$_3$)$_2$, 4-OCF$_2$H
2,5-(CH$_3$)$_2$, 4-OCF$_2$CF$_2$H
2,5-(CH$_3$)$_2$, 4-OCF$_2$CFHCF$_3$
2,5-(CH$_3$)$_2$, 4-OCH$_2$CF$_3$
2,5-(CH$_3$)$_2$, 4-OC$_6$H$_5$
2,5-(CH$_3$)$_2$, 4-OCH$_2$C$_6$H$_5$
2,5-(CH$_3$)$_2$, 4-cyclopentyloxy
2,5-(CH$_3$)$_2$, 4-cyclohexyloxy
3,5-(CH$_3$)$_2$, 4-OCH$_3$
3,5-(CH$_3$)$_2$, 4-OCH$_2$CH$_3$
3,5-(CH$_3$)$_2$, 4-OCH$_2$CH$_2$CH$_3$
3,5-(CH$_3$)$_2$, 4-OCH(CH$_3$)$_2$
3,5-(CH$_3$)$_2$, 4-OCH$_2$(CH$_2$)$_2$CH$_3$
3,5-(CH$_3$)$_2$, 4-OCH(CH$_3$)CH$_2$CH$_3$
3,5-(CH$_3$)$_2$, 4-OCH$_2$CH(CH$_3$)$_2$
3,5-(CH$_3$)$_2$, 4-OC(CH$_3$)$_3$
3,5-(CH$_3$)$_2$, 4-OCF$_3$
3,5-(CH$_3$)$_2$, 4-OCF$_2$Br
3,5-(CH$_3$)$_2$, 4-OCF$_2$H
3,5-(CH$_3$)$_2$, 4-OCF$_2$CF$_2$H
3,5-(CH$_3$)$_2$, 4-OCF$_2$CFHCF$_3$
3,5-(CH$_3$)$_2$, 4-OCH$_2$CF$_3$
3,5-(CH$_3$)$_2$, 4-OC$_6$H$_5$
3,5-(CH$_3$)$_2$, 4-OCH$_2$C$_6$H$_5$
3,5-(CH$_3$)$_2$, 4-cyclopentyloxy
3,5-(CH$_3$)$_2$, 4-cyclohexyloxy
3,5-Cl$_2$, 4-OCH$_3$
3-OC$_6$H$_4$(p-F)
3,5-Cl$_2$, 4-OCH$_2$CH$_3$
3,5-Cl$_2$, 4-OCH$_2$CH$_2$CH$_3$
3,5-Cl$_2$, 4-OCH(CH$_3$)$_2$
3 5-Cl$_2$, 4-OCH$_2$(CH$_2$)$_2$CH$_3$
3,5-Cl$_2$, 4-OCH(CH$_3$)CH$_2$CH$_3$
3,5-Cl$_2$, 4-OCH$_2$CH(CH$_3$)$_2$
3,5-Cl$_2$, 4-OC(CH$_3$)$_3$
3,5-Cl$_2$, 4-OCF$_3$
3,5-Cl$_2$, 4-OCF$_2$Br
3,5-Cl$_2$, 4-OCF$_2$H
3,5-Cl$_2$, 4-OCF$_2$CF$_2$H
3,5-Cl$_2$, 4-OCF$_2$CFHCF$_3$
3,5-Cl$_2$, 4-OCH$_2$CF$_3$
3,5-Cl$_2$, 4-OC$_6$H$_5$
3,5-Cl$_2$, 4-OCH$_2$C$_6$H$_5$
3,5-Cl$_2$, 4-cyclopentyloxy
3,5-Cl$_2$, 4-cyclohexyloxy
2-F, 5-OC$_6$H$_4$(p-F)
2-Br, 5-(OC$_6$H$_5$)
4-(OC$_6$H$_4$p-CF$_3$)
3-OC$_6$H$_4$(p-F)
4-OH
3-SF$_5$
4-SF$_5$
2,3,4-Cl$_3$
2,5,6-Cl$_3$
2,4,5-Cl$_3$
2,3,4,6-Cl$_4$
3,4-OCF$_2$O—
2,6-Cl$_2$, 4-OCH$_2$CH═C(Cl)$_2$
4-C$_6$H$_4$-(p-OCF$_3$)

TABLE 13

R$^1$ = 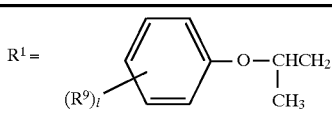

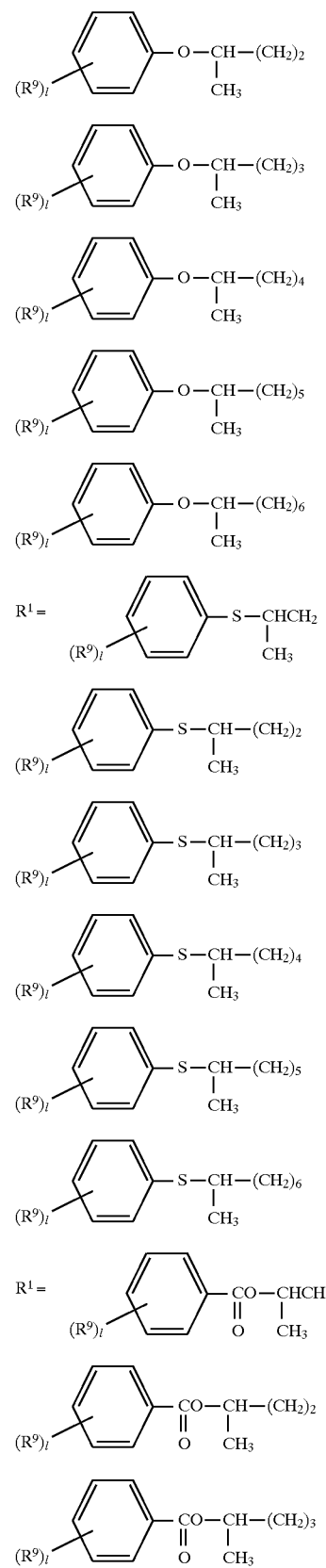

TABLE 13-continued

[Structures shown with (R⁹)ₗ substituted phenyl groups:]

- Phenyl—CO—O—CH(CH₃)—(CH₂)₄
- Phenyl—CO—O—CH(CH₃)—(CH₂)₅
- Phenyl—CO—O—CH(CH₃)—(CH₂)₆

R¹ =
- Phenyl—NH—CH(CH₃)—CH₂
- Phenyl—NH—CH(CH₃)—(CH₂)₂
- Phenyl—NH—CH(CH₃)—(CH₂)₃
- Phenyl—NH—CH(CH₃)—(CH₂)₄
- Phenyl—NH—CH(CH₃)—(CH₂)₅
- Phenyl—NH—CH(CH₃)—(CH₂)₆

R¹ =
- Phenyl—N(CH₃)—(CH₂)₂
- Phenyl—N(CH₃)—(CH₂)₃
- Phenyl—N(CH₃)—(CH₂)₄
- Phenyl—N(CH₃)—(CH₂)₅
- Phenyl—N(CH₃)—(CH₂)₆
- Phenyl—N(CH₃)—(CH₂)₇

R¹ =
- Phenyl—CH(CH₃)—CH₂
- Phenyl—CH(CH₃)—(CH₂)₂
- Phenyl—CH(CH₃)—(CH₂)₃
- Phenyl—CH(CH₃)—(CH₂)₄
- Phenyl—CH(CH₃)—(CH₂)₅
- Phenyl—CH(CH₃)—(CH₂)₆
- Phenyl—CH(CH₃)—(CH₂)₇

((R⁹)l in Table 13 is as defined below.)

| (R⁹)l |
| --- |
| H |
| 2-F |
| 2-CF₃ |
| 2-Cl |
| 2-Br |
| 2-I |
| 2-OCH₃ |
| 2-OCH₂CH₃ |
| 2-CN |
| 3-CH₃ |
| 3-F |
| 3-CF₃ |
| 3-Cl |
| 3-Br |
| 3-I |
| 3-OCH₃ |
| 3-OC₆H₅ |
| 3-OCH₂C₆H₅ |
| 3-OCF₃ |
| 3-OCF₂CF₂H |
| 3-NO₂ |
| 3-OC₆H₄(p-CH₃) |
| 3-OC₆H₄(p-C(CH₃)₃) |
| 3-OC₆H₄(m-CF₃) |
| 3-OC₆H₄(p-Cl) |
| 3-OC₆H₄(3,4-Cl₂) |

TABLE 13-continued

3-OC$_6$H$_3$(3,5-Cl$_2$)
3-OC$_6$H$_4$(p-OCH$_3$)
3-CN
3-CH$_3$
3-CH$_2$CH$_3$
3-CH$_2$CH$_2$CH$_3$
3-CH(CH$_3$)$_2$
3-C(CH$_3$)$_3$
3-OCF$_2$Br
3-OCF$_2$H
3-OCF$_2$CFHCF$_3$
3-OCH$_2$CF$_3$
3-OCH$_2$CH$_3$
3-OCH$_2$CH$_2$CH$_3$
3-OCH$_2$(CH$_2$)$_2$CH$_3$
3-OCH(CH$_3$)$_2$
3-OCH(CH$_3$)CH$_2$CH$_3$
3-OCH$_2$CH(CH$_3$)CH$_3$
3-OC(CH$_3$)$_3$
3-OCH$_2$CH=CH$_2$
3-OCH$_2$CH=C(Cl)$_2$
3-OCH$_2$CH=C(Br)$_2$
3-OCH$_2$CH=CH(Cl)
3-OCH$_2$C(Cl)=CH(Cl)
3-OCH$_2$CH=C(CH$_3$)$_2$
3-OCH$_2$CH=CH(CH$_3$)
3-OCH$_2$C(CH$_3$)=CH$_2$
3-OCH$_2$CBr=CH(Br)
3-OCH$_2$C≡CH
3-OCH$_2$C≡C—Cl
3-OCH$_2$C≡C—Br
3-OCH$_2$C≡C—CH$_3$
3-OCH(CH$_3$)C≡CH
3-cyclopentyl
3-cyclohexyl
3-(3-cyclopentenyl)
3-(4-cyclopentenyl)

3-C(=O)—OCH$_3$

3-C(=O)—OCH$_2$CH$_3$

3-C(=O)—OCH$_2$CH$_2$CH$_3$

3-C(=O)—OCH(CH$_3$)$_2$

3-C(=O)—OC(CH$_3$)$_3$ 3-cyclopropyloxy
3-cyclobutyloxy
3-cyclopentyloxy
3-cyclohexyloxy
3-(3-cyclohexenyl)
3-(4-cyclohexenyl)
3-(5-cyclohexenyl)
3-(3-cyclopentenyloxy)
3-(4-cyclopentenyloxy)
3-(3-cyclohexenyloxy)
3-(4-cyclohexenyloxy)
3-(5-cyclohexenyloxy)
3-CH$_2$C$_6$H$_5$
3-OCH$_2$CH=C(Cl)(CH$_3$)
3-OCH$_2$CH=C(CH$_3$)(CF$_3$)
3-OC$_6$H$_4$(o-Cl)
3-OC$_6$H$_4$(o-F)
3-OC$_6$H$_4$(o-CH$_3$)

TABLE 13-continued

3-OC$_6$H$_4$(o-Cl)
3-OC$_6$H$_4$(m-F)
3-OC$_6$H$_4$(m-CH$_3$)
3-OCH$_2$C$_6$H$_4$(o-Cl)
3-OCH$_2$C$_6$H$_4$(o-F)
3-OCH$_2$C$_6$H$_4$(o-Br)
3-OCH$_2$C$_6$H$_4$(o-CH$_3$)
3-OCH$_2$C$_6$H$_4$(o-CF$_3$)
3-OCH$_2$C$_6$H$_4$(m-Cl)
3-OCH$_2$C$_6$H$_4$(m-F)
3-OCH$_2$C$_6$H$_4$(m-Br)
3-OCH$_2$C$_6$H$_4$(m-CH$_3$)
3-OCH$_2$C$_6$H$_4$(m-CF$_3$)
3-OCH$_2$C$_6$H$_4$(p-Cl)
3-OCH$_2$C$_6$H$_4$(p-Br)
3-OCH$_2$C$_6$H$_4$(p-F)
3-OCH$_2$C$_6$H$_4$(p-CH$_3$)
3-OCH$_2$C$_6$H$_4$(p-CF$_3$)
3-SCF$_2$CF$_2$H
3-SCH$_3$
3-SCH$_2$CH$_3$
3-OCH$_2$C(Cl)=CH$_2$
4-CH$_3$
4-CH$_2$CH$_3$
4-CH(CH$_3$)$_2$
4-C(CH$_3$)$_3$
4-CH$_2$(CH$_2$)$_2$CH$_3$
4-F
4-CF$_3$
4-Cl
4-Br
4-OCH$_3$
4-OCH$_2$CH$_3$
4-OCH$_2$(CH$_2$)$_2$CH$_3$
4-OCF$_3$
4-C$_6$H$_5$
4-OCH$_2$C$_6$H$_5$
4-OCH$_2$CH$_2$CH$_3$
4-OCF$_3$
4-SCH$_3$
4-NO$_2$
4-OC$_6$H$_5$
4-CH$_2$(CH$_2$)$_3$CH$_3$
4-CH$_2$(CH$_2$)$_4$CH$_3$
4-CH$_2$(CH$_2$)$_5$CH$_3$
4-CH$_2$(CH$_2$)$_6$CH$_3$
4-CH=CH$_2$
4-I
4-OCH$_2$(CH$_2$)$_3$CH$_3$
4-OCH$_2$(CH$_2$)$_4$CH$_3$
4-OCH$_2$(CH$_2$)$_5$CH$_3$
4-OCH(CH$_3$)$_2$
4-(2-cyclohexenyl)
4-SCH$_2$CH$_3$
4-C$_6$H$_4$(p-CH$_2$CH$_3$)
4-CN
4-OCF$_2$Br
4-OCF$_2$H
4-OCF$_2$CFHCF$_3$
4-OCH$_2$CF$_3$
4-OCF$_2$CF$_2$H
4-SCF$_2$CF$_2$H
4-SCH(CH$_3$)$_2$
4-OCH$_2$CH=CH$_2$
4-OCH$_2$CH=C(Cl)$_2$
4-OCH$_2$CH=C(Br)$_2$
4-OCH$_2$CH=CH(Cl)
4-OCH$_2$C(Cl)=CH(Cl)
4-OCH$_2$CH=C(CH$_3$)$_2$
4-OCH$_2$CH=CH(CH$_3$)
4-OCH$_2$C(CH$_3$)=CH$_2$
4-OCH$_2$C(Cl)=CH$_2$
4-OCH$_2$C(Br)=CH$_2$(Br)
4-OCH$_2$C≡CH 4-OCH$_2$C≡C—Cl 4-OCH$_2$C≡C—Br

TABLE 13-continued

4-OCH$_2$C≡C—CH$_3$
4-OCH(CH$_3$)C≡CH 4-cyclopentyl
4-cyclohexyl
4-(3-cyclopentenyl)
4-(4-cyclopentenyl)

4-COCH$_3$
‖
O

4-COCH$_2$CH$_3$
‖
O

4-COCH$_2$CH$_2$CH$_3$
‖
O

4-COCH(CH$_3$)$_2$
‖
O

4-COC(CH$_3$)$_3$
‖
O 4-cyclopropyloxy
4-cyclobutyloxy
4-cyclopentyloxy
4-cyclohexyloxy
4-(3-cyclohexenyl)
4-(4-cyclohexenyl)
4-(5-cyclohexenyl)
4-(3-cyclopentenyloxy)
4-(4-cyclopentenyloxy)
4-(3-cyclohexenyloxy)
4-(4-cyclohexenyloxy)
4-(5-cyclohexenyloxy)
4-CH$_2$C$_6$H$_5$
4-OCH$_2$CH═C(Cl)CH$_3$
4-OCH$_2$CH═C(CH$_3$)CF$_3$
4-OC$_6$H$_4$(o-Cl)
4-OC$_6$H$_4$(o-F)
4-OC$_6$H$_4$(o-CH$_3$)
4-OC$_6$H$_4$(m-Cl)
4-OC$_6$H$_4$(m-F)
4-OC$_6$H$_4$(m-CH$_3$)
4-OCH$_2$C$_6$H$_4$(o-Cl)
4-OCH$_2$C$_6$H$_4$(o-F)
4-OCH$_2$C$_6$H$_4$(o-Br)
4-OCH$_2$C$_6$H$_4$(o-CH$_3$)
4-OCH$_2$C$_6$H$_4$(o-CF$_3$)
4-OCH$_2$C$_6$H$_4$(m-Cl)
4-OCH$_2$C$_6$H$_4$(m-F)
4-OCH$_2$C$_6$H$_4$(m-Br)
4-OCH$_2$C$_6$H$_4$(m-CH$_3$)
4-OCH$_2$C$_6$H$_4$(m-CF$_3$)
4-OCH$_2$C$_6$H$_4$(p-Cl)
4-OCH$_2$C$_6$H$_4$(p-Br)
4-OCH$_2$C$_6$H$_4$(p-F)
4-OCH$_2$C$_6$H$_4$(p-CH$_3$)
4-OCH$_2$C$_6$H$_4$(p-CF$_3$)
4-SCF$_2$CF$_2$H
4-OCH$_2$C(Cl)═CH$_2$
4-F, 3-OC$_6$H$_5$
4-F, 3-OCH$_2$C$_6$H$_5$
4-Cl, 3-OC$_6$H$_5$
4-Cl, 3-OCH$_2$C$_6$H$_5$
4-CH$_3$, 3-OC$_6$H$_5$
4-CH$_3$, 3-OCH$_2$C$_6$H$_5$
4-Br, 3-OCH$_2$C$_6$H$_5$
3-F, 4-OC$_6$H$_5$
3-Cl, 4-OC$_6$H$_5$
3-CH$_3$, 4-OC$_6$H$_5$
3-F, 4-OCH$_2$C$_6$H$_5$
3-Cl, 4-OCH$_2$C$_6$H$_5$
3-Br, 4-OCH$_2$C$_6$H$_5$
3-CH$_3$, 4-OCH$_2$C$_6$H$_5$

TABLE 14

$R^1 = $ 4-ethyl-1-isopropylphenyl with $(R^9)_l$ substituent (R$^9$)l

H
3-F
3-CF$_3$
3-Cl
3-Br
3-OC$_6$H$_5$
3-OCH$_2$C$_6$H$_5$
4-F, 3-OC$_6$H$_5$
4-F, 3-OCH$_2$C$_6$H$_5$
4-Cl, 3-OC$_6$H$_5$
4-Cl, 3-OCH$_2$C$_6$H$_5$
4-CH$_3$, 3-OC$_6$H$_5$
4-CH$_3$, 3-OCH$_2$C$_6$H$_5$
4-Br, 3-OCH$_2$C$_6$H$_5$
3-F, 4-OC$_6$H$_5$
3-F, 4-OCH$_2$C$_6$H$_5$
3-Cl, 4-OC$_6$H$_5$
3-Cl, 4-OCH$_2$C$_6$H$_5$
3-CH$_3$, 4-OC$_6$H$_5$
3-CH$_3$, 4-OCH$_2$C$_6$H$_5$
3-Br, 4-OCH$_2$C$_6$H$_5$
3-cyclohexyl
3-cyclopentyl
3-cyclohexyloxy
3-cyclopentyloxy
4-cyclohexyl
4-cyclopentyl
4-cyclohexyloxy
4-cyclopentyloxy
4-F
4-CF$_3$
4-Cl
4-Br
4-OC$_6$H$_5$
4-OCH$_2$C$_6$H$_5$
3-OCH$_2$CH═C(Cl)$_2$
3-OCH$_2$CH═C(Br)$_2$
4-OCH$_2$CH═C(Cl)$_2$
4-OCH$_2$CH═C(Br)$_2$
3-Cl, 4-OCH$_2$CH═C(Cl)$_2$
3-Cl, 4-OCH$_2$CH═C(Br)$_2$

TABLE 15

$R^1 = $ 4-propyl-1-isopropylphenyl with $(R^9)_l$ substituent (R$^9$)l

H
3-F
3-CF$_3$
3-Cl
3-Br
3-OC$_6$H$_5$
3-OCH$_2$C$_6$H$_5$

TABLE 15-continued

R¹ = [phenyl ring with positions 1-6, CH₂CH₂CH₃ at position 1, (R⁹)ₗ at position 4]

(R⁹)l

4-F, 3-OC₆H₅
4-F, 3-OCH₂C₆H₅
4-Cl, 3-OC₆H₅
4-Cl, 3-OCH₂C₆H₅
4-CH₃, 3-OC₆H₅
4-CH₃, 3-OCH₂C₆H₅
4-Br, 3-OCH₂C₆H₅
3-F, 4-OC₆H₅
3-F, 4-OCH₂C₆H₅
3-Cl, 4-OC₆H₅
3-Cl, 4-OCH₂C₆H₅
3-CH₃, 4-OC₆H₅
3-CH₃, 4-OCH₂C₆H₅
3-Br, 4-OCH₂C₆H₅
3-cyclohexyl
3-cyclopentyl
3-cyclohexyloxy
3-cyclopentyloxy
4-cyclohexyl
4-cyclopentyl
4-cyclohexyloxy
4-cyclopentyloxy
4-F
4-CF₃
4-Cl
4-Br
4-OC₆H₅
4-OCH₂C₆H₅
3-OCH₂CH=C(Cl)₂
3-OCH₂CH=C(Br)₂
4-OCH₂CH=C(Cl)₂
4-OCH₂CH=C(Br)₂
3-Cl, 4-OCH₂CH=C(Cl)₂
3-Cl, 4-OCH₂CH=C(Br)₂

TABLE 16

R¹ = [phenyl ring with positions 1-6, CH(CH₃)₂ at position 1, (R⁹)ₗ at position 4]

(R⁹)l

H
3-F
3-CF₃
3-Cl
3-Br

TABLE 16-continued

R¹ = [phenyl ring with positions 1-6, CH(CH₃)₂ at position 1, (R⁹)ₗ at position 4]

(R⁹)l

3-OC₆H₅
3-OCH₂C₆H₅
4-F, 3-OC₆H₅
4-F, 3-OCH₂C₆H₅
4-Cl, 3-OC₆H₅
4-Cl, 3-OCH₂C₆H₅
4-CH₃, 3-OC₆H₅
4-CH₃, 3-OCH₂C₆H₅
4-Br, 3-OCH₂C₆H₅
3-F, 4-OC₆H₅
3-F, 4-OCH₂C₆H₅
3-Cl, 4-OC₆H₅
3-Cl, 4-OCH₂C₆H₅
3-CH₃, 4-OC₆H₅
3-CH₃, 4-OCH₂C₆H₅
3-Br, 4-OCH₂C₆H₅
3-cyclohexyl
3-cyclopentyl
3-cyclohexyloxy
3-cyclopentyloxy
4-cyclohexyl
4-cyclopentyl
4-cyclohexyloxy
4-cyclopentyloxy
4-F
4-CF₃
4-Cl
4-Br
4-OC₆H₅
4-OCH₂C₆H₅
3-OCH₂CH=C(Cl)₂
3-OCH₂CH=C(Br)₂
4-OCH₂CH=C(Cl)₂
4-OCH₂CH=C(Br)₂
3-Cl, 4-OCH₂CH=C(Cl)₂
3-Cl, 4-OCH₂CH=C(Br)₂

TABLE 17

$R^1 =$ (naphthalene structure with positions 1-8, substituents $(R^9)_m$, $(R^{12})_q$, and group $Q_{10}$: $A-[\underset{R^{11}}{\overset{R^{10}}{|}}]_p-\overset{R^7}{\underset{|}{CH}}$)

| $(R^4)_m$ | $(R^{12})_a$ | position of $[\underset{R^{11}}{\overset{R^{10}}{|}}]_p-\overset{R^7}{\underset{|}{CH}}$ | A | p | $R^7$ | $R^{10}$ | $R^{11}$ |
|---|---|---|---|---|---|---|---|
| H | H | 1 | O | 1 | H | H | H |
| H | H | 2 | O | 1 | H | H | H |
| H | H | 1 | O | 2 | H | H | H |
| H | H | 2 | O | 2 | H | H | H |
| H | H | 1 | O | 3 | H | H | H |
| H | H | 2 | O | 3 | H | H | H |
| H | H | 1 | O | 4 | H | H | H |
| H | H | 2 | O | 4 | H | H | H |
| H | H | 1 | NH | 2 | H | H | H |
| H | H | 2 | NH | 3 | H | H | H |
| H | H | 1 | S | 2 | H | H | H |
| H | H | 2 | S | 3 | H | H | H |

The aldehyde compound of the general formula [X], which is an intermediate for use in the production of the present compounds, can be produced, for example, according to the following scheme:

SCHEME 1

[VI] + L—CH$_2$CH(OC$_2$H$_5$)$_2$

↓

$R^1-Z$—(phenyl ring with $R^2$, $R^3$, $(R^{14})_r$)—Y—CH$_2$CH(OC$_2$H$_5$)$_2$ ↓ H$_3$O$^{\oplus}$(ex. conc. HCl/AcOH)

[IX]

wherein all variables are as defined above.

The compounds of the general formula [IV], [V] or [VI], which are intermediate for use in the production of the present compounds, can be produced, for example, according to the following scheme:

SCHEME 2

(when Y and Z are both oxygen)

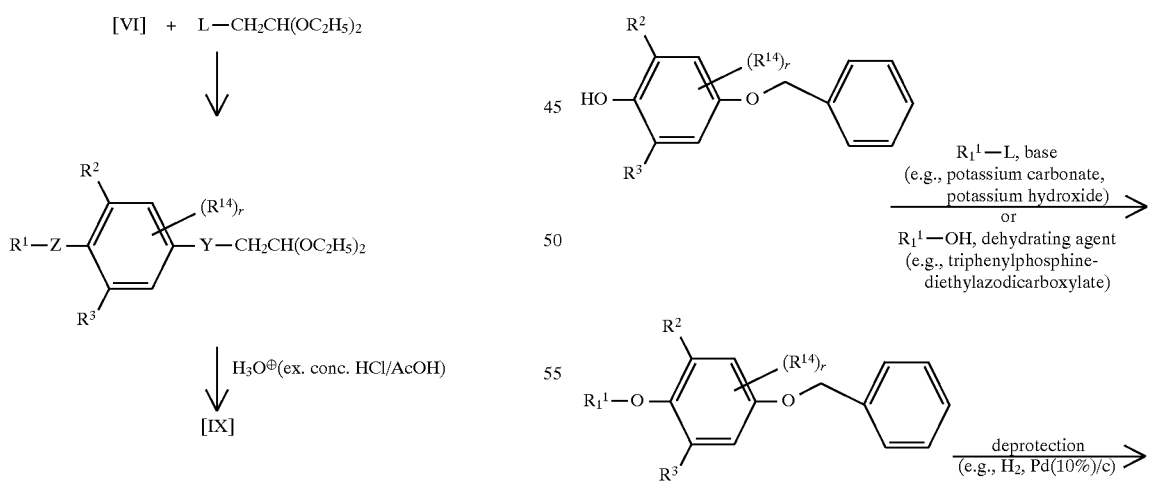

chlorination, bromination, iodination or methylation *1)

$R_1^1$—L, base (e.g., potassium carbonate, potassium hydroxide) or $R_1^1$—OH, dehydrating agent (e.g., triphenylphosphine-diethylazodicarboxylate)

deprotection (e.g., H$_2$, Pd(10%)/c)

-continued
SCHEME 2

*1): see, e.g., Tetrahedron Lett., 889(1974)).

wherein $R^1$ is $C_1$–$C_{10}$ alkyl, $C_1$–$C_5$ haloalkyl, $C_2$–$C_{10}$ alkenyl, $C_2$–$C_6$ haloalkenyl, $C_3$–$C_9$ alkynyl, $C_3$–$C_5$ haloalkynyl, $C_2$–$C_7$ alkoxyalkyl, $C_2$–$C_7$ alkylthioalkyl; $C_3$–$C_6$ cycloalkyl which may be substituted with $C_1$–$C_4$ alkyl, $C_1$–$C_3$ alkoxy or $C_1$–$C_3$ haloalkoxy; $C_4$–$C_9$ cycloalkylalkyl which may be substituted with $C_1$–$C_4$ alkyl; or $C_6$–$C_8$ cycloalkenylalkyl which may be substituted with $C_1$–$C_4$ alkyl, and $R^2$, $R^3$, $R^{14}$, r and L are each as defined above.

SCHEME 3

(when Y and Z are both oxygen)

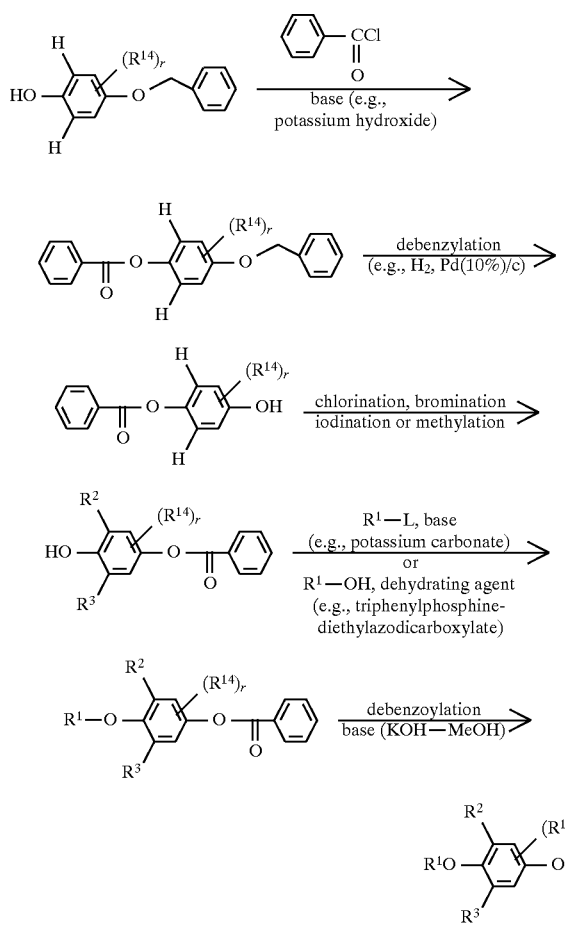

wherein $R^1$, $R^2$, $R^3$, $R^{14}$, r and L are each as defined above.

SCHEME 4

(when Y and Z are not both oxygen)

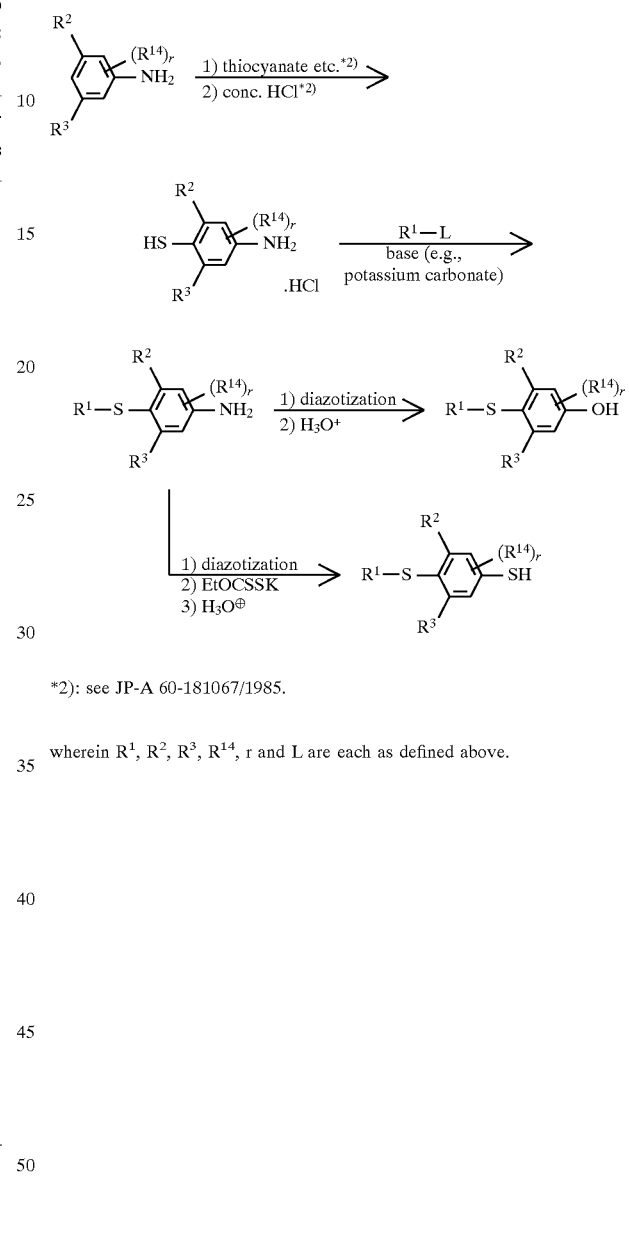

*2): see JP-A 60-181067/1985.

wherein $R^1$, $R^2$, $R^3$, $R^{14}$, r and L are each as defined above.

SCHEME 5
(when Y and Z are not both oxygen)
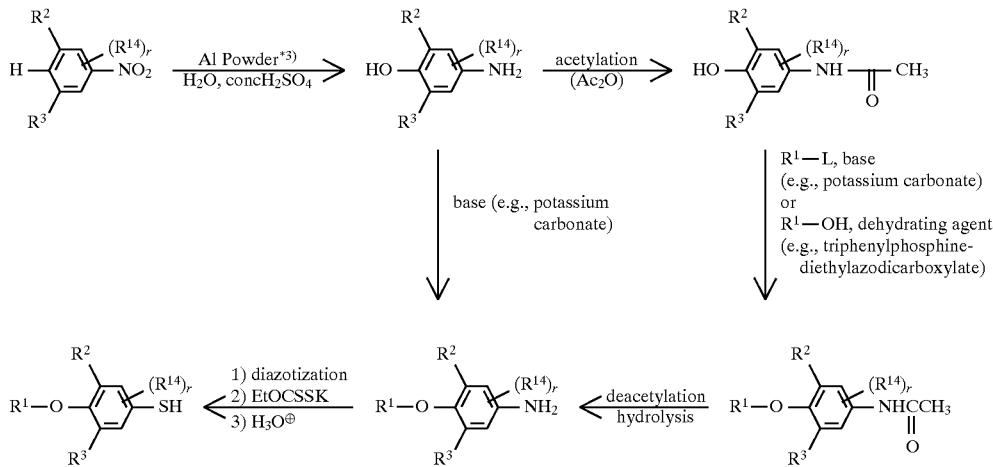
*3): see H. J. Shine, "Aromatic Rearrangement", Elsevier, 182 (1967).
wherein $R^1$, $R^2$, $R^3$, $R^{14}$, r and L are each as defined above.
SCHEME 6-1
(when Y is oxygen)
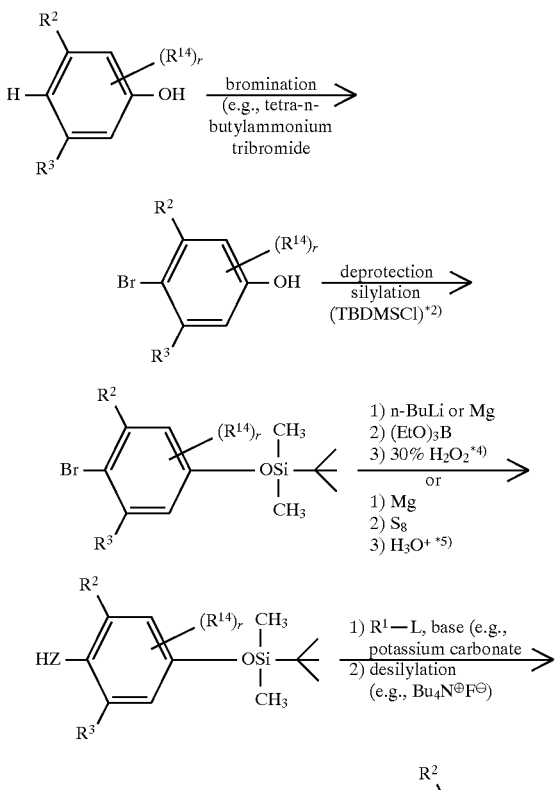
-continued
SCHEME 6-1
*4): see J. Org. Chem., 22, 1001 (1957).
*5): see Ber., 72, 594 (1939).
wherein $R^1$, $R^2$, $R^3$, $R^{14}$, r, L and Z are each as defined above.
SCHEME 6-2
(when Y is oxygen)
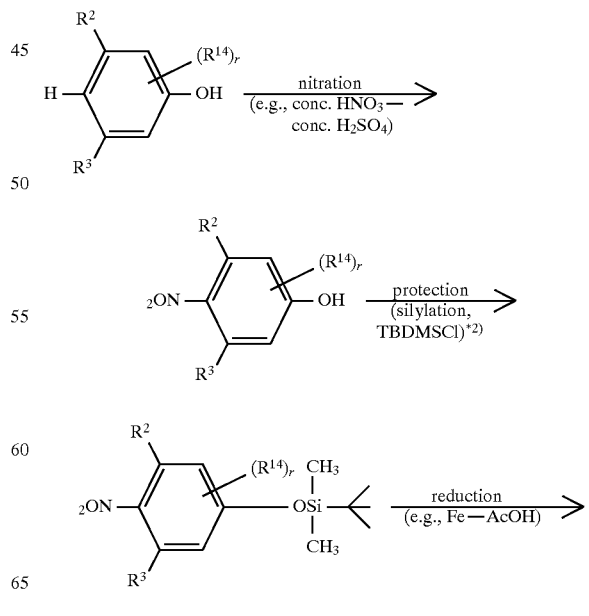

SCHEME 6-2 (continued)

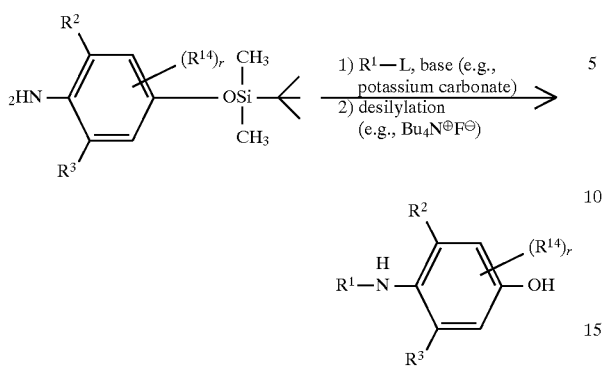

wherein $R^1$, $R^2$, $R^3$, $R^{14}$, r and L are each as defined above.

The compounds of the general formula [III] or [X], which are intermediates for use in the production of the present compound, can be produced, for example, according to the following scheme:

The compounds of the general formula [II], [XIII] or [XIV], which are intermediates for use in the production of the present compound, can be produced, for example, according to the following scheme:

SCHEME 7

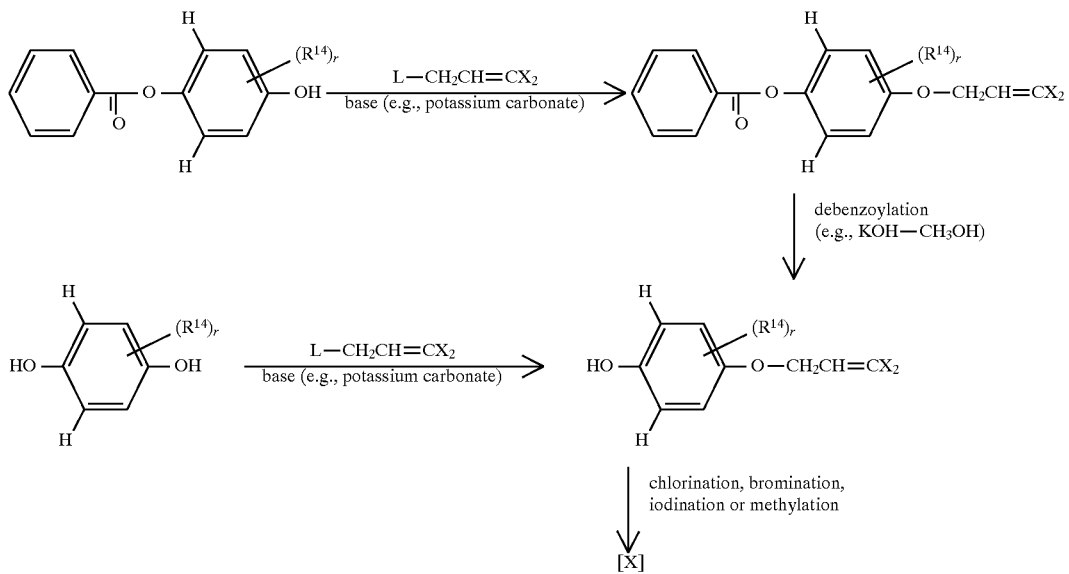

wherein the general formula [X] represents the compound [III] when r is o.

SCHEME 8

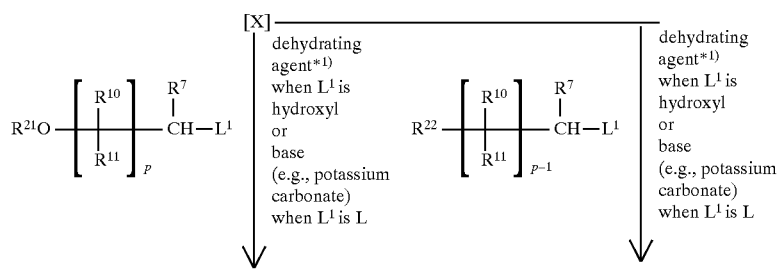

-continued
SCHEME 8

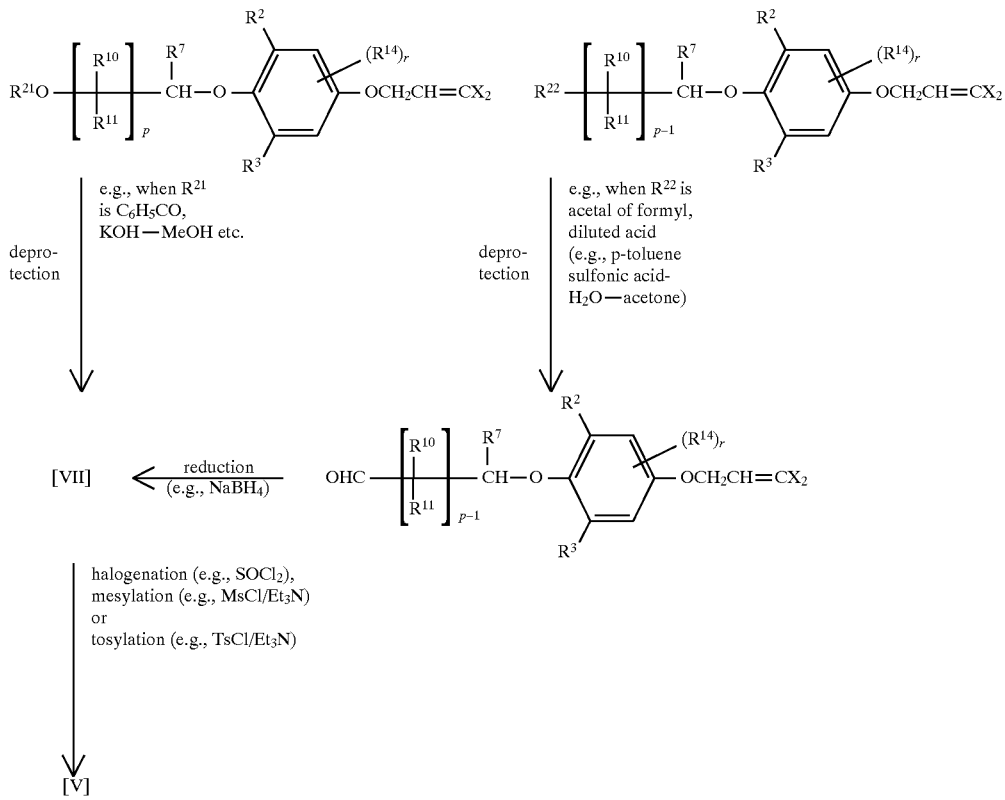

*1): triphenylphosphine-diethylazodicarboxylate etc.

wherein the general formula [XIV] represents the compound [II] wherein $L^1$ is OH when r is 0, the general formula [XIII] represents the compound [II] wherein $L^1$ is L when r is 0, $R^{21}$ is a protecting group (e.g., benzoyl) for alcohols, Ms is mesyl, Ts is tosyl, and other variables are each as defined above.

SCHEME 9

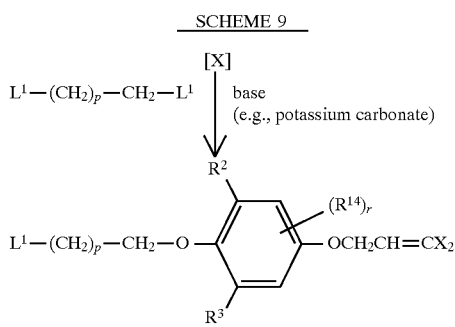

wherein the produced compounds are the compound [XIII] or [XIV] wherein $R^7$, $R^{10}$ and $R^{11}$ are all hydrogen and the compound [II] wherein r is 0, and all the variables are each as defined above.

The compound of the general formula [VII] and the alcohol compound of the general formula [VIII], which are intermediates for use in the production of the present compounds, are commercially available or can be produced, for example, according to the following scheme:

SCHEME 10

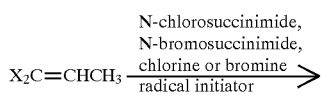

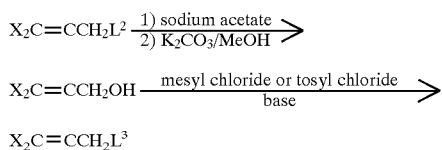

$X_2C=CCH_2L^3$ wherein $L^2$ is chlorine or bromine, $L^3$ is mesyloxy or tosyloxy, and X is as defined above.

The present compounds are satisfactory effective for the control of various noxious insects, mites and ticks, examples of which are as follows:

Hemiptera

Delphacidae such as *Laodelphax striatellus, Nilaparvata lugens* and *Sogatella furcifera*, Deltocephalidae such as *Nephotettix cincticeps* and *Nephotettix virescens*, Aphididae, Pentatomidae, Aleyrodidae, Coccidae, Tingidae, Psyllidae, etc.

Lepidoptera

Pyralidae such as *Chilo suppressalis, Cnaphalocrocis medinalis, Ostrinia nubilalis, Parapediasia teterrella, Notarcha derogata* and *Plodia interpunctella*, Noctuidae such as *Spodoptera litura, Spodoptera exigua, Spodoptera litoralis, Pseudaletia separata, Mamestra brassicae, Agrotis ipsilon*, Trichoplusia spp., Heliothis spp., Helicoverpa spp. and Earias spp., Pieridae such as *Pieris rapae crucivora*, Tortricidae such as Adoxophyes spp., *Grapholita molesta* and *Cydia pomonella*, Carposinidae such as *Carposina niponensis*, Lyonetiidae such as Lyonetia spp., Lymantriidae such as Lymantria spp. and Euproctis spp., Yponomeutidae such as *Plutella xylostella*, Gelechiidae such as *Pectinophora gossypiella*, Arctiidae such as *Hyphantria cunea*, Tineidae such as *Tinea translucens* and *Tineola bisselliella*, etc.

Diptera

Culex such as *Culex pipiens pallens* and *Cules tritaeniorhynchus*, Aedes such as *Aedes albopictus* and *Aedes aegypti*, Anopheles such as *Anophelinae sinensis*, Chironomidae, Muscidae such as *Musca domestica* and *Muscina stabulans*, Calliphoridae, Sarcophagidae, *Fannia canicularis*, Anthomyiidae such as *Delia Platura* and *Delia antigua*, Trypetidae, Drosophilidae, Psychodidae, Tabanidae, Simuliidae, Stomoxyinae, etc.

Coleoptera

Diabrotica such as *Diabrotica virgifera* and *Diabrotica undecimpunctata*, Scarabaeidae such as *Anomala cuprea* and *Anomala rufocuprea*, Curculionidae such as Lissorphoptrus oryzophilus, *Hypera pastica*, and *Calosobruchys chinensis*, Tenebrionidae such as *Tenebrio molitor* and *Tribolium castaneum*, Chrysomelidae such as *Phyllotreta striolata* and *Aulacophora femoralis*, Anobiidae, Epilachna spp. such as *Henosepilachna vigintioctopunctata*, Lyctidae, Bostrychidae, Cerambycidae, *Paederus fuscipes*, etc.

Dictyoptera

*Blattella germanica, Periplaneta fuliginosa, Peroplaneta americana, Periplaneta brunnea, Blatta orientalis*, etc.

Thysanoptera

*Thrips palmi, Thrips hawaiiensis*, etc.

Hymenoptera

Formicidae, Vespidae, Bethylidae, Tenthredinidae such as *Athalia rosae japonensis*, etc.

Orthoptera

Gryllotalpidae, Acrididae, etc.

Siphonaptera

*Purex irritans*, etc.

Anoplura

*Pediculus humanus capitis, Phthirus pubis*, etc.

Isoptera (termites)

*Reticulitermes speratus, Coptotermes formosanus*, etc.

Acarina plant patasitic Tetranychidae such as *Tetranychus uriticae, Panonychus citri*, Tetranychus cinnabarinus and *Panonychus ulmi*, animal parasitic Ixodidae such as *Boophilus microphus*, house dust mites, etc.

The present compounds are also effective for the control of various noxious insects, mites and ticks having resistance to conventional insecticides and acaricides.

When the present compound is used as an active ingredient of insecticidal/acaricidal agents, it may be used as such without any addition of other ingredients. The present compound is, however, usually formulated into a dosage form such as oil sprays, emulsifiable concentrates, wettable powders, flowables, granules, dusts, aerosols, fumigants (foggings) and poison baits. These formulations are usually prepared by mixing the present compound with a solid carrier, a liquid carrier, a gaseous carrier or a bait, and if necessary, adding a surfactant and other auxiliaries used for formulation.

Each of the formulations usually contains the present compound as an active ingredient in an amount of 0.01% to 95% by weight.

Examples of the solid carrier to be used for the formulation are fine powder or granules of clay materials such as kaolin clay, diatomaceous earth, synthetic hydrated silicon oxide, bentonite, Fubasami clay and acid clay; various kinds of talc, ceramics, other inorganic minerals such as sericite, quartz, sulfur, active carbon, calcium carbonate and hydrated silica; and chemical fertilizers such as ammonium sulfate, ammonium phosphate, ammonium nitrate, urea and ammonium chloride.

Examples of the liquid carrier are water; alcohols such as methanol and ethanol; ketones such as acetone and methyl ethyl ketone; aromatic hydrocarbons such as benzene, toluene, xylene, ethylbenzene and methylnaphthalene; aliphatic hydrocarbons such as hexane, cyclohexane, kerosine and gas oil; esters such as ethyl acetate and butyl acetate; nitriles such as acetonitrile and isobutyronitrile; ethers such as diisopropyl ether and dioxane; acid amides such as N,N-dimethylformamide and N,N-dimethylacetamide; halogenated hydrocarbons such as dichloromethane, trichloroethane and carbon tetrachloride; dimethyl sulfoxide; and vegetable oils such as soybean oil and cottonseed oil.

Examples of the gaseous carrier or propellant are flon gas, butane gas, LPG (liquefied petroleum gas), dimethyl ether and carbon dioxide.

Examples of the surfactant are alkyl sulfates, alkyl sulfonates, alkyl arylsulfonates, alkyl aryl ethers and their polyoxyethylene derivatives, polyethylene glycol ethers, polyhydric alcohol esters and sugar alcohol derivatives.

Examples of the auxiliaries used for formulation, such as fixing agents or dispersing agents, are casein, gelatin, polysaccharides such as starch, gum arabic, cellulose derivatives and alginic acid, lignin derivatives, bentonite, sugars, and synthetic water-soluble polymers such as polyvinyl alcohol, polyvinyl pyrrolidone and polyacrylic acid.

Examples of the stabilizer are PAP (isopropyl acid phosphate), BHT (2,6-di-tert-4-methylphenol), BHA (mixtures of 2-t-butyl-4-methoxyphenol and 3-tert-butyl-4-methoxyphenol), vegetable oils, mineral oils, surfactants, fatty acids and their esters.

Examples of the base material to be used in the poison baits are bait materials such as grain powder, vegetable oils, sugars and crystalline cellulose; antioxidants such as dibutylhydroxytoluene and nordihydroguaiaretic acid; preservatives such as dehydroacetic acid; substances for preventing erroneous eating, such as red pepper powder, attractant flavors such as cheese flavor or onion flavor.

The formulation thus obtained is used as such or after diluted with water. The formulation may also be used in combination with other insecticides, nematocides, acaricides, bactericides, fungicides, herbicides, plant growth regulators, synergists, fertilizers, soil conditioners and/or animal feed under non-mixing conditions or premixing conditions.

Examples of the insecticide, acaricide and/or nematocide which can be used are organophosphorus compounds such as Fenitrothion [(O,O-dimethyl O-(3-methyl-4-nitrophenyl) phosphorothioate], Fenthion [O,O-dimethyl O-(3-methyl-4-methylthio)phenyl)phosphorothioate], Diazinon [O,O-diethyl-O-2-isopropyl-6-methylpyrimidin-4-ylphosphorothioate], Chlorpyriphos [O,O-diethyl-O-3,5,6-trichloro-2-pyridylphosphorothioate], Acephate [O,S-dimethylacetylphosphoramidothioate], Methidachion [S-2,3-dihydro-5-methoxy-2-oxo-1,3,4thiadiazol-3-ylmethyl O,O-dimethylphosphorodithioate], Disulfotone [O,O-diethyl S-2-ethylthioethylphosphorothioate], DDVP [2,2-dichlorovinyldimethylphosphate], Sulprofos [O-ethyl O-4-(methylthio)phenyl S-propyl phosphorodithioate], Cyanophos O-4-cyanophenyl O,O-dimethylphosphorothioate], Dioxabenzofos [2-methoxy- 4H-1,3,2-benzodioxaphosphinin-2-sulfide], Dimethoate [O,O-dimethyl-S-(N-methylcarbamoylmethyl) dithiophosphate], Phenthoate [ethyl 2-dimethoxyphosphinothioylthio(phenyl)acetate], Malathion [diethyl(dimethoxyphosphinothioylthio) succinate], Trichlorfon [dimethyl 2,2,2-trichloro-1-hydroxyethylphosphonate], Azinphos-methyl [S-3,4-dihydro-4-oxo-1,2,3-benzotriazin-3-ylmethyl-O,O-dimethylphosphorodithioate], Monocrotophos [dimethyl (E)-1-methyl-2-(methylcarbamoyl)vinylphosphate], Profenfos [O-4-bromo-2-chlorophenyl O-ethyl S-propylphosphorothioate] and Ethion [O,O,O',O'-tetraethyl S,S'-methylenebis(phosphorodithioate)]; carbamate compounds such as BPMC [2-sec-butylphenylmethylcarbamate], Benfuracarb [ethyl N-[2,3-dihydro-2,2-dimethylbenzofuran-7-yloxycarbonyl(methyl) aminothio]-N-isopropyl-β-alaninate], Propoxur [2-isopropoxyphenyl N-methylcarbamate], Carbosulfan [2,3-dihydro-2,2-dimethyl-7-benzo[b]-furanyl N-dibutylaminothio-N-methylcarbamate], Carbaril [1-naphthyl-N-methylcarbamate], Methomyl [S-methyl-N-[(methylcarbamoyl)oxy]thioacetoimidate], Ethiofencarb [2-(ethylthiomethyl)phenylmethylcarbamate], Aldicarb [2-methyl-2-(methylthio)propanaldehyde O-methylcarbamoyloxime], Oxamyl [N,N-dimethyl-2-methylcarbamoyloxyimino-2-(methylthio)acetamide], Thiodicarb [3,7,9,13-tetramethyl-5,11-dioxa-2,8,14-trithia-4,7,9,12-tetraazapentadeca-3,12-dien-6,10-dione], Alanylcarb [ethyl (Z)-N-benzyl-N-{[[methyl(1-methylthioethylideneaminooxycarbonyl)amino]thio }-β-alanylate] and Fenothiocarb [S-4phenoxybutyl)-N,N-dimethylthiocarbamate]; pyrethroid compounds such as Etofenprox [2-(4-ethoxyphenyl)-2-methylpropyl-3-phenoxybenzylether], Fenvalerate [(RS)-α-cyano-3-phenoxybenzyl (RS)-2-(4-chlorophenyl)-3-methylbutyrate], Esfenvalerate [(S)-α-cyano-3-phenoxybenzyl (S)-2-(4-chlorophenyl)-3-methylbutyrate], Fenpropathrin[(RS)-α-cyano-3-phenoxybenzyl 2,2,3,3-tetramethylcyclopropanecarboxylate], Cypermethrin [(RS)-α-cyano-3-phenoxybenzyl (1RS,3RS)-3-(2,2-dichlorovinyl) -2,2-dimethylcyclopropanecarboxylate], Permethrin [3-phenoxybenzyl (1RS,3RS)-3-(2,2-dichlorovinyl)-2,2-dimethylcyclopropanecarboxylate], Cyhalothrin [(RS)-α-cyano-3-phenoxybenzyl (Z)-(1RS,3RS)-3-(2-chloro-3,3,3-trifluoropropenyl)-2,2-dimethylcyclopropanecarboxylate], Deltamethrin [(S)-α-cyano-m-phenoxybenzyl (1R,3R)-3-(2, 2-dibromovinyl)-2,2-dimethylcyclopropanecarboxylate], Cycloprothrin [(RS)-(α-cyano-3-phenoxybenzyl (RS)-2,2-dichloro-1-(4-ethoxyphenyl)cyclopropanecarboxylate], Fluvalinate [α-cyano-3-phenoxybenzyl N-(2-chloro-α, α, α-trifluoro-p-tolyl)-D-valinate], Bifenthrin [2-methylbiphenyl-3-ylmethyl)(Z)-(1RS)-cis -3-(2-chloro-3,3,3-trifluoropropen-1-yl)-2,2-dimethylcyclopropanecarboxylate], Acrinathrin [cyano-(3-phenoxyphenyl)methyl [1R-{1((S*),3α(Z)}]-2,2-dimethyl-3-[3-oxo-3-(2,2,2-trifluoro-1-(trifluoromethyl)-ethoxy 1-propenyl]cyclopropanecarboxylate], 2-methyl-2-(4-bromodifluoromethoxyphenyl)propyl (3-phenoxybenzyl) ether, Traromethrin [(S)-α-cyano-3-phenoxylbenzyl (1R, 3R)-3-[(1'RS)(1',1',2'-tetrabromoethyl)]-2,2-dimethylcyclopropanecarboxylate] and Silafluofen [4-ethoxylphenyl [3-(4-fluoro-3-phenoxyphenyl)propyl] dimethylsilane]; thiadiazine derivatives such as Buprofezin [2-tert-butylimino-3-isopropyl-5-phenyl-1,3,5-thiadiazin-4-one]; nitroimidazolidine derivatives such as Imidacloprid [1-(6-chloro-3-pyridylmethyl)-N-nitroimidazolidin-2-ylidenamine]; Nereistoxin derivatives such as Cartap [S,S'-(2-dimethylaminotrimethylene)bisthiocarbamate], Thiocyclam [N,N-dimethyl-1,2,3-trithian-5-ylamine] and Bensultap [S,S'-2-dimethylaminotrimethylene di(benzenethiosulfonate)]; N-cyanoamidine derivatives such as acetamiprid [N-cyano-N'-methyl-N'-(6-chloro-3-pyridylmethyl)acetamidine]; chlorinated hydrocarbons such as Endosulfan [6,7,8,9,10,10-hexachloro-1,5,5a,6,9,9a-hexahydro-6,9-methano-2,4,3-benzodioxathiepinoxide], γ-BHC [1,2,3,4,5,6-hexachlorocyclohexane] and Kelthane 1,1-bis-(chlorophenyl)-2,2,2-trichloroethanol]; benzoylphenylurea compounds such as Chlorfluazuron [1-(3,5-dichloro-4-(3-chloro-5-trifluoromethylpyridin-2-yloxy) phenyl)-3-(2,6-difluorobenzoyl) urea], Teflubenzuron [1-(3, 5-dichloro-2,4-difluorophenyl)-3-(2,6-difluorobenzoyl) urea] and Fulphenoxron [1-(4-(2-chloro-4-trifluoromethylphenoxy)-2-fluorophenyl)-3-(2,6-difluorobenzoyl)urea]; formamidine derivatives such as Amitraz [N,N'-[(methylimino)dimethylidine]-di-2,4-xylidine] and Chlordimeform [N'-(4-chloro-2-methylphenyl)-N,N-dimethylmethanimidamide]; thiourea derivatives such as Diafenthiuron (N-(2,6-diisopropyl-4-phenoxyphenyl)-N'-tert-butylcarbodiimide]; Fipronyl [5-amino-1-(2,6-dichloro-α, α, α,-trifluoro -p-tolyl)-4-trifluoromethylsulfinylpyrazole-3-carbonitrite], Tebfenozide [N-tert-butyl-N'-(4-ethylbenzoyl)-3,5-dimethylbenzohydrazide], 4-bromo-2-(4-chlorophenyl)-1-ethoxymethyl-5-trifluoromethylpyrrole-3-carbonitrile, Chlorfenapyl [4-bromo-2-(4-chlorophenyl)-1-ethoxy methyl-S -trifluoromethylpyrole-3-carbonitril], Bromopropylate [isopropyl 4,4'-dibromobenzylate], Tetradifon[4-chlorophenyl-2,4,5-trichlorophenyl sulfone], Quinomethionate [S,S-6-methylquinoxaline-2,3-diyldithiocarbonate], Propargite [2-(4-tert-butylphenoxy) cyclohexyl prop-2-yl sulfite], Fenbutatin oxide [bis[tris(2-methyl-2-phenylpropyl)tin)oxide], Hexythiazox [(4RS, 5RS)-5-(4-chlorophenyl)-N-chlorohexyl-4-methyl-2-oxo-1, 3-thiazolidine-3-carboxamide], Chlofentezine [3,6-bis(2-chlorophenyl)-1,2,4,5-tetrazine], Pyridaben [2-tert-butyl-5-(4-tert-butylbenzylthio)-4-chloropyridazin-3(2H)-one], Fenpyroximate [tert-butyl(E)-4-[(1,3-dimethyl-5-phenoxypyrazol-4-yl)methyleneaminooxymethyl] benzoate], Tebfenpyrad [N-4-tert-butylbenzyl)-4-chloro-3-ethyl-1-methyl-5-pyrazol carboxamide], polynactin complexes including tetranactin, trinactin and dinactin; Milbemectin, Avermectin, Ivermectin, Azadilactin [AZAD], Pyrimidifen [5-chloro-N-[2-{4-(2-ethoxyethyl)-2,3-dimethylphenoxy}ethyl]-6-ethylpyrimidin-4-amine] and Pimetrozine [2,3,4,5-tetrahydro-3-oxo-4-[(pyridin-3-yl)-methyleneamino]-6-methyl-1,2,4-triazine].

When the present compound is used as an active ingredient of insecticidal/acaricidal agents for agriculture, the application amount thereof is usually in the range of 0.1 to 100 g per 10 ares. In the case of emulsifiable concentrates, wettable powders and flowable concentrates, which are used after diluted with water, the application concentration thereof is usually in the range of 0.1 to 500 ppm. In the case of granules and dusts, they are applied as such without any dilution. When the present compound is used as an active ingredient of insecticidal/acaricidal agents for epidemic prevention, it is formulated into a dosage form such as emulsifiable concentrates, wettable powders and flowable concentrates, which are applied after diluted with water to a typical concentration of 0.1 to 500 ppm; or it is formulated into a dosage form such as oil sprays, aerosols, fumigants and poisonous baits, which are applied as such without any dilution.

The application amount and application concentration may vary depending upon various conditions such as formulation type, application time, place and method, kind of noxious insects, mites and ticks, and degree of damage, and they can be increased or decreased without limitation to the above range.

The present invention will be further illustrated by the following production examples, formulation examples and test examples, which are not to be construed to limit the scope thereof.

The following are production examples for the present compounds according to various production processes.

PRODUCTION EXAMPLE 1

Production of Compound (64) by Production Process E

To a solution of 0.30 g of 4-(3,3-dichloro-2-propenyloxy)-2,6-dichlorophenol, 0.16 g of 4-phenyl-1-butanol and 0.27 g of triphenylphosphine dissolved in 10 ml of tetrahydrofuran was added dropwise a solution of 0.21 g of diethylazodicarboxylate dissolved in 5 ml of tetrahydrofuran was added dropwise, while stirring at room temperature. After stirring at room temperature for 24 hours, the reaction mixture was concentrated to obtain a residue. The residue was subjected to silica gel chromatography, which afforded 0.32 g of 3,5-dichloro-1-(3,3-dichloro-2-propenyloxy)-4-(4-phenylbutyloxy)benzene (73% yield), $n_D^{26.0}$ 1.5716.

PRODUCTION EXAMPLE 2

Production of Compound (77) by Production Process E

To a solution of 0.30 g of 2,6-dichloro-4-(3,3-dichloro-2-propenyloxy)phenol, 0.16 g of 3-phenoxy-1-propanol and 0.27 g of triphenylphosphine dissolved in 10 ml of tetrahydrofuran was added dropwise a solution of 0.21 g of diisopropylazodicarboxylate dissolved in 5 ml of tetrahydrofuran, while stirring at room temperature. After stirring at room temperature for 24 hours, the reaction mixture was concentrated to obtain a residue. The residue was subjected to silica gel chromatography, which afforded 0.36 g of 3,5-dichloro-1-(3,3-dichloro-2-propenyloxy)-4-(3-phenoxypropyloxy)benzene (82% yield), $n_D^{25.0}$ 1.5762.

PRODUCTION EXAMPLE 3

Production of Compound (34) by Production Process B

To a solution of 0.33 g of 4-(3,3-dichloro-2-propenyloxy)-2,6-dichlorophenol, 0.23 g of m-phenoxybenzyl alcohol and 0.34 g of triphenylphosphine dissolved in 10 ml of tetrahydrofuran was added dropwise a solution of 0.26 g of diisopropylazodicarboxylate dissolved in 5 ml of tetrahydrofuran, while stirring at room temperature. After stirring at room temperature for 12 hours, the reaction mixture was concentrated, and then mixed with 20 ml of diethyl ether. The precipitate was filtered, and the filtrate was concentrated. The residue was subjected to silica gel chromatography, which afforded 0.31 g of 3,5-dichloro-4-(3-phenoxybenzyl)-1-(3,3-dichloro-2-propenyloxy)-benzene (57% yield), $n_D^{25.5}$ 1.6066.

PRODUCTION EXAMPLE 4

Production of Compound (35) by Production Process E

To a solution of 0.46 g of 4-(3,3-dichloro-2-propenyloxy)-2,6-dichlorophenol, 0.32 g of p-phenoxybenzyl alcohol and 0.46 g of triphenylphosphine dissolved in 10 ml of tetrahydrofuran was added dropwise a solution of 0.35 g of diisopropylazodicarboxylate dissolved in 5 ml of tetrahydrofuran, while stirring at room temperature. After stirring at room temperature for 12 hours, the reaction mixture was concentrated, and then mixed with 20 ml of diethyl ether. The precipitate was filtered, and the filtrate was concentrated. The residue was subjected to silica gel chromatography, which afforded 0.51 g of 3,5-dichloro-4-(4-phenoxybenzyl)-1-(3,3-dichloro-2-propenyloxy)benzene (68% yield), $n_D^{25.5}$ 1.6084.

PRODUCTION EXAMPLE 5

Production of Compound (63) by Production Process E

To a solution of 0.30 g of 4-(3,3-dichloro-2-propenyloxy)-2,6-dichlorophenol, 0.16 g of 4-chloro-β-phenetyl alcohol and 0.27 g of triphenylphosphine dissolved in 10 ml of tetrahydrofuran was added dropwise a solution of 0.21 g of diethylazodicarboxylate dissolved in 5 ml of tetrahydrofuran, while stirring at room temperature. After stirring at room temperature for 24 hours, the reaction mixture was concentrated to obtain a residue. The residue was subjected to silica gel chromatography, which afforded 0.32 g of 4-(4-chloro-β-phenetyloxy)-3,5-dichloro-1-(3,3-dichloro-2-propenyloxy)benzene (72% yield), $n_D^{24.5}$ 1.5868.

PRODUCTION EXAMPLE 6

Production of Compound (1) by Production Process A

To a mixture of 600 mg of 3,5-dichloro-4-(1,1,2,2-tetrafluoroethoxy)phenol, 330 mg of potassium carbonate and 10 ml of N,N-dimethylformamide was added dropwise a solution of 340 mg of 1,1,3-trichloro-1-propene dissolved in 3 ml of N,N-dimethylformamide, while stirring at room temperature. After stirring continued at room temperature for 5 hours, the reaction mixture was poured into ice-water, and extracted twice with 40 ml of diethyl ether. The combined ether layer was washed with water, dried with anhydrous magnesium sulfate, and concentrated to obtain a crude product. The crude product was subjected to silica gel chromatography, which afforded 630 mg of 3,5-dichloro-4-(1,1,2,2-tetrafluoroethoxy)-1-(3,3-dichloro-2-propenyloxy) benzene (82% yield), $n_D^{24.6}$ 1.5067.

PRODUCTION EXAMPLE 7

Production of Compound (41) by Production Process A

To a mixture of 1.10 g of 3,5-dichloro-4-(4-fluoro-3-phenoxy)benzyloxyphenol, 0.44 g of potassium carbonate and 20 ml of N,N-dimethylformamide was added dropwise a solution of 0.89 g of 1,1,3-tribromopropene dissolved in 5 ml of N,N-dimethylformamide, while stirring at room temperature. After stirring at room temperature for 7 hours, the reaction mixture was poured into ice-water, and extracted twice with 50 ml of diethyl ether. The combined ether layer was washed with water, dried with anhydrous magnesium sulfate, and concentrated to obtain a crude product. The crude product was subjected to silica gel chromatography, which afforded 1.16 g of 3,5-dichloro-4-(4-fluoro-3-phenoxy)benzyloxy-1(3,3-dibromo-2-propenyloxy)benzene (69% yield), $n_D^{22.5}$ 1.6062.

PRODUCTION EXAMPLE 8

Production of Compound (3) by Production Process B

To a solution of 0.54 g of 4-(3,3-dichloro-2-propenyloxy)-3,5-dichlorophenol, 0.24 g of 3,3-dichloroallyl alcohol and 0.49 g of triphenylphosphine dissolved in 15 ml of tetrahydrofuran was added dropwise a solution of 0.38 g of diisopropylazodicarboxylate dissolved in 5 ml of tetrahydrofuran, while stirring at room temperature. After stirring at room temperature for 24 hours, the reaction mixture was concentrated to obtain a residue. The residue was subjected to silica gel chromatography, which afforded 0.52 g of 4-(31(3,3-dichloro-2-propenyloxy)benzene (70% yield), m.p. 75.8° C.

PRODUCTION EXAMPLE 9

Production of Compound (47) by Production Process C

In a reaction vessel were placed 0.26 g of zinc dust, 1.0 g of triphenylphosphine, 1.3 g of carbon tetrabromide and 20 ml of methylene chloride, followed by stirring at room temperature. After 24 hours, a solution of 0.70 g of (4-(2-chlorobenzyloxy)-3,5-dichlorophenoxy)acetaldehyde dissolved in 5 ml of methylene chloride was added dropwise to the above solution, while stirring at room temperature. After stirring at room temperature for 6 hours, the reaction mixture was concentrated to obtain a residue. The residue was subjected to silica gel chromatography, which afforded 0.63 g of 4-(2-chlorobenzyloxy)-3,5-dichloro-1-(3,3-dibromo-2-propenyloxy)benzene (63% yield), m.p. 83.5° C.

PRODUCTION EXAMPLE 10

Production of Compound (23) by Production Process D

To a mixture of 0.51 g of 2,6-dichloro-4-(3,3,-dichloro-2-propenyloxy)phenol, 0.27 g of potassium carbonate and 20 ml of N,N-dimethylformamide was added dropwise a solution of 0.29 g of m-chlorobenzyl chloride dissolved in 5 ml of N,N-dimethylformamide, while stirring at room temperature. After stirring at room temperature for 7 hours, the reaction mixture was poured into ice-water, and extracted twice with 50 ml of diethyl ether. The combined ether layer was washed with water, dried with anhydrous magnesium sulfate, and concentrated to obtain a crude product. The crude product was subjected to silica gel chromatography, which afforded 0.50 g of 3,5-dichloro-4-(3-chlorobenzyloxy)-1-(3,3-dichloro-2-propenyloxy)benzene (69% yield), m.p. 87.0° C.

PRODUCTION EXAMPLE 11

Production of Compound (27) by Production Process D

To a mixture of 0.72 g of 2,6-dichloro-4-(3,3,-dichloro-2-propenyloxy)phenol, 0.38 g of potassium carbonate and 20 ml of N,N-dimethylformamide was added dropwise a solution of 0.71 g of 3-fluoro-4-phenoxybenzylbromide dissolved in 5 ml of N,N-dimethylformamide, while stirring at room temperature. After stirring at room temperature for 7 hours, the reaction mixture was poured into ice-water, and extracted twice with 50 ml of diethyl ether. The combined ether layer was washed with water, dried with anhydrous magnesium sulfate, and concentrated to obtain a crude product. The crude product was subjected to silica gel chromatography, which afforded 1.05 g of 3,5-dichloro-4-(3-fluoro-4-phenoxy)benzyloxy-1-(3,3-dichloro-2-propenyloxy)benzene (86% yield), $n_D^{22.5}$ 1.5973.

PRODUCTION EXAMPLE 12

Production of Compound (37) by Production Process E

To a solution of 0.41 g of 4-(3,3-dichloro-2-propenyloxy)-2,6-dichlorophenol, 0.17 g of (α-phenetyl alcohol and 0.37 g of triphenylphosphine dissolved in 10 ml of tetrahydrofuran was added dropwise a solution of 0.29 g of diisopropylazodicarboxylate dissolved in 5 ml of tetrahydrofuran, while stirring at room temperature. After stirring at room temperature for 12 hours, the reaction mixture was concentrated, and then mixed with 20 ml of diethyl ether. The precipitate was filtered, and the filtrate was concentrated. The residue was subjected to silica gel chromatography, which afforded 0.27 g of 3,5-dichloro-4-α-phenetyloxy-1-(3,3-dichloro-2-propenyloxy)benzene (48% yield), $n_D^{26.0}$ 1.5830.

PRODUCTION EXAMPLE 13

Production of Compound (42) by Production Process E

To a solution of 0.30 g of 4-(3,3-dichloro-2-propenyloxy)-2,6-dichlorophenol, 0.12 g of P-phenetyl alcohol and 0.27 g of triphenylphosphine dissolved in 10 ml of tetrahydrofuran was added dropwise a solution of 0.21 g of diisopropylazodicarboxylate dissolved in 5 ml of tetrahydrofuran, while stirring at room temperature. After stirring at room temperature for 12 hours, the reaction mixture was concentrated and mixed with 20 ml of diethyl ether. The precipitate was filtered, and the filtrate was concentrated. The residue was subjected to silica gel chromatography, which afforded 0.25 g of 3,5-dichloro-4-β-phenetyloxy-1-(3,3-dichloro-2-propenyloxy)benzene (61% yield), $n_D^{28.5}$ 1.5816.

PRODUCTION EXAMPLE 14

Production of Compound (19) by Production Process D

To a mixture of 0.51 g of 2,6-dichloro-4-(3,3,-dichloro-5-propenyloxy)phenol, 0.27 g of potassium carbonate and 20 ml of N,N-dimethylformamide was added dropwise a solution of 0.31 g of 2-(α-chloromethyl)naphthalene dissolved in 5 ml of N,N-dimethylformamide, while stirring at room temperature. After stirring at room temperature for 7 hours, the reaction mixture was poured into ice-water, and extracted twice with 50 ml of diethyl ether. The combined ether layer was washed with water, dried with anhydrous magnesium sulfate, and concentrated to obtain a crude product. The crude product was subjected to silica gel chromatography, which afforded 0.58 g of 3,5-dichloro-4-(2-naphthylmethyloxy)-1-(3,3-dichloro-2-propenyloxy)benzene (76% yield), m.p. 86.7° C.

PRODUCTION EXAMPLE 15

Production of Compound (16) by Production Process D

To a mixture of 0.62 g of 2,6-dichloro-4-(3,3,-dichloro-2-propenyloxy)phenol, 0.33 g of potassium carbonate and 20 ml of N,N-dimethylformamide was added dropwise a solution of 0.43 g of cinnamyl bromide dissolved in 5 ml of N,N-dimethylformamide, while stirring at room temperature. After stirring at room temperature for 7 hours, the reaction mixture was poured into ice-water, and extracted twice with 50 ml of diethyl ether. The combined ether layer was washed with water, dried with anhydrous magnesium sulfate, and concentrated to obtain a crude product. The crude product was subjected to silica gel chromatography, which afforded 0.70 g of 3,5-dichloro-4-(cinnamyloxy)-1-(3,3-dichloro-2-propenyloxy)benzene (80% yield), m.p. 51.3° C.

PRODUCTION EXAMPLE 16

Production of Compound (68) by Production Process D

To a mixture of 0.51 g of 2,6-dichloro-4-(3,3,-dichloro-2-propenyloxy)phenol, 0.17 g of potassium carbonate and 20 ml of N,N-dimethylformamide was added dropwise a solution of 0.34 g of 2-fluoro-5-(4-fluorophenoxy)benzyl bromide dissolved in 5 ml of N,N-dimethylformamide, while stirring at room temperature. After stirring at room temperature for 24 hours, the reaction mixture was poured into ice-water, and extracted twice with 50 ml of diethyl ether. The combined ether layer was washed with water, dried with anhydrous magnesium sulfate, and concentrated to obtain a crude product. The crude product was subjected to silica gel chromatography, which afforded 0.50 g of 3,5-dichloro-1-(3,3-dichloro-2-propenyloxy)-4-(2-fluoro-5-(4-fluorophenoxy) benzyloxy)benzene (68% yield), $n_D^{26.0}$ 1.5871.

PRODUCTION EXAMPLE 17

Production of Compound (84) by Production Process E

To a solution of 0.30 g of 2,6-dichloro-4-(3,3-dichloro-2-propenyloxy)phenol, phenol, 0.16 g of 3-chlorophenetyl alcohol and 0.27 g of triphenylphosphine dissolved in 10 ml of tetrahydrofuran was added dropwise a solution of 0.21 g of diisopropylazodicarboxylate dissolved in 5 ml of tetrahydrofuran, while stirring at room temperature. After siring at room temperature for 24 hours, the reaction mixture was concentrated to obtain a residue. The residue was subjected to silica gel chromatography, which afforded 0.36 g of 3,5-dichloro-1-(3,3-dichloro-2-propenyloxy)-4-(2-(3-chlorophenyl)ethoxy)benzene (81% yield), $n_D^{26.0}$ 1.5897.

PRODUCTION EXAMPLE 18

Production of Compound (86) by Production Process E

To a solution of 0.30 g of 2,6-dichloro-4-(3,3-dichloro-2-propenyloxy)phenol, 0.20 g of 3-(trifluoromethyl) phenetyl alcohol and 0.27 g of triphenylphosphine dissolved in 10 ml of tetrahydrofuran was added dropwise a solution of 0.21 g of diisopropylazodicarboxylate dissolved in 5 ml of tetrahydrofuran, while stirring at room temperature. After stirring at room temperature for 24 hours, the reaction mixture was concentrated to obtain a residue. The residue was subjected to silica gel chromatography, which afforded 0.39 g of 3,5-dichloro-1-(3,3-dichloro-2-propenyloxy)-4-(2-(3-(trifluoromethyl) phenyl)ethoxy)benzene (81% yield), $n_D^{26.0}$ 1.5497.

PRODUCTION EXAMPLE 19

Production of Compound (91) by Production process E

A mixture of 1.14 g of 2,6-dichloro-4-(3,3-dichloro-2-propenyloxy)phenol, 1.20 g of 3-(4-chlorophenoxy)propyl bromide, 0.83 g of potassium carbonate and 20 ml of N,N-dimethylformamide was stirred at 80° C. for 6 hours. The reaction mixture was poured into ice-water, and extracted twice with 50 ml of diethyl ether. The combined ether layer was washed with water, dried with anhydrous magnesium sulfate, and concentrated to obtain a crude product. The crude product was subjected to silica gel chromatography, which afforded 1.01 g of 3,5-dichloro-1-(3,3-dichloro-2-propenyloxy)-4-(3-(4-chlorophenoxy) propyloxy)benzene (55% yield), $n_D^{25.0}$ 1.5822.

PRODUCTION EXAMPLE 20

Production of Compound (99) by Production Process E

To a solution of 0.30 g of 2,6-dichloro-4-(3,3-dichloro-2-propenyloxy)phenol, 0.24 g of 3-(4-bromophenoxy)-1-propanol and 0.27 g of triphenylphosphine dissolved in 10 ml of tetrahydrofuran was added dropwise a solution of 0.21 g of diisopropylazodicarboxylate dissolved in 5 ml of tetrahydrofuran, while stirring at room temperature. After stirring at room temperature for 24 hours, the reaction mixture was concentrated to obtain a residue. The residue was subjected to silica gel chromatography, which afforded 0.34 g of 3,5-dichloro-1-(3,3-dichloro-2-propenyloxy)-4-(3-(4-bromophenoxy) propyloxy)benzene (65% yield), $n_D^{25.0}$ 1.5917.

PRODUCTION EXAMPLE 21

Production of Compound (100) by Production Process E

To a solution of 0.30 g of 2,6-dichloro-4-(3,3-dichloro-2-propenyloxy)phenol, 0.25 g of 3-(4-trifluoromethoxy) phenoxy)-1-propanol and 0.27 g of triphenylphosphine dissolved in 10 ml of tetrahydrofuran was added dropwise a solution of 0.21 g of diisopropylazodicarboxylate dissolved in 5 ml of tetrahydrofuran, while stirring at room temperature. After stirring at room temperature for 24 hours, the reaction mixture was concentrated to obtain a residue. The residue was subjected to silica gel chromatography, which afforded 0.41 g of 3,5-dichloro-1-(3,3-dichloro-2-propenyloxy)-4-(3-(4-(trifluoromethoxy) phenoxy) propyloxy)benzene (78% yield), $n_D^{25.0}$ 1.5342.

PRODUCTION EXAMPLE 22

Production of Compound (166) by Production Process F

A mixture of 0.56 g of 3,5-dichloro-4-(3-bromopropyloxy)-1-(3,3-dichloro-2-propenyloxy)benzene, 0.22 g of 4-trifluoromethylphenol, 0.21 g of potassium carbonate and 20 ml of N,N-dimethylformamide was stirred at room temperature. After stirring for 7 hours, the reaction mixture was poured into ice-water, and extracted twice with 50 ml of diethyl ether. The combined ether layer was washed with water, dried with anhydrous magnesium sulfate, and concentrated to obtain a crude product. The crude product was subjected to silica gel chromatography, which afforded 0.48 g of 3,5-dichloro-4-(3-(4-trifluoromethylphenoxy) propyloxy)-1-(3,3-dichloro-2-propenyloxy)benzene (71% yield), $n_D^{24.4}$ 1.5390.

PRODUCTION EXAMPLE 23

Production of Compound (203) by Production Process F

A mixture of 0.88 g of 3,5-dichloro-4-(4-bromobutyloxy)-1-(3,3-dichloro-2-propenyloxy) propenyloxy)benzene, 0.32 g of 4-isopropoxyphenol, 0.32 g of potassium carbonate and 20 ml of N,N-dimethylformamide was stirred at room temperature. After 7 hours, the reaction mixture was poured into ice-water, and extracted twice with 50 ml of diethyl ether. The combined ether layer was washed with water, dried with anhydrous magnesium sulfate, and concentrated to obtain a crude product. The crude product was subjected to silica gel chromatography, which afforded 0.54 g of 3,5-dichloro-4-(4-(4-iso-propoxyphenoxy) butyloxy)-1-(3,3-dichloro-2-propenyloxy)benzene (51% yield), $n_D^{23.0}$ 1.5578.

PRODUCTION EXAMPLE 24

Production of Compound (222) by Production Process F

A mixture of 0.61 g of 3,5-dichloro-4-(4-bromobutyloxy)-1-(3,3-dichloro-2-propenyloxy) benzene, 0.19 g of 4-chlorophenol, 0.22 g of potassium carbonate and 20 ml of N,N-dimethylformamide was stirred at room temperature. After 7 hours, the reaction mixture was poured into ice-water, and extracted twice with 50 ml of diethyl ether. The combined ether layer was washed with water, dried with anhydrous magnesium sulfate, and concentrated to obtain a crude product. The crude product was subjected to silica gel chromatography, which afforded 0.54 g of 3,5-dichloro-4-(4-(4-chlorophenoxy) butyloxy)-1-(3,3-dichloro-2-propenyloxy)benzene (59% yield), m.p. 54.5° C.

PRODUCTION EXAMPLE 25

Production of Compound (152) by Production Process F

In a reaction vessel were placed 0.29 g of 3,5-dichloro-4-(3-bromopropyloxy)-1-(3,3-dichloro-2-propenyloxy) benzene, 0.12 g of 4-ethoxybenzoic acid, 0.12 g of potassium carbonate and 10 ml of N,N-dimethylformamide, followed by stirring at room temperature for 12 hours. The reaction mixture was poured into water, and extracted twice with 50 ml of diethyl ether. The combined ether layer was washed with water, dried with anhydrous magnesium sulfate, and concentrated to obtain a crude product. The crude product was subjected to silica gel chromatography, which afforded 0.30 g of 3,5-dichloro-4-(3-(4-ethoxybenzoyloxy)propyloxy)-1-(3,3-dichloro-2-propenyloxy)-benzene (86% yield), $n_D^{24.0}$ 1.5715.

PRODUCTION EXAMPLE 26

Production of Compound (235) by Production Process F

In a reaction vessel were placed 0.20 g of 3,5-dichloro-4-(3-bromopropyloxy)-1-(3,3-dichloro-2-propenyloxy) benzene, 0.10 g of 4-chlorophenylacetic acid, 0.08 g of potassium carbonate and 5 ml of N,N-dimethylformamide, followed by stirring at room temperature for 12 hours. The reaction mixture was poured into water, and extracted twice with 30 ml of diethyl ether. The combined ether layer was washed with water, dried with anhydrous magnesium sulfate, and concentrated to obtain a crude product. The crude product was subjected to silica gel chromatography, which afforded 0.22 g of 3,5-dichloro-4-(3-(4-chlorophenylacetyloxy)propyloxy)-1-(3,3-dichloro-2-propenyloxy) benzene (90% yield), $n_D^{22.0}$ 1.5698.

PRODUCTION EXAMPLE 27

Production of Compound (236) by Production Process F

In a reaction vessel were placed 0.20 g of 3,5-dichloro-4-(3-bromopropyloxy)-1-(3,3-dichloro-2-propenyloxy) benzene, 0.11 g of 4-chlorocinnamic acid, 0.08 g of potassium carbonate and 5 ml of N,N-dimethylformamide, followed by stirring at room temperature for 12 hours. The reaction mixture was poured into water, and extracted twice with 30 ml of diethyl ether. The combined ether layer was washed with water, dried with anhydrous magnesium sulfate, and concentrated to obtain a crude product. The crude product was subjected to silica gel chromatography, which afforded 0.24 g of 3,5-dichloro-4-(3-(4-chlorophenylacetyloxy)propyloxy)-1-(3,3-dichloro-2-propenyloxy) benzene (96% yield), m.p. 62.2° C.

PRODUCTION EXAMPLE 27

Production of Compound (237) by Production Process F

In a reaction vessel were placed 0.20 g of 3,5-dichloro-4-(3-bromopropyloxy)-1-(3,3-dichloro-2-propenyloxy) benzene, 0.11 g of 4-chlorophenoxyacetic acid, 0.08 g of potassium carbonate and 5 ml of N,N-dimethylformamide, followed by stirring at room temperature for 12 hours. The reaction mixture was poured into water, and extracted twice with 30 ml of diethyl ether. The combined ether layer was washed with water, dried with anhydrous magnesium sulfate, and concentrated to obtain a crude product. The crude product was subjected to silica gel chromatography, which afforded 0.23 g of 3,5-dichloro-4-(3-(4-chlorophenoxyacetyloxy)propyloxy)-1-(3,3-dichloro-2-propenyloxy) benzene (91% yield), $n_D^{22.0}$ 1.5709.

PRODUCTION EXAMPLE 29

Production of Compound (185) by Production Process G

To a solution of 1.10 g of 3,5-dichloro-4-(3-hydroxypropoxy)-1-(3,3-dichloro-2-propenyloxy)benzene, 0.56 g of 3-trifluoromethoxyphenol and 0.83 g of triphenylphosphine dissolved in 20 ml of tetrahydrofuran was added dropwise a solution of 0.64 g of diisopropylazodicarboxylate dissolved in 10 ml of tetrahydrofuran, while stirring at room temperature. After stirring at room temperature for 24 hours, the reaction mixture was concentrated to obtain a residue. The residue was subjected to silica gel chromatography, which afforded 1.03 g of 3,5-dichloro-4-(3-(4-trifluoromethoxyphenoxy) propoxy)-1-(3,3-dichloro-2-propenyloxy)benzene (64% yield), $n_D^{23.4}$ 1.5343.

PRODUCTION EXAMPLE 30

Production of Compound (276) by Production Process F

A mixture of 3.9 g of 4-(trifluoromethyl)aniline and 0.50 g of 1-(3-bromopropyloxy)-2,6-dichloro-4-(3,3-dichloro-2-propenyloxy)benzene was stirred at 90° C. to 100° C. for 3 hours. After cooling to room temperature, the reaction mixture was subjected to silica gel chromatography, which afforded 0.37 g of 3,5-dichloro-1-(3,3-dichloro-2-propenyloxy)-4-(3-(4-(trifluoromethyl)phenylamino) propyloxy)benzene (62% yield), $n_D^{23.5}$ 1.5617.

PRODUCTION EXAMPLE 31

Production of Compound (277)

A mixture of 0.37 g of 3,5-dichloro-1-(3,3-dichloro-2-propenyloxy)-4-(3-(4-(trifluoromethyl) phenylamino) propyloxy)benzene, 0.1 ml of methyl iodide, 0.12 g of potassium carbonate and 10 ml of N,N-dimethylformamide was stirred at 50° C. for 3 hours. After cooling to room temperature, the reaction mixture was poured into ice-water, and extracted twice with 50 ml of ethyl acetate. The combined ethyl acetate layer was washed with water, dried with anhydrous magnesium sulfate, and concentrated to obtain a crude product. The crude product was subjected to silica gel chromatography, which afforded 0.26 g of 3,5-dichloro-1-(3,3-dichloro-2-propenyloxy)-4-(3-(methyl(4-(trifluoromethyl)phenyl)amino)propyloxy)benzene (68% yield), $n_D^{25.5}$ 1.5593.

PRODUCTION EXAMPLE 32

Production of Compound (182) according to Production Process F

A mixture of 0.47 g of 4-chlorothiophenol, 1.33 g of 1-(3-bromopropyloxy)-2,6-dichloro-4-(3,3-dichloro-2-propenyloxy)benzene, 0.49 g of potassium carbonate and 20 ml of N,N-dimethylformamide was stirred at room temperature for 24 hours. The reaction mixture was poured into ice-water, and extracted twice with 50 ml of diethyl ether. The combined ether layer was washed with water, dried with anhydrous magnesium sulfate, and concentrated to obtain a crude product. The crude product was subjected to silica gel chromatography, which afforded 1.24 g of 1-(3-(4-chlorophenylthio) propyloxy)-2,6-dichloro-4-(3,3-dichloro-2-propenyloxy)benzene (81% yield), $n_D^{26.0}$ 1.6035.

PRODUCTION EXAMPLE 33

Production of Compound (268)

A mixture of 0.50 g of 1-(3-(4-chlorophenylthio)propyloxy)-2,6-dichloro-4-(3,3-dichloro-2-propenyloxy) benzene and 20 ml of methylene chloride was stirred under cooling with ice-water, to which 0.26 g of m-chloroperbenzoic acid was added. After stirring at room temperature for 24 hours, the methylene chloride layer was separated, washed successively with saturated aqueous sodium sulfite solution, saturated aqueous sodium hydrogencarbonate solution and saturated saline solution, dried with magnesium sulfate, and concentrated to obtain a crude product. The crude product was subjected to silica gel chromatography, which afforded 0.38 g of 1-(3-(4-chlorophenylsulfinyl)propyloxy)-2,6-dichloro-4-(3,3-dichloro-2-propenyloxy)benzene (73% yield), $n_D^{24.5}$ 1.5962.

PRODUCTION EXAMPLE 34

Production of Compound (285)

A mixture of 0.50 g of 1-(3-(4-chlorophenylthio)propyloxy)-2,6-dichloro-4-(3,3-dichloro-2-propenyloxy)benzene and 20 ml of methylene chloride was stirred under cooling with ice-water, to which 0.52 g of m-chloroperbenzoic acid was added. After stirring at room temperature for 24 hours, the methylene chloride layer was separated, washed successively with saturated aqueous sodium sulfite solution, saturated aqueous sodium hydrogencarbonate solution and saturated saline solution, dried with magnesium sulfate, and concentrated to obtain a crude product. The crude product was subjected to silica gel chromatography, which afforded 0.44 g of 1-(3-(4-chlorophenylsulfonyl)propyloxy)-2,6-dichloro-4-(3,3-dichloro-2-propenyloxy)benzene (82% yield), $n_D^{24.5}$ 1.5863.

PRODUCTION EXAMPLE 35

Production of Compound (242) by Production Process E

In a reaction vessel were placed 0.53 g of 4-(3-fluorophenyl)-3-buten-1-ol and 50 ml of ethyl acetate, and the air in the vessel was exchanged for nitrogen. Then, 0.1 g of 10% palladium carbon was added thereto, and the nitrogen in the vessel was exchanged for hydrogen, followed by vigorous stirring at room temperature for 24 hours. After the hydrogen in the vessel was exchanged for nitrogen, the reaction solution was filtered through a celite bed, and the filtrate was concentrated. The residue was subjected to silica gel chromatography, which afforded 0.48 g of 4-(3-fluorophenyl)-1-butanol.

To a solution of 0.18 g of 4-(3-fluorophenyl)-1-butanol, 0.30 g of 2,6-dichloro-4-(3,3-dichloro-2-propenyloxy) phenol and 0.27 g of triphenylphosphine dissolved in 10 ml of tetrahydrofuran, a solution of 0.20 ml of N,N-diisopropylazodicarboxylate dissolved in 5 ml of tetrahydrofuran was added dropwise, while stirring at room temperature. After stirring at room temperature for 24 hours, the reaction mixture was concentrated to obtain a residue. The residue was subjected to silica gel chromatography, which afforded 0.38 g of 3,5-dichloro-1-(3,3-dichloro-2-propenyloxy)-4-(4-(3-fluorophenyl) butyloxy)benzene (83% yield), $n_D^{25.0}$ 1.5620.

PRODUCTION EXAMPLE 36

Production of Compound (239) by Production Process E

A mixture of 4.0 g of (3-hydroxypropyl)triphenylphosphonium bromide and 20 ml of tetrahydrofuran was cooled to 0° C., to which 12.5 ml of 1.6M n-butyl lithium (as a hexane solution) was slowly added dropwise. The reaction mixture was stirred at 0° C. for 30 minutes, to which a mixture of 1.24 g of 3-fluorobenzaldehyde and 10 ml of tetrahydrofuran was slowly added dropwise at the same temperature, followed by further stirring at room temperature for 6 hours. The reaction mixture was poured into ice-water, acidified by the addition of 10% hydrochloric acid, and extracted twice with 50 ml of diethyl ether. The combined ether layer was washed with saturated saline solution, dried with anhydrous magnesium sulfate, and concentrated to obtain a crude product. The crude product was subjected to silica gel chromatography, which afforded 0.70 g of 4-(3-fluorophenyl)-3-buten-1-ol.

To a solution of 0.17 g of 4-(3-fluorophenyl)-3-buten-1-ol, 0.30 g of 2,6-dichloro-4-(3,3-dichloro-2-propenyloxy) phenol and 0.27 g of triphenylphosphine dissolved in 10 ml of tetrahydrofuran was added dropwise a solution of 0.20 ml of N,N-diisopropylazodicarboxylate dissolved in 5 ml of tetrahydrofuran, while stirring at room temperature. After the stirring was continued at room temperature for 24 hours, the reaction mixture was concentrated to obtain a residue. The residue was subjected to silica gel chromatography, which afforded 0.38 g of 3,5-dichloro-1-(3,3-dichloro-2-propenyloxy)-4-(4-(3-fluorophenyl)-3-butenyloxy)benzene (84% yield), $n_D^{25.5}$ 1.5857.

PRODUCTION EXAMPLE 37

Production of Compound (270) by Production Process E

To a mixture of 20.4 g of 1,3-dibromopropane, 7.1 g of potassium carbonate and 100 ml of N,N-dimethylformamide was added dropwise a solution of 9 g of 4-trifluoromethoxyphenol dissolved in 30 ml of N,N-dimethylformamide, while stirring at room temperature. After stirring at room temperature for 24 hours, the reaction mixture was filtered, and the solvent was removed from the filtrate by distillation under reduced pressure. The residue was subjected to silica gel chromatography, which afforded 9.1 g of 1-(3-bromopropyloxy)4-trifluoromethoxybenzene (60% yield).

To a mixture of 0.6 g of 3,5-diethyl-4-[3-(4-(trifluoromethoxy)phenoxy)propyloxy]phenol thus obtained, 0.21 g of potassium carbonate and 10 ml of N,N-dimethylformamide was added dropwise a solution of 0.30 g of 1,1,3-trichloro-1-propene dissolved in 5 ml of N,N-dimethylformamide, while stirring at room temperature. After stirring at room temperature for 12 hours, the reaction mixture was poured into ice-water, and extracted twice with 100 ml of diethyl ether. The combined ether layer was washed with water, dried with anhydrous magnesium sulfate, and concentrated to obtain a crude product. The crude product was subjected to silica gel chromatography, which afforded 0.56 g of 3,5-diethyl-4-[3-(4-trifluoromethoxyphenoxy)propyloxyl-1-(3,3-dichloro-2-propenyloxy)benzene (80% yield), $n_D^{25.9}$ 1.5115.

PRODUCTION EXAMPLE 38

Production of Compound (216) by Production Process D

First, 0.35 g of 1-(3-bromopropyloxy)-4-trifluoromethylbenzene (prepared in the same manner as described above for 1-(3-bromopropyloxy)-4-trifluoromethoxybenzene) and 0.2 g of potassium carbonate were dissolved in 100 ml of N,N-dimethylformamide, to which 0.3 g of 2-chloro-6-methyl-4-(3,3-dichloro-2-propenyloxy)phenol was added, and the mixture was stirred at room temperature for 24 hours. The reaction mixture was mixed with 200 ml of diethyl ether, washed with water, dried with anhydrous magnesium sulfate, and concentrated to obtain a crude product. The crude product was subjected to silica gel chromatography, which afforded 0.50 g of 3-chloro-4-[3-(4-trifluoromethylphenoxy) propyloxy]-5-methyl-1-(3,3-dichloro-2-propenyloxy)benzene (94% yield), $n_D^{23.0}$ 1.5330.

Production Example 39

Production of compound (272) by production process A

To a mixture of 0.6 g of 3-ethyl-4-[3-(4-trifluoromethoxyphenoxy)propyloxy]-5-methylphenol, 0.22 g of potassium carbonate and 10 ml of N,N-dimethylformamide was added dropwise a solution of 0.31 g of 1,1,3-trichloro-1-propene dissolved in 5 ml of N,N-dimethylformamide, while stirring at room temperature. After stirring at room temperature for 12 hours, the reaction mixture was poured into ice-water, and extracted twice with 100 ml of diethyl ether. The combined ether layer was washed with water, dried with anhydrous magnesium sulfate, and concentrated to obtain a crude product. The crude product was subjected to silica gel chromatography, which afforded 0.5 g of 3-ethyl-4-[3-(4-trifluoromethoxyphenoxy)propyloxy]-5-methyl-1-(3,3-dichloro-2-propenyloxy)benzene (71% yield), $n_D^{23.5}$ 1.5150.

The following are specific examples of the present compounds under the corresponding compound numbers with their physical properties, if measured.

(1) 3,5-Dichloro-4-(1,1,2,2-tetrafluoroethoxy)-1-(3,3-dichloro-2-propenyloxy)benzene $n_D^{24.6}$ 1.5067
(2) 3,5-Dichloro-4-(1,1,2,2-tetrafluoroethoxy)-1-(3,3-dibromo-2-propenyloxy)benzene $n_D^{24.6}$ 1.5333
(3) 2,6-Dichloro-4-(3,3-dichloro-2-propenyloxy)-1-(3,3-dichloro-2-propenyloxy)benzene m.p. 75.8° C.
(4) 2,6-Dichloro-4-(3,3-dibromo-2-propenyloxy)-1-(3,3-dibromo -2-propenyloxy)benzene $n_D^{22.5}$ 1.6459
(5) 3,5-Dichloro-4-ethoxy-1-(3,3-dichloro-2-propenyloxy) benzene $n_D^{24.5}$ 1.5561
(6) 3,5-Dichloro-4-ethoxy-1-(3,3-dibromo-2-propenyloxy) benzene $n_D^{24.5}$ 1.5865
(7) 3,5-Dichloro-4-(3,3-dibromo-2-propenyloxy)-1-(3,3-dichloro-2-propenyloxy)benzene m.p 51.9° C.
(8) 3,5-Dichloro-4-(4-trifluoromethylbenzyloxy)-1-(3,3-dichloro-2-propenyloxy)benzene m.p. 77.1° C.
(9) 3,5-Dichloro-4-(3-methyl-2-butenyloxy)-1-(3,3-dichloro-2-propenyloxy)benzene $n_D^{24.0}$ 1.5556
(10) 3,5-Dichloro-4-(3-chloro-2-butenyloxy)-1-(3,3-dichloro-2-propenyloxy)benzene $n_D^{24.0}$ 1.5552
(11) 3,5-Dichloro-4-(3-chloro-2-propenyloxy)-1-(3,3-dichloro-2-propenyloxy)benzene $n_D^{24.0}$ 1.5694
(12) 3,5-Dichloro-4-(3-trifluoromethylbenzyloxy)-1-(3,3-dichloro-2-propenyloxy)benzene m.p. 51.6° C.
(13) 3,5-Dichloro-4-(4-tert-butoxycarbonylbenzyloxy)-1-(3,3-dichloro-2-propenyloxy)benzene m.p. 78.3° C.
(14) 3,5-Dichloro-4-(4-tert-butylbenzyloxy)-1-(3,3-dichloro-2-propenyloxy)benzene $n_D^{24.5}$ 1.5670
(15) 3,5-Dichloro-4-(4-methoxy benzyloxy)-1-(3,3-dichloro-2-propenyloxy)benzene m.p. 95.4° C.
(16) 3,5-Dichloro-4-(4-cynnamyloxy)-1-(3,3-dichloro-2-propenyloxy)benzene m.p. 51.3° C.
(17) 3,5-Dichloro-4-(3,5-bis(trifluoromethyl)benzyloxy)-1-(3,3-dichloro-2-propenyloxy)benzene m.p. 58.8° C.
(18) 3,5-Dichloro-4-(3-methoxybenzyloxy)-1-(3,3-dichloro-2-propenyloxy)benzene m.p. 73.9° C.
(19) 3,5-Dichloro-4-(2-naphthylmethyloxy)-1-(3,3-dichloro-2-propenyloxy)benzene m.p. 86.7° C.
(20) 3,5-Dichloro-4-(1-naphthylmethoxy)-1-(3,3-dichloro-2-propenyloxy)benzene m.p. 84.1° C.
(21) 3,5-Dichloro-4-(3-cyanobenzyloxy)-1-(3,3-dichloro-2-propenyloxy)benzene m.p. 122.9° C.
(22) 3,5-Dichloro-4-(3-fluorobenzyloxy)-1-(3,3-dichloro-2-propenyloxy)benzene m.p. 75.3° C.
(23) 3,5-Dichloro-4-(3-chlorobenzoyloxy)-1-(3,3-dichloro-2-propenyloxy)benzene m.p. 87.0° C.
(24) 3,5-Dichloro-4-(3-bromobenzyloxy)-1-(3,3-dichloro-2-propenyloxy)benzene m.p. 73.6° C.
(25) 3,5-Dichloro-4-benzyloxy-1-(3,3-dichloro-2-propenyloxy)benzene m.p. 46.8° C.
(26) 3,5-Dichloro-4-(3-methylbenzyloxy)-1-(3,3-dichloro-2-propenyloxy)benzene m.p. 43.6° C.
(27) 3,5-Dichloro-4-(3-fluoro-4-phenoxy)benzyl oxy)-1-(3,3-dichloro-2-propenyloxy) benzene $n_D^{22.5}$ 1.5973
(28) 3,5-Dichloro-4-(4-chlorobenzyloxy)-1-(3,3-dichloro-2-propenyloxy)benzene m.p. 67.8° C.
(29) 3,5-Dichloro-4-(2-chlorobenzyloxy)-1-(3,3-dichloro-2-propenyloxy)benzene m.p. 82.0° C.
(30) 3,5-Dichloro-4-(2,4-dichloro benzyloxy)-1-(3,3-dichloro-2-propenyloxy)benzene m.p. 89.3° C.
(31) 3,5-Dichloro-4-(2,5-dichloro benzyloxy)-1-(3,3-dichloro-2-propenyloxy)benzene m.p. 98.9° C.
(32) 3,5-Dichloro-4-(3,4-dichloro benzyloxy)-1-(3,3-dichloro-2-propenyloxy)benzene m.p. 95.2° C.
(33) 3,5-Dichloro-4-(4-bromobenzyloxy)-1-(3,3-dichloro-2-propenyloxy)benzene m.p. 85.5° C.
(34) 3,5-Dichloro -4-(3-phenoxybenzyloxy)-1-(3,3-dichloro -2-propenyloxy)benzene $n_D^{25.5}$ 1.6066

(35) 3,5-Dichloro-4-(4-phenoxy benzyloxy)-1-(3,3-dichloro-2-propenyloxy)benzene $n_D^{25.5}$ 1.6084
(36) 3,5-Dichloro-4-(4-phenylbenzyloxy)-1-(3,3-dichloro-2-propenyloxy)benzene m.p. 112.6° C.
(37) 3,5-Dichloro-4-((α-phenethyloxy)-1-(3,3-dichloro-2-propenyloxy)benzene $n_D^{26.0}$ 1.5830.
(38) 3,5-Dichloro-4-(3,4-methylenedioxybenzyloxy)-1-(3,3-dichloro-2-propenyloxy)benzene m.p. 97.3° C.
(39) 3,5-Dichloro-4-(3-benzyloxybenzyloxy)-1-(3,3-dichloro-2-propenyloxy)benzene $n_D^{25.0}$ 1.6040
(40) 3,5-Dichloro-4-(1-(2-methylnaphthyl)methoxy)-1-(3,3-dichloro-2-propenyloxy)benzene m.p. 120.3° C.
(41) 3,5-Dichloro-4-(4-fluoro-3-phenoxy)benzyloxy)-1-(3,3-dibromo-2-propenyloxy)benzene $n_D^{22.5}$ 1.6062
(42) 3,5-Dichloro-4-(β-phenethyloxy)-1-(3,3-dichloro-2-propenyloxy)benzene $n_D^{28.5}$ 1.5816
(43) 3,5-Dichloro-4-(2-methyl-3-phenylbenzyloxy)-1-(3,3-dichloro-2-propenyloxy)benzene $n_D^{28.5}$ 1.6125
(44) 3,5-Dichloro-4-(2-phenylbenzyloxy)-1-(3,3-dichloro-2-propenyloxy)benzene $n_D^{28.5}$ 1.6164
(45) 3,5-Dichloro-4-(4-fluorobenzyloxy)-1-(3,3-dichloro-2-propenyloxy)benzene m.p. 72.0° C.
(46) 3,5-Dichloro-4-(2-methylbenzyloxy)-1-(3,3-dichloro-2-propenyloxy)benzene m.p. 52.9° C.
(47) 4-(2-Chlorobenzyloxy)-3,5-dichloro-1-(3,3-dibromo-2-propenyloxy)benzene m.p. 83.5° C.
(48) 3,5-Dichloro-4-(2-bromobenzyloxy)-1-(3,3-dichloro-2-propenyloxy)benzene m.p. 82.5° C.
(49) 3,5-Dichloro-4-(2-fluorobenzyloxy)-1-(3,3-dichloro-2-propenyloxy)benzene m.p. 60.6° C.
(50) 3,5-Dichloro-4-(2,6-dichloro benzyloxy)-1-(3,3-dichloro-2-propenyloxy)benzene m.p. 135.6° C.
(51) 3,5-Dichloro-4-(2-bromoethoxy)-1-(3,3-dichloro-2-propenyloxy)benzene $n_D^{24.0}$ 1.5813
(52) 3,5-Dichloro-4-(2,2-dichloroethoxy)-1-(3,3-dichloro-2-propenyloxy)benzene $n_D^{24.0}$ 1.5719
(53) 3,5-Dichloro-4-(4-(methylthio)butoxy)-1-(3,3-dichloro-2-propenyloxy)benzene $n_D^{24.0}$ 1.5673
(54) 3,5-Dichloro-4-(3-phenylpropoxy)-1-(3,3-dichloro-2-propenyloxy)benzene $n_D^{23.5}$ 1.5794
(55) 3,5-Dichloro-4-(3-isopropoxy-4-chlorobenzyloxy)-1-(3,3-dichloro-2-propenyloxy)benzene $n_D^{22.5}$ 1.5780
(56) 3,5-Dichloro-4-(4-benzyloxybenzyloxy)-1-(3,3-dichloro-2-propenyloxy)benzene $n_D^{23.5}$ 1.6047
(57) 3,5-Dichloro-4-(4-chloro-3-phenoxybenzyloxy)-1-(3,3-dichloro-2-propenyloxy)benzene $n_D^{23.0}$ 1.6112
(58) 3,5-Dichloro-4-(4-methoxy-3-benzyloxybenzyloxy)-1-(3,3-dichloro-2-propenyloxy)benzene $n_D^{22.0}$ 1.5958
(59) 3,5-Dichloro-4-(3-(3,4-dichlorophenoxy)benzyloxy)-1-(3,3-dichloro-2-propenyloxy)benzene $n_D^{22.0}$ 1.6160
(60) 3,5-Dichloro-4-(3-(3-trifluoromethylbenzyloxy)benzyloxy)-1-(3,3-dichloro-2-propenyloxy)benzene $n_D^{22.0}$ 1.5713
(61) 3,5-Dichloro-4-(3-(4-chlorophenoxy)benzyloxy)-1-(3,3-dichloro-2-propenyloxy)benzene $n_D^{22.5}$ 1.6087
(62) 3,5-Dichloro-1-(3,3-dichloro-2-propenyloxy)-4-(3-(3-phenoxyphenyl)propoxy)benzene $n_D^{25.0}$ 1.5928
(63) 3,5-Dichloro-1-(3,3-dichloro-2-propenyloxy)-4-(4-chloro phenethyloxy)benzene $n_D^{24.5}$ 1.5868
(64) 3,5-Dichloro-1-(3,3-dichloro-2-propenyloxy)-4-((4-phenyl)butyloxy)benzene $n_D^{26.0}$ 1.5716
(65) 3,5-Dichloro-1-(3,3-dichloro-2-propenyloxy)-4-((5-phenyl)pentyloxy)benzene $n_D^{26.0}$ 1.5690
(66) 3,5-Dichloro-1-(3,3-dichloro-2-propenyloxy)-4-(1-indanyloxy)benzene $n_D^{26.0}$ 1.5982
(67) 3,5-Dichloro-1-(3,3-dichloro-2-propenyloxy)-4-(2-methyl-1-(4-phenoxyphenyl)-n-propoxy)benzene $n_D^{26.0}$ 1.5885
(68) 3,5-Dichloro-1-(3,3-dichloro-2-propenyloxy)-4-(2-fluoro-5-(4-fluorophenoxy)benzyloxy)benzene $n_D^{26.0}$ 1.5871
(69) 3,5-Dichloro-1-(3,3-dichloro-2-propenyloxy)-4-(4-fluorophenethyloxy)benzene $n_D^{26.5}$ 1.5711
(70) 3,5-Dichloro-1-(3,3-dichloro-2-propenyloxy)-4-(4-bromophenethyloxy)benzene $n_D^{26.5}$ 1.5985
(71) 3,5-Dichloro-1-(3,3-dichloro-2-propenyloxy)-4-(4-methylphenethyloxy)benzene $n_D^{26.5}$ 1.5815
(72) 3,5-Dichloro-1-(3,3-dichloro-2-propenyloxy)-4-(4-methoxyphenethyloxy)benzene $n_D^{26.5}$ 1.5806
(73) 3,5-Dichloro-1-(3,3-dichloro-2-propenyloxy)-4-(1-(4-phenoxyphenyl)ethoxy)benzene $n_D^{25.0}$ 1.6007
(74) 3,5-Dichloro-1-(3,3-dichloro-2-propenyloxy)-4-(2-chloro phenethyloxy)benzene $n_D^{24.5}$ 1.5872
(75) 3,5-Dichloro-1-(3,3-dichloro-2-propenyloxy)-4-(2-(1-naphthyl)ethoxy)benzene $n_D^{24.4}$ 1.6189
(76) 3,5-Dichloro-1-(3,3-dichloro-2-propenyloxy)-4-(2-phenoxyethoxy)benzene $n_D^{25.0}$ 1.5836
(77) 3,5-Dichloro-1-(3,3-dichloro-2-propenyloxy)-4-(3-phenoxypropyloxy)benzene $n_D^{25.0}$ 1.5762
(78) 3,5-Dichloro-1-(3,3-dichloro-2-propenyloxy)-4-(2-bromo-5-phenoxybenzyloxy)benzene $n_D^{26.5}$ 1.6188
(79) 3,5-Dichloro-1-(3,3-dichloro-2-propenyloxy)-4-(4-(4-(trifluoromethyl)phenoxy)benzyloxy)benzene $n_D^{26.5}$ 1.5730
(80) 3,5-Dichloro-1-(3,3-dichloro-2-propenyloxy)-4-(3-(4-tert-butylphenoxy)benzyloxy)benzene $n_D^{26.5}$ 1.5889
(81) 3,5-Dichloro-1-(3,3-dichloro-2-propenyloxy)-4-(6-phenylhexyloxy)benzene $n_D^{26.0}$ 1.5702
(82) 3,5-Dichloro-1-(3,3-dichloro-2-propenyloxy)-4-(3-(4-methylphenoxy)benzyloxy)benzene $n_D^{26.0}$ 1.6019
(83) 3,5-Dichloro-1-(3,3-dichloro-2-propenyloxy)-4-(3-(3,5-dichlorophenoxy)benzyloxy)benzene $n_D^{26.0}$ 1.6148
(84) 3,5-Dichloro-1-(3,3-dichloro-2-propenyloxy)-4-(2-(3-chlorophenyl)ethoxy)benzene $n_D^{26.0}$ 1.5897
(85) 3,5-Dichloro-1-(3,3-dichloro-2-propenoyloxy)-4-(2-(2-(trifluoromethyl)phenyl)ethoxy)benzene $n_D^{26.0}$ 1.5516
(86) 3,5-Dichloro-1-(3,3-dichloro-2-propenyloxy)-4-(2-(3-trifluoromethylphenyl)ethoxy)benzene
(87) 3,5-Dichloro-4-methoxymethoxy-1-(3,3-dichloro-2-propenyloxy)benzene $n_D^{26.5}$ 1.5596
(88) 3,5-Dichloro-4-(3-(3-trifluoromethylphenyl)propyloxy)-1-(3,3-dichloro-2-propenyloxy)benzene $n_D^{24.0}$ 1.5430
(89) 3,5-Dichloro-4-(3-(3-chlorophenyl)propyloxy)-1-(3,3-dichloro-2-propenyloxy)benzene $n_D^{24.0}$ 1.5828
(90) 3,5-Dichloro-4-(3-(4-chlorophenyl)propyloxy)-1-(3,3-dichloro-2-propenyloxy)benzene $n_D^{25.0}$ 1.5832
(91) 3,5-Dichloro-4-(3-(4-chlorophenoxy)propyloxy)-1-(3,3-dichloro-2-propenyloxy)benzene $n_D^{25.0}$ 1.5822
(92) 3,5-Dichloro-4-(2-(4-chlorophenoxy)ethoxy)-1-(3,3-dichloro-2-propenyloxy)benzene m.p. 78.6° C.
(93) 3,5-Dichloro-4-(3-(4-fluorophenoxy)benzyloxy)-1-(3,3-dichloro-2-propenyloxy)benzene $n_D^{25.5}$ 1.5961
(94) 3,5-Dichloro-4-(4-ethoxybenzyloxy)-1-(3,3-dichloro-2-propenyloxy)benzene m.p. 84.0° C.
(95) 3,5-Dichloro-4-(2-(phenylthio)ethoxy)-1-(3,3-dichloro-2-propenyloxy)benzene $n_D^{25.5}$ 1.6063
(96) 3,5-Dichloro-4-(3-trifluoromethoxybenzyloxy)-1-(3,3-dichloro-2-propenyloxy)benzene $n_D^{25.0}$ 1.5416
(97) 3,5-Dichloro-4-(4-trifluoromethoxybenzyloxy)-1-(3,3-dichloro-2-propenyloxy)benzene m.p. 72.1° C.
(98) 3,5-Dichloro-4-(3-(3-chlorophenoxy)propyloxy)-1-(3,3-dichloro-2-propenyloxy)benzene $n_D^{25.0}$ 1.5817
(99) 3,5-Dichloro-4-(3-(4-bromophenoxy)propyloxy)-1-(3,3-dichloro-2-propenyloxy)benzene $n_D^{25.0}$ 1.5917

(100) 3,5-Dichloro-4-(3-(4-trifluoromethoxyphenoxy) propyloxy)-1-(3,3-dichloro-2-propenyloxy)benzene $n_D^{25.0}$ 1.5342
(101) 3-(2,6-Dichloro-4-(3,3-dichloro-2-propenyloxy) phenoxy)propyl benzoate $n_D^{25.0}$ 1.5698
(102) 3,5-Dimethyl-4-benzyloxy-1-(3,3-dichloro-2-propenyloxy)benzene $n_D^{21.0}$ 1.5697
(103) 3,5-Dimethyl-4-benzyloxy-1-(3,3-dibromo-2-propenyloxy)benzene m.p. 70.2° C.
(104) 3-Chloro-5-methyl-4-benzyloxy-1-(3,3-dichloro-2-propenyloxy)benzene $n_D^{25.0}$ 1.5793
(105) 3-Chloro-5-methyl-4-benzyloxy-1-(3,3-dibromo-2-propenyloxy)benzene $n_D^{25.0}$ 1.5998
(106) 4-(2,6-dichloro-4-(3,3-dichloro-2-propenyloxy) phenoxy)butyl benzoate $n_D^{23.5}$ 1.5711
(107) 3,5-Dichloro-4-(3-(4-tert-butylphenoxy)propyloxy)-1-(3,3-dichloro-2-propenyloxy)benzene $n_D^{23.8}$ 1.5601
(108) 3,5-Dichloro-4-(3-(4-ethylphenoxy)propyloxy)-1-(3,3-dichloro-2-propenyloxy)benzene $n_D^{23.8}$ 1.5673
(109) 3,5-Dichloro-4-(3-(3-(trifluoromethyl)phenoxy) propyloxy)-1-(3,3-dichloro-2-propenyloxy)benzene $n_D^{24.0}$ 1.5443
(110) 3,5-Dichloro-4-(3-(3-fluorophenoxy)propyloxy)-1-(3,3-dichloro-2-propenyloxy)benzene $n_D^{24.0}$ 1.5647
(111) 3,5-Dichloro-4-(3-(4-ethoxyphenoxy)propyloxy)-1-(3,3-dichloro-2-propenyloxy)benzene $n_D^{24.0}$ 1.5620
(112) 3,5-Dichloro-4-(3-(4-benzylphenoxy)propyloxy)-1-(3,3-dichloro-2-propenyloxy)benzene $n_D^{24.3}$ 1.5761
(113) 3,5-Dichloro-4-(3-(4-bromopropyloxy)-1-(3,3-dichloro-2-propenyloxy)benzene $n_D^{24.0}$ 1.5693
(114) 3,5-Dichloro-4-(3-(4-fluorophenoxy)propyloxy)-1-(3,3-dichloro-2-propenyloxy)benzene $n_D^{22.3}$ 1.5689
(115) 3,5-Dichloro-4-(3-((4-(trifluoromethoxy)phenyl)) phenoxy)propyloxy)-1-(3,3-dichloro-2-propenyloxy) benzene $n_D^{22.3}$ 1.5751
(116) 3,5-Dichloro-4-(3-(3-chloro-4-(3-chloro-5-trifluoromethyl-2-pyridyloxy)-phenoxy)propyloxy) 1-(3,3-dichloro-2-propenyloxy)benzene $n_D^{22.3}$ 1.5710
(117) 3,5-Dichloro-4-(3-(4-(1,1,3,3-tetramethylbutyl) phenoxy)propyloxy)-1(3,3-dichloro-2-propenyloxy) benzene $n_D^{22.3}$ 1.5570
(118) 3,5-Dichloro-4-(3-(4-n-octyloxyphenoxy)propyloxy)-1-(3,3-dichloro-2-propenyloxy)benzene $n_D^{22.3}$ 1.5526
(119) 3,5-Dichloro-4-(2-(3-fluorophenyl)ethoxy)-1-(3,3-dichloro-2-propenyloxy)benzene $n_D^{23.0}$ 1.5548
(120) 3,5-Dichloro-4-(2-(3-bromophenyl)ethoxy)-1-(3,3-dichloro-2-propenyloxy)benzene $n_D^{23.0}$ 1.5900
(121) 3,5-Dichloro-4-(3-(3-fluorophenyl)propyloxy)-1-(3,3-dichloro-2-propenyloxy)benzene $n_D^{22.0}$ 1.5730
(122) 3,5-Dichloro-4-(3-(4-fluorophenyl)propyloxy)-1-(3,3-dichloro-2-propenyloxy)benzene $n_D^{23.5}$ 1.5669
(123) 3,5-Dichloro-4-(3-(3,4-dichlorophenoxy)propyloxy)-1-(3,3-dichloro-2-propenyloxy)benzene $n_D^{25.7}$ 1.5837
(124) 3,5-Dichloro-4-(3-(2,3,4-trichlorophenoxy) propyloxy)-1-(3,3-dichloro-2-propenyloxy)benzene $n_D^{25.5}$ 1.5857
(125) 3,5-Dichloro-4-(3-(2,4,6-trichlorophenoxy) propyloxy)-1-(3,3-dichloro-2-propenyloxy)benzene $n_D^{25.5}$ 1.5799
(126) 3,5-Dichloro-4-(3-(2,3,6-trichlorophenoxy) propyloxy)-1-(3,3-dichloro-2-propenyloxy)benzene $n_D^{25.7}$ 1.5857
(127) 3,5-Dichloro-4-(3-(2,4,5-trichlorophenoxy) propyloxy)-1-(3,3-dichloro-2-propenyloxy)benzene $n_D^{25.7}$ 1.5870
(128) 3,5-Dichloro-4-(3-(2,3,4,6-tetrachlorophenoxy) propyloxy)-1-(3,3-dichloro-2-propenyloxy)benzene $n_D^{25.7}$ 1.5870
(129) 3,5-Dichloro-4-(3-(4-methylthiophenoxy)propyloxy)-1-(3,3-dichloro-2-propenyloxy)benzene $n_D^{25.7}$ 1.5898
(130) 3,5-Dichloro-4-(3-(3-ethoxylphenoxy)propyloxy)-1-(3,3-dichloro-2-propenyloxy)benzene $n_D^{25.7}$ 1.5628
(131) 3,5-Dichloro-4-(3-(3-methoxylphenoxy)propyloxy)-1-(3,3-dichloro-2-propenyloxy)benzene $n_D^{25.7}$ 1.5625
(132) 2-(2,6-Dichloro-4-(3,3-dichloro-2-propenyloxy) phenoxy)ethyl (4-chloro)benzoate m.p. 72.3° C.
(133) 2-(2,6-Dichloro-4-(3,3-dibromo-2-propenyloxy) phenoxy)ethyl (4-chloro)benzoate $n_D^{24.0}$ 1.5811
(134) 2-(2,6-Dichloro-4-(3,3-dibromo-2-propenyloxy) phenoxy)ethyl benzoate $n_D^{23.5}$ 1.5794
(135) 3,5-Dichloro-4-(3-(3-trifluoromethoxylphenyl) propyloxy)-1-(3,3-dichloro-2-propenyloxy)benzene $n_D^{25.5}$ 1.5354
(136) 3,5-Dichloro-4-(3-(4-trifluoromethoxylphenyl) propyloxy)-1-(3,3-dichloro-2-propenyloxy)benzene $n_D^{24.0}$ 1.5337
(137) 2-(2,6-Dichloro-4-(3,3-dibromo-2-propenyloxy) phenoxy)ethyl (4-trifluoromethoxy)benzoate $n_D^{22.5}$ 1.5320
(138) 2-(2,6-Dichloro-4-(3,3-dibromo-2-propenyloxy) phenoxy)ethyl (3,5-dichloro)benzoate m.p. 86.1° C.
(139) 3,5-Dichloro-4-(3-(4-(1,1,2,2-tetrafluoroethoxy) phenoxy)propyloxy)-1-(3,3-dichloro-2-propenyloxy) benzene $n_D^{23.5}$ 1.5262
(140) 3,5-Dichloro-4-(3-(4-(1,1,2,2-tetrafluoro-2-bromoethoxy)phenoxy)propyloxy)-1-(3,3-dichloro-2-propenyloxy)benzene $n_D^{23.5}$ 1.5302
(141) 3,5-Dichloro-4-(3-(4-bromodifluoromethoxyphenoxy)propyloxy)-1-(3,3-dichloro-2-propenyloxy)benzene $n_D^{23.5}$ 1.5481
(142) 3,5-Dichloro-4-(2-(4-trifluoromethylphenyl)ethoxy)-1-(3,3-dichloro-2-propenyloxy)benzene $n_D^{22.0}$ 1.5462
(143) 3,5-Dichloro-4-(3-(3-bromophenyl)propyloxy)-1-(3,3-dichloro-2-propenyloxy)benzene $n_D^{22.0}$ 1.5913
(144) 3,5-Dichloro-4-(4-(4-chlorophenyl)-3-butenyloxy)-1-(3,3-dichloro-2-propenyloxy)benzene m.p. 53.6° C.
(145) 3,5-Dichloro-4-(4-(4-fluorophenyl)butyloxy)-1-(3,3-dichloro-2-propenyloxy)benzene $n_D^{22.0}$ 1.5653
(146) 3,5-Dichloro-4-(4-(4-trifluoromethylphenyl) butyloxy)-1-(3,3-dichloro-2-propenyloxy)benzene $n_D^{22.0}$ 1.5409
(147) 3,5-Dichloro-4-(4-(4-trifluoromethoxyphenyl) butyloxy)-1-(3,3-dichloro-2-propenyloxy)benzene $n_D^{22.0}$ 1.5325
(148) 2-(2,6-Dichloro-4-(3,3-dichloro-2-propenyloxy) phenoxy)ethyl phenylacetate $n_D^{21.5}$ 1.5717
(149) 3-(2,6-Dichloro-4-(3,3-dichloro-2-propenyloxy) phenoxy)propyl (2-chloro)benzoate $n_D^{24.0}$ 1.5744
(150) 3-(2,6-Dichloro-4-(3,3-dichloro-2-propenyloxy) phenoxy)propyl (3-chloro)benzoate $n_D^{24.0}$ 1.5766
(151) 3-(2,6-Dichloro-4-(3,3-dichloro-2-propenyloxy) phenoxy)propyl (4-chloro)benzoate $n_D^{24.0}$ 1.5791
(152) 3-(2,6-Dichloro-4-(3,3-dichloro-2-propenyloxy) phenoxy)propyl (4-ethoxy)benzoate $n_D^{24.0}$ 1.5715
(153) 3-(2,6-Dichloro-4-(3,3-dichloro-2-propenyloxy) phenoxy)propyl (4-trifluoromethoxy)benzoate $n_D^{24.0}$ 1.5370
(154) 2-(2,6-Dichloro-4-(3,3-dichloro-2-propenyloxy) phenoxy)ethyl (2-chloro)benzoate M.p. 51.9° C.
(155) 2-(2,6-Dichloro-4-(3,3-dichloro-2-propenyloxy) phenoxy)ethyl (3-chloro)benzoate $n_D^{24.8}$ 1.5793
(156) 3,5-Dichloro-4-(2-(4-chlorophenylthio)ethoxy)-1-(3,3-dichloro-2-propenyloxy)benzene $n_D^{22.5}$ 1.6121
(157) 3-(2,6-Dichloro-4-(3,3-dichloro-2-propenyloxy) phenoxy)propyl (3-phenoxy)benzoate $n_D^{24.5}$ 1.5753

(158) 3-(2,6-Dichloro-4-(3,3-dichloro-2-propenyloxy) phenoxy)propyl (4-fluoro)benzoate $n_D^{24.5}$ 1.5627

(159) 3-(2,6-Dichloro-4-(3,3-dichloro-2-propenyloxy) phenoxy)propyl (4bromo)benzoate $n_D^{24.5}$ 1.5832

(160) 3-(2,6-Dichloro-4-(3,3-dichloro-2-propenyloxy) phenoxy)propyl (2-fluoro-4-trifluoromethyl)benzoate $n_D^{24.5}$ 1.5351

(161) 3-(2,6-Dichloro-4-(3,3-dichloro-2-propenyloxy) phenoxy)propyl (3,5-bistrifluoromethyl)benzoate $n_D^{24.5}$ 1.5146

(162) 3,5-Dichloro-4-(3-(4-isopropoxyphenoxy)propyloxy) -1-(3,3-dichloro-2-propenyloxy)benzene $n_D^{24.4}$ 1.5608

(163) 3,5-Dichloro-4-(3-(3-isopropoxyphenoxy)propyloxy) -1-(3,3-dichloro-2-propenyloxy)benzene $n_D^{24.4}$ 1.5611

(164) 3,5-Dichloro-4-(3-(4-(2,2,2-trifluoroethoxy)phenoxy) propyloxy)-1-(3,3-dichloro-2-propenyloxy)benzene $n_D^{24.4}$ 1.5371

(165) 3,5-Dichloro-4-(3-(3-(2,2,2-trifluoroethoxy)phenoxy) propyloxy)-1-(3,3-dichloro-2-propenyloxy)benzene $n_D^{24.4}$ 1.5361

(166) 3,5-Dichloro-4-(3-(4-trifluoromethylphenoxy) propyloxy)-1-(3,3-dichloro-2-propenyloxy)benzene $n_D^{24.4}$ 1.5390

(167) 3,5-Dichloro-4-(3-(3-(1,1,2,2-tetrafluoroethoxy) phenoxy)propyloxy)-1-(3,3-dichloro-2-propenyloxy) benzene $n_D^{23.4}$ 1.5267

(168) 3,5-Dichloro-4-(3-(3-(2-bromo-1,1,2,2-tetrafluoroethoxy)phenoxy)propyloxy)-1-(3,3-dichloro-2-propenyloxy)benzene $n_D^{23.4}$ 1.5343

(169) 3-(2,6-Dichloro-4-(3,3-dichloro-2-propenyloxy) phenoxy)propyl (2,4-dichloro)benzoate $n_D^{25.0}$ 1.5850

(170) 3-(2,6-Dichloro-4-(3,3-dichloro-2-propenyloxy) phenoxy)propyl (3,4-diethoxy)benzoate $n_D^{25.0}$ 1.5664

(171) 3-(2,6-Dichloro-4-(3,3-dichloro-2-propenyloxy) phenoxy)propyl (3-trifluoromethyl)benzoate $n_D^{25.0}$ 1.5410

(172) 3-(2,6-Dichloro-4-(3,3-dichloro-2-propenyloxy) phenoxy)propyl (3,4-dimethoxy)benzoate m.p. 66.2° C.

(173) 3-(2,6-Dichloro-4-(3,3-dichloro-2-propenyloxy) phenoxy)propyl (4-isopropyl)benzoate (174) 3,5-Dichloro-4-(4-bromobutyloxy)-1-(3,3-dichloro-2-propenyloxy)benzene $n_D^{25.0}$ 1.5666

(175) 3,5-Dichloro-4-(3-(2,6-dichloro-4-(3,3-dichloro-2-propenyloxy)phenoxy)propyloxy)-1-(3,3-dichloro-2-propenyloxy)benzene m.p. 115.0° C.

(176) 3,5-Dichloro-4-(4-(2,6-dichloro-4-(3,3-dichloro-2-propenyloxy)phenoxy)butyloxy)-1-(3,3-dichloro-2-propenyloxy)benzene m.p. 111.0° C.

(177) 3-Chloro-5-methyl4-(2-(4-bromophenyl)ethoxy)-1-(3,3-dichloro-2-propenyloxy)benzene $n_D^{24.2}$ 1.5865

(178) 3-Chloro-5-methyl-4-(3-(4-chlorophenoxy) propyloxy)-1-(3,3-dichloro-2-propenyloxy)benzene $n_D^{24.0}$ 1.5720

(179) 3-Chloro-5-methyl-4-(4-phenylbutyloxy)-1-(3,3-dichloro-2-propenyloxy)benzene $n_D^{24.5}$ 1.5625

(180) 3-Chloro-5-methyl-4-(2-(4-bromophenyl)ethoxy)-1-(3,3-dibromo-2-propenyloxy)benzene m.p. 70.7° C.

(181) 3,5-Dichloro-4-(3-(phenylthio)propyloxy) 1-(3,3-dibromo-2-propenyloxy)benzene $n_D^{26.0}$ 1.5997

(182) 3,5-Dichloro-4-(3-(4-chlorophenylthio)propyloxy)-1-(3,3-dibromo-2-propenyloxy)benzene $n_D^{26.0}$ 1.6035

(183) 3-(2,6-Dichloro-4-(3,3-dichloro-2-propenyloxy) phenoxy)propyl 1-naphthoate $n_D^{25.5}$ 1.5978

(184) 3-(2,6-Dichloro-4-(3,3-dichloro-2-propenyloxy) phenoxy)propyl 2-naphthoate m.p. 71.4° C.

(185) 3,5-Dichloro-4-(3-(3-trifluoromethoxyphenoxy) propyloxy)-1-(3,3-dichloro-2-propenyloxy)benzene $n_D^{23.4}$ 1.5343

(186) 4-(2,6-Dichloro-4-(3,3-dichloro-2-propenyloxy) phenoxy)butyl (4-ethoxy)benzoate $n_D^{24.0}$ 1.5652

(187) 2-(2,6-Dichloro-4-(3,3-dichloro-2-propenyloxy) phenoxy)ethyl (4-isopropoxy)benzoate $n_D^{24.0}$ 1.5703

(188) 3-(2,6-Dichloro-4-(3,3-dichloro-2-propenyloxy) phenoxy)propyl (4-isopropoxy)benzoate $n_D^{24.0}$ 1.5650

(189) 2-(2,6-Dichloro-4-(3,3-dichloro-2-propenyloxy) phenoxy)ethyl (4-ethoxy)benzoate m.p. 77.8° C.

(190) 3,5-Dichloro-4-(3,7-dimethyloctyloxy)-1-(3,3-dichloro-2-propenyloxy)benzene $n_D^{23.7}$ 1.5340

(191) 3,5-Dichloro-4-(3,7-dimethyl-6-octenyloxy)-1-(3,3-dichloro-2-propenyloxy)benzene $n_D^{23.7}$ 1.5446

(192) 3,5-Dichloro(3,7-dimethyl-2,6-octadienoxy)-1-(3,3-dichloro-2-propenyloxy)benzene $n_D^{23.7}$ 1.5762

(193) 3,5-Dichloro-4-(n-octyloxy)-1-(3,3-dichloro-2-propenyloxy)benzene $n_D^{20.5}$ 1.5297

(194) 3,5-Dichloro-4-(2-(4-chlorobenzyloxy)ethoxy)-1-(3,3-dichloro-2-propenyloxy)benzene $n_D^{23.7}$ 1.5777

(195) 4-(2,6-Dichloro-4-(3,3-dichloro-2-propenyloxy) phenoxy)butyl (2-chloro)benzoate $n_D^{23.5}$ 1.5734

(196) 4-(2,6-Dichloro-4-(3,3-dichloro-2-propenyloxy) phenoxy)butyl (3-chloro)benzoate $n_D^{23.5}$ 1.5732

(197) 4-(2,6-Dichloro-4-(3,3-dichloro-2-propenyloxy) phenoxy)butyl (4-chloro)benzoate $n_D^{23.5}$ 1.5746

(198) 4-(2,6-Dichloro-4-(3,3-dichloro-2-propenyloxy) phenoxy)butyl (4-trifluoromethoxy)benzoate $n_D^{23.5}$ 1.5326

(199) 4-(2,6-Dichloro-4-(3,3-dichloro-2-propenyloxy) phenoxy)butyl (4-isopropoxy)benzoate $n_D^{23.5}$ 1.5622

(200) 3,5-Dichloro-4-(3-(4-trifluoromethylphenylthio) propyloxy)-1-(3,3-dichloro-2-propenyloxy)benzene $n_D^{25.0}$ 1.5635

(201) 3,5-Dichloro-4-(3-(4-tert-butylphenylthio)propyloxy) -1-(3,3-dichloro-2-propenyloxy)benzene $n_D^{25.0}$ 1.5777

(202) 3,5-Dichloro-4-(4-(4-trifluoromethoxyphenoxy) butyloxy)-1-(3,3-dichloro-2-propenyloxy)benzene $n_D^{23.0}$ 1.5367

(203) 3,5-Dichloro-4-(4-(4-isopropyloxyphenoxy)butyloxy) -1-(3,3-dichloro-2-propenyloxy)benzene $n_D^{23.0}$ 1.5578

(204) 3,5-Dibromo-4-(2-(4-bromophenyl)ethoxy)-1-(3,3-dichloro-2-propenyloxy)benzene $n_D^{23.0}$ 1.6180

(205) 3,5-Dibromo-4-(3-(4-chlorophenoxy)propyloxy)-1-(3,3-dichloro-2-propenyloxy)benzene $n_D^{23.0}$ 1.5983

(206) 3,5-Dibromo-4-(4-phenylbutyloxy)-1-(3,3-dichloro-2-propenyloxy)benzene $n_D^{23.0}$ 1.5918

(207) 3,5-Dibromo-4-(4-(4-chlorophenyl)butyloxy)-1-(3,3-dichloro-2-propenyloxy)benzene $n_D^{21.5}$ 1.5721

(208) 2-(2,6-Dichloro-4-(3,3-dichloro-2-propenyloxy) phenoxy)ethyl (3-ethoxy)benzoate $n_D^{24.5}$ 1.5716

(209) 3-(2,6-Dichloro-4-(3,3-dichloro-2-propenyloxy) phenoxy)propyl (3-ethoxy)benzoate $n_D^{24.5}$ 1.5646

(210) 4-(2,6-Dichloro-4-(3,3-dichloro-2-propenyloxy) phenoxy)butyl (3-ethoxy)benzoate $n_D^{24.5}$ 1.5585

(211) 2-(2,6-Dichloro-4-(3,3-dichloro-2-propenyloxy) phenoxy)ethyl (4-trifluoromethyl)benzoate $n_D^{25.5}$ 1.5427

(212) 3-(2,6-Dichloro-4-(3,3-dichloro-2-propenyloxy) phenoxy)propyl (4-trifluoromethyl)benzoate $n_D^{25.5}$ 1.5396

(213) 3,5-Dichloro-4-(3-methyl-3-(4-chlorophenoxy) propyloxy)-1-(3,3-dichloro-2-propenyloxy)benzene $n_D^{23.5}$ 1.5693

(214) 3,5-Dichloro-4-(1-methyl-3-(4-chlorophenoxy) propyloxy)-1-(3,3-dichloro-2-propenyloxy)benzene $n_D^{23.5}$ 1.5613

(215) 3,5-Dichloro-4-(3-methyl-3-butenyloxy)-1-(3,3-dichloro-2-propenyloxy)benzene (216) 3-Chloro-5-methyl-4-(3-(4-trifluoromethylphenoxy) propyloxy)-1-(3,3-dichloro-2-propenyloxy)benzene $n_D^{23.0}$ 1.5330

(217) 3,5-Dichloro-4-(3-(4-methoxyphenylthio)propyloxy)-1-(3,3-dichloro-2-propenyloxy)benzene $n_D^{25.5}$ 1.5990
(218) 3,5-Dichloro-4-(3-(4-fluorophenylthio)propyloxy)-1-(3,3-dichloro-2-propenyloxy)benzene $n_D^{25.5}$ 1.5844
(219) 3,5-Dichloro-4-(3-(2,3,5,6-tetrafluorophenylthio)propyloxy)-1-(3,3-dichloro-2-propenyloxy)benzene $n_D^{25.5}$ 1.5619
(220) 3,5-Dichloro-4-(3-(3-chlorophenylthio)propyloxy)-1-(3,3-dichloro-2-propenyloxy)benzene $n_D^{25.5}$ 1.6004
(221) 3,5-Dichloro-4-(3-(4-bromophenylthio)propyloxy)-1-(3,3-dichloro-2-propenyloxy)benzene $n_D^{25.5}$ 1.6117
(222) 3,5-Dichloro-4-(4-(4-chlorophenoxy)butyloxy)-1-(3,3-dichloro-2-propenyloxy)benzene m.p. 54.5° C.
(223) 3,5-Dichloro-4-(4-(3-isopropoxyphenoxy)butyloxy)-1-(3,3-dichloro-2-propenyloxy)benzene $n_D^{20.3}$ 1.5615
(224) 3,5-Dichloro-4-(4-(3-trifluoromethoxyphenoxy)butyloxy)-1-(3,3-dichloro-2-propenyloxy)benzene $n_D^{20.3}$ 1.5355
(225) 3,5-Dichloro-4-(4-(4-(1,1,2,2-tetrafluoroethoxy)phenoxy)butyloxy)-1-(3,3-dichloro-2-propenyloxy)benzene $n_D^{20.3}$ 1.5283
(226) 3,5-Dichloro-4-(4-(3-(1,1,2,2-tetrafluoroethoxy)phenoxy)butyloxy)-1-(3,3-dichloro-2-propenyloxy)benzene $n_D^{20.3}$ 1.5298
(227) 3,5-Dichloro-4-(4-(4-(2,2,2-trifluoroethoxy)phenoxy)butyloxy)-1-(3,3-dichloro-2-propenyloxy)benzene $n_D^{20.3}$ 1.5384
(228) 3,5-Dichoro-4-(4-(3-(2,2,2-trifluoroethoxy)phenoxy)butyloxy)-1-(3,3-dichloro-2-propenyloxy)benzene $n_D^{20.3}$ 1.5431
(229) 3,5-Dichloro-4-(4-(4-difluoromethoxyphenoxy)butyloxy)-1-(3,3-dichloro-2-propenyloxy)benzene $n_D^{20.3}$ 1.5484
(230) 3,5-Dichloro-4-(4-(3-difluoromethoxyphenoxy)butyloxy)-1-(3,3-dichloro-2-propenyloxy)benzene $n_D^{23.3}$ 1.5446
(231) 3,5-Dichloro-4-(3-(4-difluoromethoxyphenoxy)propyloxy)-1-(3,3-dichloro-2-propenyloxy)benzene $n_D^{20.3}$ 1.5519
(232) 3,5-Dichloro-4-(3-(3-difluoromethoxyphenoxy)propyloxy)-1-(3,3-dichloro-2-propenyloxy)benzene $n_D^{23.3}$ 1.5500
(233) 3,5-Dichloro-4-(4-(4-trifluoromethylphenoxy)butyloxy)-1-(3,3-dichloro-2-propenyloxy)benzene $n_D^{20.3}$ 1.5418
(234) 3,5-Dichloro-4-(4-(3-trifluoromethylphenoxy)butyloxy)-1-(3,3-dichloro-2-propenyloxy)benzene $n_D^{20.3}$ 1.5375
(235) 3-(2,6-Dichloro-4-(3,3-dichloro-2-propenyloxy)phenoxy)propyl (4-chloro)phenylacetate $n_D^{22.0}$ 1.5698
(236) 3-(2,6-Dichloro-4-(3,3-dichloro-2-propenyloxy)phenoxy)propyl (4-chloro)cinnamate m.p. 62.2° C.
(237) 3-(2,6-Dichloro-4-(3,3-dichloro-2-propenyloxy)phenoxy)propyl (4-chloro)phenoxyacetate $n_D^{22.0}$ 1.5709
(238) 3,5-Dichloro-4-(3-(N-methylanilino)propyloxy)-1-(3,3-dichloro-2-propenyloxy)benzene $n_D^{25.5}$ 1.5887
(239) 3,5-Dichloro-4-(4-(3-fluorophenyl)-3-butenyloxy)-1-(3,3-dichloro-2-propenyloxy)benzene $n_D^{25.5}$ 1.5857
(240) 3,5-Dichloro-4-(4-(3-trifluoromethylphenyl)-3-butenyloxy)-1-(3,3-dichloro-2-propenyloxy)benzene $n_D^{25.5}$ 1.5588
(241) 3,5-Dichloro-4-(4-(3-trifluoromethoxyphenyl)-3-butenyloxy)-1-(3,3-dichloro-2-propenyloxy)benzene $n_D^{25.5}$ 1.5502
(242) 3,5-Dichloro-4-(4-(3-fluorophenyl)butyloxy)-1-(3,3-dichloro-2-propenyloxy)benzene $n_D^{25.0}$ 1.5620
(243) 3,5-Dichloro-4-(4-(3-trifluoromethylphenyl)butyloxy)-1-(3,3-dichloro-2-propenyloxy)benzene $n_D^{25.0}$ 1.5373
(244) 3,5-Dichloro-4-(4-(3-trifluoromethoxyphenyl)butyloxy)-1-(3,3-dichloro-2-propenyloxy)benzene $n_D^{25.0}$ 1.5314
(245) 2-(2,6-Dichloro-4-(3,3-dichloro-2-propenyloxy)phenoxy)ethyl (4-(2,2,2-trifluoroethoxy)benzoate m.p. 57.6° C.
(246) 3-(2,6-Dichloro-4-(3,3-dichloro-2-propenyloxy)phenoxy)propyl (4-(2,2,2-trifluoroethoxy)benzoate m.p. 53.9° C.
(247) 3,5-Dichloro-4-((3-ethoxycarbonyl)propyloxy)-1-(3,3-dichloro-2-propenyloxy)benzene $n_D^{22.0}$ 1.5367
(248) 3,5-Dichloro-4-(3-(4-(trifluoromethoxy)phenoxycarbonyl)propyloxy)-1-(3,3-dichloro-2-propenyloxy)benzene $n_D^{23.0}$ 1.5307
(249) 3,5-Dichloro-4-(2-methyl-3-(4-chlorophenoxy)propyloxy)-1-(3,3-dichloro-2-propenyloxy)benzene
(250) 3-Chloro-5-methyl-4-(3-(4-trifluoromethoxyphenoxy)propyloxy)-1-(3,3-dichloro-2-propenyloxy)benzene $n_D^{23.0}$ 1.5279
(251) 3-(2-Chloro-6-methyl-4-(3,3-dichloro-2-propenyloxy)phenoxy)propyl (4-bromo)benzoate $n_D^{24.0}$ 1.5798
(252) 3,5-Dichloro-4-(2-(4-isopropoxyphenyl)ethoxy)-1-(3,3-dichloro-2-propenyloxy)benzene $n_D^{25.0}$ 1.5632
(253) 3,5-Dichloro-4-(2-(4-(trifluoromethoxy)phenyl)ethoxy)-1-(3,3-dichloro-2-propenyloxy)benzene $n_D^{25.0}$ 1.5370
(254) 3,5-Dichloro-4-(3-(4-bromophenyl)propyloxy)-1-(3,3-dichloro-2-propenyloxy)benzene $n_D^{25.0}$ 1.5891
(255) 3,5-Dichloro-4-(3-(4-(trifluoromethyl)phenyl)propyloxy)-1-(3,3-dichloro-2-propenyloxy)benzene $n_D^{25.0}$ 1.5367
(256) 3,5-Dimethyl-4-(3-(4-chlorophenoxy)propyloxy)-1-(3,3-dichloro-2-propenyloxy)benzene $n_D^{23.0}$ 1.5638
(257) 3,5-Dichloro-4-(4-(4-chlorophenoxy)-2-(Z)-butenyloxy)-1-(3,3-dichloro-2-propenyloxy)benzene $n_D^{21.9}$ 1.5827
(258) 3,5-Dichloro-4-(4-(4-chlorophenoxy)-2-(E)-butenyloxy)-1-(3,3-dichloro-2-propenyloxy)benzene $n_D^{21.9}$ 1.5824
(259) 3-(2,6-Dichloro-4-(3,3-dichloro-2-propenyloxy)phenoxy)propyl (4-difluoromethyl)benzoate $n_D^{23.0}$ 1.5535
(260) 3-(2,6-Dichloro-4-(3,3-dichloro-2-propenyloxy)phenoxy)propyl (4-(1,1,2,2-tetrafluoroethoxy))benzoate $n_D^{23.0}$ 1.5329
(261) 3-(2,6-Dichloro-4-(3,3-dichloro-2-propenyloxy)phenoxy)propyl (3-methyl-2-(4-chlorophenyl))butyrate $n_D^{23.0}$ 1.5565
(262) 3,5-Dichloro-4-(4-(4-chlorophenylthio)butyloxy)-1-(3,3-dichloro-2-propenyloxy)benzene $n_D^{22.5}$ 1.5910
(263) 3,5-Dichloro-4-(4-(4-trifluoromethylphenylthio)butyloxy)-1-(3,3-dichloro-2-propenyloxy)benzene $n_D^{22.5}$ 1.5608
(264) 3,5-Dichloro-4-(4-(4-hydroxyphenylthio)butyloxy)-1-(3,3-dichloro-2-propenyloxy)benzene $n_D^{22.5}$ 1.5998
(265) 3,5-Dimethyl-4-(3-(4-trifluoromethoxyphenoxy)propyloxy)-1-(3,3-dichloro-2-propenyloxy)benzene $n_D^{22.0}$ 1.5183
(266) 3,5-Dichloro-4-(4-(4-methoxyphenylthio)butyloxy)-1-(3,3-dichloro-2-propenyloxy)benzene $n_D^{24.0}$ 1.5831
(267) 3,5-Dichloro-4-(4-(4-isopropoxyphenylthio)butyloxy)-1-(3,3-dichloro-2-propenyloxy)benzene $n_D^{24.0}$ 1.5718
(268) 3,5-Dichloro-4-(3-(4-chlorophenylsulfenyl)propyloxy)-1-(3,3-dichloro-2-propenyloxy)benzene $n_D^{24.5}$ 1.5962
(269) 3,5-Diisopropyl-4-(4-(4-trifluoromethoxyphenoxy)butyloxy)-1-(3,3-dichloro-2-propenyloxy)benzene $n_D^{23.0}$ 1.5070

(270) 3,5-Diethyl-4-(4-(4-trifluoromethoxyphenoxy)butyloxy)-1-(3,3-dichloro-2-propenyloxy)benzene $n_D^{25.9}$ 1.5115

(271) 3,5-Diethyl-4-(4-(4-trifluoromethoxyphenoxy)butyloxy)-1-(3,3-bromo-2-propenyloxy)benzene $n_D^{25.9}$ 1.5292

(272) 3-Ethyl-5-methyl-4-(4-(4-trifluoromethoxyphenoxy)butyloxy)-1-(3,3-dibromo-2-propenyloxy)benzene $n_D^{23.5}$ 1.5150

(273) 3-(2,6-Dichloro-4-(3,3-dichloro-2-propenyloxy)phenoxy)propyl (4-trifluoromethyl)cinnamate $n_D^{25.5}$ 1.5542

(274) 3,5-Dichloro-4-(3-(4-trifluoromethoxyanilino)propyloxy)-1-(3,3-dichloro-2-propenyloxy)benzene $n_D^{25.0}$ 1.5503

(275) 3,5-Dichloro-4-(3-anilino)propyloxy)-1-(3,3-dichloro-2-propenyloxy)benzene $n_D^{20.0}$ 1.5974

(276) 3,5-Dichloro-4-(3-(4-trifluoromethoxyanilino)propyloxy)-1-(3,3-dichloro-2-propenyloxy)benzene $n_D^{23.5}$ 1.5617

(277) 3,5-Dichloro-4-(3-(N-methyl-4-trifluoromethylanilino)propyloxy)-1-(3,3-dichloro-2-propenyloxy)benzene $n_D^{25.5}$ 1.5593

(278) 3,5-Dichloro-4-(3-(N-acetyl-4-trifluoromethylanilino)propyloxy)-1-(3,3-dichloro-2-propenyloxy)benzene $n_D^{25.5}$ 1.5395

(279) 3,5-Dichloro-4-(3-(4-trifluoromethoxyphenylthio)propyloxy)-1-(3,3-dichloro-2-propenyloxy)benzene $n_D^{23.5}$ 1.5569

(280) 3,5-Dichloro-4-(4-trifluoromethylbenzyloxy)-1-(3,3-dichloro-2-propenylthio)benzene (281) 3,5-Dichloro-4-(2-(4-trifluoromethylphenyl)ethoxy-1-(3,3-dichloro-2-propenyloxy) benzene (282) 3,5-Dichloro-4-(3-(4-trifluoromethylphenyl)propyloxy)-1-(3,3-dichloro-2-propenyloxy)benzene $n_D^{25.0}$ 1.5367

(283) 3,5-Dichloro-4-(3-(4-trifluoromethylphenoxy)propyloxy)-1-(3,3-dichloro-2-propenyloxy)benzene m.p. 52.1° C.

(284) 3-Ethyl-5-methyl-4-(3-(4-trifluoromethylphenoxy)propyloxy)-1-(3,3-dichloro-2-propenyloxy)benzene $n_D^{21.5}$ 1.5234

(285) 3,5-Dichloro-4-(3-(4-chlorophenylsulfonyl)propyloxy)-1-(3,3-dichloro-2-propenyloxy)benzene $n_D^{24.5}$ 1.5863

(286) 2,3,5,6-Tetrachloro-4-(3-(4-trifluoromethylphenoxy)propyloxy)-1-(3,3-dichloro-2-propenylthio)benzene (287) 2,3,5,6-Tetrachloro-1,4-bis(3,3-dichloro-2-propenyloxy)benzene (288) 3,5-Dichloro-4-(4-anilino)butyloxy)-1-(3,3-dichloro-2-propenyloxy)benzene $n_D^{21.5}$ 1.5919

(289) 3,5-Dichloro-4-(4-(4-trifluoromethylanilino)butyloxy)-1-(3,3-dichloro-2-propenyloxy)benzene $n_D^{21.5}$ 1.5606

(290) 3,5-Dichoro-4-(4-(4-trifluoromethoxyanilino)butyloxy)-1-(3,3-dichloro-2-propenyloxy)benzene $n_D^{21.5}$ 1.5491

(291) 3,5-Diethyl-4-(3-(4-trifluoromethylphenoxy)propyloxy)-1-(3,3-dichloro-2-propenyloxy)benzene $n_D^{20.0}$ 1.5230

(292) 3,5-Dichloro-4-(3-(4-isopropoxycarbonylphenoxy)propyloxy)-1-(3,3-dichloro-2-propenyloxy)benzene $n_D^{22.7}$ 1.5440

(293) 3,5-Dichloro-4-(3-(4-methoxycarbonylphenoxy)propyloxy)-1-(3,3-dichloro-2-propenyloxy)benzene $n_D^{22.7}$ 1.5519

(294) 3-Chloro-5-methyl-4-(4-(4-trifluoromethoxyphenoxy)butyloxy)-1-(3,3-dichloro-2-propenyloxy)benzene $n_D^{23.0}$ 1.5208

(295) 3-Chloro-5-methyl-4-(4-(4-trifluoromethylphenoxy)butyloxy)-1-(3,3-dichloro-2-propenyloxy)benzene $n_D^{23.0}$ 1.5285

(296) 3-Chloro-5-methyl-4-(4-(4-chlorophenoxy)butyloxy)-1-(3,3-dichloro-2-propenyloxy)benzene m.p. 54.5° C.

(297) 3-Chloro-5-methyl-4-(3-(4-bromophenoxy)propyloxy)-1-(3,3-dichloro-2-propenyloxy)benzene $n_D^{24.0}$ 1.5812

(298) 3-Chloro-5-methyl-4-(4-(4-bromophenoxy)butyloxy)-1-(3,3-dichloro-2-propenyloxy)benzene m.p. 51.6° C.

(299) 3-Chloro-5-methyl-4-(3-(4-isopropoxyphenoxy)propyloxy)-1-(3,3-dichloro- 2-propenyloxy)benzene $n_D^{24.0}$ 1.5485

(300) 3-Chloro-5-methyl-4-(4-(4-isopropoxyphenoxy)butyloxy)-1-(3,3-dichloro-2-propenyloxy)benzene $n_D^{24.0}$ 1.5482

(301) 3-Ethyl-5-methyl-4-(4-(4-trifluoromethoxyphenoxy)butyloxy)-1-(3,3-dichloro-2-propenyloxy)benzene $n_D^{23.0}$ 1.5150

(302) 3-Ethyl-5-methyl-4-(4-(4-trifluoromethylphenoxy)butyloxy)-1-(3,3-dichloro-2-propenyloxy)benzene $n_D^{23.0}$ 1.5221

(303) 3-Ethyl-5-methyl-4-(3-(4-chlorophenoxy)propyloxy)-1-(3,3-dichloro-2-propenyloxy)benzene $n_D^{23.5}$ 1.5562

(304) 3-Ethyl-5-methyl-4-(4-(4-chlorophenoxy)butyloxy)-1-(3,3-dichloro-2-propenyloxy)benzene $n_D^{21.3}$ 1.5554

(305) 3-Ethyl-5-methyl-4-(3-(4-bromophenoxy)propyloxy)-1-(3,3-dichloro-2-propenyloxy)benzene $n_D^{23.5}$ 1.5670

(306) 3-Ethyl-5-methyl-4-(4-(4-bromophenoxy)butyloxy)-1-(3,3-dichloro-2-propenyloxy)benzene $n_D^{21.3}$ 1.5620

(307) 3-Ethyl-5-methyl-4-(3-(4-isopropoxyphenoxy)propyloxy)-1-(3,3-dichloro-2-propenyloxy)benzene $n_D^{23.5}$ 1.5430

(308) 3-Ethyl -5-methyl-4-(4-(4-isopropoxyphenoxy)butyloxy)-1-(3,3-dichloro-2-propenyloxy)benzene $n_D^{21.3}$ 1.5429

(309) 3,5-Diethyl-4-(4-(4-trifluoromethoxyphenoxy)butyloxy)-1-(3,3-dichloro-2-propenyloxy)benzene (310) 3,5-Diethyl-4-(4-(4-trifluoromethylphenoxy)butyloxy)-1-(3,3-dichloro-2-propenyloxy)benzene (311) 3,5-Diethyl-4-(3-(4-chlorophenoxy)propyloxy)-1-(3,3-dichloro-2-propenyloxy)benzene (312) 3,5-Diethyl-4-(4-(4-chlorophenoxy)butyloxy)-1-(3,3-dichloro-2-propenyloxy)benzene (313) 3,5-Diethyl-4-(3-(4-bromophenoxy)butyloxy)-1-(3,3-dichloro-2-propenyloxy)benzene (314) 3,5-Diethyl-4-(4-(4-bromophenoxy)butyloxy)-1-(3,3-dichloro-2-propenyloxy)benzene (315) 3,5-Diethyl-4-(3-(4-isopropoxyphenoxy)propyloxy)-1-(3,3-dichloro-2-propenyloxy)benzene (316) 3,5-Diethyl-4-(4-(4-isopropoxyphenoxy)butyloxy)-1-(3,3-dichloro-2-propenyloxy)benzene (317) 3,5-Diisopropyl-4-(4-(4-trifluoromethoxyphenoxy)butyloxy)-1-(3,3-dichloro-2-propenyloxy)benzene (318) 3,5-Diisopropyl-4-(3-(4-trifluoromethylphenoxy)propyloxy)-1-(3,3-dichloro-2-propenyloxy)benzene (319) 3,5-Diisopropyl-4-(4-(4-trifluoromethylphenoxy)butyloxy)-1-(3,3-dichloro-2-propenyloxy)benzene (320) 3,5-Diisopropyl-4-(3-(4-chlorophenoxy)propyloxy)-1-(3,3-dichloro-2-propenyloxy)benzene (321) 3,5-Diisopropyl-4-(4-(4-chlorophenoxy)butyloxy)-1-(3,3-dichloro-2-propenyloxy)benzene (322) 3,5-Diisopropyl-4-(3-(4-bromophenoxy)propyloxy)-1-(3,3-dichloro-2-propenyloxy)benzene (323) 3,5-Diisopropyl-4-(4-(4-bromophenoxy)butyloxy)-1-(3,3-dichloro-2-propenyloxy)benzene (324) 3,5-Diisopropyl-4-(3-(4-isopropoxyphenoxy)propyloxy)-1-(3,3-dichloro-2-propenyloxy)benzene (325) 3,5-Diisopropyl-1-4-(4-(4-isopropoxyphenoxy) butyloxy)-1-(3,3-dichloro-2-propenyloxy)benzene The following are production examples for the intermediate compounds of the general formula [IV], [V] or [VI].

Intermediate Production Example 1

Production of Intermediate Compound 1)

A reaction vessel was charged with 25.5 g of hydroquinone monobenzyl ether, 17.9 g of benzoyl chloride, 0.50 g of tetrabutylammonium bromide and 100 ml of toluene, to which 78.6 g of 10% potassium hydroxide solution was slowly added dropwise, while stirring under ice cooling. After 24 hours, the reaction mixture was made weakly acidic by the addition of 20% hydrochloric acid, and the deposited crystals were collected by filtration. The crystals thus obtained were successively washed with 10% hydrochloric acid and water, and dried, which afforded 38 g of 4-benzyloxyphenyl benzoate (98% yield).

A reaction vessel was charged with 38 g of 4-benzyloxyphenyl benzoate and 500 ml of ethanol, and the air in the vessel was replaced with nitrogen. Then, 1.0 g of 10% palladium carbon was added thereto, and the nitrogen in the vessel was replaced with hydrogen, followed by vigorous stirring at room temperature for 24 hours. The hydrogen in the vessel was replaced with nitrogen, after which the reaction mixture was filtered though celite, and the filtrate was concentrated, which afforded 24.5 g of 4-hydroxyphenyl benzoate (94% yield).

A reaction vessel was charged with 24.5 g of 4-hydroxyphenyl benzoate and 500 ml of carbon tetrachloride, to which a solution of 24.8 g of t-butyl hypochlorite dissolved in 20 ml of carbon tetrachloride was slowly added dropwise, while stirring under ice cooling. After 24 hours, the reaction mixture was poured into water, followed by phase separation. The organic layer (i.e., carbon tetrachloride layer) was washed with water, dried with anhydrous magnesium sulfate, and concentrated to obtain a crude product. The crude product was subjected to silica gel chromatography, which afforded 29.5 g of 3,5-dichloro-4-hydroxyphenyl benzoate (91% yield).

A reaction vessel was charged with 1.54 g of 3,5-dichloro-4-hydroxyphenyl benzoate, 0.83 g of potassium carbonate, 1.53 g of 4-fluoro-3-phenoxybenzyl bromide, and 10 ml of N,N-dimethylformamide, followed by stirring at room temperature for 5 hours. The reaction mixture was poured into water, and extracted twice with 50 m of diethyl ether. The combined ether layer was washed with water, dried with anhydrous magnesium sulfate, and concentrated to obtain a crude product. The crude product was subjected to silica gel chromatography, which afforded 2.32 g of 3,5-dichloro-4-(4-fluoro-3-phenoxybenzyloxy)phenyl benzoate (88% yield).

A reaction vessel was charged with 1.36 g of 3,5-dichloro-4-(4-fluoro-3-phenoxybenzyloxy)phenyl benzoate and 10 ml of methanol, to which 4.2 g of 10% potassium hydroxide solution was slowly added dropwise under ice cooling. After stirring for 1 hour, the reaction mixture was made weakly acidic by the addition of 10% hydrochloric acid, and extracted twice with 50 ml of diethyl ether under salting out. The combined ether layer was washed with water, dried with anhydrous magnesium sulfate, and concentrated to obtain a crude product. The crude product was subjected to silica gel chromatography, which afforded 0.97 g of 3,5-dichloro-4-(4-fluoro-3-phenoxybenzyloxy)phenol (91% yield), m.p. 144.8° C.

Intermediate Production Example 2

Production of Intermediate Compound 2)

A mixture of 2.27 g of 4-benzoyloxy-2,6-dichlorophenol, 1.29 g of 2-chlorobenzyl chloride, 1.21 g of potassium carbonate and 50 ml of N,N-dimethylformamide was stirred at 80° C. for 6 hours. The reaction mixture was cooled to room temperature, poured in ice water, and extracted twice with 50 ml of diethyl ether. The combined ether layer was washed with water, and dried with anhydrous magnesium sulfate, followed by removal of the solvent by distillation under reduced pressure. The residue was subjected to silica gel chromatography, which afforded 2.87 g of 1-benzoyloxy-4-(2-chlorobenzyloxy)-3,5-dichlorobenzene (88% yield).

To a mixture of 2.87 g of 1-benzoyloxy-4-(2-chlorobenzyloxy)-3,5-dichlorobenzene and 100 ml of methanol was added dropwise 5.1 g of 10% (w/w) aqueous potassium hydroxide solution, while stirring at room temperature. After stirring at room temperature for 6 hours, the reaction mixture was made weakly acidic by the addition of 10% hydrochloric acid, and the methanol was removed by distillation under reduced pressure. The residue was extracted twice with 100 ml of ethyl acetate. The combined ether layer was washed with water, and dried with anhydrous magnesium sulfate, followed by removal of the solvent by distillation under reduced pressure. The residue was subjected to silica gel chromatography, which afforded 1.17 g of 4-(2-chlorobenzyloxy)-3,5-dichlorophenol (55% yield), m.p. 108.3° C.

Intermediate Production Example 3

Production of Intermediate Compound 264)

A mixture of 27 g of 2-ethyl-6-methylaniline, 36 ml of concentrated sulfuric acid and 100 ml of water was stirred at a temperature of 0°–5° C., to which a solution of 16.1 g of sodium nitrite dissolved in 50 ml of water was added dropwise. Then, 150 g of cold water, 1.5 g of urea and 150 g of ice were added thereto.

This aqueous solution was added dropwise to a mixture of 100 ml of sulfuric acid, 100 ml of water and 150 g of sodium sulfate, while heating to 135° C. under stirring. At the same time, the mixture was subjected to steam distillation. After completion of the addition, an aqueous solution obtained by the steam distillation was subjected to salting out with sodium chloride, dried with anhydrous magnesium sulfate, and concentrated to obtain a crude product. The crude product was subjected to silica gel chromatography, which afforded 16 g of 2-ethyl-6-methylphenol (59% yield).

Then, 16 g of 2-ethyl-6-methylphenol was dissolved in 200 ml of chloroform, followed by stirring at 0° C., to which 56.6 g of tetrabutylammonium tribromide was added in small portions. After stirring at room temperature for 1 hour, the solvent was removed by distillation under reduced pressure, and the residue was dissolved in 300 ml of diethyl ether. The solution was successively washed with 10% hydrochloric acid and water, dried with anhydrous magnesium sulfate, and concentrated to obtain a crude product. The crude product was subjected to silica gel chromatography, which afforded 23 g of 4-bromo-2-ethyl-6-methylphenol (92% yield).

To a mixture of 10 g of 4-bromo-2-ethyl-6-methylphenol, 14.0 g of 1-(3-bromopropyloxy)-4-trifluoromethoxybenzene and 100 ml of N,N-dimethylformamide was added 7 g of potassium carbonate, while stirring at room temperature.

After stirring at room temperature for 12 hours, the reaction mixture was poured into ice water, and extracted twice with 200 ml of diethyl ether. The combined ether layer was washed with water, dried with anhydrous magnesium sulfate, and concentrated to obtain a crude product. The crude product was subjected to silica gel chromatography, which afforded 18.1 g of 4-bromo-2-ethyl-6-methyl-1-[3-(4-trifluoromethoxyphenoxy)propyloxy]benzene 90% yield).

Then, 6.6 g of 4-bromo-2-ethyl-6-methyl-1-[3-(4-trifluoromethoxyphenoxy)propyloxy]benzene was dissolved in 200 ml of tetrahydrofuran, and the solution was stirred at −70° C., to which 9.6 ml of n-butyl lithium solution (in hexane, 1.58 mol/liter) was added dropwise, followed by further stirring at −70° C. for 2 hours. To this reaction mixture was added dropwise a solution of 2.2 g of triethoxy borane dissolved in 60 ml of tetrahydrofuran. Then, the reaction mixture was stirred for 1 hour, while warming to room temperature, and 13 ml of 10% aqueous hydrochloric acid solution was added in small portions, followed by stirring at room temperature for 20 minutes. The tetrahydrofuran layer was washed with water, dried with anhydrous magnesium sulfate, and concentrated, to which 50 ml of toluene was added, and the mixture was heated at 70° C. under stirring, to which 6 ml of 30% aqueous hydrogen peroxide solution was added dropwise. The mixture was heated under reflux for 1 hour, and washed once with water, twice with 10% aqueous ammonium ferrous sulfate solution, and once with water. The toluene layer was dried with anhydrous magnesium sulfate, and concentrated to obtain a crude product. The crude product was subjected to silica gel chromatography, which afforded 3.4 g of 3-ethyl-4-[3-(4-trifluoromethoxyphenoxy)propyloxy]-5-methylphenol (61% yield), $n_D^{25.4}$ 1.4955.

Intermediate Production Example 4

Production of Intermediate Compound 263)

To a mixture of 10 g of 4-bromo-2,6-diethylphenol, 13.5 g of 1-(3-bromopropyloxy)-4-trifluoromethoxybenzene and 100 ml of N,N-dimethylformamide was added 6.6 g of potassium carbonate, while stirring at room temperature. After stirring at room temperature for 12 hours, the reaction mixture was poured into ice water, and extracted twice with 200 ml of diethyl ether. The combined ether layer was washed with water, dried with anhydrous magnesium sulfate, and concentrated to obtain a crude product. The crude product was subjected to silica gel chromatography, which afforded 14.8 g of 4-bromo-2-ethyl-6-methyl-1-[3-(4-trifluoromethoxyphenoxy)propyloxy]benzene (76% yield).

Then, 7.0 g of 4-bromo-2-ethyl-6-methyl-1-[3-(4-trifluoromethoxyphenoxy)propyloxy]benzene was dissolved in 200 ml of tetrahydrofuran, followed by stirring at −70° C., to which 10.0 ml of n-butyl lithium solution (in hexane, 1.58 mol/liter) was added dropwise, followed by further stirring at −70° C. for 2 hours. To this reaction mixture was added dropwise a solution of 2.4 g of trimethoxy borane dissolved in 60 ml of tetrahydrofuran. The reaction mixture was stirred for 1 hour, while warming to room temperature, and 13 ml of 10% aqueous hydrochloric acid solution was added in small portions, followed by stirring at room temperature for 20 minutes. The tetrahydrofuran layer was washed with water, dried with anhydrous magnesium sulfate, and concentrated, to which 50 ml of toluene was added, and the mixture was heated at 70° C. under stirring, to which 6 ml of 30% aqueous hydrogen peroxide solution was added dropwise. The mixture was heated under reflux for 1 hours, and washed once with water, and twice with 10% aqueous ammonium ferrous sulfate solution and once with water. The toluene layer was dried with anhydrous magnesium sulfate, and concentrated to obtain a crude product. The crude product was subjected to silica gel chromatography, which afforded 4.3 g of 3,5-diethyl-4-[3-(4-trifluoromethoxyphenoxy)propyloxy]phenol (50% yield), $n_D^{25.4}$ 1.5060.

The following are specific examples of the intermediate compounds of the general formula [IV], [V] or [VI] under the corresponding compound numbers with their physical properties, if measured.

1) 3,5-Dichloro-4-(4-fluoro-3-phenoxybenzyloxy)phenol m.p. 144.8° C.
2) 4-(2-Chlorobenzyloxy)-3,5-dichlorophenol m.p. 108.3° C.
3) 3,5-Dichloro-4-(1,1,2,2-tetrafluoroethoxy)phenol
4) 3,5-Dichloro-4-(3,3-dichloro-2-propenyloxy)phenol
5) 3,5-Dichloro-4-(3,3-dibromo-2-propenyloxy)phenol
6) 3,5-Dichloro-4-ethoxyphenol
7) 3,5-Dichloro-4-(4-trifluoromethylbenzyloxy)phenol
8) 3,5-Dichloro-4-(3-methyl-2-butenyloxy)phenol
9) 3,5-Dichloro-4-(3-chloro-2-butenyloxy)phenol
10) 3,5-Dichloro-4-(3-chloro-2-propenyloxy)phenol
11) 3,5-Dichloro-4-(4-tert-butoxycarbonylbenzyloxy)phenol
12) 3,5-Dichloro-4-benzyloxyphenol
13) 3,5-Dichloro-4-(3-methylbenzyloxy)phenol
14) 3,5-Dichloro-4-(4-chlorobenzyloxy)phenol
15) 3,5-Dichloro-4-(2,4-dichlorobenzyloxy)phenol
16) 3,5-Dichloro-4-(2,5-dichlorobenzyloxy)phenol
17) 3,5-Dichloro-4-(3,4-dichlorobenzyloxy)phenol
18) 3,5-Dichloro-4-(4-bromobenzyloxy)phenol
19) 3,5-Dichloro-4-(3-phenoxybenzyloxy)phenol
20) 3,5-Dichloro-4-(4-phenoxybenzyloxy)phenol
21) 3,5-Dichloro-4-(4-phenylbenzyloxy)phenol
22) 3,5-Dichloro-4-(α-methylbenzyloxy)phenol
23) 3,5-Dichloro-4-(4-tert-butylbenzyloxy)phenol
24) 3,5-Dichloro-4-(4-methoxybenzyloxy)phenol
25) 3,5-Dichloro-4-(3-phenyl-2-propenyloxy)phenol
26) 3,5-Dichloro-4-(3,5-bis(trifluoromethyl)benzyloxy)phenol
27) 3,5-Dichloro-4-(3-methoxybenzyloxy)phenol
28) 3,5-Dichloro-4-(2-naphthylmethoxy)phenol
29) 3,5-Dichloro-4-(1-naphthylmethoxy)phenol
30) 3,5-Dichloro-4-(3-cyanobenzyloxy)phenol
31) 3,5-Dichloro-4-(3-fluorobenzyloxy)phenol
32) 3,5-Dichloro-4-(3-chlorobenzyloxy)phenol
33) 3,5-Dichloro-4-(3-bromobenzyloxy)phenol
34) 3,5-Dichloro-4-(3,4-methylenedioxybenzyloxy)phenol
35) 3,5-Dichloro-4-(3-benzyloxybenzyloxy)phenol
36) 3,5-Dichloro-4-(1-(2-methylnaphthyl))methoxyphenol
37) 3,5-Dichoro-4-(phenethyloxy)phenol
38) 3,5-Dichloro-4-(2-methyl-3-phenylbenzyloxy)phenol
39) 3,5-Dichloro-4-(2-phenylbenzyloxy)phenol
40) 3,5-Dichloro-4-(4-fluorobenzyloxy)phenol
41) 3,5-Dichloro-4-(2-methylbenzyloxy)phenol
42) 3,5-Dichloro-4-(2-bromobenzyloxy)phenol
43) 3,5-Dichloro-4-(2-fluorobenzyloxy)phenol
44) 3,5-Dichloro-4-(2,6-dichlorobenzyloxy)phenol
45) 3,5-Dichloro-4-(2-bromoethoxy)phenol
46) 3,5-Dichloro-4-(2,2-dichloroethoxy)phenol
47) 3,5-Dichloro-4-(4-(methylthio)butoxy)phenol
48) 3,5-Dichloro-4-(3-phenylpropoxy)phenol
49) 3,5-Dichloro-4-(4-chloro-3-isopropoxybenzyloxy)phenol
50) 3,5-Dichloro-4-(4-benzyloxy)benzyloxyphenol
51) 3,5-Dichloro-4-(4-chloro-3-phenoxy)benzyloxyphenol 52) 3,5-Dichloro-4-(4-methoxy-3-benzyloxy)benzyloxyphenol
53) 3,5-Dichloro-4-(3-(3,4-dichlorophenoxy)benzyloxy)phenol
54) 3,5-Dichloro-4-(3-(3-trifluoromethylbenzyloxy)benzyloxy)phenol
55) 3,5-Dichloro-4-(3-(4-chlorophenoxy)benzyloxy)phenol
56) 3,5-Dichloro-4-(3-trifluoromethylbenzyloxy)phenol
57) 3,5-Dichloro-4-(3-(3-phenoxyphenyl)propyloxy)phenol
58) 3,5-Dichloro-4-(2-(4-chlorophenyl)ethoxy)phenol
59) 3,5-Dichloro-4-(4-phenylbutoxy)phenol
60) 3,5-Dichloro-4-(5-phenylpentyloxy)phenol
61) 3,5-Dichloro-4-(1-indanyloxy)phenol
62) 3,5-Dichloro-4-(2-methyl-1-(4-phenoxyphenyl)propyloxy)phenol
63) 3,5-Dichloro-4-(2-fluoro-5-(4-fluorophenoxy)benzyloxy)phenol
64) 3,5-Dichloro-4-(2-(4-fluorophenyl)ethoxy)phenol
65) 3,5-Dichloro-4-(2-(4-bromophenyl)ethoxy)phenol
66) 3,5-Dichloro-4-(2-(4-methylphenyl)ethoxy)phenol
67) 3,5-Dichloro-4-(2-(4-methoxyphenyl)ethoxy)phenol
68) 3,5-Dichloro-4-(2-(4-phenoxyphenyl)ethoxy)phenol
69) 3,5-Dichloro-4-(2-(2-chlorophenyl)ethoxy)phenol
70) 3,5-Dichloro-4-(2-(2-naphthyl)ethoxy)phenol
71) 3,5-Dichloro-4-(2-phenoxyethoxy)phenol
72) 3,5-Dichloro-4-(3-phenoxyethoxy)phenol
73) 3,5-Dichloro-4-(2-bromo-5-phenoxybenzyloxy)phenol
74) 3,5-Dichloro-4-(4-(4-trifluoromethylphenoxy)benzyloxy)phenol
75) 3,5-Dichloro-4-(3-(4-tert-butylphenoxy)benzyloxy)phenol
76) 3,5-Dichloro-4-(6-phenylhexyloxy)phenol
77) 3,5-Dichloro-4-(3-(4-methylphenoxy)benzyloxy)phenol
78) 3,5-Dichloro-4-(3-(3,5-dichlorophenoxy)benzyloxy)phenol
79) 3,5-Dichloro-4-(2-(3-chlorophenyl)ethoxy)phenol
80) 3,5-Dichloro-4-(2-(2-trifluoromethylphenyl)ethoxy)phenol
81) 3,5-Dichloro-4-(2-(3-trifluoromethylphenyl)ethoxy)phenol
82) 3,5-Dichloro-4-methoxymethoxyphenol
83) 3,5-Dichloro-4-(3-(3-trifluoromethylphenyl)propyloxy)phenol
84) 3,5-Dichloro-4-(3-(3-chlorophenyl)propyloxy)phenol
85) 3,5-Dichloro-4-(3-(4-chlorophenyl)propyloxy)phenol
86) 3,5-Dichloro-4-(3-(4-chlorophenoxy)propyloxy)phenol $n_D^{26.0}$ 1.5525
87) 3,5-Dichloro-4-(2-(4-chlorophenoxy)ethoxy)phenol
88) 3,5-Dichloro-4-(3-(4-fluorophenoxy)benzyloxy)phenol
89) 3,5-Dichloro-4-(4-ethoxybenzyloxy)phenol
90) 3,5-Dichloro-4-(2-phenylthioethoxy)phenol
91) 3,5-Dichloro-4-(3-trifluoromethoxybenzyloxy)phenol
92) 3,5-Dichloro-4-(4-trifluoromethoxybenzyloxy)phenol
93) 3,5-Dichloro-4-(3-(3-chlorophenoxy)propyloxy)phenol
94) 3,5-Dichloro-4-(3-(4-bromophenoxy)propyloxy)phenol
95) 3,5-Dichloro-4-(3-(4-trifluoromethoxyphenoxy)propyloxy)phenol $n_D^{25.0}$ 1.5000
96) 3-(2,6-Dichloro-4-hydroxyphenoxy)propylbenzoate
97) 3,5-Dimethyl-4-benzyloxyphenol m.p. 81.6° C.
98) 3-Chloro-5-methyl-4-benzyloxyphenol $n_D^{25.0}$ 1.5842
99) 4-(2,6-Dichloro-4-hydroxyphenoxy)butylbenzoate
100) 3,5-Dichloro-4-(3-(4-tert-butylphenoxy)propyloxy)phenol
101) 3,5-Dichloro-4-(3-(4-ethylphenoxy)propyloxy)phenol
102) 3,5-Dichloro-4-(3-(3-trifluoromethyl)phenoxy)propyloxy)phenol
103) 3,5-Dichloro-4-(3-(3-trifluoromethoxyphenoxy)propyloxy)phenol
104) 3,5-Dichloro-4-(3-(4-ethoxyphenoxy)propyloxy)phenol
105) 3,5-Dichloro-4-(3-(4-benzylphenoxy)propyloxy)phenol
106) 3,5-Dichloro-4-(3-bromopropyloxy)phenol
107) 3,5-Dichloro-4-(3-(4-fluorophenoxy)propyloxy)phenol
108) 3,5-Dichloro-4-(3-(4-(4-trifluoromethoxyphenyl)phenoxy)propyloxy)phenol
109) 3,5-Dichloro-4-(3-(3-chloro-4-(3-chloro-5-trifluoromethyl-2-pyridyloxy) phenoxy)propyloxy)phenol
110) 3,5-Dichloro-4-(3-(4-(1,1,3,3-tetramethylbutyl)phenoxy)propyloxy)phenol
111) 3,5-Dichloro-4-(3-(4-n-octyloxyphenoxy)propyloxy)phenol
112) 3,5-Dichloro-4-(2-(3-fluorophenyl)ethoxy)phenol
113) 3,5-Dichloro-4-(2-(3-bromophenyl)ethoxy)phenol
114) 3,5-Dichloro-4-(3-(3-fluorophenyl)propyloxy)phenol
115) 3,5-Dichloro-4-(3-(4-fluorophenyl)propyloxy)phenol
116) 3,5-Dichloro-4-(3-(3,4-dichlorophenoxy)propyloxy)phenol
117) 3,5-Dichloro-4-(3-(2,3,4-trichlorophenoxy)propyloxy)phenol
118) 3,5-Dichloro-4-(3-(2,4,6-trichlorophenoxy)propyloxy)phenol
119) 3,5-Dichloro-4-(3-(2,3,6-trichlorophenoxy)propyloxy)phenol
120) 3,5-Dichloro-4-(3-(2,4,5-trichlorophenoxy)propyloxy)phenol
121) 3,5-Dichloro-4-(3-(2,3,4,6-tetrachlorophenoxy)propyloxy)phenol
122) 3,5-Dichloro-4-(3-(4-methylthiophenoxy)propyloxy)phenol
123) 3,5-Dichloro-4-(3-(3-ethoxyphenoxy)propyloxy)phenol
124) 3,5-Dichloro-4-(3-(3-methoxyphenoxy)propyloxy)phenol
125) 2-(2,6-Dichloro-4-hydroxyphenoxy)ethyl (4-chloro)benzoate
126) 2-(2,6-Dichloro-4-hydroxyphenoxy)ethyl (4-bromo)benzoate
127) 2-(2,6-Dichloro-4-hydroxyphenoxy)ethyl benzoate
128) 3,5-Dichloro-4-(3-(3-trifluoromethoxyphenyl)propyloxy)phenol
129) 3,5-Dichloro-4-(3-(4-trifluoromethoxyphenyl)propyloxy)phenol
130) 2-(2,6-Dichloro-4-hydroxyphenoxy)ethyl (4-trifluoromethoxy)benzoate
131) 2-(2,6-Dichloro-4-hydroxyphenoxy)ethyl (3,5-dichloro)benzoate
132) 3,5-Dichloro-4-(3-(4-(1,1,2,2-tetrafluoroethoxy)phenoxy)propyloxy)phenol
133) 3,5-Dichloro-4-(3-(4-(1,1,2,2-tetrafluoro-2-bromoethoxy)phenoxy)propyloxy)phenol
134) 3,5-Dichloro-4-(3-(4-bromodifluoromethoxyphenoxy)propyloxy)phenol
135) 3,5-Dichloro-4-(2-(4-trifluoromethylphenyl)ethoxy)phenol
136) 3,5-Dichloro-4-(3-(3-bromophenyl)propyloxy)phenol
137) 3,5-Dichloro-4-(4-(4-chlorophenyl)-3-butenyloxy)phenol
138) 3,5-Dichloro-4-(4-(4-fluorophenyl)butyloxy)phenol
139) 3,5-Dichloro-4-(4-(4-trifluoromethylphenyl)propyloxy)phenol
140) 3,5-Dichloro-4-(4-(4-trifluoromethoxyphenyl)propyloxy)phenol
141) 2-(2,6-Dichloro-4-hydroxyphenoxy)ethyl phenylacetate 142) 3-(2,6-Dichloro-4-hydroxyphenoxy)propyl (2-chloro) benzoate
143) 3-(2,6-Dichloro-4-hydroxyphenoxy)propyl (3-chloro) benzoate
144) 3-(2,6-Dichloro-4-hydroxyphenoxy)propyl (4-chloro) benzoate
145) 3-(2,6-Dichloro-4-hydroxyphenoxy)propyl (4-ethoxy) benzoate
146) 3-(2,6-Dichloro-4-hydroxyphenoxy)propyl (4-trifluoromethoxy)benzoate
147) 2-(2,6-Dichloro-4-hydroxyphenoxy)ethyl (2-chloro) benzoate
148) 2-(2,6-Dichloro-4-hydroxyphenoxy)ethyl (3-chloro) benzoate
149) 3,5-Dichloro-4-(2-(4-chlorophenylthio)ethoxy)phenol
150) 3-(2,6-Dichloro-4-hydroxyphenoxy)propyl (3-phenoxy)benzoate
151) 3-(2,6-Dichloro-4-hydroxyphenoxy)propyl (4-fluoro) benzoate
152) 3-(2,6-Dichloro-4-hydroxyphenoxy)propyl (4-bromo) benzoate
153) 3-(2,6-Dichloro-4-hydroxyphenoxy)propyl (2-fluoro-4-trifluoromethyl)benzoate
154) 3-(2,6-Dichloro-4-hydroxyphenoxy)propyl (3,5-bistrifluoromethyl)benzoate
155) 3,5-Dichloro-4-(3-(4-isopropoxyphenoxy)propyloxy) phenol
156) 3,5-Dichloro-4-(3-(3-isopropoxyphenoxy)propyloxy) phenol
157) 3,5-Dichloro-4-(3-(4-(2,2,2-trifluoroethoxy)phenoxy) propyloxy)phenol
158) 3,5-Dichloro-4-(3-(3-(2,2,2-trifluoroethoxy)phenoxy) propyloxy)phenol
159) 3,5-Dichloro-4-(3-(4-trifluoromethylphenoxy) propyloxy)phenol $n_D^{25.0}$ 1.5151
160) 3,5-Dichloro-4-(3-(3-(1,1,2,2-tetrafluoroethoxy) phenoxy)propyloxy)phenol
161) 3,5-Dichloro-4-(3-(3-(2-bromo-1,1,2,2-tetrafluoroethoxy)phenoxy)propyloxy)phenol
162) 3-(2,6-Dichloro-4-hydroxyphenoxy)propyl (2,4-dichloro)benzoate
163) 3-(2,6-Dichloro-4-hydroxyphenoxy)propyl (3,4-dichloro)benzoate
164) 3-(2,6-Dichloro-4-hydroxyphenoxy)propyl (3-trifluoromethyl)benzoate
165) 3-(2,6-Dichloro-4-hydroxyphenoxy)propyl (3,4-dimethoxy)benzoate
166) 3-(2,6-Dichloro-4-hydroxyphenoxy)propyl (4-isopropyl)benzoate
167) 3,5-Dichloro-4-(4-bromobutyloxy)phenol
168) 3,5-Dichloro-4-(3-(2,6-dichloro-4-(3,3-dichloro-2-propenyloxy)phenoxy)propyloxy)phenol
169) 3,5-Dichloro-4-(4-(2,6-dichloro-4-(3,3-dichloro-2-propenyloxy)phenoxy)butoxy)phenol
170) 3-Chloro-5-methyl-4-(2-(4-bromophenyl)ethoxy) phenol
171) 3-Chloro-5-methyl-4-(3-(4-chlorophenoxy)propyloxy) phenol
172) 3-Chloro-5-methyl-4-(4-phenylbutyloxy)phenol
173) 3-Chloro-5-methyl-4-(2-(4-bromophenyl)ethoxy) phenol
174) 3,5-Dichloro-4-(3-(phenylthio)propyloxy)phenol
175) 3,5-Dichloro-4-(3-(4-chlorophenylthio)propyloxy) phenol
176) 3-(2,6-Dichloro-4-hydroxyphenoxy)propyl 1-naphthoate
177) 3-(2,6-Dichloro-4-hydroxyphenoxy)propyl 2-naphthoate
178) 3,5-Dichloro-4-(3-(3-trifluoromethoxyphenoxy) propyloxy)phenol
179) 4-(2,6-Dichloro-4-hydroxyphenoxy)butyl (4-ethoxy) benzoate
180) 2-(2,6-Dichloro-4-hydroxyphenoxy)ethyl (4-isopropoxy)benzoate
181) 3-(2,6-Dichloro-4-hydroxyphenoxy)propyl (4-isopropoxy)benzoate
182) 2-(2,6-Dichloro-4-hydroxyphenoxy)ethyl (4-ethoxy) benzoate
183) 3,5-Dichloro-4-(3,7-dimethyloctyloxy)phenol
184) 3,5-Dichloro-4-(3,7-dimethyl-6-octenyloxy)phenol
185) 3,5-Dichloro-4-(3,7-dimethyl-2,6-octadien-1-yl-oxy) phenol
186) 3,5-Dichloro-4-(n-octyloxy)phenol
187) 3,5-Dichloro-4-(2-(4-chlorobenzyloxy)ethoxy)phenol
188) 4-(2,6-Dichloro-4-hydroxyphenoxy)butyl (2-chloro) benzoate
189) 4-(2,6-Dichloro-4-hydroxyphenoxy)butyl (3-chloro) benzoate
190) 4-(2,6-Dichloro-4-hydroxyphenoxy)butyl (4-chloro) benzoate
191) 4-(2,6-Dichloro-4-hydroxyphenoxy)butyl (4-trifluoromethoxy)benzoate
192) 4-(2,6-Dichloro-4-hydroxyphenoxy)butyl (4-isopropoxy)benzoate
193) 3,5-Dichloro-4-(3-(4-trifluoromethylphenylthio) propyloxy)phenol
194) 3,5-Dichloro-4-(3-(4-tert-butylphenylthio)propyloxy) phenol 195) 3,5-Dichloro-4-(4-(4-trifluoromethoxyphenoxy)butyloxy)phenol
196) 3,5-Dichloro-4-(4-(4-isopropyloxyphenoxy)butyloxy) pheno $n_D^{25.5}$ 1.5484
197) 3,5-Dibromo-4-(2-(4-bromophenyl)ethoxy)phenol $n_D^{26.0}$ 1.5875
198) 3,5-Dibromo-4-(3-(4-chlorophenoxy)propyloxy) phenol m.p. 80.3° C.
199) 3,5-Dibromo-4-(4-phenylbutyloxy)phenol m.p. 80.3° C.
200) 3,5-Dichloro-4-(4-(4-chlorophenyl)butyloxy)phenol
201) 2-(2,6-Dichloro-4-hydroxyphenoxy)ethyl (3-ethoxy) benzoate
202) 3-(2,6-Dichloro-4-hydroxyphenoxy)propyl (3-ethoxy) benzoate
203) 4-(2,6-Dichloro-4-hydroxyphenoxy)butyl (3-ethoxy) benzoate
204) 2-(2,6-Dichloro-4-hydroxyphenoxy)ethyl (4-trifluoromethyl)benzoate
205) 3-(2,6-Dichloro-4-hydroxyphenoxy)propyl (4-trifluoromethyl)benzoate
206) 3,5-Dichloro-4-(3-methyl-3-(4-chlorophenoxy) propyloxy)phenol 207) 3,5-Dichloro-4-(1-methyl-3-(4-chlorophenoxy)propyloxy)phenol
208) 3,5-Dichloro-4-(3-methyl-3-butenyloxy)phenol
209) 3,5-Dichloro-4-(3-(4-methoxyphenylthio)propyloxy) phenol
210) 3,5-Dichloro-4-(3-(4-fluorophenylthio)propyloxy) phenol
211) 3,5-Dichloro-4-(3-(2,3,5,6-tetrafluorophenylthio) propyloxy)phenol
212) 3,5-Dichloro-4-(3-(3-chlorophenylthio)propyloxy) phenol
213) 3,5-Dichloro-4-(3-(4-bromophenylthio)propyloxy) phenol
214) 3,5-Dichloro-4-(4-(4-chlorophenoxy)butyloxy)phenol $n_D^{25.0}$ 1.5540
215) 3,5-Dichloro-4-(4-(3-isopropoxyphenoxy)butyloxy) phenol 216) 3,5-Dichloro-4-(4-(4-trifluoromethoxyphenoxy)butyloxy)phenol
217) 3,5-Dichloro-4-(4-(4-(1,1,2,2-tetrafluoroethoxy)phenoxy)butyloxy)phenol
218) 3,5-Dichloro-4-(4-(3-(1,1,2,2-tetrafluoroethoxy)phenoxy)butyloxy)phenol
219) 3,5-Dichloro-4-(4-(4-(2,2,2-trifluoroethoxy)phenoxy)butyloxy)phenol
220) 3,5-Dichloro-4-(4-(3-(2,2,2-trifluoroethoxy)phenoxy)butyloxy)phenol
221) 3,5-Dichloro-4-(4-(4-difluoromethoxyphenoxy)butyloxy)phenol
222) 3,5-Dichloro-4-(4-(3-difluoromethoxyphenoxy)butyloxy)phenol
223) 3,5-Dichloro-4-(3-(4-difluoromethoxyphenoxy)propyloxy)phenol
224) 3,5-Dichloro-4-(3-(3-difluoromethoxyphenoxy)butyloxy)phenol
225) 3,5-Dichloro-4-(4-(4-trifluoromethylphenoxy)butyloxy)phenol
226) 3,5-Dichloro-4-(4-(3-trifluoromethylphenoxy)butyloxy)phenol
227) 3-(2,6-Dichloro-4-hydroxyphenoxy)propyl (4-chloro)phenylacetate
228) 3-(2,6-Dichloro-4-hydroxyphenoxy)propyl (4-chloro)cinnamate
229) 3-(2,6-Dichloro-4-hydroxyphenoxy)propyl (4-chloro)phenoxyacetate
230) 3,5-Dichloro-4-(3-(N-methylanilino)propyloxy)phenol
231) 3,5-Dichloro4-(4-(3-fluorophenyl)-3-butenyloxy)phenol
232) 3,5-Dichloro-4-(4-(3-trifluoromethylphenyl)-3-butenyloxy)phenol
233) 3,5-Dichloro-4-(4-(3-trifluoromethoxyphenyl)-3-butenyloxy)phenol
234) 3,5-Dichloro-4-(4-(3-fluorophenyl)butyloxy)phenol
235) 3,5-Dichloro-4-(4-(3-trifluoromethylphenyl)butyloxy)phenol
236) 3,5-Dichloro-4-(4-(3-trifluoromethoxyphenyl)butyloxy)phenol
237) 2-(2,6-Dichloro-4-hydroxyphenoxy)ethyl (4-(2,2,2-trifluoroethoxy))benzoate
238) 3-(2,6-Dichloro-4-hydroxyphenoxy)propyl (4-(2,2,2-trifluoroethoxy))benzoate
239) 3,5-Dichloro-4-((3-ethoxycarbonyl)propyloxy)phenol
240) 4-(Trifluoromethoxy)phenoxy 4-(4-hydroxy-2,6-dichlorophenoxy)butyrate
241) 3,5-Dichloro-4-(2-methyl-3-(4-chlorophenoxy)propyloxy)phenol
242) 3-Chloro-5-methyl-4-(3-(4-trifluoromethoxyphenoxy)propyloxy)phenol
243) 3-(2-Chloro-6-methyl-4-hydroxyphenoxy)propyl 4-bromobenzoate
244) 3,5-Dichloro-4-(2-(4-isopropoxyphenyl)ethoxy)phenol
245) 3,5-Dichloro-4-(2-(4-trifluoromethoxyphenyl)ethoxy)phenol
246) 3,5-Dichloro-4-(3-(4-bromophenyl)propyloxy)phenol
247) 3,5-Dichloro-4-(3-(4-trifluoromethylphenyl)propyloxy)phenol
248) 3,5-Dimethyl-4-(3-(4-chlorophenoxy)propyloxy)phenol
249) 3,5-Dichloro-4-(4-(4-chlorophenoxy)-2-(Z)-butenyloxy)phenol
250) 3,5-Dichloro-4-(4-(4-chlorophenoxy)-2-(E)-butenyloxy)phenol
251) 3-(2,6-Dichloro-4-hydroxyphenoxy)propyl 4-difluoromethylbenzoate
252) 3-(2,6-Dichloro-4-hydroxyphenoxy)propyl 4-(1,1,2,2-tetrafluoroethoxy)benzoate
253) 3-(2,6-Dichloro-4-hydroxyphenoxy)propyl 3-methyl-2-(4-chlorophenyl)butyrate
254) 3,5-Dichloro-4-(4-(4-chlorophenylthio)butyloxy)phenol
255) 3,5-Dichloro-4-(4-(4-trifluoromethylphenylthio)butyloxy)phenol
256) 3,5-Dichloro-4-(4-(4-hydroxyphenylthio)butyloxy)phenol
257) 3,5-Dimethyl-4-(3-(4-trifluoromethoxyphenoxy)propyloxy)phenol
258) 3,5-Dichloro-4-(4-(4-methoxyphenylthio)butyloxy)phenol
259) 3,5-Dichloro-4-(4-(4-isopropoxyphenylthio)butyloxy)phenol
260) 3,5-Dichloro-4-(3-(4-chlorophenylsulfenyl)propyloxy)phenol
261) 3,5-Dichloro-4-(4-(4-chlorophenoxy)butyloxy)phenol
262) 3,5-Diisopropyl-4-(4-(4-trifluoromethoxyphenoxy)butyloxy)phenol
263) 3,5-Diethyl-4-(3-(4-trifluoromethoxyphenoxy)propyloxy)phenol $n_D^{20.4}$ 1.5060
264) 3-Ethyl-5-methyl-4-(3-(4-trifluoromethoxyphenoxy)propyloxy)phenol $n_D^{25.4}$ 1.4955
265) 3-(2,6-Dichloro-4-hydroxyphenoxy)propyl (4-trifluoromethyl)cinnamate
266) 3,5-Dichloro-4-(3-(4-trifluoromethoxyanilino)propyloxy)phenol
267) 3,5-Dichloro-4-(3-anilino)propyloxy)phenol
268) 3,5-Dichloro-4-(3-(4-trifluoromethylanilino)propyloxy)phenol
269) 3,5-Dichloro-4-(3-(N-methyl-4-trifluoromethylanilino)propyloxy)phenol
270) 3,5-Dichloro-4-(3-(N-acyl-4-trifluoromethylanilino)propyloxy)phenol
271) 3,5-Dichloro-4-(3-(4trifluoromethoxyphenylthio)propyloxy)phenol
272) 3,5-Dichloro-4-(4-trifluoromethylbenzyloxy)thiophenol
273) 3,5-Dichloro-4-(2-(4-trifluoromethylphenyl)ethoxy)phenol
274) 3,5-Dichloro-4-(3-(4-trifluoromethylphenyl)propyloxy)phenol
275) 3,5-Dichloro-4-(3-(4-trifluoromethylphenoxy)propyloxy)phenol
276) 3-Ethyl-5-methyl-4-(3-(4-trifluoromethylphenoxy)propyloxy)phenol
277) 3,5-Dichloro-4-(3-(4-chlorophenylsulfonyl)propyloxy)phenol
278) 2,3,5,6-Tetrachloro-4-(3-(4-trifluoromethylphenoxy)propyloxy)phenol
279) 3,5-Dichloro-4-(4-anilino)butyloxy)phenol
280) 3,5-Dichloro-4-(4-(4-trifluoromethylanilino)butyloxy)phenol
281) 3,5-Dichloro-4-(4-(4-trifluoromethoxyanilino)butyloxy)phenol
282) 3,5-Diethyl-4-(3-(4-trifluoromethylphenoxy)propyloxy)phenol
283) 3,5-Dichloro-4-(3-(4-isopropoxycarbonylphenoxy)propyloxy)phenol
284) 3,5-Dichloro-4-(3-(4-methoxycarbonylphenoxy)propyloxy)phenol
285) 3-Chloro-5-methyl-4-(4-(4-trifluoromethoxyphenoxy)butyloxy)phenol
286) 3-Chloro-5-methyl-4-(4-(4-trifluoromethylphenoxy)butyloxy)phenol 287) 3-Chloro-5-methyl-4-(4-(4-chlorophenoxy)butyloxy) phenol
288) 3-Chloro-5-methyl-4-(3-(4-bromophenoxy)propyloxy) phenol
289) 3-Chloro-5-methyl-4-(4-(4-bromophenoxy)butyloxy) phenol
290) 3-Chloro-5-methyl-4-(3-(4-isopropoxyphenoxy) propyloxy)phenol
291) 3-Chloro-5-methyl-4-(4-(4-isopropoxyphenoxy) butyloxy)phenol
292) 3-Ethyl-5-methyl-4-(4-(4-trifluoromethoxyphenoxy) butyloxy)phenol
293) 3-Ethyl-5-methyl-4-(4-(4-trifluoromethylphenoxy) butyloxy)phenol
294) 3-Ethyl-5-methyl-4-(3-(4-chlorophenoxy)propyloxy) phenol
295) 3-Ethyl-5-methyl-4-(4-(4-chlorophenoxy)butyloxy) phenol
296) 3-Ethyl-5-methyl-4-(3-(4-bromophenoxy)propyloxy) phenol
297) 3-Ethyl-5-methyl-4-(4-(4-bromophenoxy)butyloxy) phenol
298) 3-Ethyl-5-methyl-4-(3-(4-isopropoxyphenoxy) propyloxy)phenol
299) 3-Ethyl-5-methyl-4-(4-(4-isopropoxyphenoxy) butyloxy)phenol
300) 3,5-Diethyl-4-(4-(4-trifluoromethoxyphenoxy) butyloxy)phenol
301) 3,5-Diethyl-4-(4-(4-trifluoromethylphenoxy)butyloxy) phenol
302) 3,5-Diethyl-4-(3-(4-chlorophenoxy)propyloxy)phenol
303) 3,5-Diethyl-4-(4-(4-chlorophenoxy)butyloxy)phenol
304) 3,5-Diethyl-4-(3-(4-bromophenoxy)propyloxy)phenol
305) 3,5-Diethyl-4-(4-(4-bromophenoxy)butyloxy)phenol
306) 3,5-Diethyl-4-(3-(4-isopropoxyphenoxy)propyloxy) phenol
307) 3,5-Diethyl-4-(4-(4-isopropoxyphenoxy)butyloxy) phenol
308) 3,5-Diisopropyl-4-(4-(4-trifluoromethoxyphenoxy) butyloxy)phenol
309) 3,5-Diisopropyl-4-(3-(4-trifluoromethoxyphenoxy) propyloxy)phenol
310) 3,5-Diisopropyl-4-(4-(4-trifluoromethoxyphenoxy) butyloxy)phenol
311) 3,5-Diisopropyl-4-(3-(4-chlorophenoxy)propyloxy) phenol
312) 3,5-Diisopropyl-4-(4-(4-chlorophenoxy)butyloxy) phenol
313) 3,5-Diisopropyl-4-(3-(4-bromophenoxy)propyloxy) phenol
314) 3,5-Diisopropyl-4-(4-(4-bromophenoxy)butyloxy) phenol
315) 3,5-Diisopropyl-4-(3-(4-isopropoxyphenoxy) propyloxy)phenol
316) 3,5-Diisopropyl-4-(4-(4-isopropoxyphenoxy) butyloxy)phenol The following is a production example for the intermediate compound of the general formula [IX].

Intermediate Production Example 5

Production of 4-(2-chlorobenzyloxy)-3,5-dichlorophenoxyacetaldehyde

A mixture of 0.85 g of 4-(2-chlorobenzyloxy)-3,5-dichlorophenol, 0.47 ml of bromoacetaldehyde diethyl acetal, 0.46 g of potassium carbonate and 20 ml of N,N-dimethylformamide was stirred at 90° C. for 6 hours. After cooling to room temperature, the reaction mixture was poured into ice water, and extracted twice with 50 ml of diethyl ether. The combined ether layer was washed with water, and dried with anhydrous magnesium sulfate, followed by removal of the solvent by distillation under reduced pressure. The residue was subjected to silica gel chromatography, which afforded 0.85 g of 4-(2-chlorobenzyloxy)-3,5-dichlorophenoxyacetaldehyde diethyl acetal (72% yield).

Then, 0.85 g of 4-(2-chlorobenzyloxy)-3,5-dichlorophenoxyacetaldehyde diethyl acetal was dissolved in 10 ml of acetic acid, to which 1 ml of concentrated hydrochloric acid was added dropwise, while stirring under ice cooling. After stirring under ice cooling for 2 hours, the reaction mixture was poured into ice water, and extracted twice with diethyl ether. The combined ether layer was washed with water, dried with anhydrous magnesium sulfate, followed by removal of the solvent by distillation under reduced pressure, which afforded 0.70 g of 4-(2-chlorobenzyloxy)-3,5-dichlorophenoxyacetaldehyde in crude form.

The following are production examples for the intermediate compounds of the general formula [III] or [X].

Intermediate Production Example 6

Production of Intermediate Compound 317)

A reaction vessel was charged with 30.5 g of 4-hydroxyphenyl benzoate, 21.6 g of potassium carbonate, 20.8 g of 1,1,3-trichloropropene and 100 ml of N,N-dimethylformamide. After stirring at room temperature for 15 hours, the reaction mixture was poured into water, and extracted twice with 150 ml of diethyl ether. The combined ether layer was washed with water, dried with anhydrous magnesium sulfate, and concentrated to obtain a crude product. The crude product was subjected to silica gel chromatography, which afforded 44.1 g of 4-(3,3-dichloro-2-propenyloxy)phenyl benzoate (96% yield).

A reaction vessel was charged with 44.1 g of 4-(3,3-dichloro-2-propenyloxy)phenyl benzoate and 400 ml of methanol, to which 33 g of 30% potassium hydroxide was slowly added dropwise under ice cooling. After stirring for 1 hour, the reaction mixture was made weakly acidic by the addition of 10% hydrochloric acid, and extracted twice with 150 ml of diethyl ether under salting out. The combined ether layer was washed with water, dried with anhydrous magnesium sulfate, and concentrated to obtain a crude product. The crude product was subjected to silica gel chromatography, which afforded 26.0 g of 4-(3,3-dichloro-2-propenyloxy)phenol (87% yield).

A reaction vessel was charged with 26.0 g of 4-(3,3-dichloro-2-propenyloxy)phenyl and 500 ml of carbon tetrachloride, to which a solution of 27.1 g of tert-butyl hypochlorite dissolved in 20 ml of carbon tetrachloride was slowly added dropwise, while stirring under ice cooling. After 24 hours, the reaction mixture was poured into water, followed by phase separation. The organic layer (i.e., carbon tetrachloride layer) was washed with water, dried with anhydrous magnesium sulfate, and concentrated to obtain a crude product. The crude product was subjected to silica gel chromatography, which afforded 11.0 g of 2,6-dichloro-4-(3,3-dichloro-2-propenyloxy)phenol (32% yield), $n_D^{22.5}$ 1.5895.

Intermediate Production Example 7

Production of Intermediate Compound 325)

A solution of 50 g of 4-bromo-6-chloro-2-methylphenol and 42.5 g of benzyl bromide dissolved in 200 ml of N,N-dimethylformamide was stirred at room temperature, to which 37.4 g of potassium carbonate was added, and the mixture was stirred for 12 hours. After completion of the reaction, the solvent was removed by distillation under reduced pressure, and the residue was added to 400 ml of diethyl ether, washed with water, dried with anhydrous magnesium sulfate, and concentrated to obtain a crude product. The crude product was subjected to silica gel chromatography, which afforded 63 g of 4-bromo-6-chloro-2-methyl-1-benzyloxybenzene (90% yield).

Then, 40 g of 4-bromo-6-chloro-2-methyl-1-benzyloxybenzene was dissolved in 400 ml of tetrahydrofuran, followed by stirring at −70° C., to which 76 ml of n-butyl lithium solution (in hexane, 1.69 mol/liter) was added dropwise, followed by further stirring at −70° C. for 2 hours. To this reaction mixture was added dropwise a solution of 13.3 g of trimethoxyborane dissolved in 50 ml of tetrahydrofuran. Then, the reaction mixture was stirred for 1 hours, while warming to room temperature, and 100 ml of 10% aqueous hydrochloric acid solution was added in small portions, followed by stirring for 20 minutes. The tetrahydrofuran layer was washed with water, dried with anhydrous magnesium sulfate, and concentrated. The residue was mixed with 200 ml of toluene, and heated at 70° C. under stirring, to which 36 ml of 30% aqueous hydrogen peroxide solution was added dropwise. After heating under reflux for 1 hour, the reaction mixture was washed once with water, twice with 10% aqueous ammonium ferrous sulfate solution, and once with water, followed by phase separation. The toluene layer was dried with anhydrous magnesium sulfate, and concentrated to obtain a crude product. The crude product was subjected to silica gel chromatography, which afforded 29 g of 4-benzyloxy-3-chloro-5-methylphenol (91% yield).

To a solution of 27.3 g of 4-benzyloxy-3-chloro-5-methylphenol dissolved in 250 ml of chloroform and stirred at 0° C. were added 15.4 g of benzoyl chloride and then 13.3 g of triethylamine. After stirring at room temperature for 2 hours, the chloroform layer was washed with water, dried with anhydrous magnesium sulfate, and concentrated. The residue was subjected to silica gel chromatography, which afforded 35 g of 4-benzyloxy-3-chloro-5-methyl-1-benzoyloxybenzene (90% yield).

A reaction vessel was charged with 35 g of 4-benzyloxy-3-chloro-5-methyl-1-benzoyloxybenzene and 200 ml of ethyl acetate, and the air in the vessel was replaced with nitrogen. Then, 2 g of 10% palladium carbon was added, and the nitrogen in the vessel was replaced with hydrogen, followed by vigorous stirring at room temperature for 10 hours. The hydrogen in the vessel was replaced with nitrogen, after which the reaction mixture was filtered, and the filtrate was concentrated. The residue was silica gel chromatography was subjected to silica gel chromatography, which afforded 25 g of 4-benzoyloxy-2-chloro-6-methylphenol (96% yield).

Then, 25 g of 4-benzoyloxy-2-chloro-6-methylphenol was dissolved in 250 ml of chloroform, to which 12 g of chloromethyl methyl ether was added, while stirring at 0° C., and 21 g of N-ethyldiisopropylamine was added dropwise. After heating under reflux for 1 hour, the chloroform layer was washed with water, and concentrated. The residue was subjected to silica gel chromatography, which afforded 27.4 g of 3-chloro4-methoxymethoxy-5-methyl-1-benzoyloxybenzene (96% yield).

Then, 26 g of 3-chloro-4-methoxymethoxy-5-methyl-1-benzoyloxybenzene was dissolved in 200 ml of methanol, and the solution was stirred at room temperature, while adding dropwise 60 ml of 10% aqueous potassium hydroxide solution. After completion of the reaction, the solvent was removed by distillation under reduced pressure. The residue was added to 150 ml of water, neutralized with 10% aqueous hydrochloric acid solution, and extracted with 200 ml of diethyl ether. The solvent was removed by distillation under reduced pressure, and the residue was subjected to silica gel chromatography, which afforded 17.4 g of 3-chloro-4-methoxymethoxy-5-methylphenol (96% yield).

To a mixture of 10 g of 3-chloro-4-methoxymethoxy-5-methylphenol, 7 g of potassium carbonate and 100 ml of N,N-dimethylformamide was added dropwise a solution of 8 g of 1,1,3-trichloro-1-propene dissolved in 30 ml of N,N-dimethylformamide, while stirring at room temperature. After stirring at room temperature for 12 hours, the reaction mixture was poured into ice water, and extracted with 200 ml of diethyl ether. The combined ether was washed with water, dried with anhydrous magnesium sulfate, and concentrated. The residue was subjected to silica gel chromatography, which afforded 14.1 g of 3-chloro-4-methoxymethoxy-5-methyl-1-(3,3-dichloro-2-propenyloxy)benzene (91% yield).

Then, 14.1 g of 3-chloro-4-methoxymethoxy-5-methyl-1-(3,3-dichloro-2-propenyloxy)benzene was dissolved in 100 ml of 80% aqueous acetic acid solution, followed by heating under reflux with stirring for 1 hour. After completion of the reaction, the reaction mixture was mixed with 200 ml of water, and extracted twice with 200 ml of diethyl ether. The combined ether layer was washed with water, dried with anhydrous magnesium sulfate, and concentrated. The residue was subjected to silica gel chromatography, which afforded 11.3 g of 2-chloro-6-methyl-(3,3-dichloro-2-propenyloxy)phenol (93% yield), m.p. 70.0° C.

The following are specific examples of the intermediate compounds of the general formula [III] or [X] under the corresponding compound numbers with their physical properties, if measured.

317) 2,6-Dichloro-4-(3,3-dichloro-2-propenyloxy)phenol
$^1$H-NMR (CDCl$_3$/TMS) δ(ppm): 4.57 (2H, d), 5.50 (1H, brs), 6.11 (1H, t), 6.85 (2H, s)
318) 2,6-Dichloro-4-(3,3-dibromo-2-propenyloxy)phenol
319) 2-Chloro-6-bromo-4-(3,3-dichloro-2-propenyloxy)phenol
320) 2-Chloro-6-bromo-4-(3,3-dibromo-2-propenyloxy)phenol
321) 2,6-Dibromo-4-(3,3-dichloro-2-propenyloxy)phenol
322) 2,6-Dibromo-4-(3,3-dibromo-2-propenyloxy)phenol
323) 2,6-Dimethyl-4-(3,3-dichloro-2-propenyloxy)phenol
324) 2,6-Dimethyl-4-(3,3-dibromo-2-propenyloxy)phenol
325) 2-Chloro-6-methyl-4-(3,3-dichloro-2-propenyloxy)phenol m.p. 70.0° C.
326) 2-Chloro-6-methyl-4-(3,3-dibromo-2-propenyloxy)phenol
327) 2,6-Diethyl-4-(3,3-dichloro-2-propenyloxy)phenol
328) 2,6-Diethyl-4-(3,3-dibromo-2-propenyloxy)phenol
329) 2,6-Diisopropyl-4-(3,3-dichloro-2-propenyloxy)phenol
330) 2,6-Diisopropyl-4-(3,3-dibromo-2-propenyloxy)phenol 331) 2-Ethyl-6-methyl-4-(3,3-dichloro-2-propenyloxy)phenol
332) 2-Ethyl-6-methyl-4-(3,3-dibromo-2-propenyloxy)phenol
333) 2-Ethyl-6-chloro-4-(3,3-dichloro-2-propenyloxy)phenol
334) 2-Ethyl-6-chloro-4-(3,3-dibromo-2-propenyloxy)phenol 335) 2,6-Difluoro-4-(3,3-dichloro-2-propenyloxy)phenol
336) 2,6-Difluoro-4-(3,3-dibromo-2-propenyloxy)phenol
337) 2-Chloro-6-fluoro-4-(3,3-dichloro-2-propenyloxy) phenol
338) 2-Chloro-6-fluoro-4-(3,3-dibromo-2-propenyloxy) phenol
339) 2-Isopropyl-6-methyl-4-(3,3-dichloro-2-propenyloxy) phenol
340) 2-Isopropyl-6-methyl-4-(3,3-dibromo-2-propenyloxy) phenol
341) 2-Isopropyl-6-ethyl-4-(3,3-dichloro-2-propenyloxy) phenol
342) 2-Isopropyl-6-ethyl-4-(3,3-dibromo-2-propenyloxy) phenol
343) 2-Isopropyl-6-chloro-4-(3,3-dichloro-2-propenyloxy) phenol
344) 2-Isopropyl-6-chloro-4-(3,3-dibromo-2-propenyloxy) phenol
345) 2-Bromo-6-methyl-4-(3,3-dichloro-2-propenyloxy) phenol
346) 2-Bromo-6-methyl-4-(3,3-dibromo-2-propenyloxy) phenol
347) 2-Bromo-6-ethyl-4-(3,3-dichloro-2-propenyloxy) phenol
348) 2-Bromo-6-ethyl-4-(3,3-dibromo-2-propenyloxy) phenol
349) 2-Bromo-6-isopropyl-4-(3,3-dichloro-2-propenyloxy) phenol
350) 2-Bromo-6-isopropyl-4-(3,3-dibromo-2-propenyloxy) phenol
351) 2-Fluoro-6-methyl-4-(3,3-dichloro-2-propenyloxy) phenol
352) 2-Fluoro-6-methyl-4-(3,3-dibromo-2-propenyloxy) phenol
353) 2-Fluoro-6-ethyl-4-(3,3-dichloro-2-propenyloxy) phenol
354) 2-Fluoro-6-ethyl-4-(3,3-dibromo-2-propenyloxy) phenol
355) 2-Fluoro-6-isopropyl-4-(3,3-dichloro-2-propenyloxy) phenol
356) 2-Fluoro-6-isopropyl-4-(3,3-dibromo-2-propenyloxy) phenol
357) 2-Bromo-6-fluoro-4-(3,3-dichloro-2-propenyloxy) phenol
358) 2-Bromo-6-fluoro-4-(3,3-dibromo-2-propenyloxy) phenol
359) 2-Chloro-6-trifluoromethyl-4-(3,3-dichloro-2-propenyloxy)phenol
360) 2-Chloro-6-trifluoromethyl-4-(3,3-dibromo-2-propenyloxy)phenol
361) 2-Fluoro-6-trifluoromethyl-4-(3,3-dichloro-2-propenyloxy)phenol
362) 2-Fluoro-6-trifluoromethyl-4-(3,3-dibromo-2-propenyloxy)phenol The following are production examples for the intermediate compounds of general formula [II] or [XIII].

Intermediate Production Example 8

Production of intermediate compound 363)

A reaction vessel was charged with 10.6 g of 1,3-dibromopropane, 5.53 g of potassium carbonate and 100 ml of N,N-dimethylformamide, to which a solution of 30.5 g of 2,6-dichloro-4-(3,3-dichloro-2-propenyloxy)phenol dissolved in 40 ml of N,N-dimethylformamide was slowly added dropwise. After stirring at room temperature for 24 hours, the reaction mixture was poured into water, and extracted twice with 150 ml of diethyl ether. The combined ether layer was washed with water, dried with anhydrous magnesium sulfate, and concentrated to obtain a crude product. The crude product was subjected to silica gel chromatography, which afforded 11.1 g of 3,5-dichloro-4-(3-bromopropyloxy)-1-(3,3-dichloro-2-propenyloxy) benzene (77% yield), $n_D^{24.0}$ 1.5693.

Intermediate Production Example 9

Production of Intermediate Compound 365)

A reaction vessel was charged with 22.67 g of 1,4-dibromobutane, 11.06 g of potassium carbonate and 200 ml of N,N-dimethylformamide, to which a solution of 20.16 g of 2,6-dichloro-4-(3,3-dichloro-2-propenyloxy)phenol dissolved in 80 ml of N,N-dimethylformamide was slowly added dropwise. After stirring at room temperature for 24 hours, the reaction mixture was poured into water, and extracted twice with 300 ml of diethyl ether. The combined ether layer was washed with water, dried with anhydrous magnesium sulfate, and concentrated to obtain a crude product. The crude product was subjected to silica gel chromatography, which afforded 21.7 g of 3,5-dichloro-4-(4-bromobutyloxy)-1-(3,3-dichloro-2-propenyloxy)benzene (74% yield), $n_D^{25.0}$ 1.5666.

The following are production examples for the intermediate compounds of general formula [II] or [XIV].

Intermediate Production Example 10

Production of Intermediate Compound 367)

A reaction vessel was charged with 1.1 g of 3,5-dichloro-4-(3-bromopropyloxy)-1-(3,3-dichloro-2-propenyloxy) benzene, 3.31 g of benzoic acid, 3.90 g of potassium carbonate and 50 ml of N,N-dimethylformamide. After stirring at room temperature for 24 hours, the reaction mixture was poured into water, and extracted twice with 150 ml of diethyl ether. The combined ether layer was washed with water, dried with anhydrous magnesium sulfate, and concentrated to obtain a crude product. The crude product was subjected to silica gel chromatography, which afforded 11.6 g, of 3,5-dichloro-4-(3-benzoyloxypropyloxy)-1-(3,3-dichloro-2-propenyloxy)benzene (95% yield).

A reaction vessel was charged with 11.6 g of 3,5-dichloro-4-(3-benzoyloxypropyloxy)-1-(3,3-dichloro-2-propenyloxy)benzene, 15.2 g of 10% aqueous potassium hydroxide solution and 300 ml of methanol. After stirring at room temperature for 24 hours, and the reaction mixture was concentrated. The concentrate was poured into water, and extracted twice with 150 ml of diethyl ether. The combined ether layer was washed with water, dried with anhydrous magnesium sulfate, and concentrated to obtain a crude product. The crude product was subjected to silica gel chromatography, which afforded 7.41 g of 3-(2,6-dichloro-4-(3,3-dichloro-2-propenyloxy)phenoxy)-1-propyl alcohol (83%o yield), m.p. 56.6° C.

The following are specific examples of the intermediate compounds of the general formula [II], [XIII] or [XIV] under the corresponding compound numbers with their physical properties, if measured.
363) 3,5-Dichloro-4-(3-bromopropyloxy)-1-(3,3-dichloro-2-propenyloxy)benzene $n_D^{24.0}$ 1.5693
364) 3,5-Dichloro-4-(3-chloropropyloxy)-1-(3,3-dichloro-2-propenyloxy)benzene
365) 3,5-Dichloro-4-(4-bromobutyloxy)-1-(3,3-dichloro-2-propenyloxy)benzene $n_D^{22.5}$ 1.5666

366) 3,5-Dichloro-4-(4-chlorobutyloxy)-1-(3,3-dichloro-2-propenyloxy)benzene
367) 3,5-Dichloro-4-(3-hydroxypropyloxy)-1-(3,3-dichloro-2-propenyloxy)benzene m.p. 56.6° C.
368) 3,5-Dichloro-4-(3-hydroxybutyloxy)-1-(3,3-dichloro-2-propenyloxy)benzene
369) 3,5-Dichloro-4-(3-bromopropyloxy)-1-(3,3-dibromo-2-propenyloxy)benzene
370) 3,5-Dichloro-4-(3-chloropropyloxy)-1-(3,3-dibromo-2-propenyloxy)benzene
371) 3,5-Dichloro-4-(4-bromobutyloxy)-1-(3,3-dibromo-2-propenyloxy)benzene
372) 3,5-Dichloro-4-(4-chlorobutyloxy)-1-(3,3-dibromo-2-propenyloxy)benzene
373) 3,5-Dichloro-4-(3-hydroxypropyloxy)-1-(3,3-dibromo-2-propenyloxy)benzene m.p. 56.6° C.
374) 3,5-Dichloro-4-(4-hydroxybutyloxy)-1-(3,3-dibromo-2-propenyloxy)benzene
375) 3-Chloro-5-methyl-4-(3-bromopropyloxy)-1-(3,3-dichloro-2-propenyloxy)benzene
376) 3-Chloro-5-methyl-4-(3-chloropropyloxy)-1-(3,3-dichloro-2-propenyloxy)benzene
377) 3-Chloro-5-methyl-4-(4-bromobutyloxy)-1-(3,3-dichloro-2-propenyloxy)benzene
378) 3-Chloro-5-methyl-4-(4-chlorobutyloxy)-1-(3,3-dichloro-2-propenyloxy)benzene
379) 3-Chloro-5-methyl-4-(3-hydroxypropyloxy)-1-(3,3-dichloro-2-propenyloxy)benzene
380) 3-Chloro-5-methyl-4-(4-hydroxybutyloxy)-1-(3,3-dichloro-2-propenyloxy)benzene
381) 3-Chloro-5-methyl-4-(3-bromopropyloxy)-1-(3,3-dibromo-2-propenyloxy)benzene
382) 3-Chloro-5-methyl-4-(3-chloropropyloxy 1-(3,3-dibromo-2-propenyloxy)benzene
383) 3-Chloro-5-methyl-4-(4-bromobutyloxy)-1-(3,3-dibromo-2-propenyloxy)benzene
384) 3-Chloro-5-methyl-4-(4-chlorobutyloxy)-1-(3,3-dibromo-2-propenyloxy)benzene
385) 3-Chloro-5-methyl-4-(3-hydroxypropyloxy)-1-(3,3-dibromo-2-propenyloxy)benzene
386) 3-Chloro-5-methyl-4-(4-hydroxybutyloxy)-1-(3,3-dibromo-2-propenyloxy)benzene
387) 3-Ethyl-5-methyl-4-(3-bromopropyloxy)-1-(3,3-dichloro-2-propenyloxy)benzene
388) 3-Ethyl-5-methyl-4-(3-chloropropyloxy)-1-(3,3-dichloro-2-propenyloxy)benzene
389) 3-Ethyl-5-methyl-4-(4-bromobutyloxy)-1-(3,3-dichloro-2-propenyloxy)benzene
390) 3-Ethyl-5-methyl-4-(4-chlorobutyloxy)-1-(3,3-dichloro-2-propenyloxy)benzene
391) 3-Ethyl-5-methyl-4-(3-hydroxypropyloxy)-1-(3,3-dichloro-2-propenyloxy)benzene
392) 3-Ethyl-5-methyl-4-(4-hydroxybutyloxy)-1-(3,3-dichloro-2-propenyloxy)benzene
393) 3-Ethyl-5-methyl-4-(3-bromopropyloxy)-1-(3,3-dibromo-2-propenyloxy)benzene
394) 3-Ethyl-5-methyl-4-(3-chloropropyloxy)-1-(3,3-dibromo-2-propenyloxy)benzene
395) 3-Ethyl-5-methyl-4-(3-bromobutyloxy)-1-(3,3-dibromo-2-propenyloxy)benzene
396) 3-Ethyl-5-methyl-4-(4-chlorobutyloxy)-1-(3,3-dibromo-2-propenyloxy)benzene
397) 3-Ethyl-5-methyl-4-(3-hydroxy propyloxy)-1-(3,3-dibromo-2-propenyloxy)benzene
398) 3-Ethyl-5-methyl-4-(4-hydroxybutyloxy)-1-(3,3-dibromo-2-propenyloxy)benzene
399) 3,5-Dibromo-4-(3-bromopropyloxy)-1-(3,3-dichloro-2-propenyloxy)benzene
400) 3,5-Dibromo-4-(3-chloropropyloxy)-1-(3,3-dichloro-2-propenyloxy)benzene
401) 3,5-Dibromo-4-(3-bromobutyloxy)-1-(3,3-dichloro-2-propenyloxy)benzene
402) 3,5-Dibromo-4-(4-chlorobutyloxy)-1-(3,3-dichloro-2-propenyloxy)benzene
403) 3,5-Dibromo-4-(3-hydroxypropyloxy)-1-(3,3-dichloro-2-propenyloxy)benzene
404) 3,5-Dibromo-4-(4-hydroxybutyloxy)-1-(3,3-dichloro-2-propenyloxy)benzene
405) 3,5-Dibromo-4-(3-bromopropyloxy)-1-(3,3-dibromo-2-propenyloxy)benzene
406) 3,5-Dibromo-4-(3-chloropropyloxy)-1-(3,3-dibromo-2-propenyloxy)benzene
407) 3,5-Dibromo-4-(4-bromobutyloxy)-1-(3,3-dibromo-2-propenyloxy)benzene
408) 3,5-Dibromo-4-(4-chlorobutyloxy)-1-(3,3-dibromo-2-propenyloxy)benzene
409) 3,5-Dibromo-4-(3-hydroxypropyloxy)-1-(3,3-dibromo-2-propenyloxy)benzene
410) 3,5-Dibromo-4-(4-hydroxybutyloxy)-1-(3,3-dibromo-2-propenyloxy)benzene
411) 3,5-Dimethyl-4-(3-bromopropyloxy)-1-(3,3-dichloro-2-propenyloxy)benzene
412) 3,5-Dimethyl-4-(3-chloropropyloxy)-1-(3,3-dichloro-2-propenyloxy)benzene
413) 3,5-Dimethyl-4-(4-bromobutyloxy)-1-(3,3-dichloro-2-propenyloxy)benzene
414) 3,5-Dimethyl-4-(4-chlorobutyloxy)-1-(3,3-dichloro-2-propenyloxy)benzene
415) 3,5-Dimethyl-4-(3-hydroxypropyloxy)-1-(3,3-dichloro-2-propenyloxy)benzene
416) 3,5-Dimethyl-4(4-hydroxybutyloxy)-1-(3,3-dichloro-2-propenyloxy)benzene
417) 3,5-Dimethyl-4-(3-bromopropyloxy)-1-(3,3-dibromo-2-propenyloxy)benzene
418) 3,5-Dimethyl-4-(3-chloropropyloxy)-1-(3,3-dibromo-2-propenyloxy)benzene
419) 3,5-Dimethyl-4-(4-bromobutyloxy)-1-(3,3-dibromo-2-propenyloxy)benzene
420) 3,5-Dimethyl-4-(4-chlorobutyloxy)-1-(3,3-dibromo-2-propenyloxy)benzene
421) 3,5-Dimethyl-4-(3-hydroxypropyloxy)-1-(3,3-dibromo-2-propenyloxy)benzene
422) 3,5-Dimethyl-4-(4-hydroxybutyloxy)-1-(3,3-dibromo-2-propenyloxy)benzene
423) 3,5-Diethyl-4-(3-bromopropyloxy)-1-(3,3-dichloro-2-propenyloxy)benzene
424) 3,5-Diethyl-4-(3-chloropropyloxy)-1-(3,3-dichloro-2-propenyloxy)benzene
425) 3,5-Diethyl-4-(4-bromobutyloxy)-1-(3,3-dichloro-2-propenyloxy)benzene
426) 3,5-Diethyl-4-(34-chlorobutyloxy)-1-(3,3-dichloro-2-propenyloxy)-benzene
427) 3,5-Diethyl-4-(3-hydroxypropyloxy)-1-(3,3-dichloro-2-propenyloxy)benzene
428) 3,5-Diethyl-4-(4-hydroxy butyloxy))-1-(3,3-dichloro-2-propenyloxy)benzene
429) 3,5-Diethyl-4-(3-bromopropyloxy)-1-(3,3-dibromo-2-propenyloxy)benzene
430) 3,5-Diethyl-4-(3-chloropropyloxy)-1-(3,3-dibromo-2-propenyloxy)benzene
431) 3,5-Diethyl-4-(4-bromobutyloxy)-l1-(3,3-dibromo-2-propenyloxy)benzene
432) 3,5-Diethyl-4-(4-chlorobutyloxy)-1-(3,3-dibromo-2-propenyloxy)benzene
433) 3,5-Diethyl-4-(3-hydroxypropyloxy)-1-(3,3-dibromo-2-propenyloxy)benzene 434) 3,5-Diethyl-4-(4-hydroxybutyloxy)-1-(3,3-dibromo-2-propenyloxy)benzene
435) 3,5-Diisopropyl-4-(3-bromopropyloxy)-1-(3,3-dichloro-2-propenyloxy)benzene
436) 3,5-Diisopropyl-4-(3-chloropropyloxy)-1-(3,3-dichloro-2-propenyloxy)benzene
437) 3,5-Diisopropyl -4-(4-bromobutyloxy)-1-(3,3-dichloro-2-propenyloxy)benzene
438) 3,5-Diisopropyl-4-(4-chlorobutyloxy)-1-(3,3-dichloro-2-propenyloxy)benzene
439) 3,5-Diisopropyl-4-(3-hydroxypropyloxy)-1-(3,3-dichloro-2-propenyloxy)benzene
440) 3,5-Diisopropyl-4-(4-hydroxybutyloxy)-1-(3,3-dichloro-2-propenyloxy)benzene
441) 3,5-Diisopropyl-4-(3-bromopropyloxy)-1-(3,3-dibromo-2-propenyloxy)benzene
442) 3,5-Diisopropyl-4-(3-chloropropyloxy)-1-(3,3-dibromo-2-propenyloxy)benzene
443) 3,5-Diisopropyl-4-(4-bromobutyloxy)-1-(3,3-dibromo-2-propenyloxy)benzene
444) 3,5-Diisopropyl-4-(4-chlorobutyloxy)-1-(3,3-dibromo-2-propenyloxy)benzene
445) 3,5-Diisopropyl-4-(3-hydroxypropyloxy)-1-(3,3-dibromo-2-propenyloxy)benzene
446) 3,5-Diisopropyl-4-(4-hydroxybutyloxy)-1-(3,3-dibromo-2-propenyloxy)benzene
447) 3,5-Difluoro-4-(3-bromopropyloxy)-1-(3,3-dichloro-2-propenyloxy)benzene
448) 3,5-Difluoro-4-(3-chloropropyloxy)-1-(3,3-dichloro-2-propenyloxy)benzene
449) 3,5-Difluoro-4-(4-bromobutyloxy)-1-(3,3-dichloro-2-propenyloxy)benzene
450) 3,5-Difluoro-4-(4-chlorobutyloxy)-1-(3,3-dichloro-2-propenyloxy)benzene
451) 3,5-Difluoro-4-(3-hydroxypropyloxy)-1-(3,3-dichloro-2-propenyloxy)benzene
452) 3,5-Difluoro-4-(4-hydroxybutyloxy)-1-(3,3-dichloro-2-propenyloxy)benzene
453) 3,5-Difluoro-4-(3-bromopropyloxy)-1-(3,3-dibromo-2-propenyloxy)benzene
454) 3,5-Difluoro-4-(3-chloropropyloxy)-1-(3,3-dibromo-2-propenyloxy)benzene
455) 3,5-Difluoro-4-(4-bromobutyloxy)-1-(3,3-dibromo-2-propenyloxy)benzene
456) 3,5-Difluoro-4-(4-chlorobutyloxy)-1-(3,3-dibromo-2-propenyloxy)benzene
457) 3,5-Difluoro-4-(3-hydroxypropyloxy)-1-(3,3-dibromo-2-propenyloxy)benzene
458) 3,5-Difluoro-4-(4-hydroxybutyloxy)-1-(3,3-dibromo-2-propenyloxy)benzene
459) 3-Chloro-5-fluoro-4-(3-bromopropyloxy)-1-(3,3-dichloro-2-propenyloxy)benzene
460) 3-Chloro-5-fluoro-4-(3-chloropropyloxy)-1-(3,3-dichloro-2-propenyloxy)benzene
461) 3-Chloro-5-fluoro-4-(4-bromo butyloxy)-1-(3,3-dichloro-2-propenyloxy)benzene
462) 3-Chloro-5-fluoro-4-(4-chlorobutyloxy)-1-(3,3-dichloro-2-propenyloxy)benzene
463) 3-Chloro-5-fluoro-4-(3-hydroxypropyloxy)-1-(3,3-dichloro-2-propenyloxy)benzene
464) 3-Chloro-5-fluoro-4-(4-hydroxybutyloxy)-1-(3,3-dichloro-2-propenyloxy)benzene
465) 3-Chloro-5-fluoro-4-(3-bromopropyloxy)-1-(3,3-dibromo-2-propenyloxy)benzene
466) 3-Chloro-5-fluoro-4-(3-chloropropyloxy)-1-(3,3-dibromo-2-propenyloxy)benzene
467) 3-Chloro -5-fluoro-4-(4-bromobutyloxy)-1-(3,3-dibromo-2-propenyloxy)benzene
468) 3-Chloro-5-fluoro-4-(4-chlorobutyloxy)-1-(3,3-dibromo-2-propenyloxy)benzene
469) 3-Chloro-5-fluoro-4-(3-hydroxypropyloxy)-1-(3,3-dibromo-2-propenyloxy)benzene
470) 3-Chloro-5-fluoro-4-(4-hydroxybutyloxy 1-(3,3-dibromo-2-propenyloxy)benzene
471) 3-Bromo-5-chloro-4-(3-bromopropyloxy)-1-(3,3-dichloro-2-propenyloxy)benzene
472) 3-Bromo-5-chloro-4-(3-chloropropyloxy)-1-(3,3-dichloro-2-propenyloxy)benzene
473) 3-Bromo-5-chloro-4-(4-bromobutyloxy)-1-(3,3-dichloro-2-propenyloxy)benzene
474) 3-Bromo -5-chloro-4-(4-chloro butyloxy)-1-(3,3-dichloro-2-propenyloxy)benzene
475) 3-Bromo -5-chloro-4-(3-hydroxypropyloxy)-1-(3,3-dichloro-2-propenyloxy)benzene
476) 3-Bromo-5-chloro-4-(4-hydroxybutyloxy)-1-(3,3-dichloro-2-propenyloxy)benzene
477) 3-Bromo-5chloro-4-(3-bromopropyloxy)-1-(3,3-dibromo-2-propenyloxy)benzene
478) 3-Bromo-5-chloro-4-(3-chloropropyloxy)-1-(3,3-dibromo-2-propenyloxy)benzene
479) 3-Bromo-5-chloro-4-(4-bromobutyloxy)-1-(3,3-dibromo-2-propenyloxy)benzene
480) 3-Bromo-5-chloro-4-(4-chlorobutyloxy)-1-(3,3-dibromo-2-propenyloxy)benzene
481) 3-Bromo -5-chloro -4-(3-hydroxypropyloxy)-1-(3,3-dibromo -2-propenyloxy)benzene
482) 3-Bromo-5-chloro -4-(3-hydroxybutyloxy)-1-(3,3-dibromo-2-propenyloxy)benzene
483) 3-Chloro -5-ethyl-4-(3-bromopropyloxy)-1-(3,3-dichloro-2-propenyloxy)benzene
484) 3-Chloro-5-ethyl-4-(3-chloropropyloxy)-1-(3,3-dichloro-2-propenyloxy)benzene
485) 3-Chloro-5-ethyl-4-(4-bromobutyloxy)-1-(3,3-dichloro-2-propenyloxy)benzene
486) 3-Chloro-5-ethyl-4-(4-chlorobutyloxy)-1-(3,3-dichloro-2-propenyloxy)benzene
487) 3-Chloro-5-ethyl-4-(3-hydroxypropyloxy)-1-(3,3-dichloro-2-propenyloxy)benzene
488) 3-Chloro-5-ethyl-4-(4-hydroxybutyloxy)-1-(3,3-dichloro-2-propenyloxy)benzene
489) 3-Chloro-5-ethyl-4-(3-bromopropyloxy)-1-(3,3-dibromo-2-propenyloxy)benzene
490) 3-Chloro -5-ethyl-4-(3-chloropropyloxy)-1-(3,3-dibromo-2-propenyloxy)benzene
491) 3-Chloro-5-ethyl-1-4-(4-bromobutyloxy)-1-(3,3-dibromo-2-propenyloxy)benzene
492) 3-Chloro-5-ethyl-4-(4-chlorobutyloxy)-1-(3,3-dibromo-2-propenyloxy)benzene
493) 3-Chloro-5-ethyl-4-(4-chlorobutyloxy)-1-(3,3-dibromo-2-propenyloxy)benzene
494) 3-Chloro-5-ethyl-4-(4-hydroxybutyloxy)-1-(3,3-dibromo-2-propenyloxy)benzene
495) 3-Chloro-5-isopropyl-4-(3-bromopropyloxy)-1-(3,3-dichloro-2-propenyloxy)benzene
496) 3-Chloro-5-isopropyl-4-(3-chloropropyloxy)-1-(3,3-dichloro-2-propenyloxy)benzene 497) 3-Chloro-5-isopropyl-4-(4-bromobutyloxy)-1-(3,3-dichloro-2-propenyloxy)benzene
498) 3-Chloro-5-isopropyl-4-(4-chlorobutyloxy)-1-(3,3-dichloro-2-propenyloxy)benzene
499) 3-Chloro-5-isopropyl-4-(3-hydroxypropyloxy)-1-(3,3-dichloro-2-propenyloxy)benzene
500) 3-Chloro-5-isopropyl-4-(4-hydroxy butyloxy)-1-(3,3-dichloro-2-propenyloxy)benzene
501) 3-Chloro-5-isopropyl -4-(3-bromopropyloxy)-1-(3,3-dibromo-2-propenyloxy)benzene 502) 3-Chloro-5-isopropyl-4-(3-chloropropyloxy)-1-(3,3-dibromo-2-propenyloxy)benzene
503) 3-Chloro-5-isopropyl-4-(4-bromobutyloxy)-1-(3,3-dibromo -2-propenyloxy)benzene
504) 3-Chloro-5-isopropyl-4-(4-chlorobutyloxy)-1-(3,3-dibromo-2-propenyloxy)benzene
505) 3-Chloro-5-isopropyl-4-(3-hydroxypropyloxy)-1-(3,3-dibromo-2-propenyloxy)benzene
506) 3-Chloro-5-isopropyl-4-(4-hydroxybutyloxy)-1-(3,3-dibromo-2-propenyloxy)benzene The following are formulation examples in which "parts" are by weight and the present compounds are designated by the corresponding compound numbers as described above.

Formulation Example 1

Emulsifiable Concentrates

Ten parts of each of the present compounds (1) to (325) are dissolved in 35 parts of xylene and 35 parts of N,N-dimethylformamide, to which 14 parts of polyoxyethylene styrylphenyl ether and 6 parts of calcium dodecylbenzenesulfonate are added, and the mixture is well stirred to give a 10% emulsifiable concentrate of each compound.

Formulation Example 2

Wettable Powders

Twenty parts of each of the present compounds (1) to (325) are added to a mixture of 4 parts of sodium lauryl sulfate, 2 parts of calcium lignin sulfonate, 20 parts of synthetic hydrated silicon oxide fine powder and 54 parts of diatomaceous earth, and the mixture is stirred with a mixer to give a 20% wettable powder of each compound.

Formulation Example 3

Granules

To 5 parts of each of the present compounds (1) to (325) are added 5 parts of synthetic hydrated silicon oxide fine powder, 5 parts of sodium dodecylbenzenesulfonate, 30 parts of bentonite and 55 parts of clay, and the mixture is well stirred. Then, a suitable amount of water is added to the mixture, which is further stirred, granulated with a granulator and then air-dried to give a 5% granule of each compound.

Formulation Example 4

Dusts

One part of each of the present compounds (1) to (325) is dissolved in a suitable amount of acetone, to which 5 parts of synthetic hydrated silicon oxide fine powder, 0.3 part of PAP and 93.7 parts of clay are added, and the mixture is stirred with a mixer. The removal of acetone by evaporation gives a I% dust of each compound.

Formulation Example 5

Flowables

Twenty parts of each of the present compounds (1) to (325) are mixed with 1.5 parts of sorbitan trioleate and 28.5 parts of an aqueous solution containing 2 parts of polyvinyl alcohol, and the mixture is pulverized into fine particles having a particle size of not more than 3 μm with a sand grinder, to which 40 parts of an aqueous solution containing 0.05 part of xanthan gum and 0.1 part of aluminum magnesium silicate are added and then 10 parts of propylene glycol are added. The mixture is stirred to give a 20% water-based suspension of each compound.

Formulation Example 6

Oil Solutions

First, 0.1 part of each of the present compounds (1) to (325) is dissolved in 5 parts of xylene and 5 parts of trichloroethane. Then, the solution was mixed with 89.9 parts of deodorized kerosine to give a 0. 1% oil solution of each compound.

Formulation Example 7

Oil-based Aerosols

First, 0.1 part of each of the present compounds (1) to (325), 0.2 part of tetramethrin, 0.1 part of d-phenothrin, and 10 parts of trichloroethane are dissolved in 59.6 parts of deodorized kerosine, and the solution is put in an aerozol vessel. Then, the vessel is equipped with a valve, through which 30 parts of a propellant (liquefied petroleum gas) are charged under increased pressure to give an oil-based aerosol of each compound.

Formulation Example 8

Water-based Aerosols

An aerosol vessel is filled with 50 parts of pure water and a mixture of 0.2 part of each of the present compounds (1) to (325), 0.2 part of d-allethrin, 0.2 part of d-phenothrin, 5 parts of xylene, 3.4 parts of deodorized kerosene and 1 part of an emulsifier [ATMOS 300 (registered trade name by Atlas Chemical Co.)]. Then, the vessel is equipped with a valve, through which 40 parts of a propellant (liquefied petroleum gas) are charged under pressure to give a water-based aerosol of each compound.

Formulation Example 9

Mosquito-coils

First, 0.3 g of each of the present compounds (1) to (325) is mixed with 0.3 g of d-allethrin, and the mixture is dissolved in 20 ml of acetone. The solution is uniformly mixed with 99.4 g of a carrier for mosquito-coils (prepared by mixing Tabu powder, pyrethrum marc powder and wood flour in the ratio of 4:3:3) under stirring. The mixture is well kneaded with 120 ml of water, molded and dried to give a mosquito-coil of each compound.

Formulation Example 10

Electric Mosquito-mats

First, 0.4 g of each of the present compounds (1) to (325), 0.4 parts of d-allethrin and 0.4 g of pipenyl butoxide are dissolved in acetone to have a total volume of 10 ml. Then, 0.5 ml of the solution is uniformly absorbed in a substrate for electric mosquito-mats having a size of 2.5 cm×1.5 cm×0.3 cm (prepared by forming a fibrillated mixture of cotton linter and pulp into a sheet) to give an electric mosquito-mat of each compound.

Formulation Example 11

Heating Smoke Formulations

First, 100 mg of each of the present compounds (1) to (325) is dissolved in a suitable amount of acetone. Then, the solution is absorbed in a porous ceramic plate having a size of 4.0 cm×4.0 cm×1.2 cm to give a heating smoke formulation of each compound.

Formulation Example 12

Poison Baits

First, 10 mg of each of the present compounds (1) to (325) is dissolved in 0.5 ml of acetone, and the solution is uniformly mixed with 5 g of solid bait powder for animals (Breeding Solid Feed Powder CE-2, trade name by Japan Clea Co., Ltd.). Then, the removal of acetone by air drying gives a 0.5% poison bait of each compound.

The following Test Examples demonstrate that the present compounds are useful as an active ingredient of insecticidal/ acaricidal agents. In these Test Examples, the present compounds are designated by the corresponding compound numbers as described above and the compounds used for comparison are designated by the corresponding compound symbols as shown in Table 18.

TABLE 18

| Compound | Chemical structure | Remarks |
| --- | --- | --- |
| (A) | ⟨○⟩—O—⟨○⟩—OCH$_2$CH=CCl$_2$ | Compound disclosed in JP-A 48-86835/1973 |
| (B) | ⟨○⟩—CH$_2$O—⟨○⟩—OCH$_2$CH=CCl$_2$ | Compound disclosed in JP-A 49-1526/1974 |

Test Example 1

Insecticidal Test Against *Spodoptera litura*

A 200-fold dilution containing an active ingredient at 500 ppm, which had been prepared by diluting with water an emulsifiable concentrate of the test compound obtained according to Formulation Example 1, was absorbed at a volume of 2 ml in 13 g of an artificial diet for *Spodoptera litura*, which had been prepared in a polyethylene cup having a diameter of 11 cm. Ten fourth-instar larvae of Spodoptera litura were set free in the cup. After 6 days, the survival of larvae was examined to determine the mortality. The test was conducted in duplicate.

As a result, it was found that the present compounds (1)–(39), (41)–(49), (51)–(66), (68)–(72), (74)–(86), (88)–(101), (104)–(172), (174)–(189), (191), (193)–(200), (202)–(246), (248), (250)–(274), (276)–(279), (284)–(286) and (288)–(308) exhibited the mortality of 80% or more. In contrast, both compounds (A) and (B) for comparison exhibited the mortality of 0%.

Test Example 2

Test Against *Tetranychus urticae* Koch

Ten female adults of *Tetranychus urticae* Koch per one leaf were allowed to parasitize to a potting bean at the primary leaf stage harvested for 7 days after seeding, and these pots were placed in a thermostated room at 25° C. After 6 days, a chemical solution containing an active ingredient at 500 ppm, which had been prepared by diluting with water an emulsifiable concentrate of the test compound obtained according to Formulation Example 1, was sprayed at a volume of 15 ml over each pot on a turntable. At the same time, 2 ml of the same solution was drenched in the soil. After 8 days, the degree of damage on the respective plants caused by *Tetranychus urticae* Koch was examined. The effects were determined according to the following criteria:

−: Damage is scarcely observed.
+: Damage is slightly observed.
++: Damage is observed at the same level as in the non-treated field.

As a result, it was found that the present compounds (7)–(8), (25)–(27), (42)–(43), (49), (63), (69)–(72), (76), (77), (102), (104), (119), (120) and evaluated as "−" or "+". In the contrast, both compounds A and B for comparison were evaluated as "++".

Test Example 3

Insecticidal Test Against *Heliothis virescens*

A dilution containing an active ingredient at 100 ppm, which had been prepared by diluting with water an emulsifiable concentrate of the test compound obtained according to Formulation Example 1, was incorporated at a volume of 0.2 ml in an artificial diet. Some second-instar larvae of H. virescens were given the diet and bred in a plastic vessel. After 6–7 days, the mortality was determined.

As a result, it was found that the present compounds (27), (34), (35), (42), (43), (54)–(57), (60), (64), (65), (68)–(70), (77), (81), (84)–(86), (88–(92), 98)–(101), (107), (108), (112), (114)–(116), (119), (122), (124), (125), (127)–(129 (146), (147), (164), (166), (185), (202), (203), (222), (224) –(226), (229), (233), (262), (263) and (272) exhibited the mortality of 80% or more. In contrast, both compounds (A) and (B) for comparison exhibited the mortality of 0%.

Test Example 4

Insecticidal Test Against *Plutella xylostella*

A chemical solution containing an active ingredient at 50 ppm, which had been prepared by diluting an emulsifiable concentrate of the test compound obtained according to Formulation Example 1 with water containing spreading agent RINOU (Nihon Nouyaku K.K.) to a degree such that the spreading agent had been 1000-fold diluted, was sprayed at a volume 25 ml over each pot of a potting cabbage at the five leaf stage. The treated plants were air dried, on which ten third-instar larvae of *Plutella xylostella* were set free. After 4 days, the mortality was determined.

As a result, it was found that the present compounds (27), (63)–(65), (68), (70), (77), (81), (84), (98), (100), (101), (106), (108), (111), (120), (130), (139)–(142), (145)–(147), (149)–(153), (157)–(159), (162), (164)–(166), (185), (188), (199), (202)–(204), (209), (212), (214), 9216), (222)–(234), (236), (242), (246(250), (251), (259), (260), (262), (263), (267), (272), (284), (292), (294)–(296), (299)–(302), (304), (306) and (308) exhibited the mortality of 80% or more. In contrast, both compounds (A) and (B) for comparison exhibited the mortality of 0%.

Industrial Applicability

The present compounds have excellent insecticidal/acaricidal activity, so that they are satisfactorily active for the control of noxious insects, mites and ticks.

We claim:

1. A dihalopropene compound of the general formula:

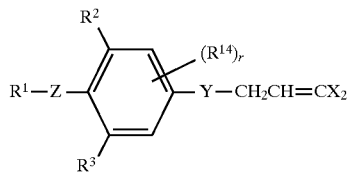

wherein $R^1$ is $C_1$–$C_{10}$ alkyl, $C_1$–$C_5$ haloalkyl, $C_2$–$C_{10}$ alkenyl, $C_2$–$C_6$ haloalkenyl, $C_3$–$C_9$ alkynyl, $C_3$–$C_5$ haloalkynyl, $C_2$–$C_7$ alkoxyalkyl, ($C_1$–$C_3$) alkoxy ($C_1$–$C_7$) carbonylalkyl, $C_2$–$C_7$ alkylthioalkyl; $C_3$–$C_6$ cycloalkyl which may be substituted with $C_1$–$C_4$ alkyl, $C_1$–$C_3$ alkoxy or $C_1$–$C_3$ haloalkoxy; $C_4$–$C_9$ cycloalkylalkyl which may be substituted with $C_1$–$C_4$ alkyl; $C_5$–$C_6$ cycloalkenyl which may be substituted with $C_1$–$C_4$ alkyl; $C_6$–$C_8$ cycloalkenylalkyl which may be substituted with $C_1$–$C_4$ alkyl; or $Q_1$, $Q_2$, $Q_3$, $Q_4$, $Q_5$, $Q_6$, $Q_7$, $Q_8$, $Q_9$ or $Q_{10}$ of the general formula:

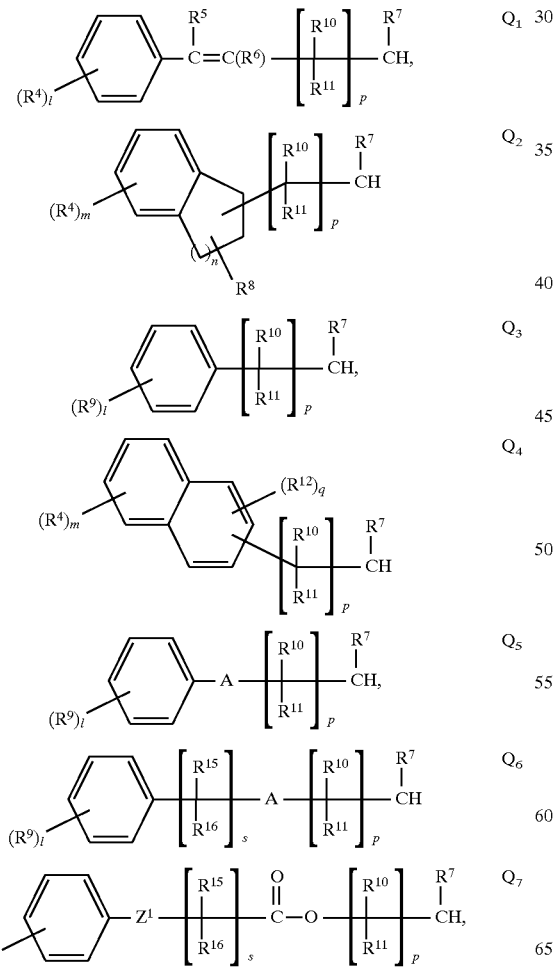

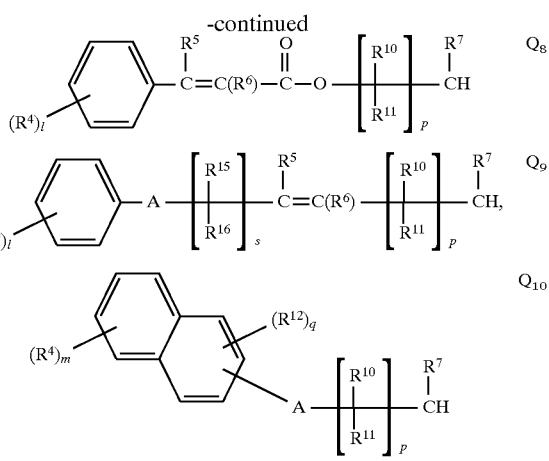

wherein $R^4$ and $R^{12}$ are independently halogen, $C_1$–$C_4$ alkyl, $C_1$–$C_3$ haloalkyl, $C_1$–$C_3$ alkoxy or $C_1$–$C_3$ haloalkoxy, $R^5$ and $R^6$ are independently hydrogen, $C_1$–$C_3$ alkyl, trifluoromethyl or halogen, $R^7$ is hydrogen or $C_1$–$C_3$ alkyl, $R^8$ is hydrogen, halogen or methyl, $R^9$ is halogen, cyano, nitro, hydroxy, pentafluorosulfanyl ($F_5S$), $C_1$–$C_8$ alkyl, $C_1$–$C_3$ haloalkyl, $C_1$–$C_8$ alkoxy, $C_1$–$C_3$ haloalkoxy, $C_1$–$C_3$ alkylthio, $C_1$–$C_3$ haloalkylthio, $C_3$–$C_6$ alkenyloxy, $C_3$–$C_6$ haloalkenyloxy, $C_1$–$C_3$ hydroxyalkyl, $C_2$–$C_4$ alkenyl, $C_2$–$C_4$ haloalkenyl, $C_2$–$C_4$ alkynyl, $C_2$–$C_4$ alkynyloxy, $C_2$–$C_4$ haloalkynyl, $C_2$–$C_4$ haloalkynyloxy, $C_2$–$C_4$ alkoxyalkyl, $C_2$–$C_4$ alkylthioalkyl, $C_3$–$C_6$ cycloalkyl, $C_5$–$C_6$ cycloalkenyl, $C_2$–$C_5$ alkoxycarbonyl, $C_3$–$C_6$ cycloalkyloxy, $C_5$–$C_6$ cycloalkenyloxy; phenyl which may be substituted with halogen, $C_1$–$C_4$ alkyl, $C_1$–$C_3$ haloalkyl, $C_1$–$C_3$ alkoxy, $C_1$–$C_3$ haloalkoxy, $C_3$–$C_6$ alkenyloxy or $C_3$–$C_6$ haloalkenyloxy; phenoxy which may be substituted with halogen, $C_1$–$C_4$ alkyl, $C_1$–$C_3$ haloalkyl, $C_1$–$C_3$ alkoxy, $C_1$–$C_3$ haloalkoxy, $C_3$–$C_6$ alkenyloxy or $C_3$–$C_6$ haloalkenyloxy; benzyl which may be substituted with halogen, $C_1$–$C_4$ alkyl, $C_1$–$C_3$ haloalkyl, $C_1$–$C_3$ alkoxy, $C_1$–$C_3$ haloalkoxy, $C_3$–$C_6$ alkenyloxy or $C_3$–$C_6$ haloalkenyloxy; benzyloxy which may be substituted with halogen, $C_1$–$C_4$ alkyl, $C_1$–$C_3$ haloalkyl, $C_1$–$C_3$ alkoxy, $C_1$–$C_3$ haloalkoxy, $C_3$–$C_6$ alkenyloxy or $C_3$–$C_6$ haloalkenyloxy; or pyridyloxy which may be substituted with halogen, $C_1$–$C_4$ alkyl, $C_1$–$C_3$ haloalkyl, $C_1$–$C_3$ alkoxy, $C_1$–$C_3$ haloalkoxy, $C_3$–$C_6$ alkenyloxy or $C_3$–$C_6$ haloalkenyloxy; or when l is an integer of 2 to 5, two adjacent $R^9$'s are taken together to form trimethylene, tetramethylene, methylenedioxy which may be substituted with halogen or $C_1$–$C_3$ alkyl; or ethylenedioxy which may be substituted with halogen or $C_1$–$C_3$ alkyl, $R^{10}$, $R^{11}$, $R^{15}$ and $R^{16}$ are independently hydrogen, $C_1$–$C_3$ alkyl or trifluoromethyl, A is oxygen, $S(O)_t$, $NR^{13}$, $C(=G^1)G^2$ or $G^1C(=G^2)$ wherein $G^1$ and $G^2$ are independently oxygen or sulfur, $R^{13}$ is hydrogen, acetyl or $C_1$–$C_3$ alkyl, and t is an integer of 0 to 2, $Z^1$ is oxygen, sulfur or $NR^{17}$ wherein $R^{17}$ is hydrogen, acetyl or $C_1$–$C_3$ alkyl, l is an integer of 0 to 5, m is an integer of 0 to 4, n is an integer of 1 or 2, p is an integer of 0 to 6, q is an integer of 0 to 3, and s is an integer of 1 to 6;

$R^2$, $R^3$ and $R^{14}$ are independently halogen, $C_1$–$C_3$ haloalkyl or $C_1$–$C_3$ alkyl, r is an integer of 0 to 2, X's are independently chlorine or bromine, Y is oxygen, NH or sulfur, and Z is oxygen, sulfur or $NR^{13}$ wherein $R^{13}$ is hydrogen, acetyl or $C_1$–$C_3$ alkyl.

2. The dihalopropene compound according to claim 1, wherein $R^2$ and $R^3$ are independently halogen or $C_1$–$C_3$ alkyl, and r is 0.

3. The dihalopropene compound according to claim 1, wherein $R^2$ and $R^3$ are independently chlorine, bromine, methyl, ethyl or isopropyl, and r is 0.

4. The dihalopropene compound according to claim 1, wherein $R^2$ and $R^3$ are both chlorine, and r is 0.

5. The dihalopropene compound according to claim 1, wherein $R^2$ is chlorine, and $R^3$ is methyl, and r is 0.

6. The dihalopropene compound according to claim 1, wherein $R^2$ is ethyl, and $R^3$ is methyl, and r is 0.

7. The dihalopropene compound according to claim 1, wherein $R^2$ and $R^3$ are both bromine and r is 0.

8. The dihalopropene compound according to claim 1, wherein $R^2$ and $R^3$ are both ethyl, and r is 0.

9. The dihalopropene compound according to claim 1, wherein $R^2$ and $R^3$ are independent halogen or $C_1$–$C_3$ alkyl, r is 1 or 2, and $R^{14}$ is halogen or $C_1$–$C_3$ alkyl.

10. The dihalopropene compound according to claim 1, wherein $R^2$ and $R^3$ are independently halogen or $C_1$–$C_3$ alkyl, r is 1 or 2, and $R^{14}$ is halogen.

11. The dihalopropene compound according to claim 1, wherein Y and Z are both oxygen.

12. The dihalopropene compound according to claim 2, wherein Y and Z are both oxygen.

13. The dihalopropene compound according to claim 1, wherein $R^1$ is $Q_3$.

14. The dihalopropene compound according to claim 1, wherein $R^1$ is $Q_3$, p is 0, and $R^9$ is halogen, $C_1$–$C_4$ alkyl, $C_1$–$C_3$ haloalkyl, $C_1$–$C_4$ alkoxy, $C_1$–$C_3$ haloalkoxy, $C_1$–$C_3$ alkylthio, $C_1$–$C_3$ haloalkylthio, cyano, nitro, or 3,4-methylenedioxy.

15. The dihalopropene compound according to claim 1, wherein $R^1$ is $Q_3$ p is 0, and $R^9$ is phenyl which may be substituted with halogen, pentafluorosulfanyl, $C_1$–$C_4$ alkyl, $C_1$–$C_3$ haloalkyl, $C_1$–$C_3$ alkoxy or $C_1$–$C_3$ haloalkoxy; benzyl which may be substituted with halogen, pentafluorosulfanyl, $C_1$–$C_4$ alkyl, $C_1$–$C_3$ haloalkyl, $C_1$–$C_3$ alkoxy or $C_1$–$C_3$ haloalkoxy; phenoxy which may be substituted with halogen, pentafluorosulfanyl, $C_1$–$C_4$ alkyl, $C_1$–$C_3$ haloalkyl, $C_1$–$C_3$ alkoxy or $C_1$–$C_3$ haloalkoxy; or benzyloxy which may be substituted with halogen, pentafluorosulfanyl, $C_1$–$C_4$ alkyl, $C_1$–$C_3$ haloalkyl, $C_1$–$C_3$ alkoxy or $C_1$–$C_3$ haloalkoxy.

16. The dihalopropene compound according to claim 1, wherein $R^1$ is $Q_3$, p is 1 to 3, $R^{10}$ and $R^{11}$ are both hydrogen, and $R^9$ is halogen, trifluoromethyl, pentafluorosulfanyl or $C_1$–$C_3$ haloalkoxy.

17. The dihalopropene compound according to claim 12, wherein $R^1$ is $Q_3$, p is 1 to 3, $R^{10}$ and $R^{11}$ are both hydrogen, and $R^9$ is halogen, trifluoromethyl, pentafluorosulfanyl or $C_1$–$C_3$ haloalkoxy.

18. The dihalopropene compound according to claim 1, wherein $R^1$ is $Q_5$.

19. The dihalopropene compound according to claim 1, wherein $R^1$ is $Q_5$, p is 1 to 4, $R^{10}$ and $R^{11}$ both hydrogen, and $R^9$ is halogen, trifluoromethyl, $C_1$–$C_3$ alkoxy, $C_1$–$C_3$ haloalkoxy, difluoromethylenedioxy or pentafluorosulfanyl.

20. The dihalopropene compound according to claim 11, wherein $R^1$ is $Q_5$ p is 2 or 3, $R^{10}$ and $R^{11}$ are both hydrogen, $R^9$ is halogen, trifluoromethyl, isopropyloxy, $C_1$–$C_3$ haloalkoxy, pentafluorosulfanyl or difluoromethylenedioxy, and A is oxygen.

21. The dihalopropene compound according to claim 11, wherein $R^1$ is $Q_5$, p is 2 or 3, $R^{10}$ and $R^{11}$ are both hydrogen, $R^9$ is halogen, trifluoromethyl, isopropyloxy or $C_1$–$C_3$ haloalkoxy, and A is oxygen.

22. The dihalopropene compound according to claim 12, wherein $R^1$ is $Q_2$.

23. The dihalopropene compound according to claim 12, wherein $R^1$ is $Q_6$.

24. The dihalopropene compound according to claim 12, wherein $R^1$ is $Q_1$.

25. The dihalopropene compound according to claim 12, wherein $R^1$ is $Q_4$.

26. The dihalopropene compound according to claim 12, wherein $R^1$ is $Q_7$.

27. The dihalopropene compound according to claim 12, wherein $R^1$ is $Q_8$.

28. The dihalopropene compound according to claim 12, wherein $R^1$ is $Q_9$.

29. The dihalopropene compound according to claim 12, wherein $R^1$ is $Q_{10}$.

30. The dihalopropene compound according to claim 1, wherein $R^1$ is $C_1$–$C_{10}$ alkyl, $C_1$–$C_5$ haloalkyl, $C_2$–$C_{10}$ alkenyl, $C_2$–$C_6$ haloalkenyl, $C_3$–$C_9$ alkynyl, $C_3$–$C_5$ haloalkynyl, $C_2$–$C_7$ alkoxyalkyl, ($C_1$–$C_3$) alkoxy ($C_1$–$C_7$) carbonylalkyl, $C_2$–$C_7$ alkylthioalkyl; $C_3$–$C_6$ cycloalkyl which may be substituted with $C_1$–$C_4$ alkyl, $C_1$–$C_3$ alkoxy or $C_1$–$C_3$ haloalkoxy; $C_4$–$C_9$ cycloalkylalkyl which may be substituted with $C_1$–$C_4$ alkyl; $C_5$–$C_6$ cycloalkenyl which may be substituted with $C_1$–$C_4$ alkyl; or $C_6$–$C_8$ cycloalkenylalkyl which may be substituted with $C_1$–$C_4$ alkyl.

31. The dihalopropene compound according to claim 1 which is 3,5-Dichloro-4-(3-(4-chlorophenoxy)propyloxy)-1-(3,3-dichloro-2-propenyloxy)benzene.

32. The dihalopropene compound according to claim 1 which is 3,5-Dichloro-4-(3-(4-bromophenoxy)propyloxy)-1-(3,3-dichloro-2-propenyloxy)benzene.

33. The dihalopropene compound according to claim 1 which is 3,5-Dichloro-4-(3-(4-trifluoromethoxy) phenoxypropyloxy)-1-(3,3-dichloro-2-propenyloxy) benzene.

34. The dihalopropene compound according to claim 1 which is 3,5-Dichloro-4-(3-(4-trifluoromethylphenoxy) propyloxy)-1-(3,3-dichloro-2-propenyloxy)benzene.

35. The dihalopropene compound according to claim 1 which is 3,5-Dichloro-4-(3-(4-isopropyloxyphenoxy) propyloxy)-1-(3,3-dichloro-2-propenyloxy)benzene.

36. The dihalopropene compound according to claim 1 which is 3,5-Dichloro-4-(3-(4-(1,1,2,2-tetrafluoroethoxy) phenoxy)propyloxy)-1-(3,3-dichloro-2-propenyloxy) benzene.

37. The dihalopropene compound according to claim 1 which is 3,5-Dichloro-4-(4-(4-chlorophenoxy)butyloxy)-1-(3,3-dichloro-2-propenyloxy)benzene.

38. The dihalopropene compound according to claim 1 which is 3,5-Dichloro-4-(4-(4-bromophenoxy)butyloxy)-1-(3,3-dichloro-2-propenyloxy)benzene.

39. The dihalopropene compound according to claim 1 which is 3,5-Dichloro-4-(4-(4-trifluoromethoxy)phenoxy) butyloxy)-1-(3,3-dichloro-2-propenyloxy)benzene.

40. The dihalopropene compound according to claim 1 which is 3, 5-Dichloro-4-(4-(4-trifluoromethylphenoxy) butyloxy)-1-(3,3-dichloro-2-propenyloxy)benzene.

41. The dihalopropene compound according to claim 1 which is 3,5-Dichloro-4-(4-(4-isopropyloxyphenoxy) butyloxy)-1-(3,3-dichloro-2-propenyloxy)benzene.

42. The dihalopropene compound according to claim 1 which is 3,5-Dichloro-4-(4-(4-(1,1,2,2-tetrafluoroethoxy) phenoxy)butyloxy)-1-(3,3-dichloro-2-propenyloxy) benezene.

43. The dihalopropene compound according to claim 1 which is 3,5-Dichloro-4-(2-(4-bromophenyl)ethoxy)-1-(3,3-dichloro-2-propenyloxy)benzene.

44. The dihalopropene compound according to claim 1 which is 3,5-Dichloro-4-(4-(4-chlorophenyl)butyloxy)-1-(3, 3-dichloro-2-propenyloxy)benzene.

45. The dihalopropene compound according to claim 1 which is 3,5-Dichloro-4-(4-(4-trifluoromethoxy)phenyl) butyloxy)-1-(3,3-dichloro-2-propenyloxy)benzene.

46. The dihalopropene compound according to claim 1 which is 3-Chloro-5-methyl-4-(3-(4-(trifluoromethoxy) phenoxy)propyloxy)-1-(3,3-dichloro-2-propenyloxy) benzene.

47. The dihalopropene compound according to claim 1 which is 3-Chloro-5-methyl-4-(3-(4-(trifluoromethyl) phenoxy) propyloxy)-1-(3,3-dichloro-2-propenyloxy) benzene.

48.) The dihalopropene compound according to claim 1 which is 3-Ethyl-5-methyl-4-(3-(4-(trifluoromethoxy) phenoxy)propyloxy)-1-(3,3-dichloro-2-propenyloxy) benzene.

49. The dihalopropene compound according to claim 1 which is 3-Ethyl-5-methyl-4-(3-(4-(trifluoromethyl) phenoxy)propyloxy-1-(3,3-dichloro-2-propenyloxy) benzene.

50. The dihalopropene compound according to claim 1 which is 3,5-Diethyl-4-(3-(4-(trifluoromethoxy) phenoxy) propyloxy)-1-(3,3-dichloro-2-propenyloxy)benzene.

51. The dihalopropene compound according to claim 1 which is 3,5-Diethyl-4-(3-(4-(trifluoromethyl)phenoxy) propyloxy)-1-(3,3-dichloro-2-propenyloxy)benzene.

52. An insecticidal/acaricidal agent comprising the dihalopropene compound according to claim 1 as an active ingredient.

53. A compound of the general formula:

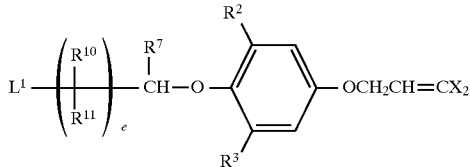

wherein $R^2$ and $R^3$ are independently halogen, $C_1$–$C_3$ alkyl or $C_1$–$C_3$ haloalkyl, $R^7$ is hydrogen or $C_1$–$C_3$ alkyl, $R^{10}$ and $R^{11}$ are independently hydrogen, $C_1$–$C_3$ alkyl or trifluoromethyl X's are independently chlorine or bromine, $L^1$ is hydroxy, halogen, methanesulfonyloxy or p-toluenesulfonyloxy, and e is an integer of 2 to 4.

54. A compound according to claim 53, wherein $R^7$, $R^{10}$ and $R^{11}$ are all hydrogen, and e is 2 or 3.

55. The compound according to claim 53 which is 3,5-Dichloro-4-(3-chloropropyloxy)-1-(3,3-dichloro-2-propenyloxy) benzene.

56. The compound according to claim 53 which is 3,5-Dichloro-4-(3-bromopropyloxy)-1-(3,3-dichloro-2-propenyloxy)benzene.

57. The compound according to claim 53 which is 3,5-Dichloro-4-(4-chlorobutyloxy)-1-(3,3-dichloro-2-propenyloxy)benzene.

58. The compound according to claim 53 which is 3,5-Dichloro-4(4-bromobutyloxy)-1-(3,3-dichloro-2-propenyloxy) benzene.

59. The compound according to claim 53 which is 3,5-Dichloro-4-(3-hydroxypropyloxy)-1-(3,3-dichloro-2-propenyloxy) benzene.

60. The compound according to claim 53 which is 3,5-Dichloro-4-(4-hydroxybutyloxy)-1-(3,3-dichloro-2-propenyloxy) benzene.

61. A compound of the general formula:

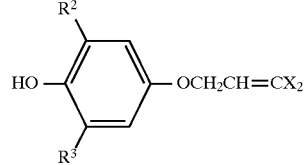

wherein $R^2$ and $R^3$ are independently halogen, $C_1$–$C_3$-alkyl or $C_1$–$C_3$ haloalkyl, and X's are independently chlorine or bromine.

62. The compound according to claim 61 which is 2,6-Dichloro-4-(3,3-dichloro-2-propenyloxy)phenol.

63. The compound according to claim 61 which is 2,6-Dichloro-4-(3,3-dibromo-2-propenyloxy)phenol.

64. The compound according to claim 61 which is 2-Chloro-6-methyl-4-(3,3-dichloro-2-propenyloxy)phenol.

65. The compound according to claim 61 which is 2-Chloro-6-methyl-4-(3,3-dibromo-2-propenyloxy)phenol.

66. The compound according to claim 61 which is 2-Ethyl-6-meth -4-(3,3-dichloro-2-propenyloxy)phenol.

67. The compound according to claim 61 which is 2-Ethyl-6-methyl-4-(3,3-dibromo-2-propenyloxy)phenol.

68. A compound of the general formula:

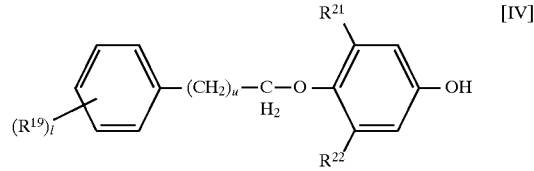

wherein $R^{21}$ and $R^{22}$ are independently halogen or $C_1$–$C_3$ alkyl, $R^{19}$ is halogen, $C_1$–$C_3$ haloalkoxy or trifluoromethyl, u is 1 to 4, and l is an integer of 0 to 5.

69. The compound according to claim 68 which is 3,5-Dichloro-4-(2-(4-bromophenyl)ethoxy)phenol.

70. The compound according to claim 68 which is 3,5-Dichloro-4-(4-(4-chlorophenyl)butoxy)phenol.

71. The compound according to claim 68 which is 3,5-Dichloro-4-(4(4-trifluoromethoxyphenyl)butoxy)phenol.

72. A compound f the general formula:

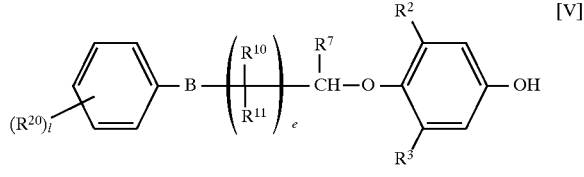

wherein $R^2$ and $R^3$ are independently halogen, $C_1$–$C_3$ alkyl or $C_1$–$C_3$ haloalkyl, $R^7$ is hydrogen or $C_1$–$C_3$ alkyl, $R^{10}$ and $R^{11}$ are independently hydrogen, $C_1$–$C_3$ alkyl or trifluoromethyl, $R^{20}$ is halogen, $C_1$–$C_3$ alkoxy, trifluoromethyl or $C_1$–$C_3$ haloalkoxy, l is an integer of 0 to 5, e is an integer of 1 to 4, and B is oxygen, $S(O)_t$ or $NR^{13}$ wherein $R^{13}$ is hydrogen, acetyl or $C_1$–$C_3$ alkyl, and t is an integer of 0 to 2.

73. The compound according to claim 72, wherein B is oxygen.

74. The compound according to claim 72, wherein $R^2$ and $R^3$ are independently halogen or $C_1$–$C_3$ alkyl, $R^7$, $R^{10}$ and $R^{11}$ are hydrogen, and e is an integer of 2 or 3.

75. The compound according to claim 72, which is 3,5-Dichloro-4-(4-chlorophenoxy)propyloxy)phenol.

76. The compound according to claim 72, which is 3,5-Dichloro-4-3-(4-bromophenoxy)propyloxy)phenol.

77. The compound according to claim 72, which is 3,5-Dichloro- n3-(4-trifluoromethylphenoxy)propyloxy)phenol.

78. The compound according to claim 72, which is 3,5-Dichloro-4-(3-(4-trifluoromethoxyphenoxy)propyloxy)phenol.

79. The compound according to claim 72, which is 3,5-Dichloro-4-(3-(4-isopropoxyphenoxy)propyloxy)phenol.

80. The compound according to claim 72, which is 3,5-Dichloro-4-(3-(4-(1,1,2,2-tetrafluoroethoxy)phenoxy)propyloxy)phenol.

81. The compound according to claim 72, which is 3,5-Dichloro-4-(4(4-chlorophenoxy)butoxy)phenol.

82. The compound according to claim 72, which is 3,5-Dichloro-4-(4(4-bromophenoxy)butoxy)phenol.

83. The compound according to claim 72, which is 3,5-Dichloro-4-(4-(4-trifluoromethylphenoxy)butoxy)phenol.

84. The compound according to claim 72, which is 3,5-Dichloro-4-(4-(4-trifluoromethoxyphenoxy)butoxy)phenol.

85. The compound according to claim 72, which is 3,5-Dichloro-4-(4-isopropoxyphenoxy)butoxy)phenol.

86. The compound according to claim 72, which is 3,5-Dichloro-4-(4-(4-(1,1,2,2-tetrafluoroethoxy)phenoxy)butoxy)phenol.

87. The compound according to claim 72, which is 3-Chloro-5-methyl-4-(3-(4-(trifluoromethoxy)phenoxy)propyloxy)phenol.

88. The compound according to claim 72, which is 3-Chloro-5-methyl-4-(3-(4-(trifluoromethyl)phenoxy)propyloxy)phenol.

89. The compound according to claim 72, which is 3-Ethyl-4-(3-(4-trifluoromethoxy)phenoxy)propyloxy)phenol.

90. The compound according to claim 72, which is 3-Ethyl-5-methyl-4-(3-(4-trifluoromethyl)phenoxy)propyloxy)phenol.

91. The compound according to claim 72, which is 3,5-Diethyl-4t3-(4-(trifluoromethoxy)phenoxy)propyloxy)phenol.

92. The compound according to claim 72, which is 3,5-Diethyl-4-(3-(4-(trifluoromethyl)phenoxy)propyloxy)phenol.

* * * * *